(12) United States Patent
Yabe et al.

(10) Patent No.: US 7,777,043 B2
(45) Date of Patent: Aug. 17, 2010

(54) COMPOUND, CHARGE TRANSPORTING MATERIAL AND ORGANIC ELECTROLUMINESCENT ELEMENT

(75) Inventors: Masayoshi Yabe, Kanagawa (JP); Hideki Sato, Kanagawa (JP); Masayo Fugono, Kanagawa (JP); Takeshi Shioya, Kanagawa (JP); Masako Takeuchi, Kanagawa (JP)

(73) Assignee: Mitsubishi Chemical Corporation, Tokyo (JP)

( * ) Notice: Subject to any disclaimer, the term of this patent is extended or adjusted under 35 U.S.C. 154(b) by 1015 days.

(21) Appl. No.: 11/342,730

(22) Filed: Jan. 31, 2006

(65) Prior Publication Data

US 2006/0186796 A1  Aug. 24, 2006

Related U.S. Application Data

(63) Continuation of application No. PCT/JP2004/011211, filed on Jul. 29, 2004.

(30) Foreign Application Priority Data

| Jul. 31, 2003 | (JP) | ............ P. 2003-204947 |
| Nov. 4, 2003 | (JP) | ............ P. 2003-374430 |
| Feb. 20, 2004 | (JP) | ............ P. 2004-045219 |

(51) Int. Cl.
   *C07D 213/04* (2006.01)
(52) U.S. Cl. .................................. 546/255
(58) Field of Classification Search .............. 546/255
   See application file for complete search history.

(56) References Cited

U.S. PATENT DOCUMENTS

| 4,882,247 | A | 11/1989 | Marugama et al. | |
| 4,937,629 | A | 6/1990 | Maruyama et al. | |
| 5,126,795 | A | 6/1992 | Maruyama et al. | |
| 5,986,121 | A | 11/1999 | Uchida et al. | |
| 6,051,319 | A | 4/2000 | Uchida et al. | |
| 6,565,994 | B2 | 5/2003 | Igarashi | |
| 6,830,829 | B2* | 12/2004 | Suzuki et al. | 428/690 |
| 6,994,922 | B2* | 2/2006 | Suzuki et al. | 428/690 |
| 2002/0055014 | A1 | 5/2002 | Okada et al. | |
| 2003/0068528 | A1 | 4/2003 | Thompson et al. | |

FOREIGN PATENT DOCUMENTS

| CN | 1376758 A | 10/2002 |
| CS | 262585 | 7/1989 |
| JP | 2-66556 | 3/1990 |
| JP | 2-195683 | 8/1990 |
| JP | 4-146442 | 5/1992 |
| JP | 2000-186066 | 7/2000 |
| JP | 2002-302671 | 10/2002 |
| JP | 2003-123987 | 4/2003 |
| JP | 2004-22334 | 1/2004 |

OTHER PUBLICATIONS

Suzuki et al. STN Accession No. 2003:271890, Document No. 138:278205, Abstract of JP 2003105332 A.*
Murase et al. STN Accession No. 2003:929770, Document No. 139:388630, Abstract of JP 4052010 B2.*
Lhotak et al. Collection of Czechoslovak Chemical Communications (1992), 57(9), 1937-46.*
Pavel Lhotak, et al., "Preparation of New Organic Luminophores Based on 3,5-Diacetylpyridines", Collect Czech. Chem. Commun., vol. 57, 1992, pp. 1937-1946 and cover page.
C. W. Tang, et al., "Organic electroluminescent diodes", Appl. Phys. Lett., vol. 51, No. 12, Sep. 21, 1987, pp. 913-915.
C. W. Tang, et al., "Electroluminescence of doped organic thin films", J. Appl. Phys. vol. 65, No. 9, May 1, 1989, pp. 3610-3616.
M. A. Baldo, et al. "Highly efficient phosphorescent emission from organic electroluminescent devices", Nature, vol. 395, Sep. 10, 1998, pp. 151-154.
M. A. Baldo, et al., Very high-efficiency green organic light-emitting devices based on electrophosphorescence, Applied Physics Letters, vol. 75, No. 1, Jul. 5, 1999, pp. 4-6.
Tetsuo Tsutsui, et al., "High Quantum Efficiency in Organic Light-Emitting Devices with Iridium-Complex as a Triplet Emissive Center", Jpn. J. Appl. Phys. vol. 38, part 2, No. 12B, Dec. 15, 1999, pp. L1502-L1504.
Raymond C. Kwong, et al., "High operational stability of electrophosphorescent devices", Applied Physics Letters, vol. 81, No. 1, Jul. 1, 2002, pp. 162-164.
Michitaka Morikawa, et al., "28a-PB-8 El cells with the emitter layer of phosphorescent dyes", Interdisciplinary Graduate School of Engineering Sciences, 1 page with English translation (Sep. 26, 1990).

* cited by examiner

*Primary Examiner*—D. Margaret Seaman
*Assistant Examiner*—Nizal S Chandrakumar
(74) *Attorney, Agent, or Firm*—Oblon, Spivak, McClelland, Maier & Neustadt, L.L.P.

(57) ABSTRACT

An object of the invention is to provide a charge transporting material having an excellent heat resistance, excellent filming properties, an excellent charge transporting ability, and excellent light-emitting characteristics and, also, to provide an organic electroluminescent element providing a high luminance and a highly luminous efficiency and having a long life.

The invention relates to a charge transporting material comprising a compound having within the molecule two or more pyridine rings substituted at 2-, 4- and 6-positions thereof, which rings do not substantially conjugate each other (provided that the 3- and 5-positions of the pyridine rings may be substituted) and an organic electroluminescent element using the charge transporting material.

14 Claims, 3 Drawing Sheets

COMPOUND, CHARGE TRANSPORTING MATERIAL AND ORGANIC ELECTROLUMINESCENT ELEMENT

FIELD OF THE INVENTION

The present invention relates to novel charge transporting materials and novel compounds and, more particularly, to charge transporting materials which are stable even when repeatedly subjected to electric oxidation or reduction and organic electroluminescent elements using the same and having high efficiency and a long life.

BACKGROUND ART

As a thin-film type electroluminescent (EL) element, those which comprise an inorganic material of the II-VI-group compound semiconductor such as ZnS, CaS or SrS doped with a light-emitting center of Mn or a rare earth element (Eu, Ce, Tb or Sm) have conventionally been popular. However, EL elements prepared from the inorganic material involve the following problems:
1) that they require countercurrent driving (50-1000 Hz);
2) that they require a high driving volt (1-200V);
3) that it is difficult to realize a full-color display (particularly blue color being difficult) by using them; and
4) that they require expensive peripheral equipment-driving circuits.

However, in recent years, development of EL elements using an organic thin film has been started in order to solve the above-mentioned problems. In particular, in order to enhance luminous efficiency, optimization has been conducted as to the kind of electrode for the purpose of improving efficiency of carrier injection from the electrode and, by the development of organic electroluminescent elements wherein a hole transport layer comprising an aromatic diamine and a light-emitting layer comprising an aluminum complex of 8-hydroxyquinoline are provided (see, non-patent document 1: Appl. Phys. Lett., 51, 913, 1987), luminous efficiency has been much more improved in comparison with the conventional EL elements using single crystal of, for example, anthracene. It has also been conducted to use an aluminum complex of 8-hydroxyquinoline as a host material and dope it with a fluorescent dye for laser such as coumarin (see, non-patent document 2: J. Appl. Phys., 65, 3610, 1989) to thereby improve luminous efficiency and conduct conversion of wavelength of emitted light. Thus, practically employable properties have approximately been obtained.

In addition to the electroluminescent elements using the low molecular materials as described above, electroluminescent elements using a high molecular material such as poly (p-phenylenevinylene), poly[2-methoxy-5-(2-ethylhexyloxy)-1,4-phenylenevinylene] or poly(3-alkylthiophene) for light-emitting layers and elements wherein a low molecular light-emitting material and an electron transfer element are mixed with a polymer material such as polyvinylcarbazole have been developed.

As an attempt to raise luminous efficiency of the element, it has also been examined to use phosphorescence instead of fluorescence. In comparison with the conventional elements using fluorescence (singlet state), elements using phosphorescence, that is, utilizing light emitted from triplet excitation state are expected to show about 3 times more improved efficiency. For this purpose, it was investigated to form a light-emitting layer comprising a coumarin derivative or a benzophenone derivative (see, non-patent document 3: 51th Oyo Butsurigakukai Rengo Koenkai, 28a-PB-7, 1990). However, there was obtained an extremely low lumninance. Thereafter, as an attempt to utilize triplet state, use of a europium complex has been investigated, but this attempt did not lead to realization of high luminous efficiency.

Recently, it has been reported that a red light can be emitted with high efficiency by using a platinum complex (T-1) shown below (non-patent document 4: Nature, 395, 151, 1998). Then, efficiency of emitting a green light has been markedly improved by doping an iridium complex (T-2) shown below into a light-emitting layer (non-patent document 5: App. Phys. Lett., 75, 4, 1999).

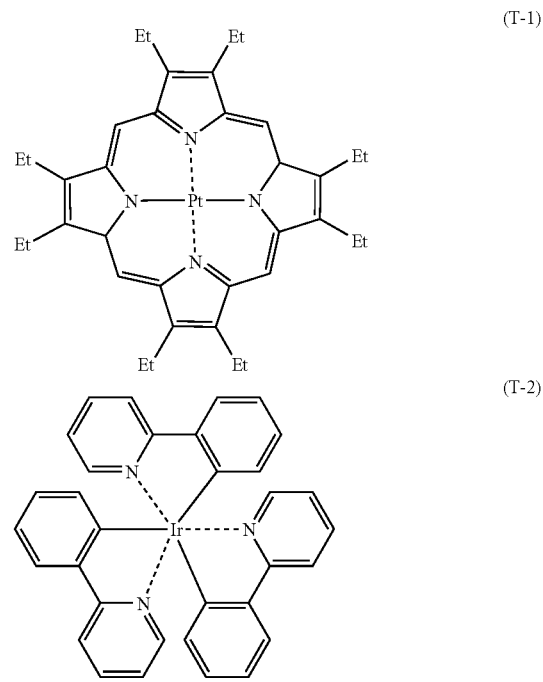

In order to apply an organic electroluminescent element to a display element such as a flat panel display, it is necessary to ensure sufficient stability upon driving as well as to improve luminous efficiency of the light-emitting element.

However, the organic electroluminescent element using the phosphorescence-emitting molecule (T-2) described in the foregoing literature shows a practically insufficient driving stability though it shows a high luminous efficiency (see, non-patent document 6: Jpn. J. Appl. Phys., 38, L1502, 1999). Thus, under the present situation, a display element showing a high efficiency is difficult to realize.

As a novel material system, patent document 1 (JP-A-2003-123983) proposes pyridine-based compounds represented by the following compounds as materials for an electron transport layer or a light-emitting layer of an organic electroluminescent element.

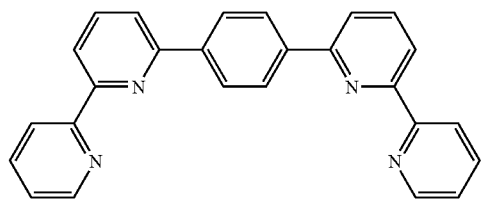

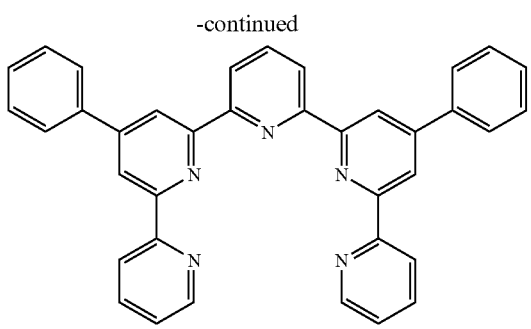

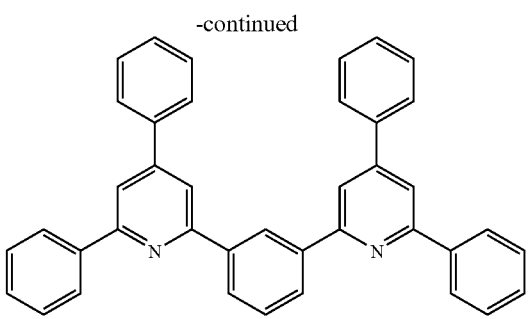

However, these compounds have a structure wherein nitrogen atoms in respective pyridine rings can be conjugated to each other, and hence they show a comparatively small oxidation-reduction potential difference.

Generally, in order to prepare organic electroluminescent elements emitting blue fluorescence or green to blue phosphorescence, it is required to use light-emitting dye having an extremely large oxidation-reduction potential difference and, in order to supply and focus charge for the dye with a high efficiency, materials surrounding the dye (a host material in a light-emitting layer and a charge transporting material constituting a layer adjacent to the light-emitting layer) are required to have a larger oxidation-reduction potential difference than that of the dye. Therefore, application of the pyridine-based compounds described in patent document 1 to the blue fluorescence-emitting element or to the phosphorescence-emitting element is considered to be difficult.

Also, since the pyridine-based compounds have hydrogen atoms at the 2-, 4- or 6-position which are Active sites on the pyridine ring, they involve a problem as to electrochemical stability. Thus, for using them as charge transporting materials in electroluminescent elements, they must be more improved.

Further, in the case where the light-emitting element is a metal complex, incorporation of a compound having a unit with a strong coordinating ability such as a bipyridyl group in a light-emitting layer or in a layer adjacent thereto can cause ligand exchange when an electric field is applied for a long time.

Non-patent document 7 (collect. Czech. Chem. Commun. (vol. 57) (1992)) proposed fluorescent materials represented by the following formulae:

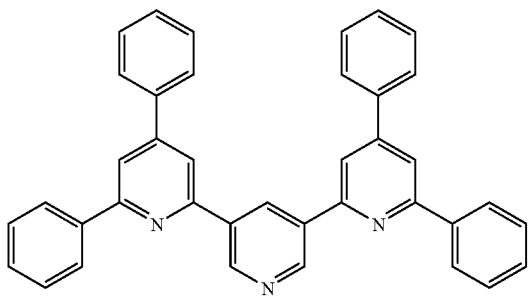

The document proposes to use the above-described compounds mainly as fluorescent dyes emitting a blue light, and does not disclose other specific applications.

By the way, in the organic electroluminescent elements having so far been reported, light emission is obtained fundamentally by the combination of a hole transport layer and an electron transport layer. The principle of emission of light is that holes injected from an anode migrate through the hole transport layer and recombine with electrons having injected from a cathode and having migrated through an electron transport layer in the vicinity of interface between the two layers to thereby excite the hole transport layer and/or the electron transport layer. Generally, a light-emitting layer is provided between the hole transport layer and the electron transport layer to thereby improve luminous efficiency.

Further, in some cases, a hole blocking layer is provided in contact with the interface with the light-emitting layer on the cathode side for the purpose of accelerating generation of excitons in the light-emitting layer to thereby enhance efficiency of light emission and purity of the color of emitted light. In particular, in an element wherein a triarylamine-based compound is used in a hole injection/transport layer and an aluminum complex is used in an electron injection/transport layer, mobility of hole tends to exceed mobility of electron, leading to the problem that holes pass through to the cathode side without contributing to emission of light. Particularly with an element wherein oxidation potential of the light-emitting layer is large and an electron transport layer uses commonly employed Alq$_3$ (an aluminum complex of 8-hydroxyquinoline), the hole blocking layer is highly required with a blue color light-emitting element or a phosphorescence-emitting element wherein holes are difficultly confined in the light-emitting layer.

With respect to the hole blocking layer, patent document 2 (JP-A-2-195683) describes, for example, to provide a hole blocking layer having a larger ionization potential than that of the light-emitting layer and, as an example thereof, it proposes to use tris(5,7-dichloroo-8-hydroxyquinolino) aluminum. Also, patent document 3 (JP-A-9-87616) proposes to use silacyclopentadiene. However, these fail to provide sufficient driving stability.

As the causes for the deterioration of driving, there have been pointed out thermal deterioration due to a low glass transition temperature (Tg) of the hole blocking material and an electrochemical factor that the hole blocking material is reduced or oxidized by injection of electrons or holes.

In an element using an iridium complex as a light-emitting dye, which emits phosphorescence with a high efficiency, an aluminum complex type hole blocking material such as Balq (aluminum(III) bis(2-methyl-8-quinolinato 4-phenylphenolate) or SAlq (aluminum(III) bis(2-methyl-8-quinolinato) triphenylsilanolate) is popularly used, succeeding in obtaining a long life to some extent (see, non-patent document 8: Appl. Phys. Lett., vol. 81, p. 162 (2002)).

However, insufficient hole blocking ability of the above-mentioned compounds has caused the problem of insufficient luminous efficiency of the element and the problem of oxidative deterioration of the material for the electron transport layer due to the fact that part of holes pass through the hole blocking material to the electron transport layer.

With the above-mentioned reasons, it has been necessary to realize rapid charge recombination in the light-emitting layer and high luminous efficiency of a dopant and to give the hole blocking material itself an enough durability against electric oxidation and reduction. Thus, further improvements and investigations have been desired with respect to materials for preparing a stable element which emits light with a high efficiency and an element structure for such materials.

[Patent Document 1]
  JP-A-2003-123987

[Patent Document 2]
  JP-A-2-195683

[Patent Document 3]
  JP-A-9-87616

[Non-Patent Document 1]
  Appl. Phys. Lett., vol. 51, p. 913, 1987

[Non-Patent Document 2]
  J. Appl. Phys., vol. 65, p. 3610, 1989

[Non-Patent Document 3]
  The 51th Oyo Butsuri-gakkai Rengo Koennkai, 28a-PB-7, 1990

[Non-Patent Document 4]
  Nature, vol. 395, p. 151, 1998

[Non-Patent Document 5]
  Appl. Phys. Lett., vol. 75, p. 4, 1999

[Non-Patent Document 6]
  Jpn. J. Phys., vol. 38, L1502, 1999

[Non-Patent Document 7]
  Collect. Czech. Chem. Commun. (Vol. 57)(1992)

[Non-Patent Document 8]
  Appl. Phys. Lett., vol 81, p. 162, 2002

DISCLOSURE OF THE INVENTION

With the above-mentioned circumstances in mind, the inventor intends to provide charge transporting materials having an excellent electron-transporting ability, an excellent durability against electric oxidation and reduction and a broad oxidation-reduction potential difference, and to provide organic electroluminescent elements emitting light with high efficiency and having high driving stability.

It is also intended to provide a compound having high amorphousness, excellent heat resistance and excellent solubility.

That is, the invention resides in a charge transporting material comprising a compound having within the molecule two or more pyridine rings substituted at 2-, 4- and 6-positions thereof, which rings do not substantially conjugate each other (provided that the 3- and 5-positions of the pyridine rings may be substituted) and in an organic electroluminescent element using the charge transporting material.

Also, the invention resides in a compound which is represented by the following formula (II) and which, when in an optimized geometry, does not form a plane structure and a compound which is represented by the following formula (II) and which, when in an optimized geometry, forms a plane structure, with p being 0:

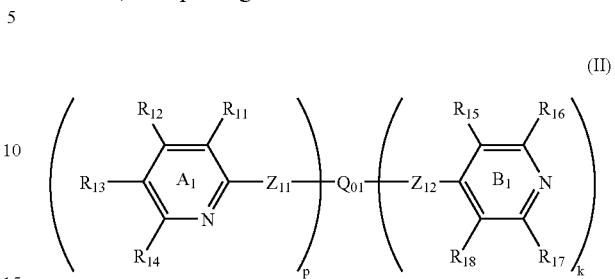

(II)

The term "compound which, when in an optimized geometry, does not form a plane structure" means that the compound has a structure which cannot form a substantially single plane structure as an optimized geometry of the molecule. The structure serves to depress π-π stacking interaction between molecules and provide excellent amorphousness, solubility and sublimation properties. Further, when formed into a film which is an aggregate of molecules, the compound of the structure can depress the phenomenon of increase in wavelength of absorption maximum and wavelength of fluorescence maximum in comparison with a solution state (wherein molecules are dispersed). Still further, it is considered that the compound can depress the phenomenon of reduction in triplet excitation level or the phenomenon of reduction in electric oxidation-reduction potential difference.

Therefore, the compound is a compound which can accumulate a large energy (of, for example, light, electricity or heat) and can discharge the accumulated energy (as, for example, light, electricity or heat).

Also, the term "compound which, when in an optimized geometry, forms a plane structure" means that the compound has a structure which forms a substantially single plane structure as an optimized geometry of the molecule. Of the compounds which are represented by the foregoing formula (II) and which, when in an optimized geometry, form a plane structure, those compounds wherein p represents 0, i.e., compounds comprising a 4-pyridyl group show an extremely high durability against repeated oxidation.

In particular, compounds, wherein pyridine rings are connected to each other through a m-phenylene group and therefore non-conjugated electron pairs on the nitrogen atoms of the respective pyridine rings cannot directly conjugate each other and wherein a conjugation structure exists between the m-phenylene ring and the pyridine ring, show a large oxidation-reduction potential difference and a particularly excellent reversibility. Amorphosness and solubility into an organic solvent can be improved by destroying symmetricalness of the pyridine rings. Such non-symmetricalness serves to provide stable filming properties without crystallization when the compound is formed into a film.

When the pyridine rings are connected to each other through a 1,3,5-substituted phenylene group (derived from a benzene ring), the non-conjugated electron pairs on the nitrogen atoms of the respective pyridine rings cannot directly conjugate each other whereas a conjugation structure exists between the 1,3,5-substituted phenylene group and the pyridine ring, thus compounds having such structure showing a large oxidation-reduction potential difference and an excellent reversibility.

Also, presence of three or more hetero rings having an electron transporting ability serves to more improve the electron transporting ability and the heat resistance of the compound. The compound has an excellent amorphousness and an excellent solubility in an organic solvent, and hence it shows good filming properties without crystallization upon formation of a film. The high glass transition temperature (Tg) of the compound serves to provide an excellent heat resistance and an excellent durability.

The organic electroluminescent element using the charge transporting material of the invention can emit light with a high luminescence and a high efficiency, showing an improved stability of the element.

The charge transporting material of the invention can be used as a light-emitting material, a host material, an electron injecting material, an electron transporting material or a hole blocking material depending upon the layer structure of the element based on its excellent heat resistance, filming properties, charge transporting ability and light-emitting properties.

Accordingly, the organic electroluminescent element by the invention can supposedly be applied to a flat panel display (e.g., for OA computers or as a wall-hanging), an onboard display element, display for a cellular phone, a light source utilizing the characteristics as a flat light-emitting body (e.g., a light source for a copying machine or a backlight source for a liquid crystal display or a meter), an indication panel or a beacon light, thus technical values of the element being large.

Since the compound of the invention has a substantially excellent oxidation-reduction stability, it is useful to utilize the compound in an electrophotographic photoreceptor as well as to in the organic electroluminescent element.

Further, the compound of the invention has an excellent amorphousness, solubility, heat resistance and durability in addition to the high performance that the charge transporting material of the invention has. Therefore, it is useful for a light-emitting material, a material for solar cell, a material for a battery (e.g., an electrolytic solution, an electrode, a separation membrane or a stabilizer), a material for medical use, a material for paint, a material for coating, a material for organic semi-conductor, a material for toiletries, a material for antistatic material and a material for thermoelectric element as well as for a charge transporting material.

Figure 1:
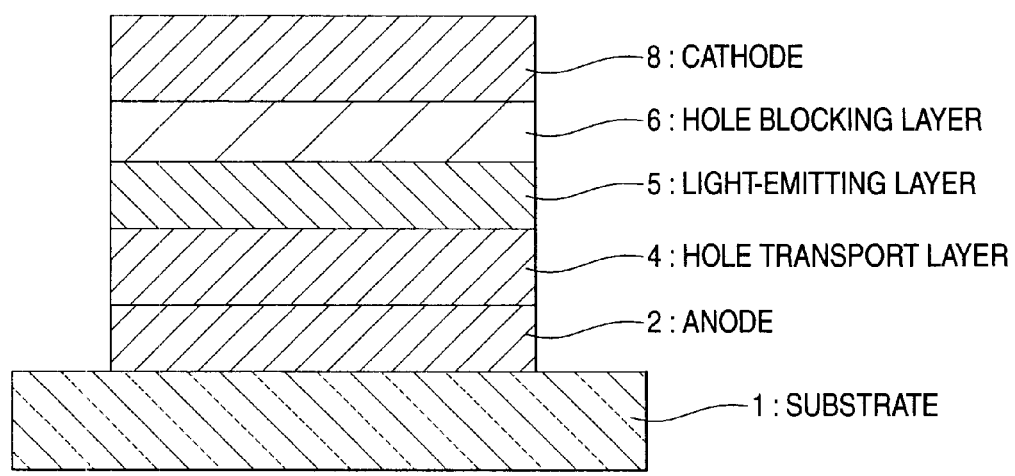
FIG. 1 is a schematic cross-sectional view showing one example of the organic electroluminescent element.

Additionally, as to numerals in the drawings, numeral 1 designates a substrate, 2 an anode, 3 an anode buffer layer, 4 a hole transport layer, 5 a light-emitting layer, 6 a hole blocking layer, 7 an electron transport layer, and 8 a cathode.

BEST MODE FOR CARRYING OUT THE INVENTION

Descriptions given below on the constituents of the invention describe one embodiment (typical example) of the invention, and do not limit the invention.

The invention relates to a charge transporting material comprising a compound which has within the molecule two or more pyridine rings substituted at 2-, 4- and 6-positions thereof, with the pyridine rings substantially not conjugating each other. The pyridine rings may be substituted at 3- and 5-positions thereof.

The charge transporting material of the invention is electrically extremely stable because it contains within the molecule pyridine rings substituted at 2-, 4- and 6-positions thereof. Therefore, use of the charge transporting material of the invention for an organic electroluminescent element or the like can provide an element having an improved stability. In addition, since the pyridine rings within the molecule do not conjugate each other as will be described hereinafter, the oxidation-reduction potential difference of the compound is difficultly reduced. The term "pyridine rings within the molecule not conjugating each other" as used herein has the meaning as will be described in detail with respect to an example of the flowing connector Q.

It suffices for the compound to have 2 or more pyridine rings within the molecule. However, the number of the pyridine rings is preferably 8 or less, because sublimation properties or solubility tends to be sacrificed and purification of the compound would become difficult.

The molecular weight of such charge transporting material is usually 4,000 or less, preferably 3,000 or less, more preferably 2,000 or less and is usually 200 or more, preferably 300 or more, more preferably 400 or more. In case when the molecular weight exceeds the upper limit, there might result seriously reduced sublimation properties which can cause troubles when a vacuum deposition method is employed for preparing a luminescent element or might result a decreased solubility in an organic solvent which makes it difficult to conduct high purification (removal of substances causing deterioration) with an increase in the amount of impurities formed in the synthesizing steps. On the other hand, in case when the molecular weight is less than the lower limit, there results a reduced glass transition temperature, reduced melting point, reduced gasification temperature and reduced filming properties, which seriously spoil heat resistance.

The hole blocking ability, which is one important characteristic property in the case of using the charge transporting material of the invention in, for example, a hole blocking and electron transport layer of the organic electroluminescent element, tends to be damaged by a diarylamine moiety within the molecule. Hence, in view of the hole blocking ability, absence of the diarylamine moiety is preferred. Further, though not so serious as the diarylamine moiety, an aryloxide moiety and an arylsulfide moiety are preferably avoided since they have a strong hole transporting ability and therefore reduce the hole blocking ability.

The term "diarylamine moiety" as used herein in the invention means an amine moiety wherein at least 2 arbitrary aromatic rings (in this specification, aromatic hydrocarbons and aromatic hetero rings are in some cases generically called "aromatic rings") exist as substituents on the nitrogen atom, and examples thereof include a diphenylamine moiety, a phenylnaphthylamine moiety and a triphenylamine moiety. Also included are those wherein substituents are connected to each other to form a ring. For example, there are illustrated a carbazole moiety, an N-phenylcarbazole moiety and an N-phenylindole moiety (provided that those moieties wherein the nitrogen atom is connected to a substituent through a double bond (e.g., acridine and phenazine) are excluded). All of them are moieties having a strong hole transporting ability.

In the invention, the aryloxide moiety means an oxide moiety wherein at least one aromatic ring exists as a substituent on the oxygen atom, and examples thereof include a phenyloxide moiety and a diphenyloxide moiety. Also included are those wherein the substituents are connected to each other to form a ring. Examples thereof include a benzofuran moiety, a dibenzofuran moiety and a dibenzo[1,4]dioxine moiety. All of them are moieties having a strong hole transporting ability.

In the invention, the arylsulfide moiety means a sulfide moiety wherein at least one aromatic ring exists as a substituent on the sulfur atom, and examples thereof include a phenylsulfide moiety and a diphenylsulfide moiety. Also included are those wherein the substituents are connected to each other to form a ring. Examples thereof include a benzothiophene moiety, a dibenzothiophene moiety and a thianthrene moiety. All of them are moieties having a strong hole transporting ability.

However, in the case of using the charge transporting material of the invention as a host material constituting a light-emitting layer, it is considered to be suitable that the charge transporting material comprises a compound having both an electron transporting ability and a hole transporting ability. In such case, a hole transporting substituent is necessary, and therefore presence of a diarylamine moiety or a carbazole ring within the molecule of the compound as a substituent capable of imparting the hole transporting ability is preferred. In particular, in order to balance with the electron transporting ability of the pyridine ring which is the main skeleton of the compound to be used as the charge transporting material of the invention, presence of at lease one carbazole ring is preferred, with 2 or more carbazole rings being more preferred, 6 or less carbazole rings being preferred, 4 or less carbazole rings being more preferred, and 3 or less carbazole rings being particularly preferred. The carbazole rings may conjugated each other within the molecule, but the pyridine rings within the molecule preferably do not conjugate the carbazole rings.

The charge transporting material of the invention is preferably a charge transporting material which comprises a compound containing within the molecule 2 to 8 pyridyl groups selected from the group consisting of an optionally substituted 2-pyridyl group and an optionally substituted 4-pyridyl group, with all of the pyridyl groups being connected to a connector Q and substantially not conjugating each other through the connector Q.

However, in the case where the compound has plural 2-pyridyl groups within the molecule, the substituents the 2-pyridyl groups have may be the same or different from each other. Also, in the case where the compound has plural 4-pyridyl groups within the molecule, the substituents the 4-pyridyl groups have may be the same or different from each other. Further, 2-, 4- and 6-positions of all pyridine rings contained in the molecule are connected to the connector Q or an arbitrary substituent.

In the charge transporting material of the invention, the connector Q is any 2- to 8-valent connector and not particularly limited as long as "all pyridyl groups in the molecule are connected to the connector Q, and any two of the pyridyl groups do not substantially conjugate each other through the connector Q".

The case where the pyridyl groups conjugate each other through the connector Q is exemplified by the case where 2 or more pyridyl groups in the molecule are connected to each other through a direct bond,

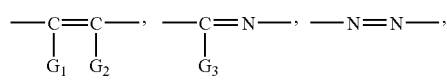

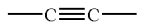

(either of cis- and trans-being possible) or a partial structure constituted by a combination of these (wherein $G_1$ to $G_3$ each independently represents a hydrogen atom or an arbitrary substituent, or constitutes part of an aromatic hydrocarbon ring or an aromatic hetero ring). That is, the above-mentioned case does not apply to the invention.

However, even when 2 or more pyridyl groups are connected through the connector Q containing the above-mentioned structure, a structure wherein the connector Q and the 2 or more pyridyl groups connected to each other through the connector Q cannot be present on the same plane (for example, the case where the connector Q is an o-phenylene group to which two pyridyl groups are connected) corresponds to the case where "(pyridyl groups) do not substantially conjugate each other through the connector Q", thus being included in the invention.

(Q)

Examples of such connector Q include $-Z_1-Q_0-Z_1-$, $-Z_1-Q_0-Z_2-$ and $-Z_2-Q_0-Z_2-$ in the formula (I) to be described hereinafter which, however, are not limitative at all.

With the charge transporting material of the invention, it is considered that conjugation between the pyridine rings contained in the molecule of the compound would reduce the oxidation-reduction potential difference of the compound or improve a hole accepting ability onto the pyridine rings, thus accelerating oxidative deterioration.

More preferred examples of the charge transporting material of the invention include compounds represented by the following formula (I):

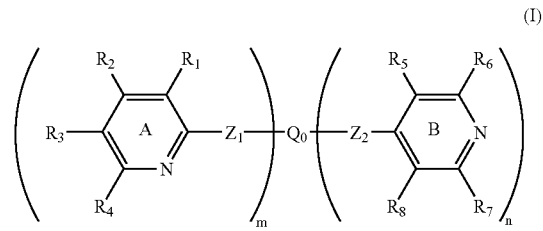

(I)

wherein $R_1$, $R_3$, $R_5$ and $R_8$ each independently represents a hydrogen atom or an arbitrary substituent, $R_2$, $R_4$, $R_6$ and $R_7$ each independently represents an arbitrary substituent, $Z_1$ represents a direct bond or a divalent connector having electrons capable of conjugating ring A, $Z_2$ represents a direct bond or a divalent connector having electrons capable of conjugating ring B, connector $Q_0$ represents a (m+n)-valent connector which makes it substantially impossible for any two members selected from the group consisting of the ring(s) A and the ring(s) B contained in the molecule to conjugate each other, m represents an integer of from 0 to 8, and n represents an integer of from 0 to 8, with the sum of m and n being an integer of from 2 to 8.

Additionally, in the case where m and/or n is 2 or more, plural $R_1$s to $R_8$s contained in the molecule may be the same or different from each other, and plural $Z_1$s and $Z_2$s contained in the molecule may be the same or different from each other.

In the formula (I), any 2 pyridyl groups selected from among the ring A and the ring B contained within the molecule do not conjugate each other through -$Z_1$-$Q_0$-$Z_1$-, -$Z_1$-$Q_0$-$Z_2$- or -$Z_2$-$Q_0$-$Z_2$-.

($Z_1$, $Z_2$)

As $Z_1$ and $Z_2$ in the formula (I), a direct bond or any connector that has conjugatable electrons and connects the connector $Q_0$ to the ring A or ring B may be employed.

Specifically, there may be illustrated:

an alkene group (derived from alkene) optionally having a substituent;

an alkyne group (derived from alkyne) optionally having a substituent;

an aromatic hydrocarbon group optionally having a substituent;

an aromatic heterocycle group optionally having a substituent; and a group comprising two or more of these connected to each other.

Specific examples thereof include those divalent groups which correspond to the monovalent groups to be described hereinafter as examples of $R_1$ to $R_8$. Also, examples of the substituents these may have include the same groups described with respect to $R_1$ to $R_8$.

In view of durability against electric reduction, $Z_1$ and $Z_2$ each preferably represents a direct bond, an optionally substituted alkene group, an optionally substituted alkyne group or an optionally substituted aromatic hydrocarbon group and, in view of obtaining a high triplet excitation level and a large oxidation-reduction potential difference, particularly preferably a direct bond or an optionally substituted aromatic hydrocarbon group. The molecular weight of each of $Z_1$ and $Z_2$ is preferably 400 or less, more preferably 250 or less, including the molecular weight of the substituent.

More preferred examples of the connector $Z_1$ or $Z_2$ are illustrated below.

Z-1

$Q_0$—

Z-2

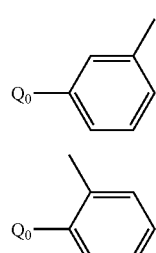

Z-3

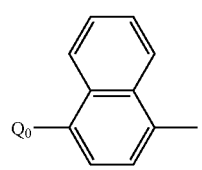

Z-4

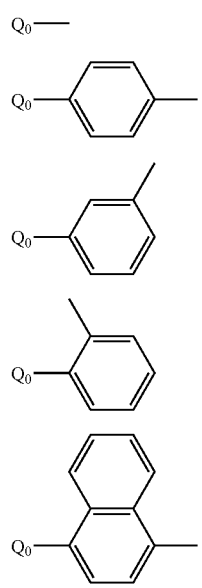

Z-5

-continued

Z-6

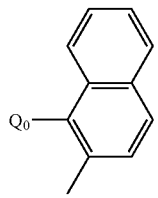

Z-7

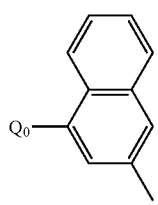

Z-8

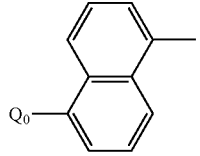

Z-9

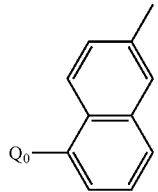

Z-10

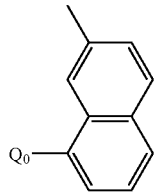

Z-11

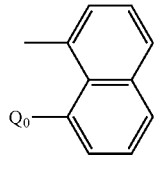

Z-12

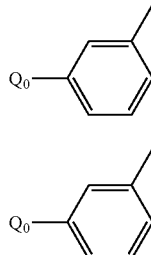

Z-13

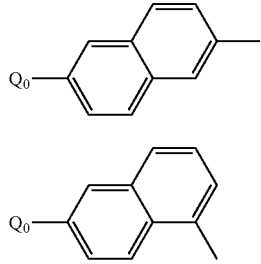

Z-14

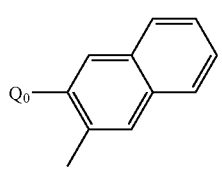

-continued
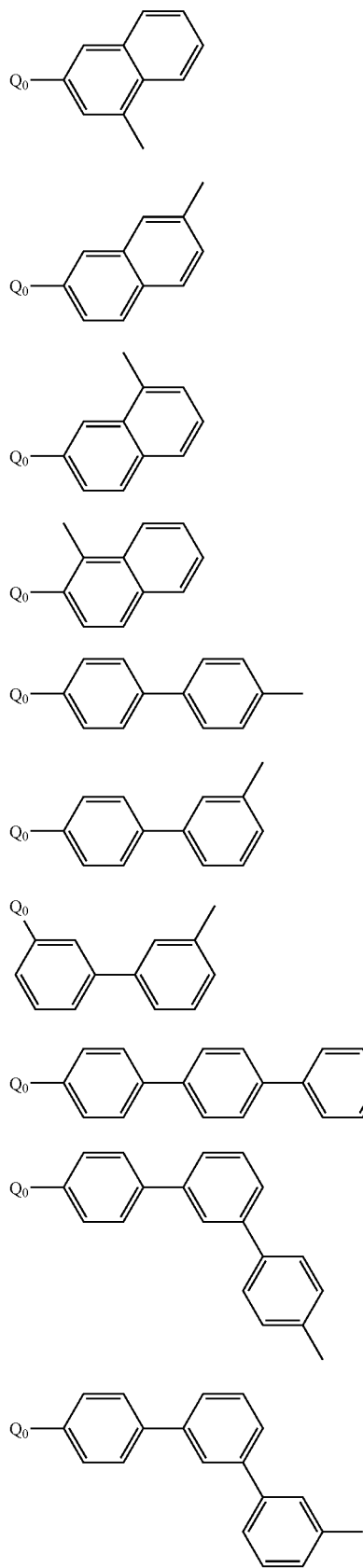
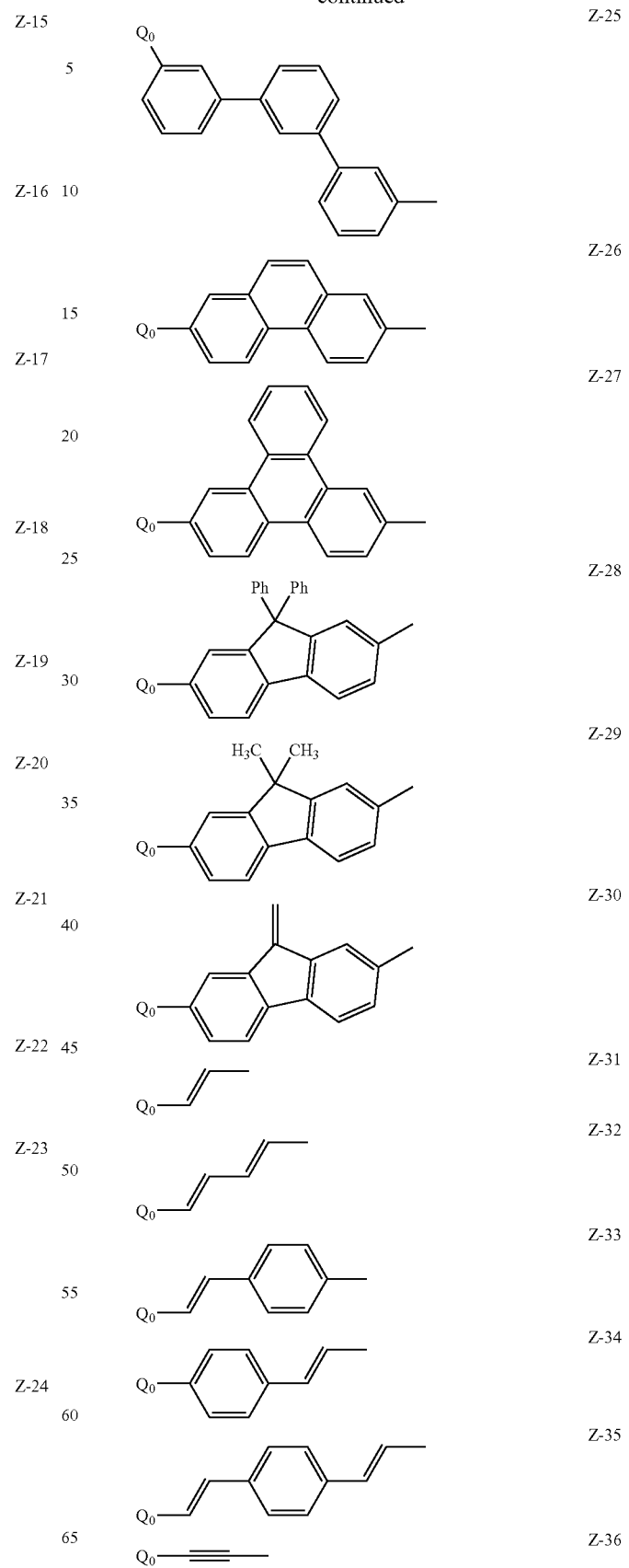

-continued
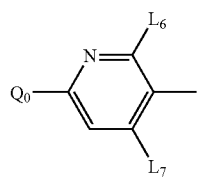 Z-37
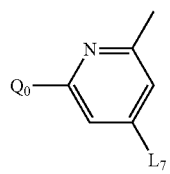 Z-38
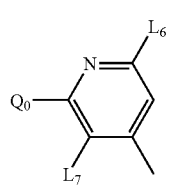 Z-39
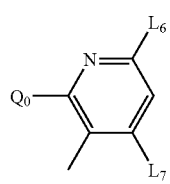 Z-40
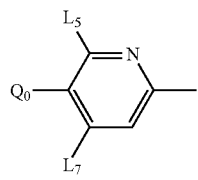 Z-41
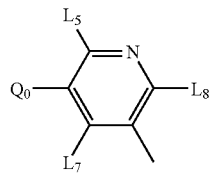 Z-42
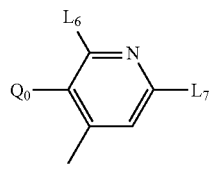 Z-43
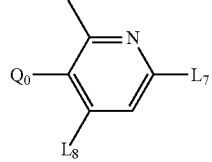 Z-44
-continued
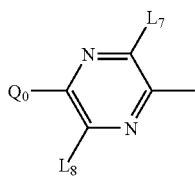 Z-45
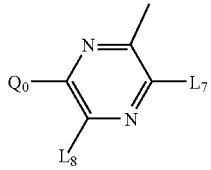 Z-46
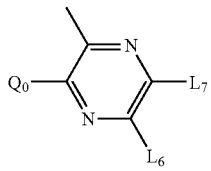 Z-47
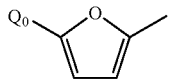 Z-48
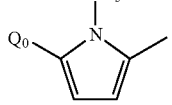 Z-49
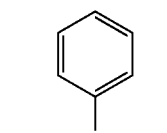 Z-50
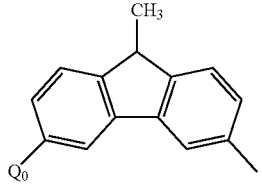 Z-51
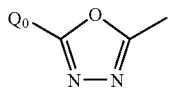 Z-52
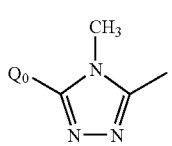 Z-53
Z-54

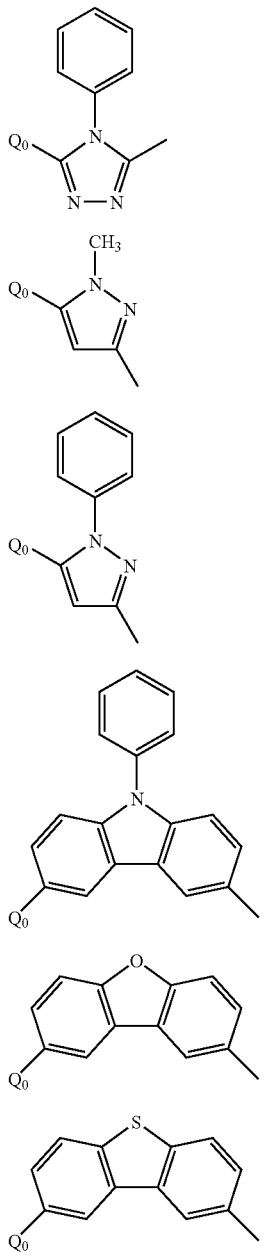

In each of the above-described structures, $L_6$ to $L_8$ each independently represents an alkyl group, an aromatic hydrocarbon group or an alkyl-substituted aromatic hydrocarbon ring.

Specific examples thereof include an alkyl group containing from about 1 to about 6 carbon atoms such as a methyl group, an ethyl group, an isopropyl group or a tert-butyl group; an aromatic hydrocarbon group containing from about 6 to about 18 carbon atoms such as a phenyl group, a naphthyl group or a fluorenyl group; and an alkyl-substituted aromatic hydrocarbon of from about 7 to about 30 in total carbon atoms such as a tolyl group, a mesityl group and a 2,6-dimethylphenyl group.

Additionally, all of the above-described structures may have a substituent in addition to $L_6$ to $L_8$. However, if the substituent exerts a strong influence on the electron state of the pyridine ring or the like to which the structure is connected, there might result a small oxidation-reduction potential difference. Therefore, it is preferred to select, as the substituent, a group which has a small electron donative property and a small electron attractive property and which difficultly lengthens the length of intramolecular conjugation. As specific examples of such group, there are also illustrated an alkyl group, an aromatic hydrocarbon group and an alkyl-substituted aromatic hydrocarbon group, and specific examples thereof include the same groups as has been illustrated as $L_6$ to $L_8$. Additionally, with compounds having 2 or more of the above-described structures within the molecule, 2 or more $L_6$s to $L_8$s contained in the molecule may be the same or different from each other.

Of the above-illustrated structures, Z-1 (direct bond), Z-2 to 21, 28, 29, 31 to 35, 48 to 52 and 56 to 60 are preferred, Z-1 (direct bond), Z-2, 3, 4, 5, 8, 10, 12, 15, 16, 17, 19, 28, 29, 31, 33, 34, 52, and 56 to 58 are more preferred, Z-1 (direct bond), Z-2, 5, 8, 12, 19, 28 and 29 are still more preferred, and Z-1 (direct bond), Z-2 and 19 are most preferred in view of sufficiently enlarging the oxidation-reduction potential difference and in view of durability against repeated electric oxidation and reduction.

($Q_o$)

The connector $Q_0$ represents a (m+n)-valent connector which makes it substantially impossible for any two members selected from the group consisting of the ring(s) A and the ring(s) B contained in the molecule to conjugate each other.

Specifically, there may be illustrated:

an alkane group (derived from alkane) optionally having a substituent;

an alkene group optionally having a substituent;

an alkyne group optionally having a substituent;

—$NR_a$— (wherein $R_a$ represents an arbitrary substituent), —O—, —CO—, —COO—, —SO—, —$SO_2$—;

an amide group optionally having a substituent;

a silyl group optionally having a substituent;

a boryl group optionally having a substituent;

a phosphino group optionally having a substituent;

an aromatic hydrocarbon group optionally having a substituent;

an aromatic heterocycle group optionally having a substituent; and a group comprising two or more of these connected to each other.

of these, in view of sufficiently enlarging the oxidation-reduction potential difference and durability against repeated electric oxidation and reduction, an alkane group optionally having a substituent, —$NR_a$—, a silyl group optionally having a substituent, an aromatic hydrocarbon group optionally having a substituent and an aromatic heterocycle group optionally having a substituent are preferred as $Q_0$. Further, since a high electron transporting ability and a high hole blocking ability are expected, an aromatic hydrocarbon group optionally having a substituent and a pyridylene group (a divalent group derived from pyridine) are more preferably illustrated, with an aromatic hydrocarbon group optionally having a substituent being particularly preferred. The molecular weight of $Q_0$ including the substituent is preferably 400 or less, more preferably 250 or less.

Additionally, in the case where $Q_0$ represents a pyridylene group, it is preferred for the compound to have, as $Z_1$ and/or $Z_2$, a group which prohibits conjugation between the pyridine rings.

Specific examples thereof include (m+n)-valent groups corresponding to mono-valent groups to be described hereinafter as examples of $R_1$ to $R_8$. Examples of the substituent they can have and preferred ones thereof are also the same as those described with respect to $R_1$ to $R_8$.

Examples of Ra also include the same ones as are described hereinafter as $R_1$ to $R_8$, and the same applies to preferred examples thereof. Specific examples of the connector $Q_0$ are described hereinafter which, however, do not limitative at all.

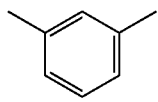
Q-1

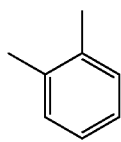
Q-2

Q-3

Q-4

Q-5

Q-6

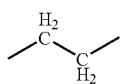
Q-7

Q-8

Q-9

Q-10

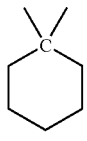
Q-11

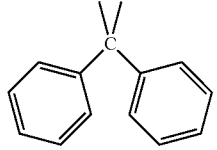
Q-12

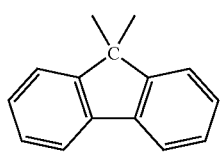

-continued

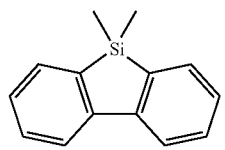
Q-13

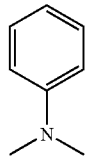
Q-14

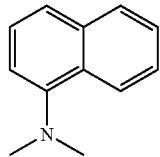
Q-15

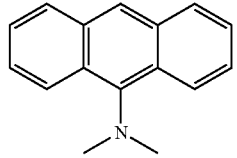
Q-16

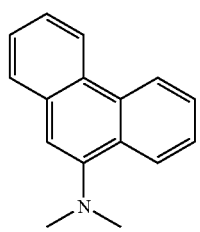
Q-17

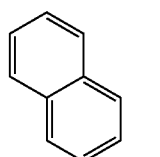
Q-18

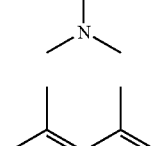
Q-19

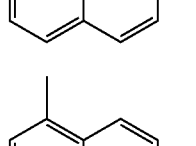
Q-20

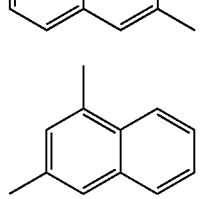
Q-21

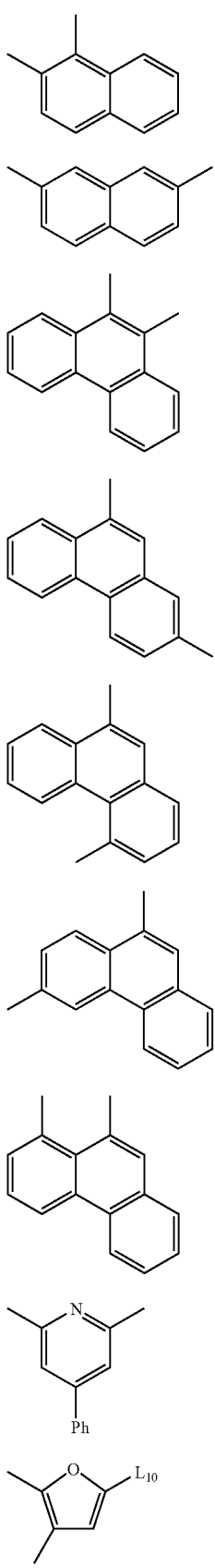
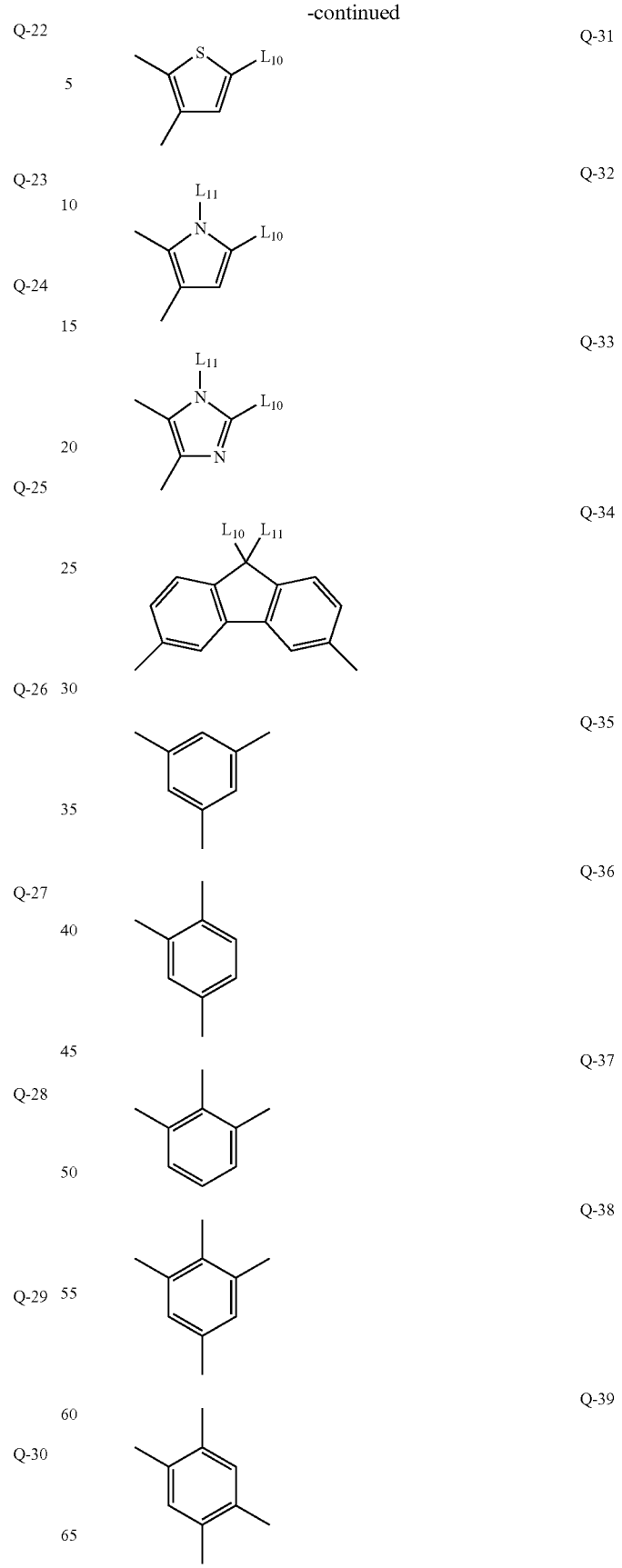

-continued
Q-40 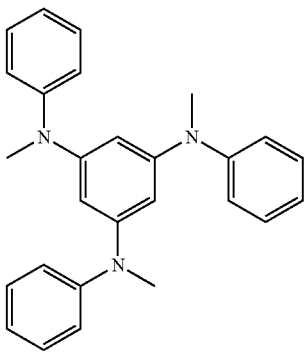
Q-41
Q-42
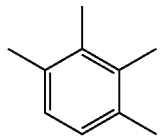
Q-43 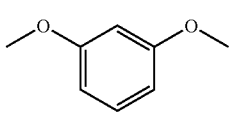
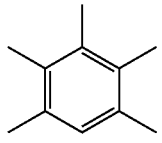
Q-44 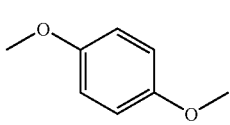
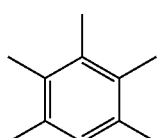
Q-45 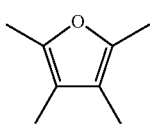
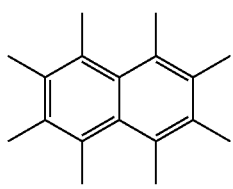
Q-46 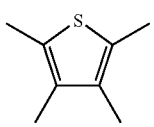
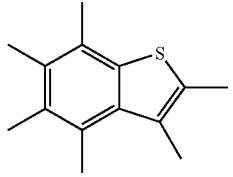
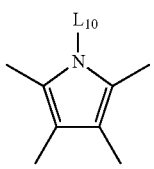
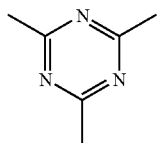
Q-47 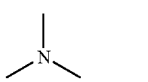
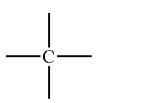
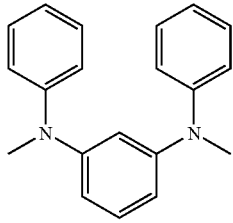
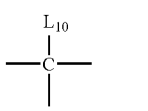
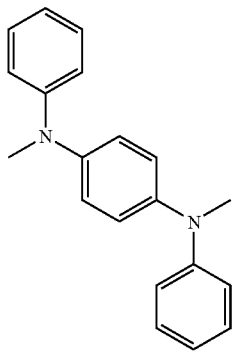
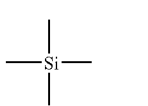
Q-48
Q-49
Q-50
Q-51
Q-52
Q-53
Q-54
Q-55
Q-56
Q-57

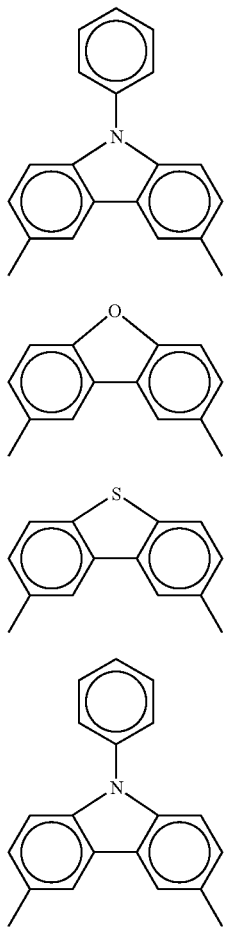

In each of the above-described structures, $L_{10}$ and $L_{11}$ each independently represents an alkyl group, an aromatic hydrocarbon group or an alkyl-substituted aromatic hydrocarbon group.

Specific examples thereof include alkyl groups containing from about 1 to about 6 carbon atoms such as a methyl group, an ethyl group, an isopropyl group and a tert-butyl group; aromatic hydrocarbon groups containing from about 6 to about 18 carbon atoms such as a phenyl group, a naphthyl group and a fluorenyl group; and alkyl-substituted aromatic hydrocarbon groups of from about 7 to about 30 in number of total carbon atoms such as a tolyl group, a mesityl group and a 2,6-dimethylphenyl group.

Additionally, all of the above-described structures may have a substituent in addition to $L_{10}$ to $L_{11}$. However, if the substituent exerts a strong influence on the electron state of the pyridine ring or the like to which the structure is connected, there might result a small oxidation-reduction potential difference. Therefore, it is preferred to select, as the substituent, a group which has a small electron donative property and a small electron attractive property and which difficultly lengthens the length of intramolecular conjugation. As specific examples of such group, there are also illustrated an alkyl group, an aromatic hydrocarbon group and an alkyl-substituted aromatic hydrocarbon group, and specific examples thereof include the same groups as has been illustrated as $L_{10}$ and $L_{11}$. Additionally, with compounds having 2 or more of the above-described structures within the molecule, 2 or more $L_{10}$s and $L_{11}$s contained in the molecule may be the same or different from each other.

Among them, in view of obtaining a sufficiently large oxidation-reduction potential difference, realizing an excellent durability against electric oxidation and reduction, and obtaining an appropriate electron transporting ability, Q-1 to 4, 7 to 13, 19 to 23, 29, 34 to 43, 45 and 51 to 61 are preferred, Q-1, 8 to 13, 19, 20, 21, 23, 34, 35 to 42, 45 and 55 to 61 are more preferred, Q-1, 8 to 12, 20, 21, 23, 34, 35, 45, 58 and 61 are still more preferred, and Q-1, 11, 12, 23 and 35 are most preferred.

($R_1$ to $R_8$)

$R_1$, $R_3$, $R_5$ and $R_8$ in the formula (I) each independently represents a hydrogen atom or an arbitrary substituent, and $R_2$, $R_4$, $R_6$ and $R_7$ each independently represents an arbitrary substituent.

Specific examples of an arbitrary substituent to be employed as $R_1$ to $R_8$ include an alkyl group optionally having a substituent (preferably a straight or branched alkyl group containing from 1 to 8 carbon atoms; e.g., methyl, ethyl, n-propyl, 2-propyl, n-butyl, isobutyl or tert-butyl); an alkenyl group optionally having a substituent (preferably an alkenyl group containing from 2 to 9 carbon atoms; e.g., vinyl, allyl or 1-butenyl); an alkynyl group optionally having a substituent (preferably an alkynyl group containing from 2 to 9 carbon atoms; e.g., ethynyl or propargyl); an arylalkyl group optionally having a substituent (preferably an arylalkyl group containing from 7 to 15 carbon atoms; e.g., benzyl); an amino group optionally having a substituent (preferably an alkylamino group having one or more alkyl groups containing from 1 to 8 carbon atoms and optionally having a substituent (e.g., methylamino, diethylamino or dibenzylamino), an arylamino group having an aromatic hydrocarbon group containing from 6 to 12 carbon atoms and optionally having a substituent (e.g., phenylamino, diphenylamino or ditolylamino), a heteroarylamino group having a 5- or 6-membered aromatic heterocycle group optionally having a substituent (e.g., pyridylamino, thienylamino or dithienylamino), an acylamino group having acyl group containing from 2 to 10 carbon atoms and optionally having a substituent (e.g., acetylamino or benzoylamino), an alkoxy group optionally having a substituent (preferably an alkoxy group containing from 1 to 8 carbon atoms and optionally having a substituent; e.g., methoxy, ethoxy or butoxy), an aryloxy group optionally having a substituent (having an aromatic hydrocarbon ring group containing preferably from 6 to 12; e.g., phenyloxy, 1-naphthyloxy or 2-naphthyloxy), a heteroaryloxy group optionally having a substituent (preferably having a 5- or 6-membered aromatic heterocycle group; e.g., pyridyloxy or thienyloxy), an acyl group optionally having a substituent (preferably an acyl group containing from 2 to 10 carbon atoms and optionally having a substituent; e.g., formyl, acetyl or benzoyl), an alkoxycarbonyl group optionally having a substituent (preferably an alkoxycarbonyl group containing from 2 to 10 carbon atoms and optionally having a substituent; e.g., methoxycarbonyl or ethoxycarbonyl), an aryloxycarbonyl group optionally having a substituent (preferably an aryloxycarbonyl group containing from 7 to 13 carbon atoms and optionally having a substituent; e.g., phenoxycarbonyl), an alkylcarbonyloxy group optionally having a substituent (preferably an alkylcarbonyloxy group containing from 2 to 10 carbon atoms and optionally having a substituent; e.g., acetoxy), a halogen atom (particularly, a fluorine atom or a chlorine atom), a carboxyl group, a cyano group, a hydroxyl group, a mercapto group, an alkylthio group optionally having a substituent (preferably an alkylthio group containing from 1 to 8 carbon atoms; e.g., methylthio or ethylthio), an arylthio group optionally having a substituent (preferably an arylthio group containing from 6 to 12 carbon atoms; e.g., phenylthio or 1-naphthylthio), a sulfonyl group optionally having a substituent (e.g., mesyl or tosyl), a silyl group optionally having a substituent (e.g., trimethylsilyl or triphenylsilyl), a boryl group optionally having a substituent (e.g., dimesitylboryl), a phosphino group optionally having a substituent (e.g., diphenylphosphino), an aromatic hydrocarbon group optionally having a substituent (e.g., a mono-valent group derived from a 5- or 6-membered single ring or from a condensed ring containing from 2 to 5 condensed rings, such as a benzene ring, a naphthalene ring, an anthracene ring, a phenanthrene ring, a perylene ring, a tetracene ring, a pyrene ring, a benzopyrene ring, a chrysene ring, a triphenylene ring or a fluoranthene) and an aromatic heterocycle group optionally having a substituent (e.g., a mono-valent group derived from a 5- or 6-membered single ring or from a condensed ring containing from 2 to 4 condensed rings, such as a furan ring, a benzofuran ring, a thiophene ring, a benzothiophene ring, a pyrrole ring, a pyrazole ring, an imidazole ring, an oxadiazole ring, an indole ring, a carbazole ring, a pyrroloimidazole ring, a pyrrolopyrazole ring, a pyrrolopyrrole ring, a thienopyrrole ring, a thienothiophene ring, a furopyrrole ring, a furofuran ring, a thienofuran ring, a benzisoxazole ring, a benzisothiazole ring, a benzimidazole ring, a pyridine ring, a pyrazine ring, a pyridazine ring, a pyrimidine ring, a triazine ring, a quinoline ring, an isoquinoline ring, a cinnoline ring, a quinoxaline ring, a benzimidazole ring, a pyrimidine ring or a quinazoline ring).

The molecular weight of each of $R_1$ to $R_8$ including that of the substituent thereof is preferably 400 or less, more preferably 250 or less.

(Substituents for $R_1$ to $R_8$)

The substituents which these can have are not particularly limited as long as the substituents do not spoil the properties of the charge transporting material of the invention, but preferred examples thereof include an alkyl group, an aromatic hydrocarbon group and an alkyl-substituted aromatic hydrocarbon group. Specific examples thereof include an alkyl group containing from about 1 to about 6 carbon atoms such as a methyl group, an ethyl group, an isopropyl group or a tert-butyl group; an aromatic hydrocarbon group containing from about 6 to about 18 carbon atoms such as a phenyl group, a naphthyl group or a fluorenyl group; and an alkyl-substituted aromatic hydrocarbon group of from about 7 to about 30 in number of total carbon atoms such as a tolyl group, a mesityl group or a 2,6-dimethylphenyl group.

$R_2$, $R_4$, $R_6$ and $R_7$ may be any of the above-mentioned groups but, in view of improving durability against electric oxidation and reduction and heat resistance, they are preferably aromatic groups (in the invention, both the aromatic hydrocarbon group and the aromatic heterocycle group are in some cases generically referred to as "aromatic groups").

Specific examples wherein $R_1$ to $R_8$ each represents an aromatic ring are illustrated below.

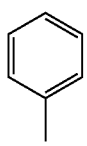
R-1

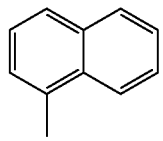
R-2

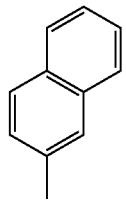
R-3

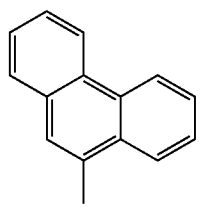
R-4

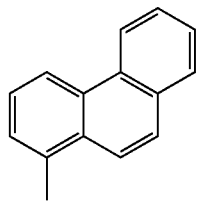
R-5

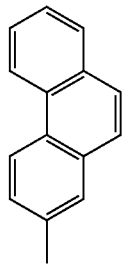
R-6

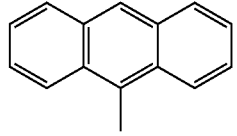
R-7

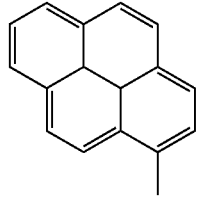
R-8

-continued
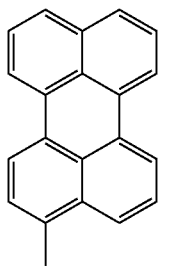
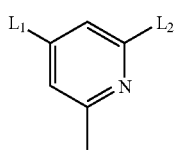
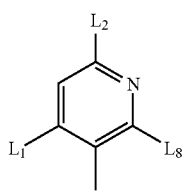
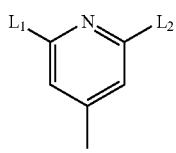
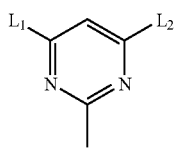
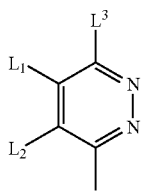
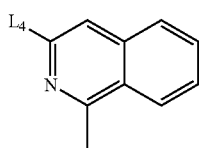
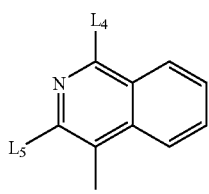
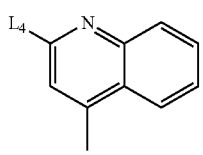
-continued
R-9
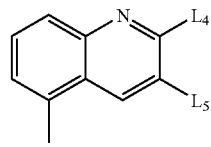
R-10
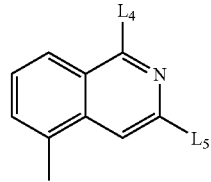
R-11
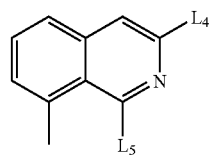
R-12
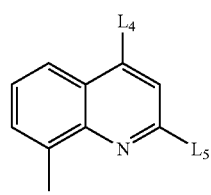
R-13
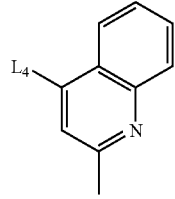
R-14
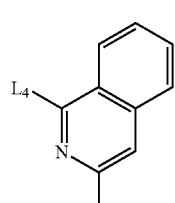
R-15
R-16
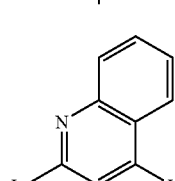
R-17
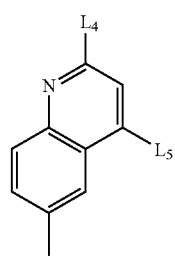
R-18
R-19
R-20
R-21
R-22
R-23
R-24
R-25

-continued
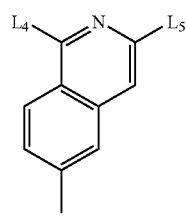
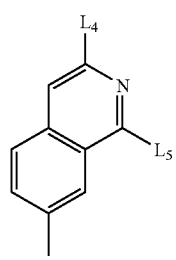
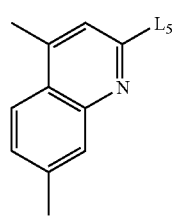
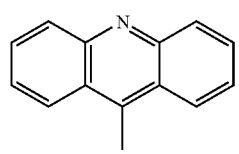
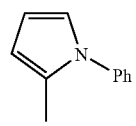
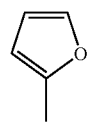
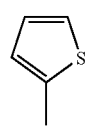
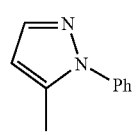
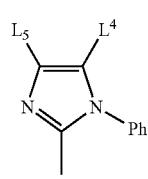
-continued
R-26 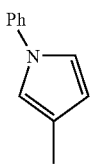
R-27 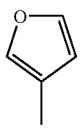
R-28 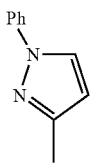
R-29 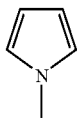
R-30 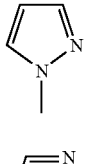
R-31 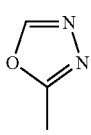
R-32 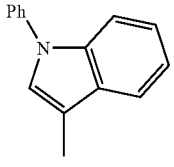
R-33 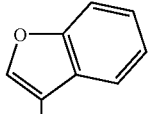
R-34 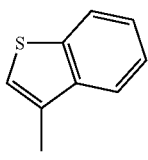
R-35
R-36
R-37
R-38
R-39
R-40
R-41
R-42
R-43
R-44

-continued

R-45 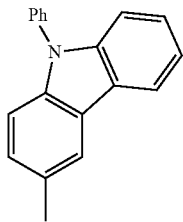

R-46 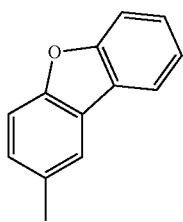

R-47 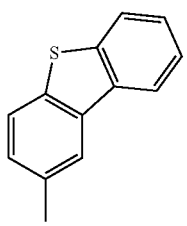

R-48 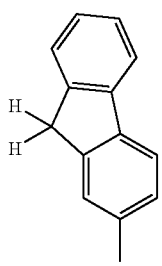

R-49 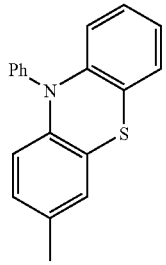

R-50 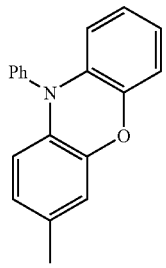

-continued

R-51 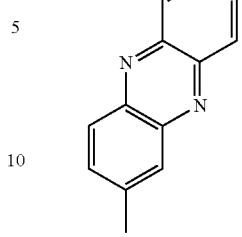

R-52 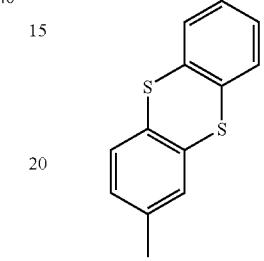

R-53 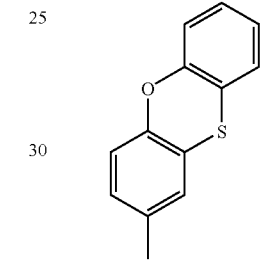

R-54 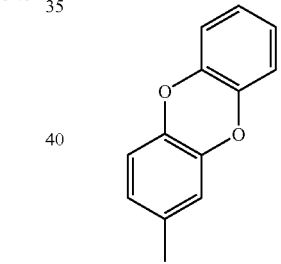

R-55 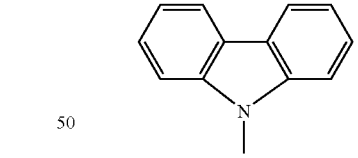

In each of the above-described structures, $L_1$ to $L_3$ each independently represents an alkyl group, an aromatic hydrocarbon group or an alkyl-substituted aromatic hydrocarbon group, and $L_4$ and $L_5$ each independently represents a hydrogen atom, an alkyl group, an aromatic hydrocarbon group or an alkyl-substituted aromatic hydrocarbon group.

Specific examples of the alkyl group, aromatic hydrocarbon group and alkyl-substituted aromatic hydrocarbon group include an alkyl group containing from about 1 to about 6 carbon atoms such as a methyl group, an ethyl group, an isopropyl group or a tert-butyl group; an aromatic hydrocarbon group containing from about 6 to about 18 carbon atoms such as a phenyl group, a naphthyl group or a fluorenyl group; and an alkyl-substituted aromatic hydrocarbon group of from about 7 to about 30 in number of total carbon atoms such as a tolyl group, a mesityl group or a 2,6-dimethylphenyl group.

Additionally, all of the above-described structures may have a substituent in addition to $L_1$ to $L_5$. However, if the substituent exerts a strong influence on the electron state of the pyridine ring to which the structure is connected, there might result a small oxidation-reduction potential difference. Therefore, it is preferred to select, as the substituent, a group which has a small electron donative property and a small electron attractive property and which difficultly lengthens the length of intramolecular conjugation. As specific examples of such group, there are also illustrated an alkyl group, an aromatic hydrocarbon group and an alkyl-substituted aromatic hydrocarbon group.

Additionally, with compounds having 2 or more of the above-described structures within the molecule, 2 or more $L_1$s to $L_5$s contained in the molecule may be the same or different from each other.

Among the above-illustrated structures, in view of obtaining a sufficiently large oxidation-reduction potential difference, R-1 to 6, 10 to 13, 33, 34, 38, 45 and 48 are preferred, R-1 to 6 and 48 are more preferred, and R-1, 4 to 6 and 48 are most preferred.

In the case of using the charge transporting material of the invention in a light-emitting layer of an organic electroluminescent element, $R_1$, $R_3$, $R_5$ and $R_8$, are preferably an alkyl group optionally having a substituent or an aromatic hydrocarbon group optionally having a substituent (particularly, an aromatic hydrocarbon group containing from about 6 to about 12 carbon atoms in view of avoiding restriction of molecular oscillation which reduces luminous efficiency, and are more preferably a hydrogen atom or an aromatic hydrocarbon group in view of imparting a large oxidation potential or a prolonged life (excellent resistance against oxidation-reduction), with a hydrogen atom or a phenyl group being particularly preferred.

The greatest characteristic of the compound represented by the foregoing formula (I) is that it has two or more pyridine rings within the molecule at positions where they cannot conjugate each other. This serves to realize the excellent electron transporting ability and the broad oxidation-reduction potential difference. On the other hand, if the number of pyridine rings is too large, there results such a strong basicity as a compound that, when incorporated in the light-emitting layer or a layer adjacent thereto, there arises a possibility of ligand exchange by application of electric field for a long time. From such standpoint, the sum of m, which represents a number of $Z_1$ connected to $Q_0$ and a number of rings A connected to $Z_1$, and n, which represents a number of $Z_2$ a connected to $Q_0$ and a number of rings B connected to $Z_2$ connected to $Q_0$ is preferably from 2 to 8, more preferably from 2 to 6, still more preferably 2 to 4, most preferably from 2 to 3.

Additionally, m is an integer of from 0 to 8, preferably from 0 to 4. Also, n is an integer of from 0 to 8, preferably from 0 to 4.

In view of enlarging the oxidation-reduction potential difference and in view of durability against repeated oxidation and reduction, m is preferably 0 or 1, and n is an integer of 1 or more.

In view of enlarging the oxidation-reduction potential difference, a 2-pyridyl group (i.e., ring A) is preferred. Thus, the case where n is 0 is preferred. In view of durability against repeated oxidation and reduction, a 4-pyridyl group (i.e., ring B) is preferred; That is, the case where m is 0 is preferred.

Also, the oxidation-reduction potential difference can be enlarged and progress of electric deterioration due to focusing of electric stress can be depressed by constituting the charge transporting material of the invention using only pyridine rings having the same electrochemical properties, thus the case where n or m is 0 being preferred. However, in the case where it is desired to improve solubility upon forming a thin film of the organic compound of the invention by applying the wet filming method, it is also an effective means to deliberately use pyridine rings having different substituents (i.e., both m and n being integers of 1 or more).

Also, in the case where n or m is 0 and the compound has only either of rings A and rings B and where substituents on the rings A or ring Bs ($R_1$ to $R_4$ or $R_5$ to $R_8$) differ with respective rings, it is also effective, as a means for finely adjusting characteristics of the material upon optimizing an element structure as an organic EL element, to properly select the substituents to thereby allow substituted pyridine rings having somewhat different electrochemical characteristics to coexist within the molecule.

Additionally, in the case of using the charge transporting material of the invention in an organic electroluminescent element—1) as a host material constituting a light-emitting layer, it is desirable for the material to have an appropriately excellent hole transporting ability and an appropriately excellent electron transporting ability. Thus, those which have an electron donative substituent (e.g., an alkyl group, an amino group or an alkoxy group) within the molecule are preferred, with those containing an aromatic amino group being particularly preferred. To have an aromatic amino group, i.e., a diarylamine moiety is preferred as mentioned above. In this case, however, a structure wherein the pyridine ring and the electron donative hetero atom cannot substantially conjugate each other. Conjugation therebetween would make the polarizing phenomenon of charge within the molecule remarkable, leading to reduction in the oxidation-reduction potential difference or reduction in the triplet excitation level. Additionally, in a system which contains as a dopant a metal complex represented by an iridium complex, usually some of the dopants themselves can accept and transport holes. Thus, in some of such system, it is not necessary to deliberately impart the hole transporting ability to the host material. In such cases, it is rather preferred to employ a structure which is considered to enhance an electron transporting ability as will be described below as 2).

In the case of 2) using as an electron transporting material and/or a hole blocking material, it is desirable to reduce the hole transporting ability and enhancing the electron transporting ability. Thus, those which do not have an electron donative substituent (e.g., an alkyl group, an amino group, an alkoxy group, an aryloxy group, an alkylthio group or an arylthio group) within the molecule are preferred, with those which do not have a group containing a diarylamine skeleton being more preferred.

(Substituents for $Q_0$)

The connector $Q_0$ in the formula (I) may be substituted by an arbitrary substituent.

Examples of the substituent include those which are the same as described hereinbefore as $R_1$ to $R_8$.

For the purpose of imparting an appropriately broad oxidation-reduction potential difference to a compound represented by the formula (I), it is preferred for $Q_0$ to be unsubstituted or substituted by a hydrocarbon group and, in view of restricting molecular oscillation, it is more preferred to be unsubstituted (hydrogen atom) or substituted by a methyl group or a phenyl group, with unsubstituted $Q_0$ being most preferred.

The molecular weight of the compound represented by the foregoing formula (I) is usually 4,000 or less, preferably 3,000 or less, more preferably 2,000 or less and is usually 200 or more, preferably 300 or more, more preferably 400 or more. In case when the molecular weight exceeds the upper limit, there might result seriously reduced sublimation properties which can cause troubles when a vacuum deposition method is employed for preparing a luminescent element and, in case when the molecular weight is less than the lower limit, there results a reduced glass transition temperature, reduced melting point and reduced gasification temperature, which seriously spoil heat resistance.

Preferred specific examples of the charge transporting material of the invention are shown below which, however, do not limit the invention.

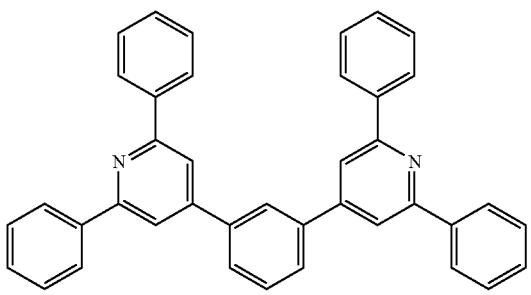

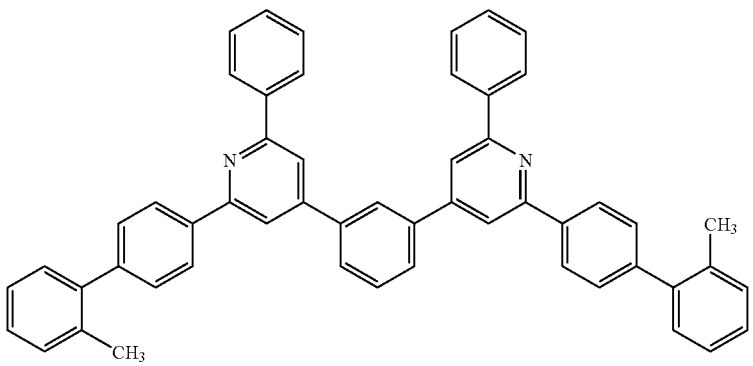

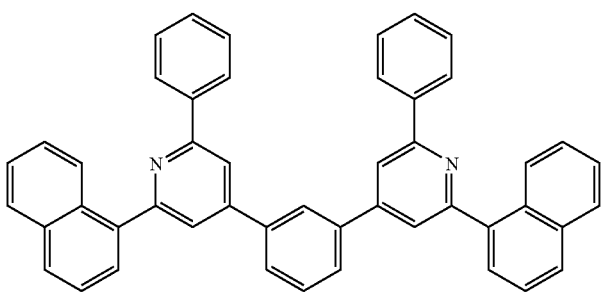

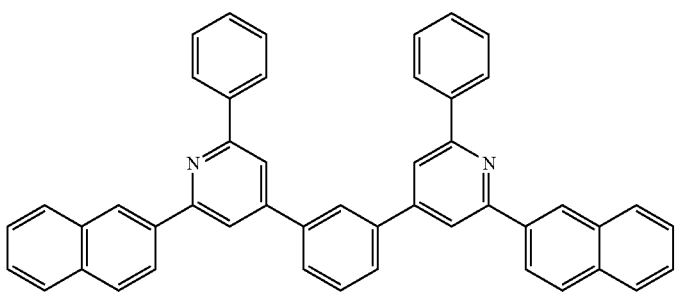

-continued
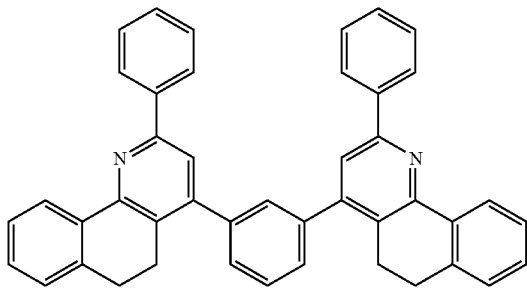
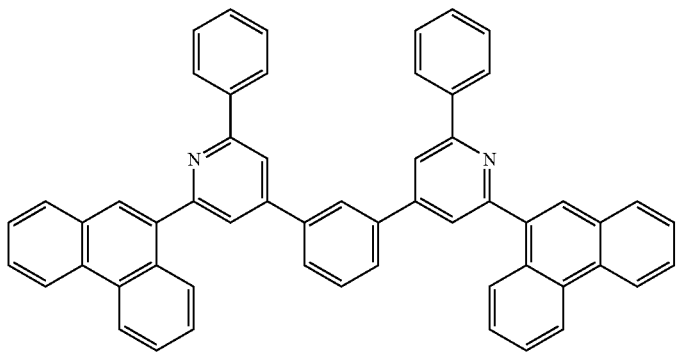
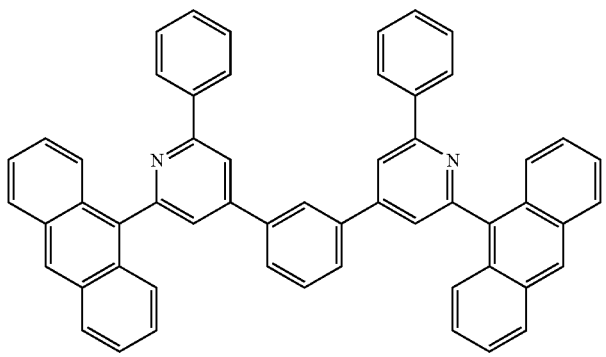
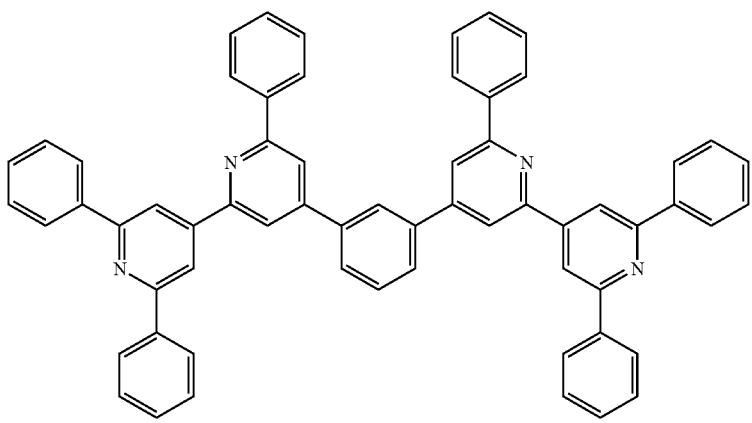

-continued
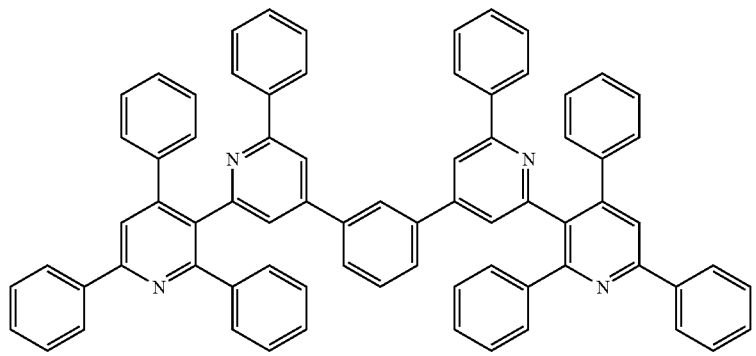
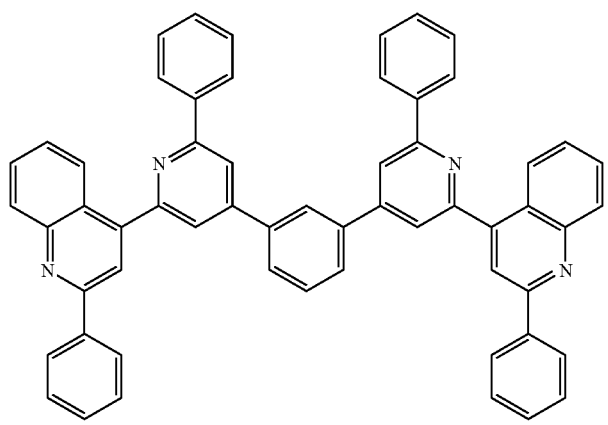
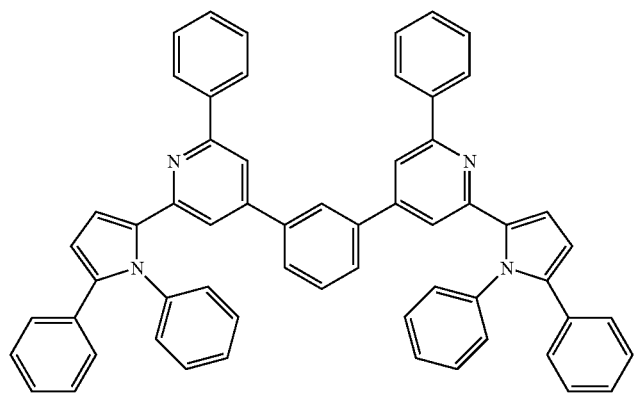
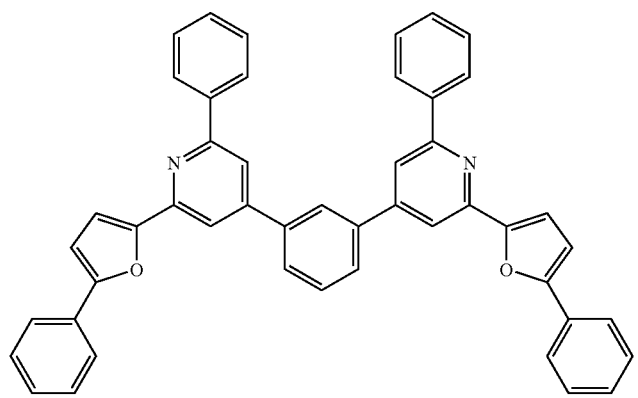

-continued
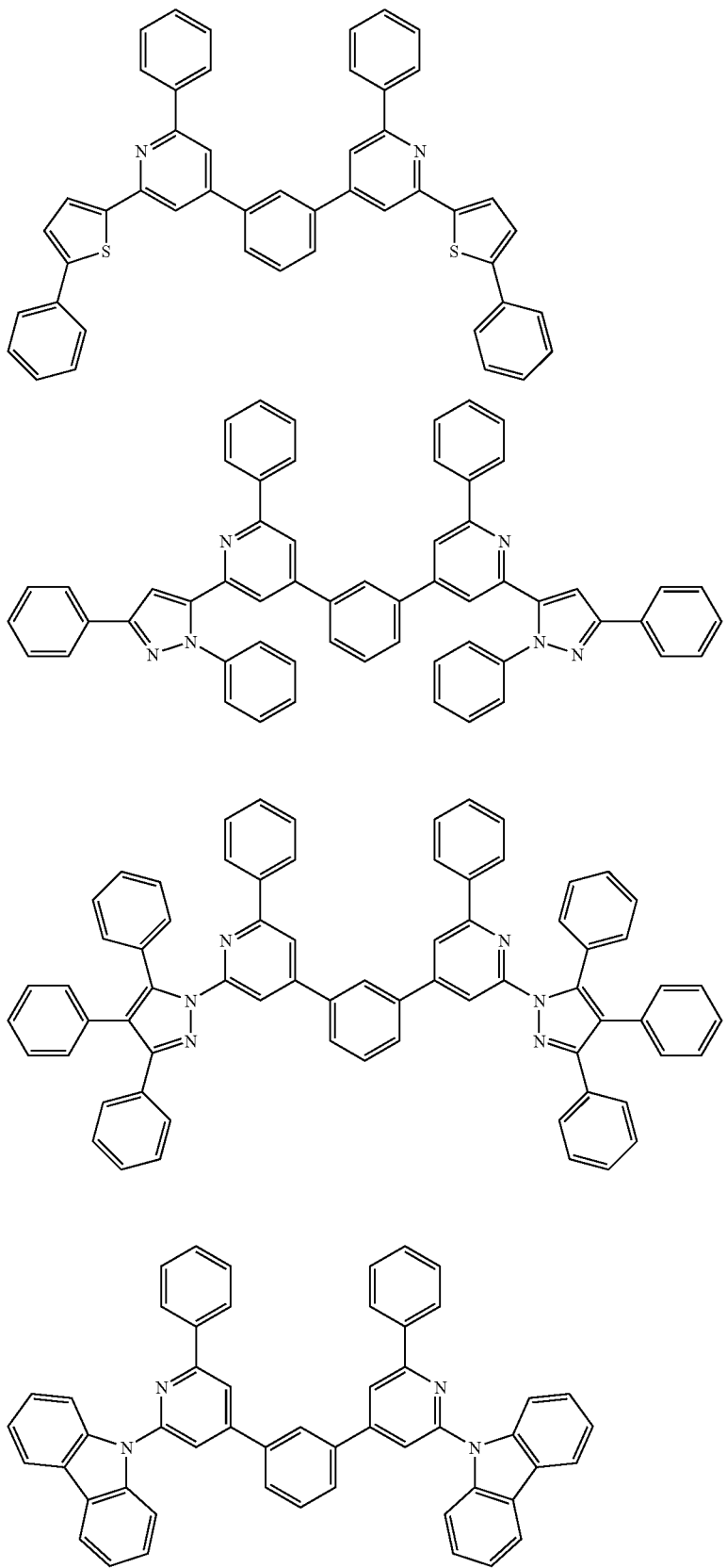

-continued
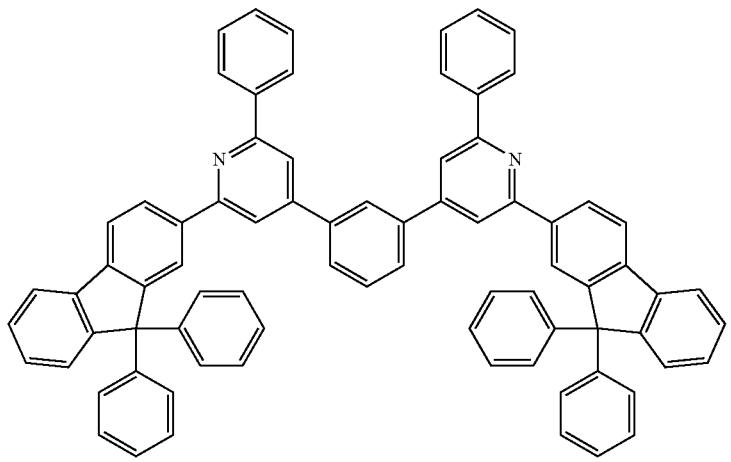
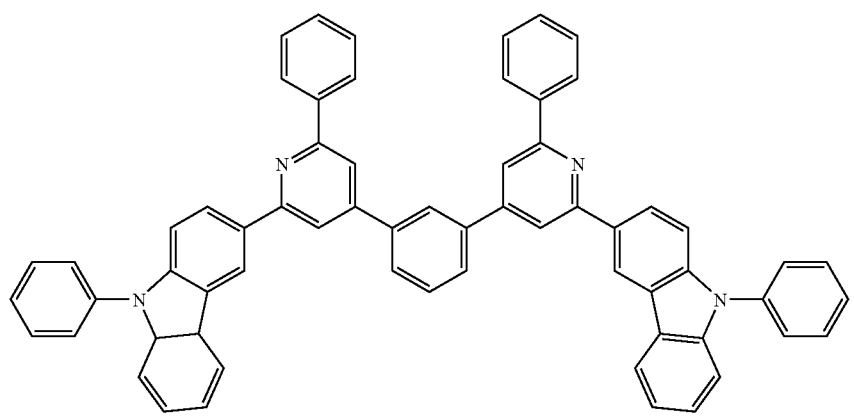
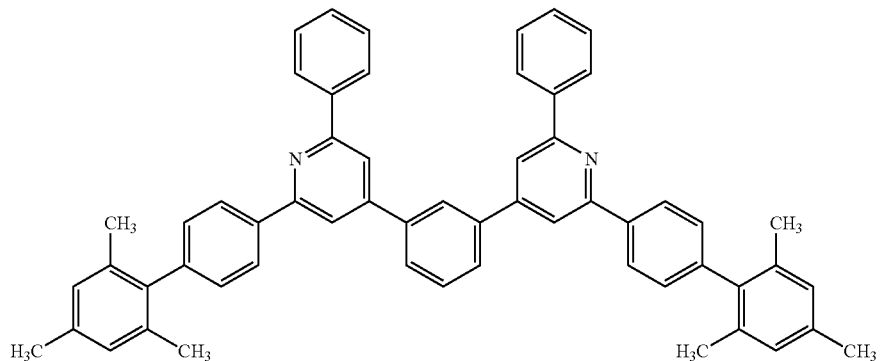
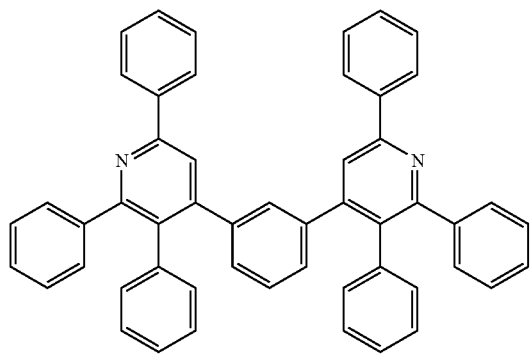

-continued
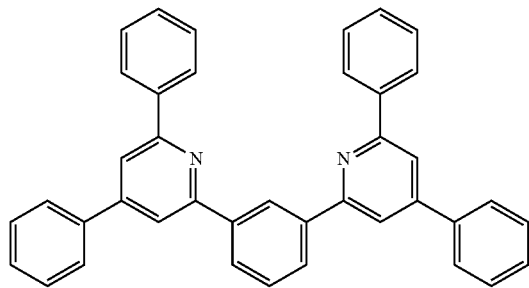
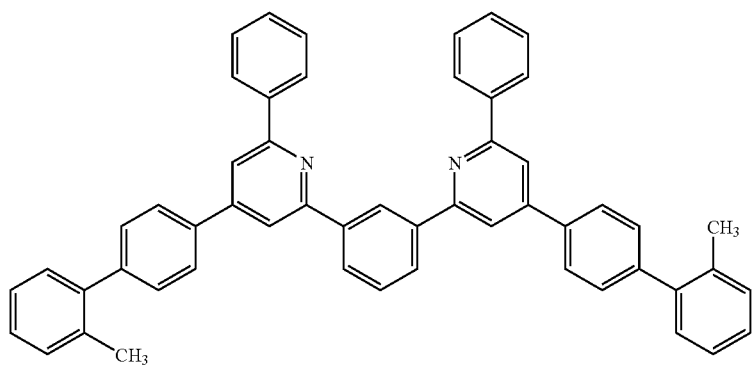
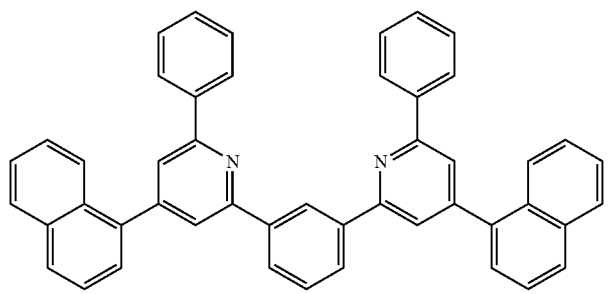
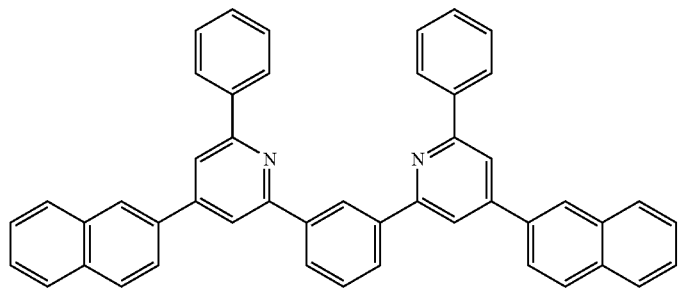
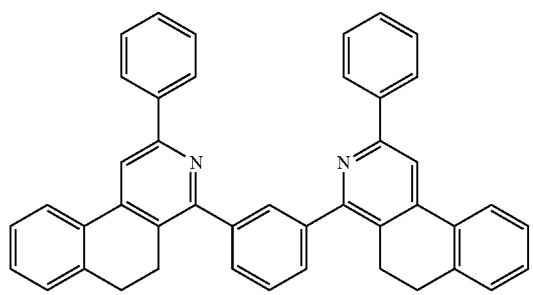

-continued
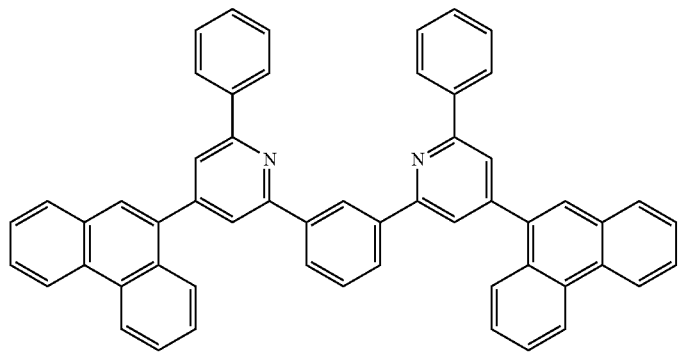
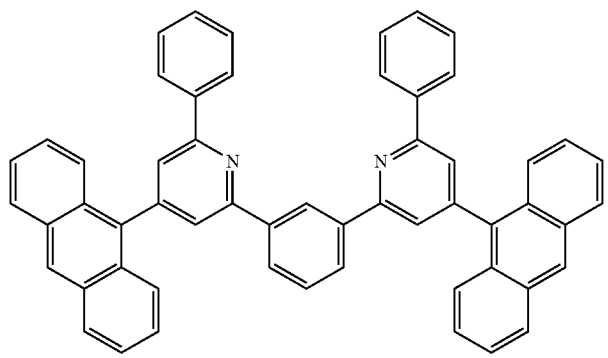
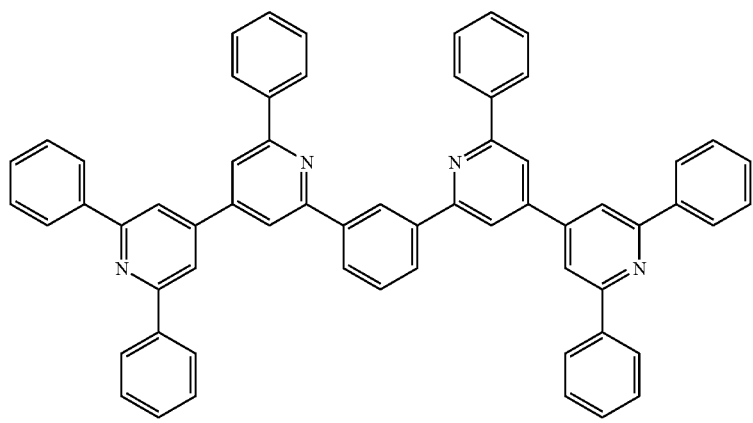
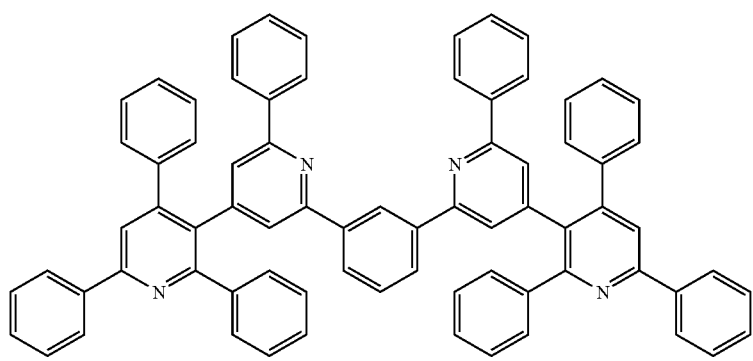

-continued
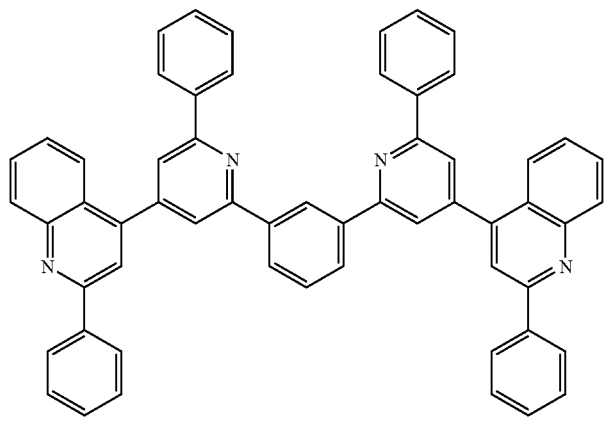
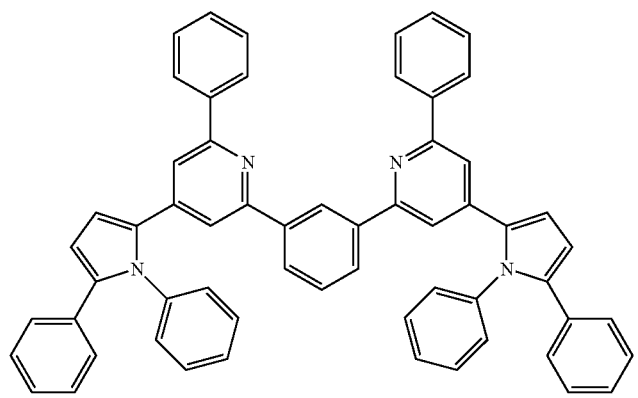
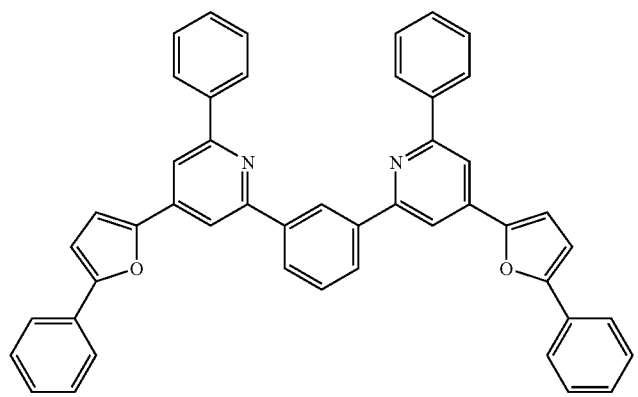
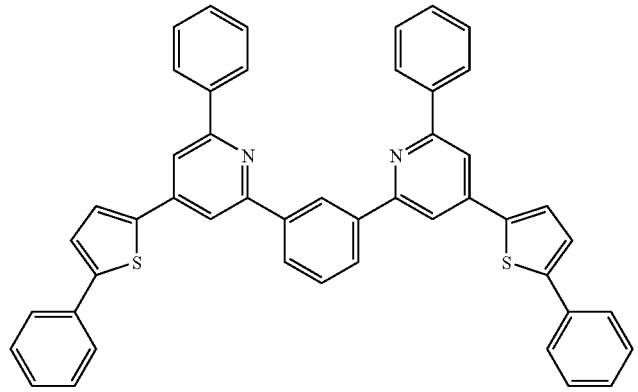

-continued
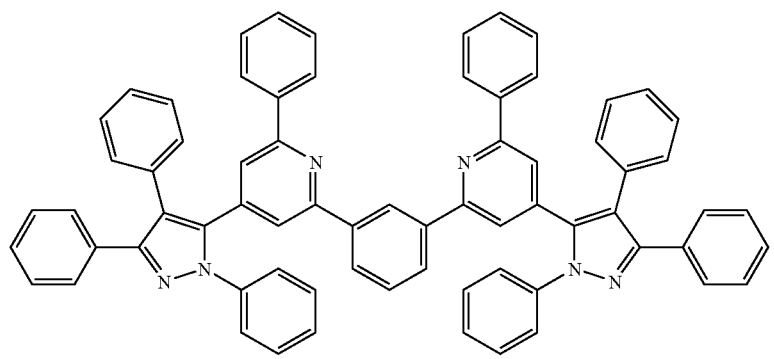
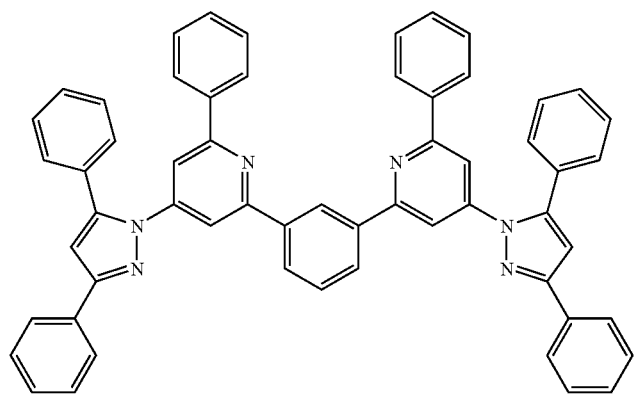
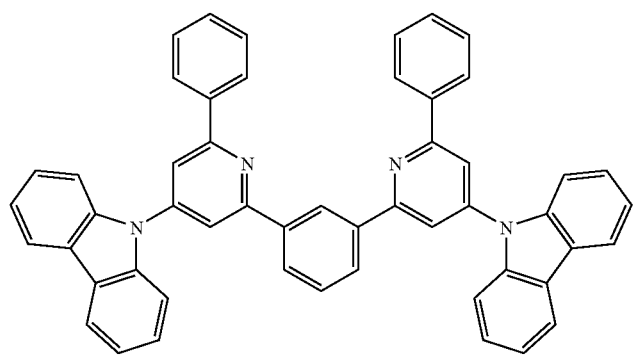
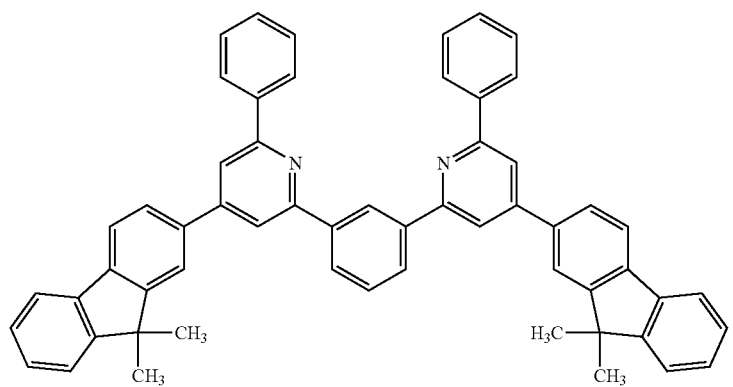

-continued
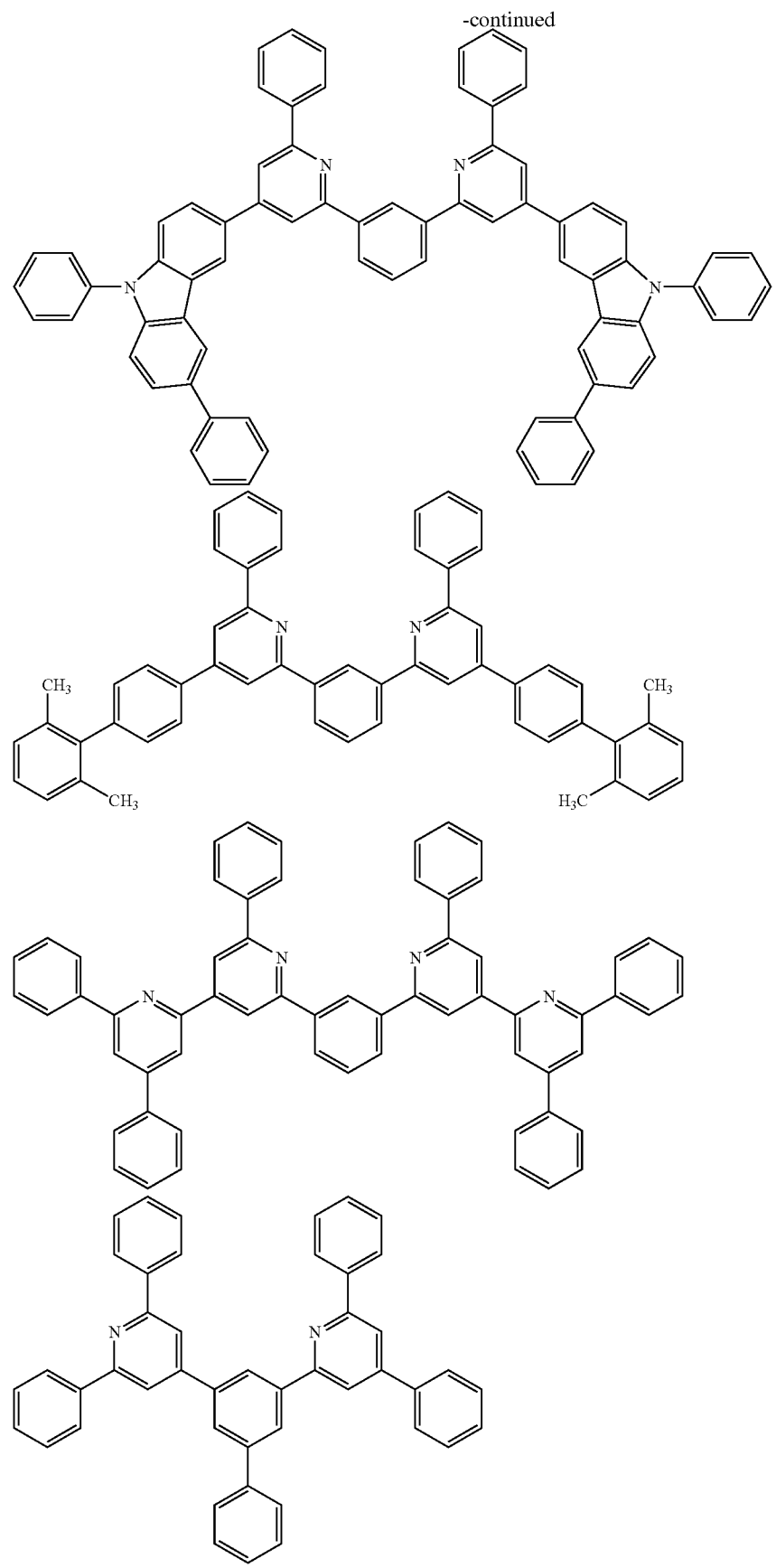

-continued
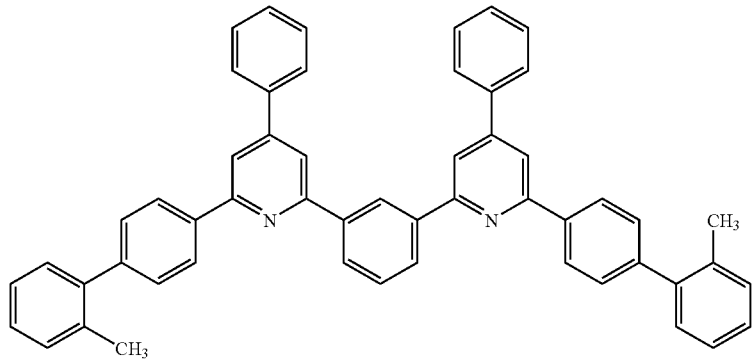
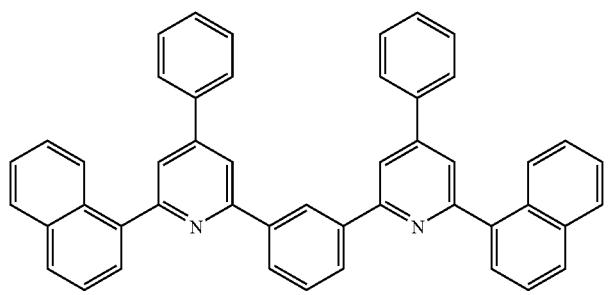
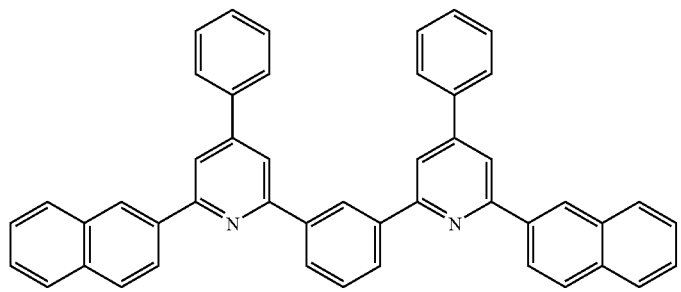
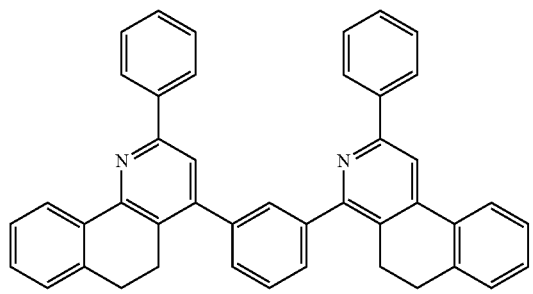
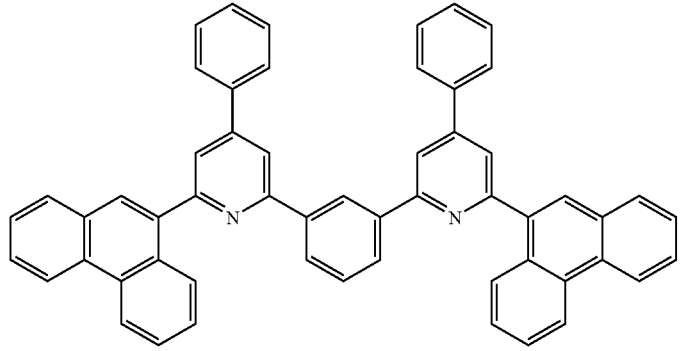

-continued
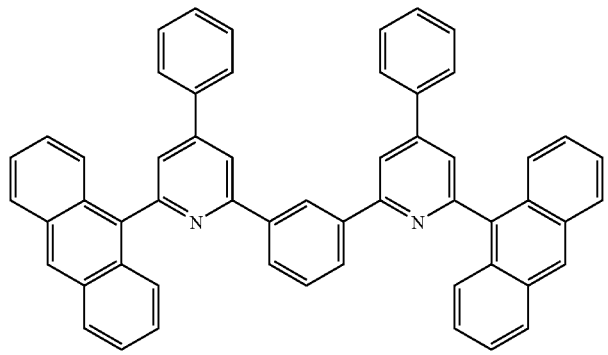
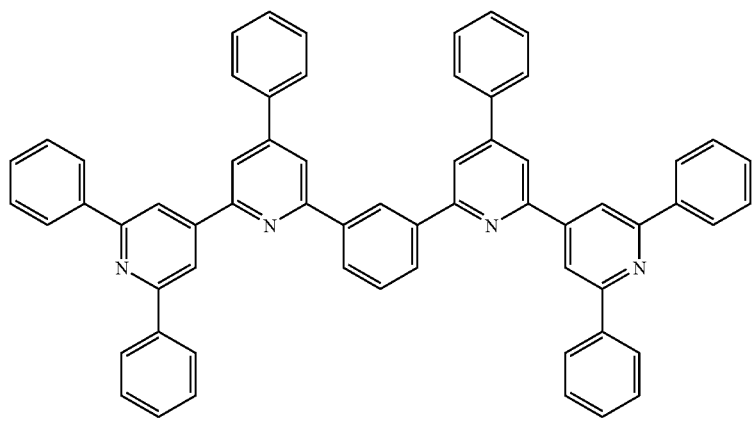
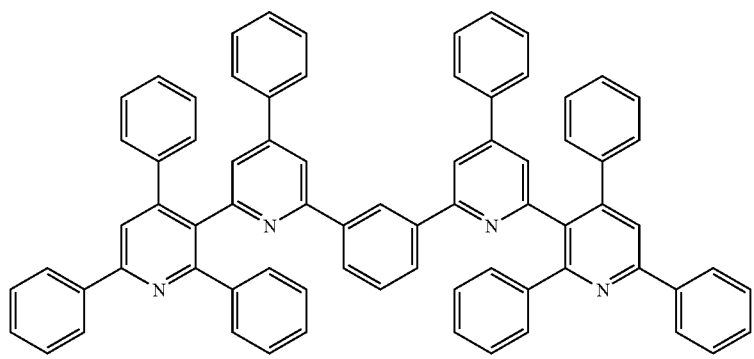
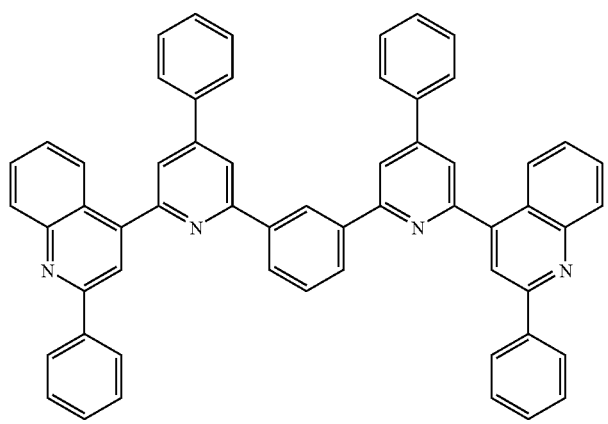

-continued
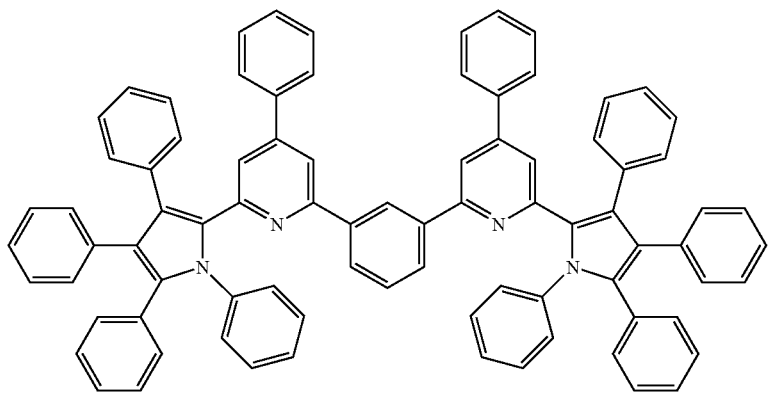
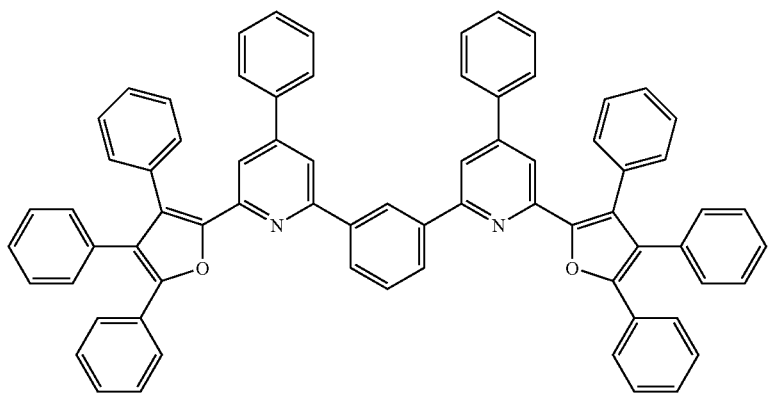
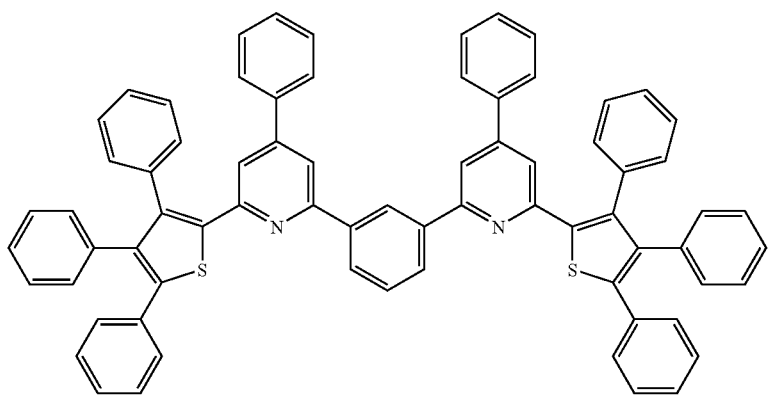
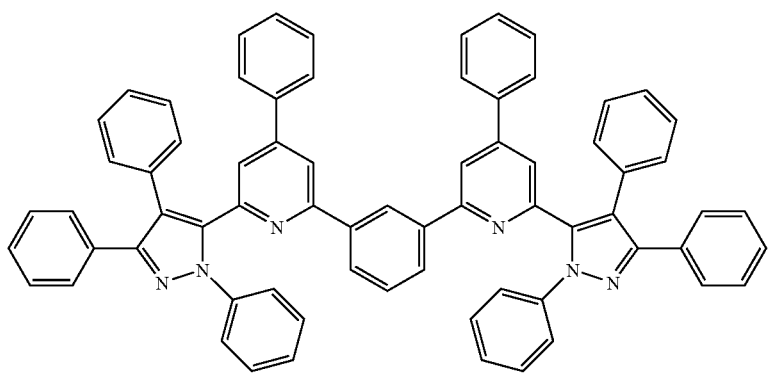

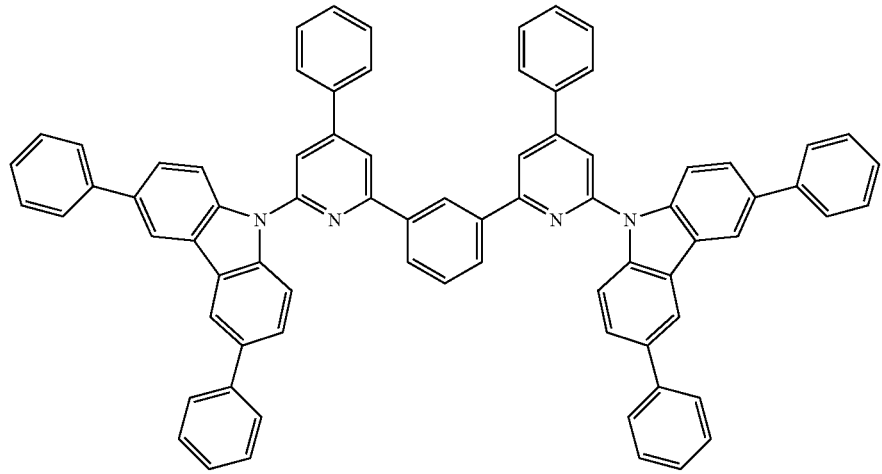
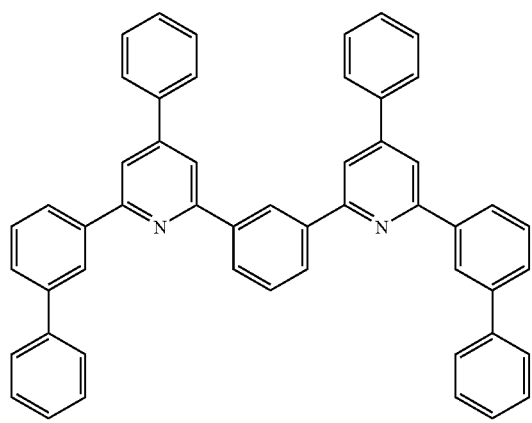
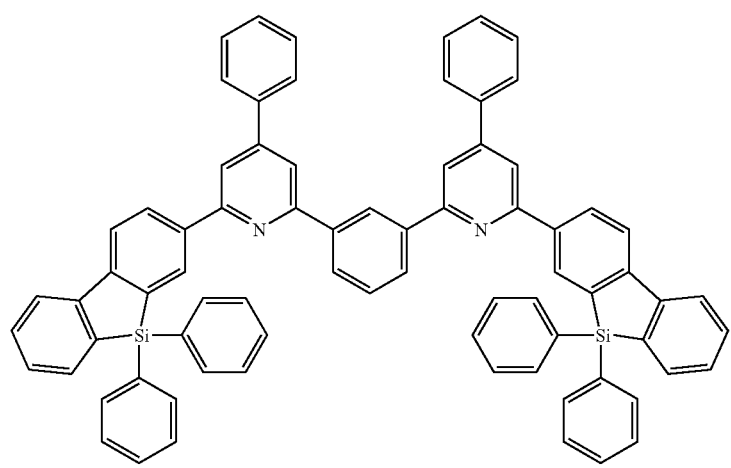

-continued
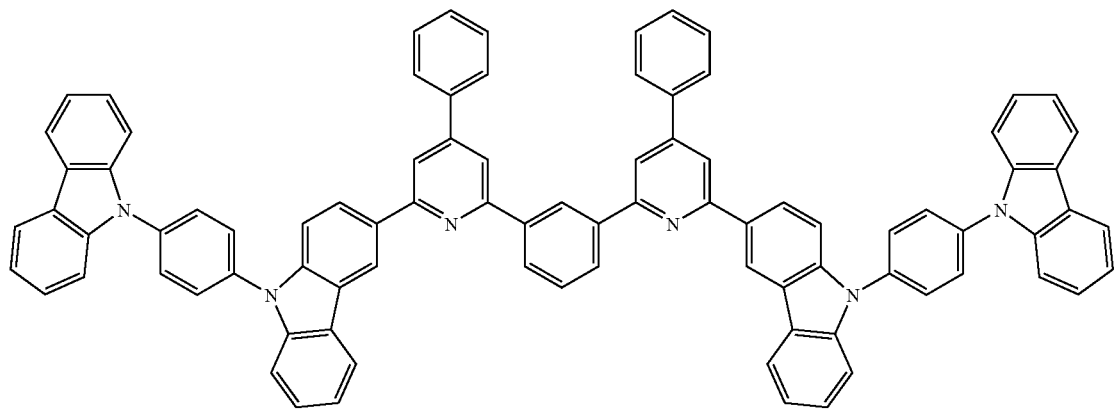
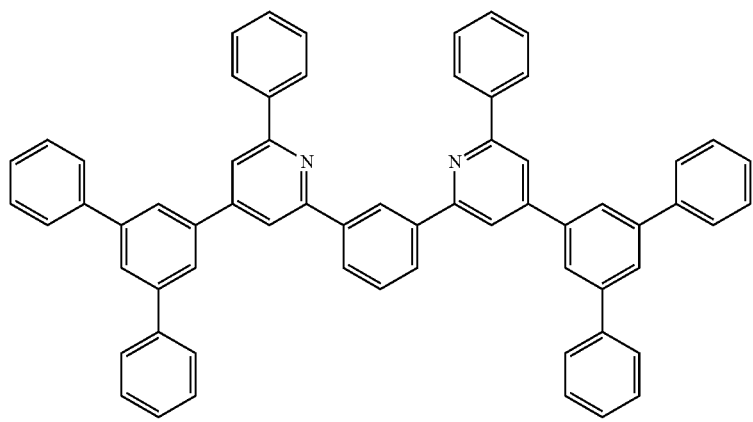
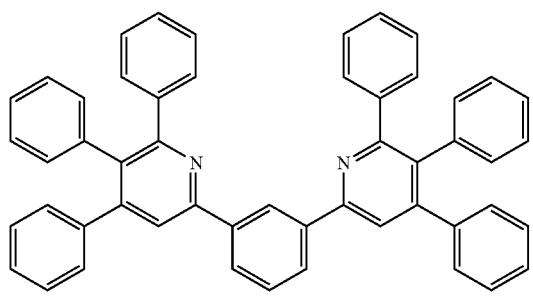
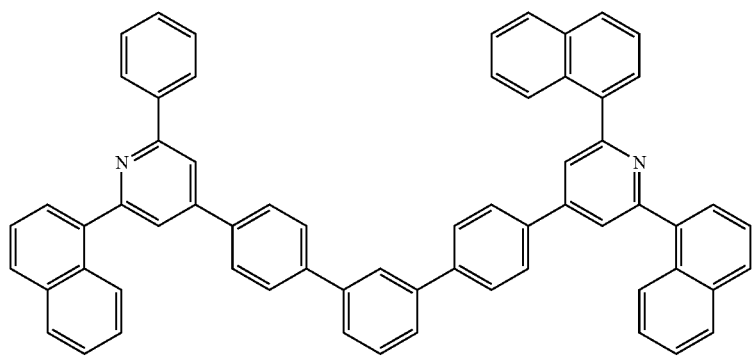

-continued
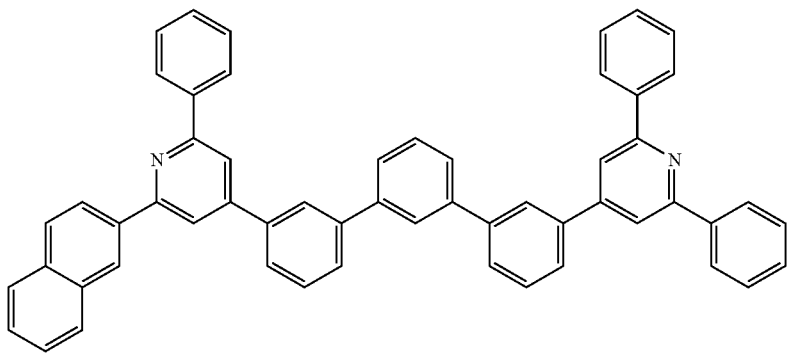
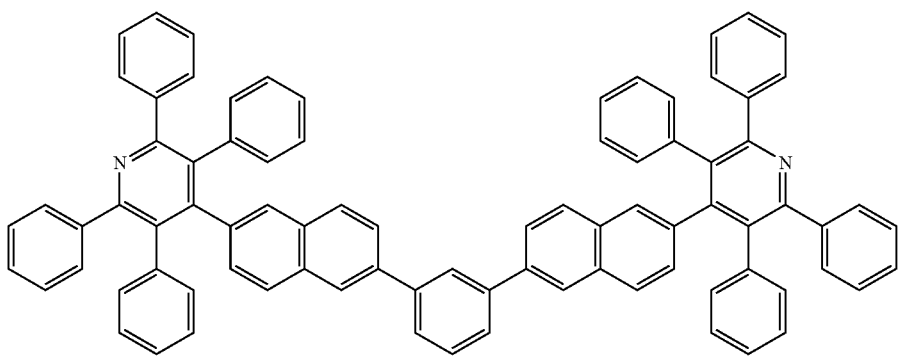
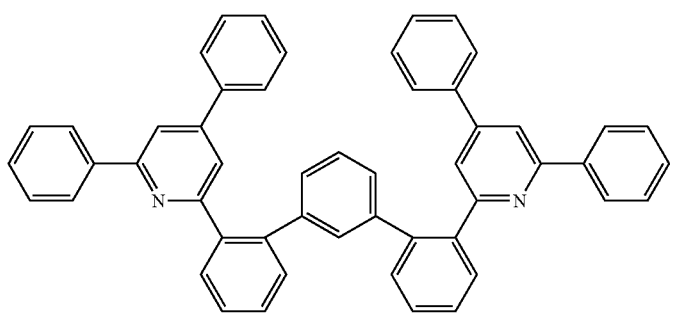
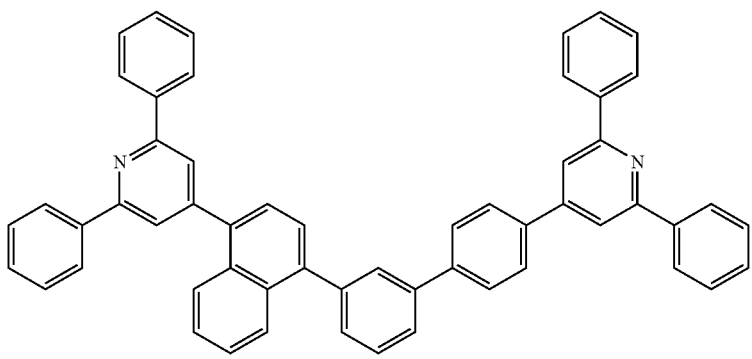

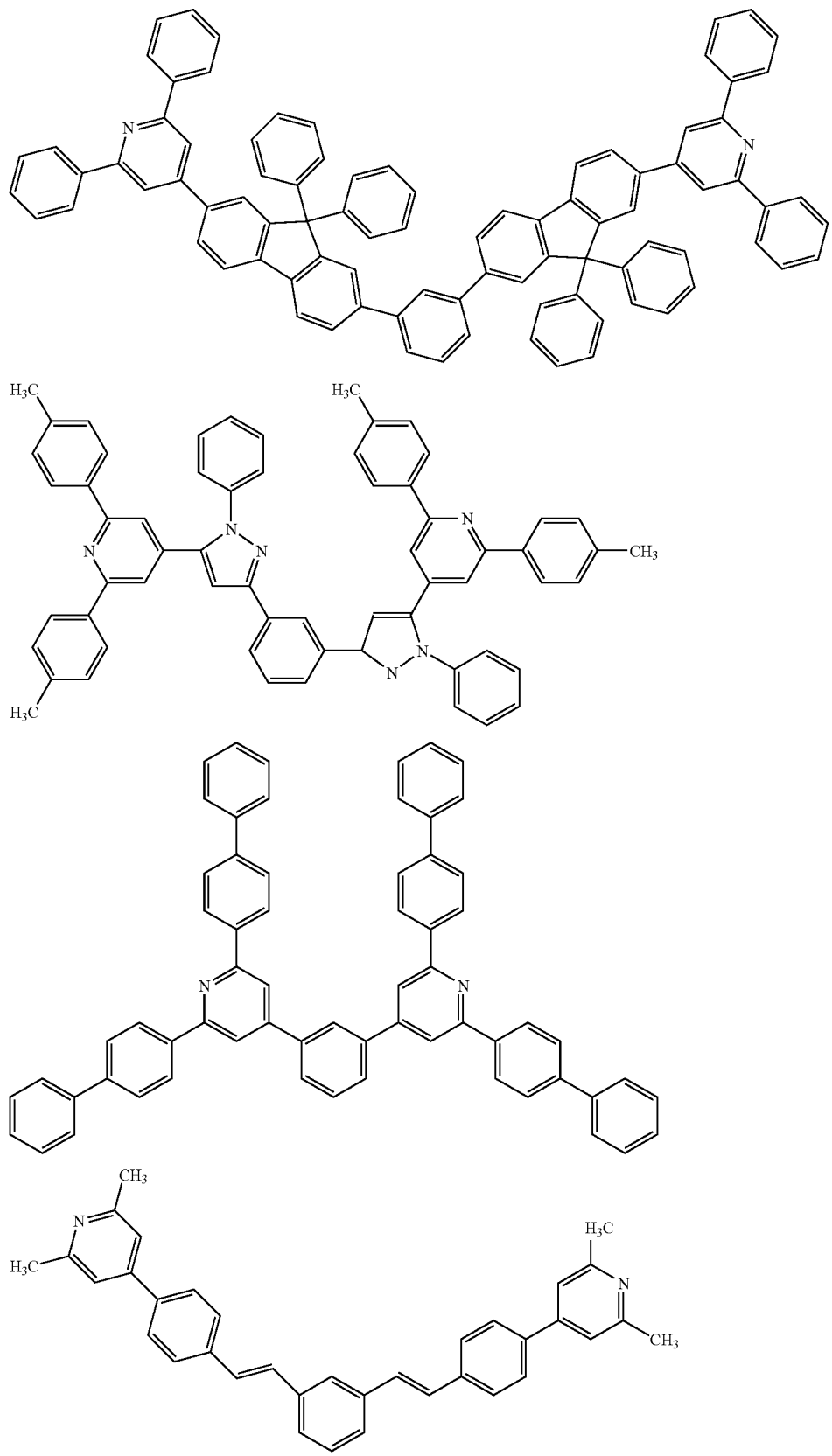

-continued
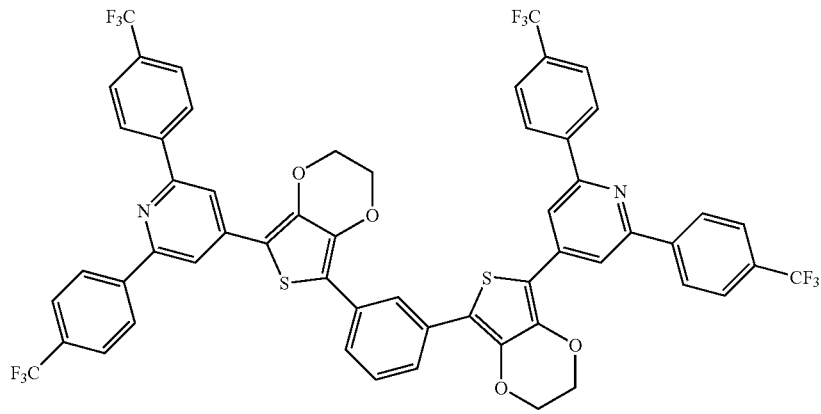
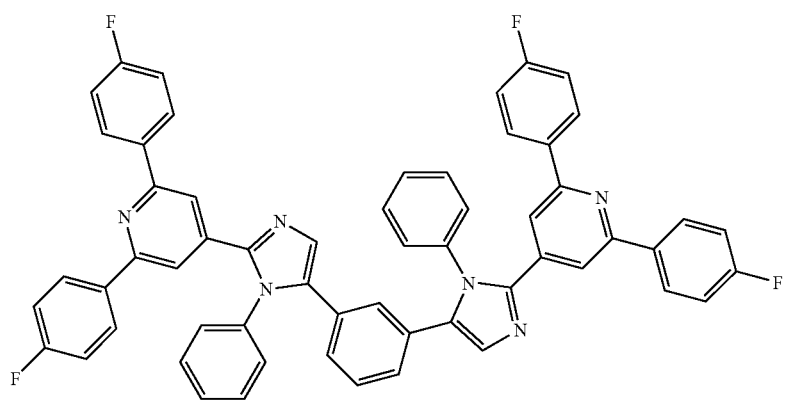
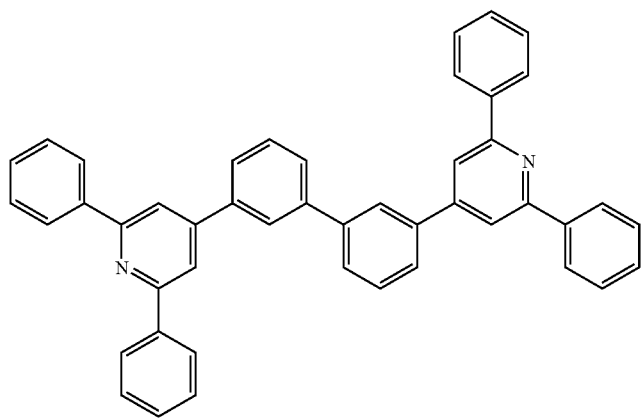

-continued
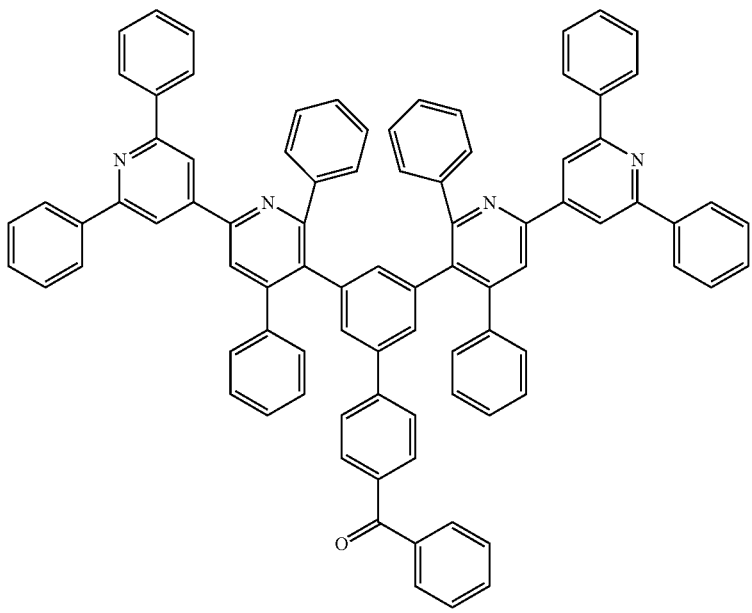
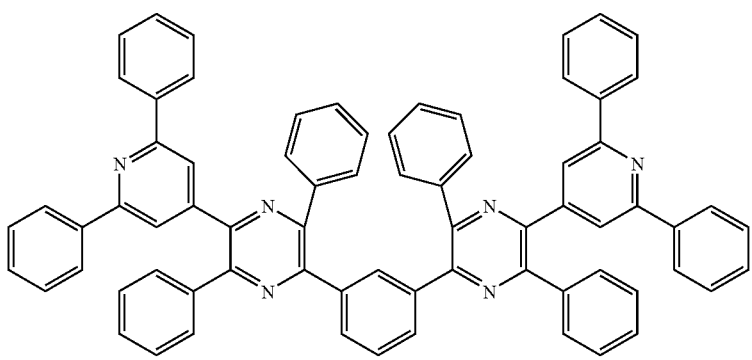
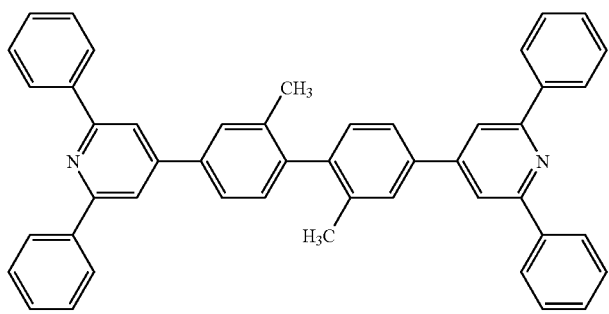
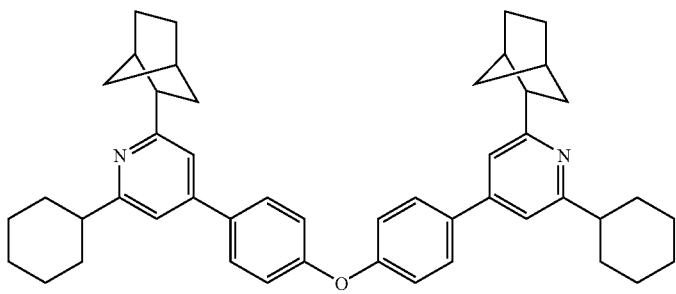

-continued
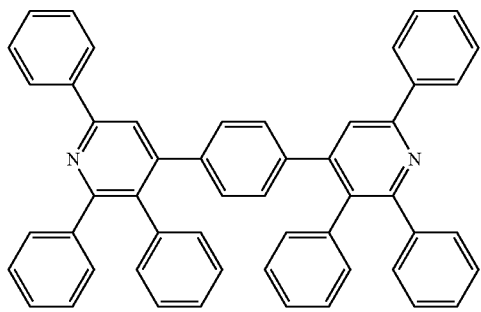
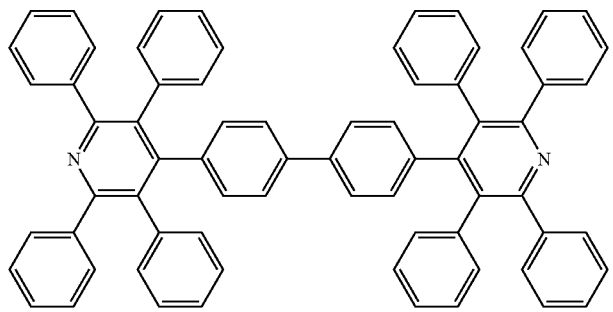
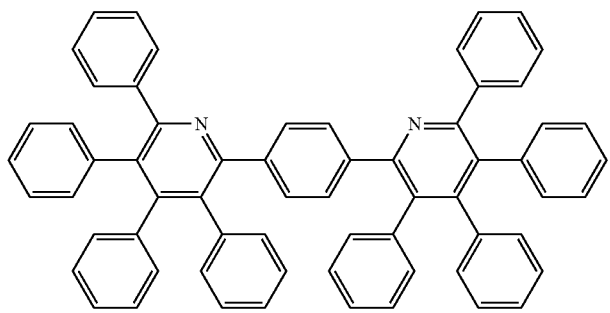
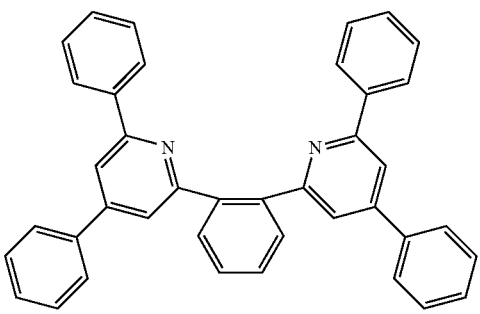
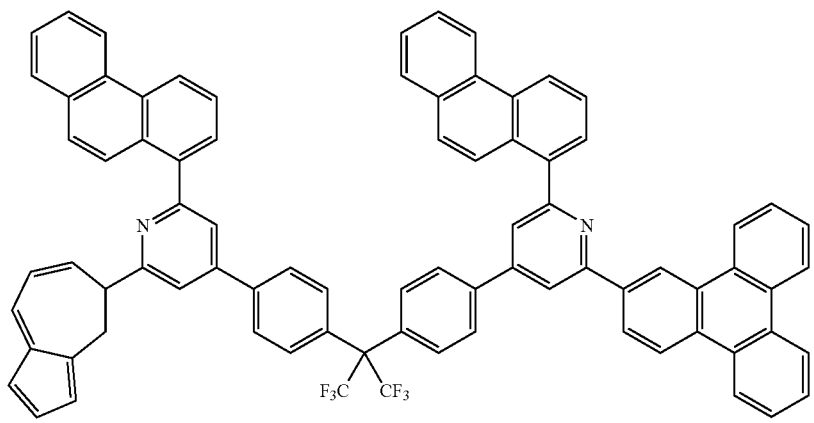
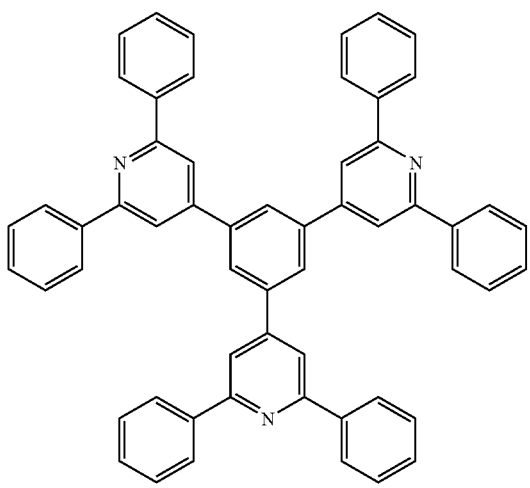
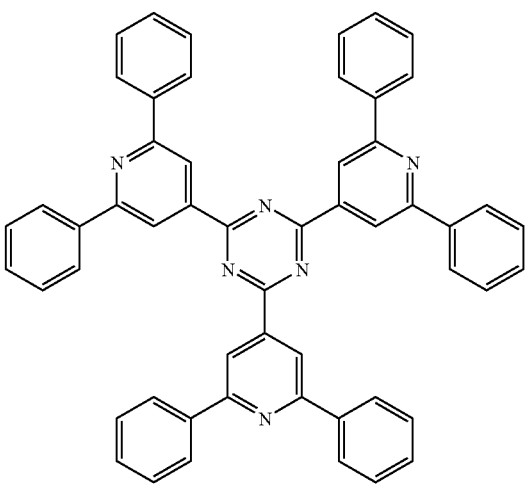

-continued
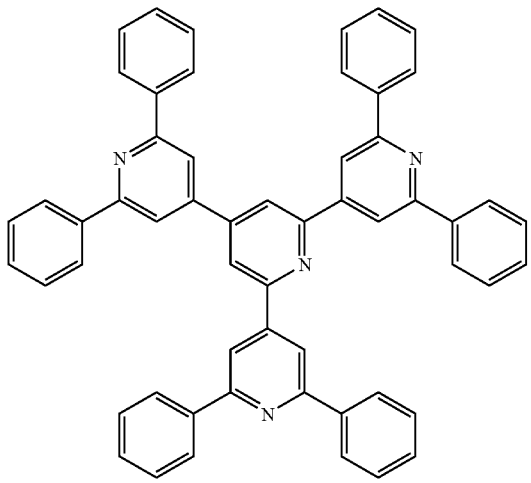
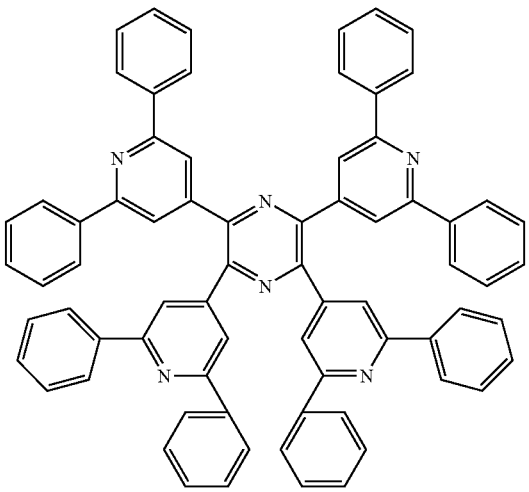
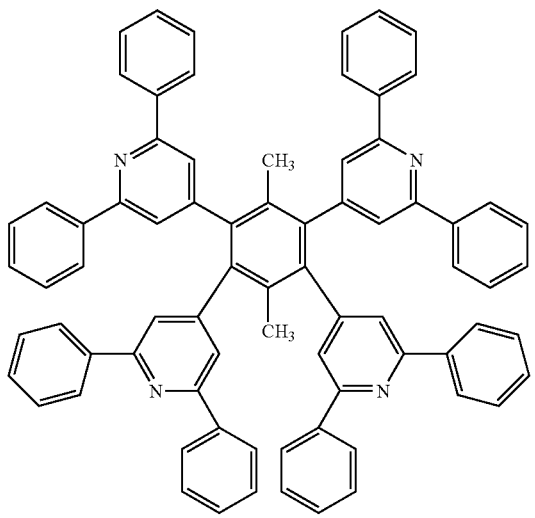
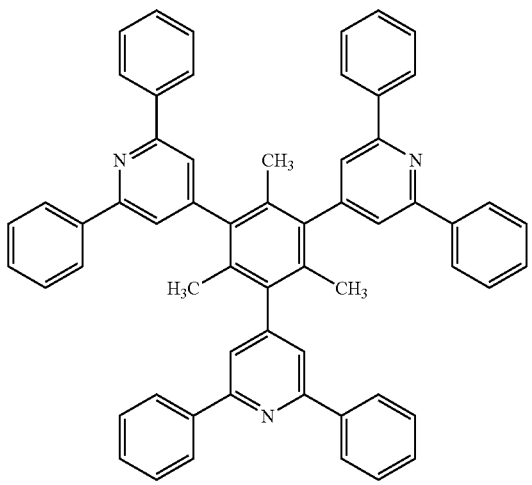
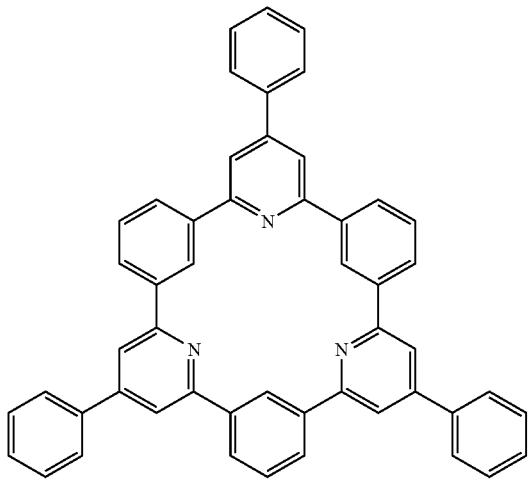
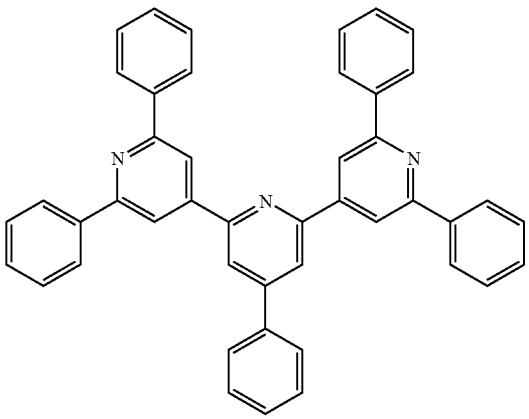

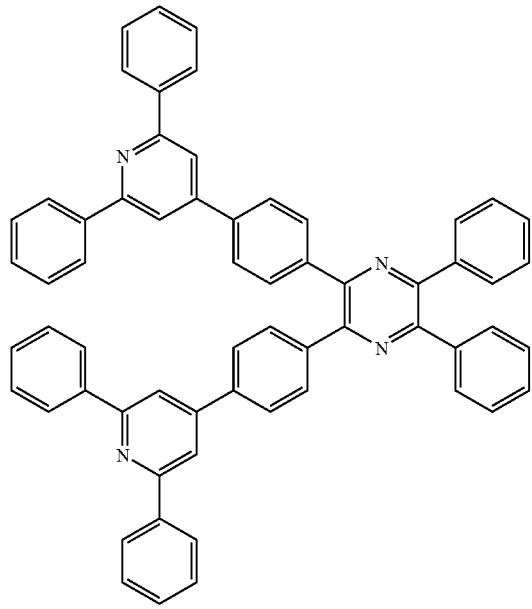
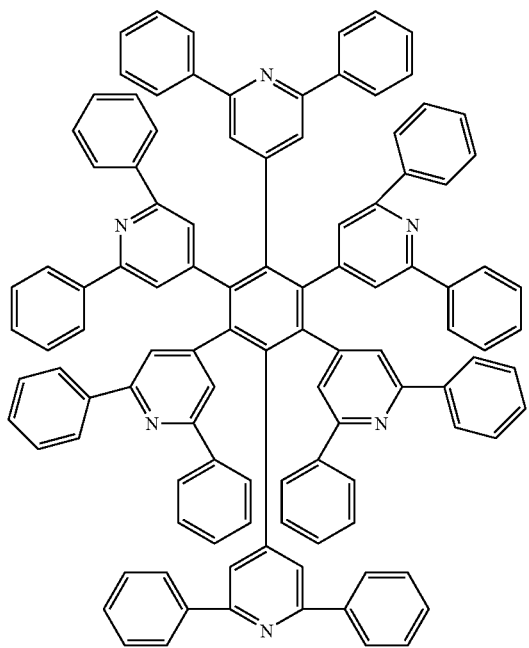
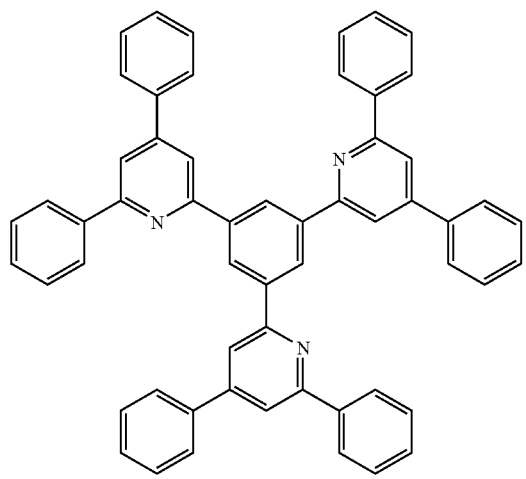

-continued
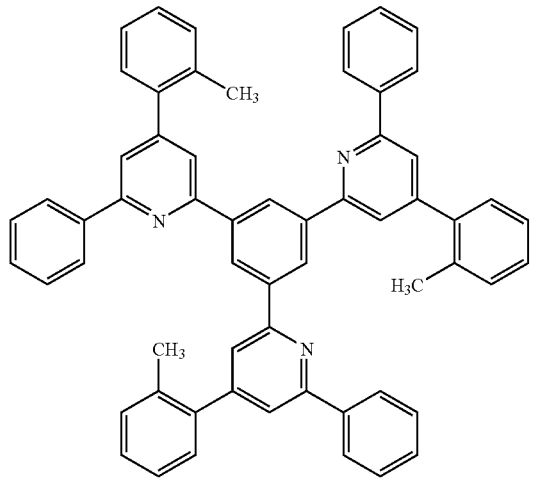
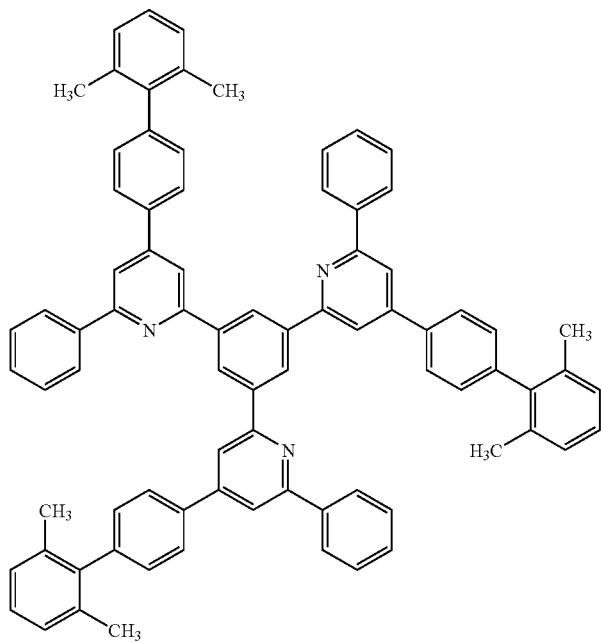
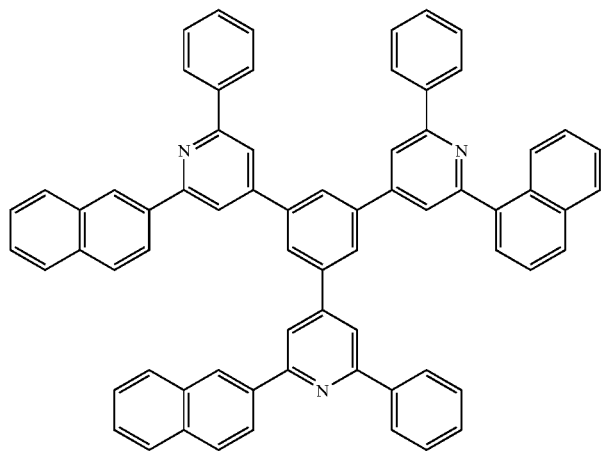

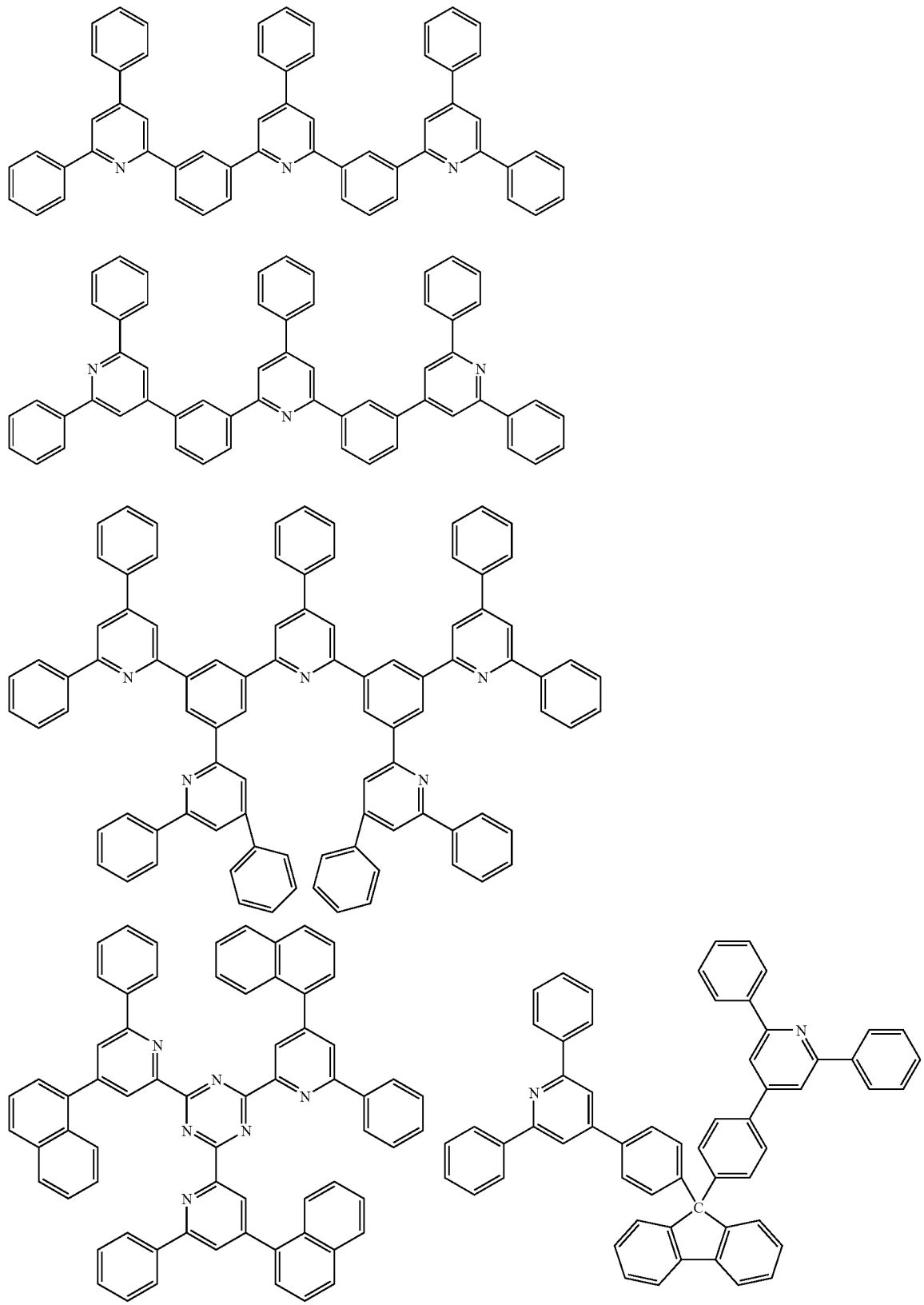

-continued
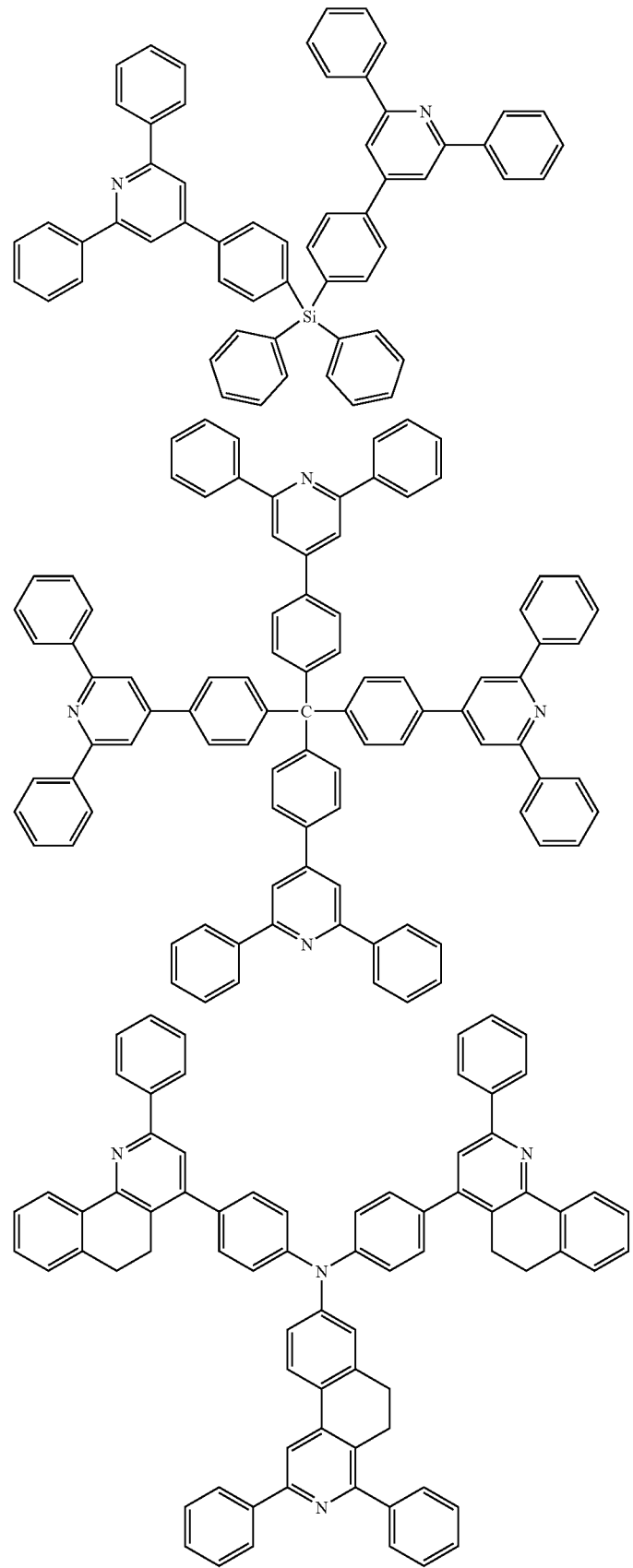

-continued
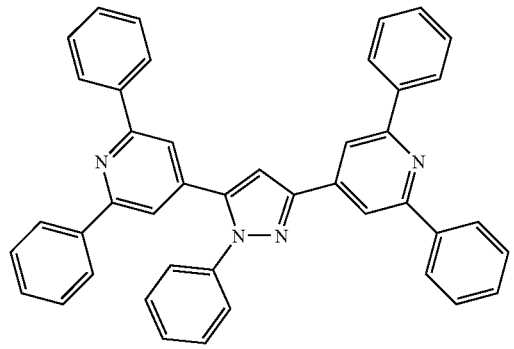
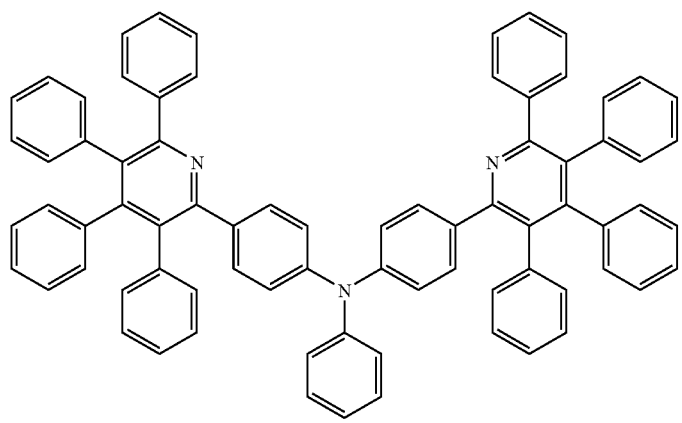
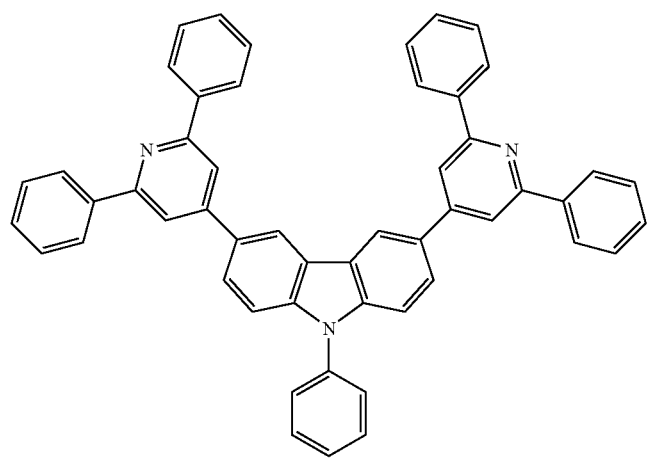
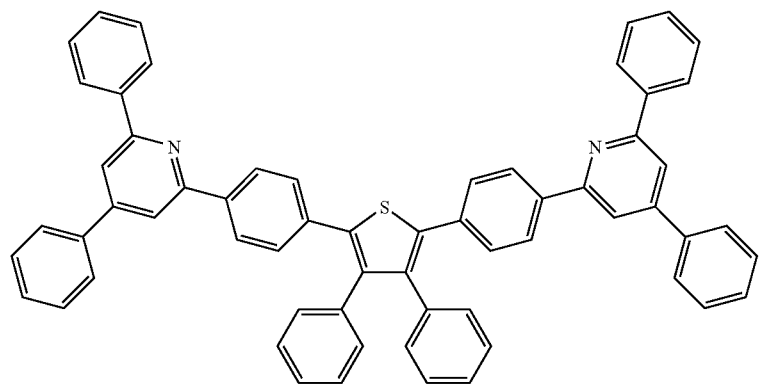

-continued
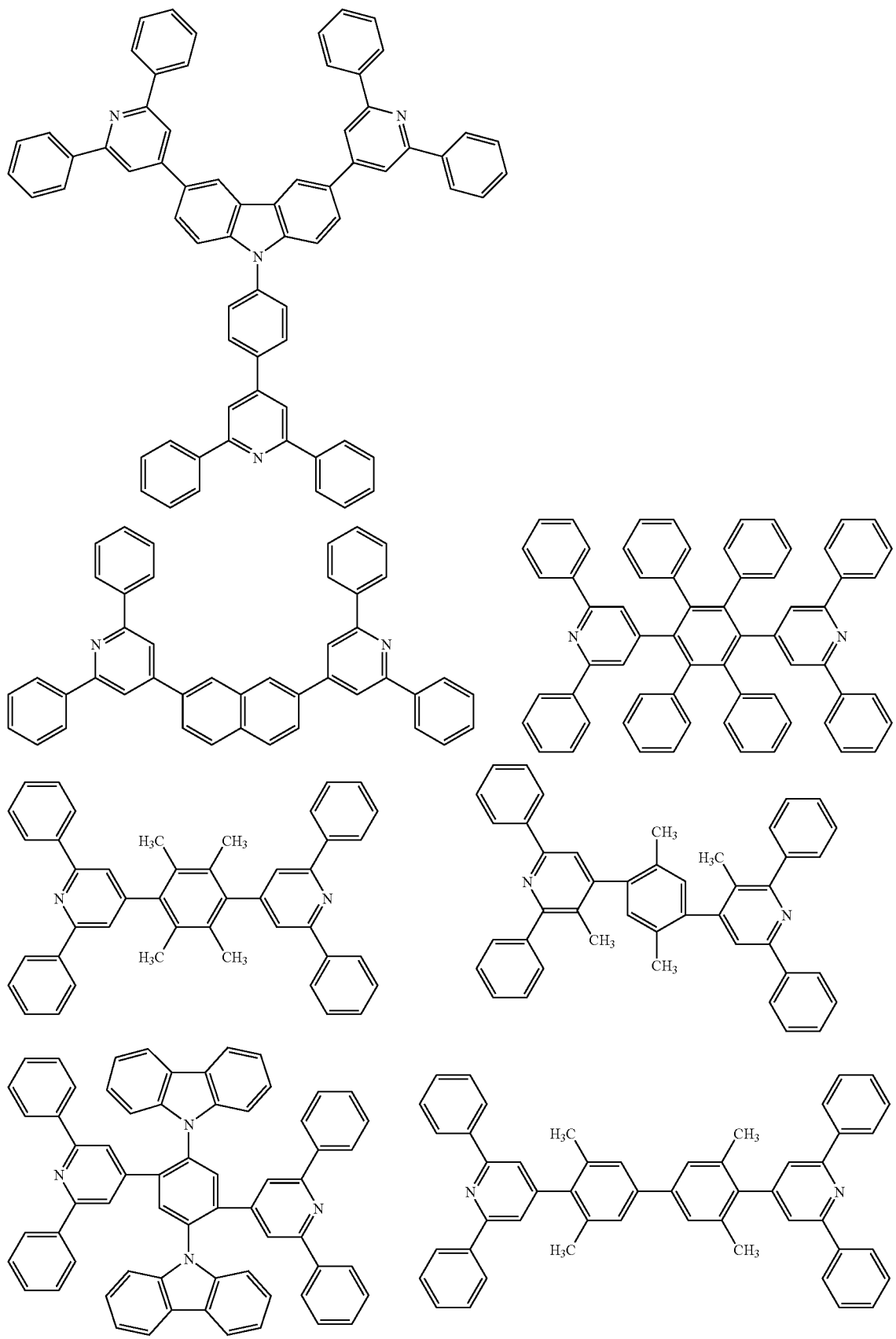

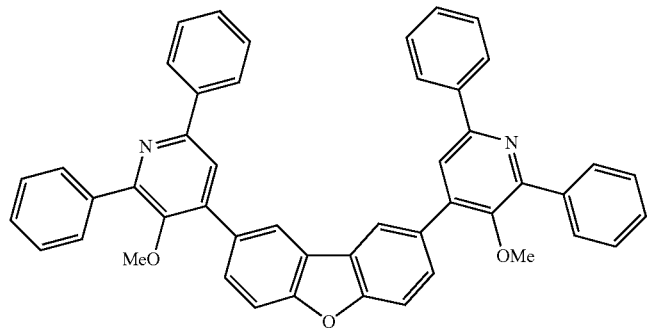
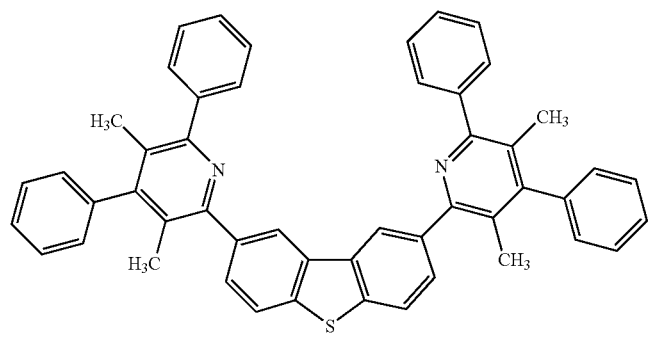
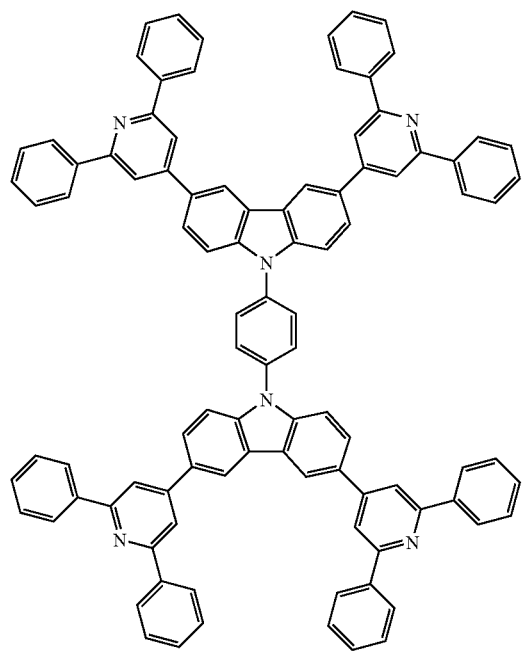

-continued
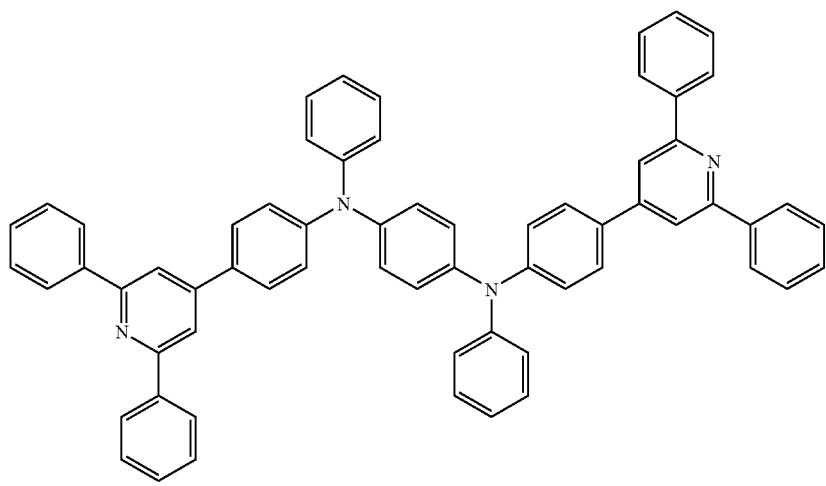
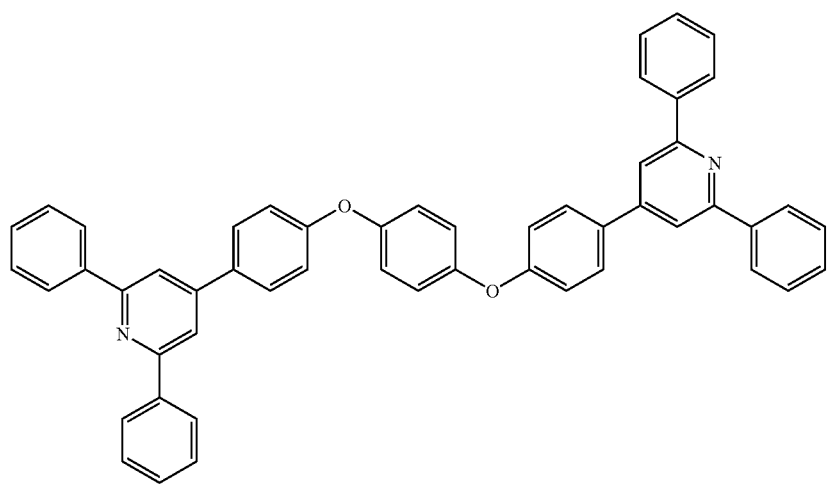
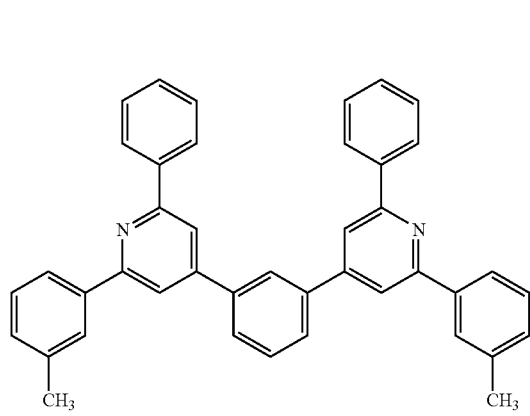
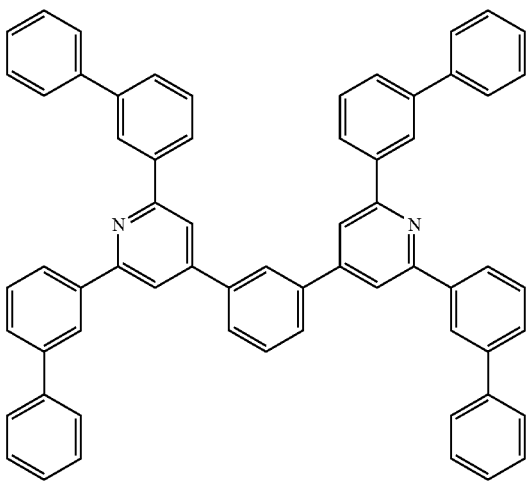

-continued
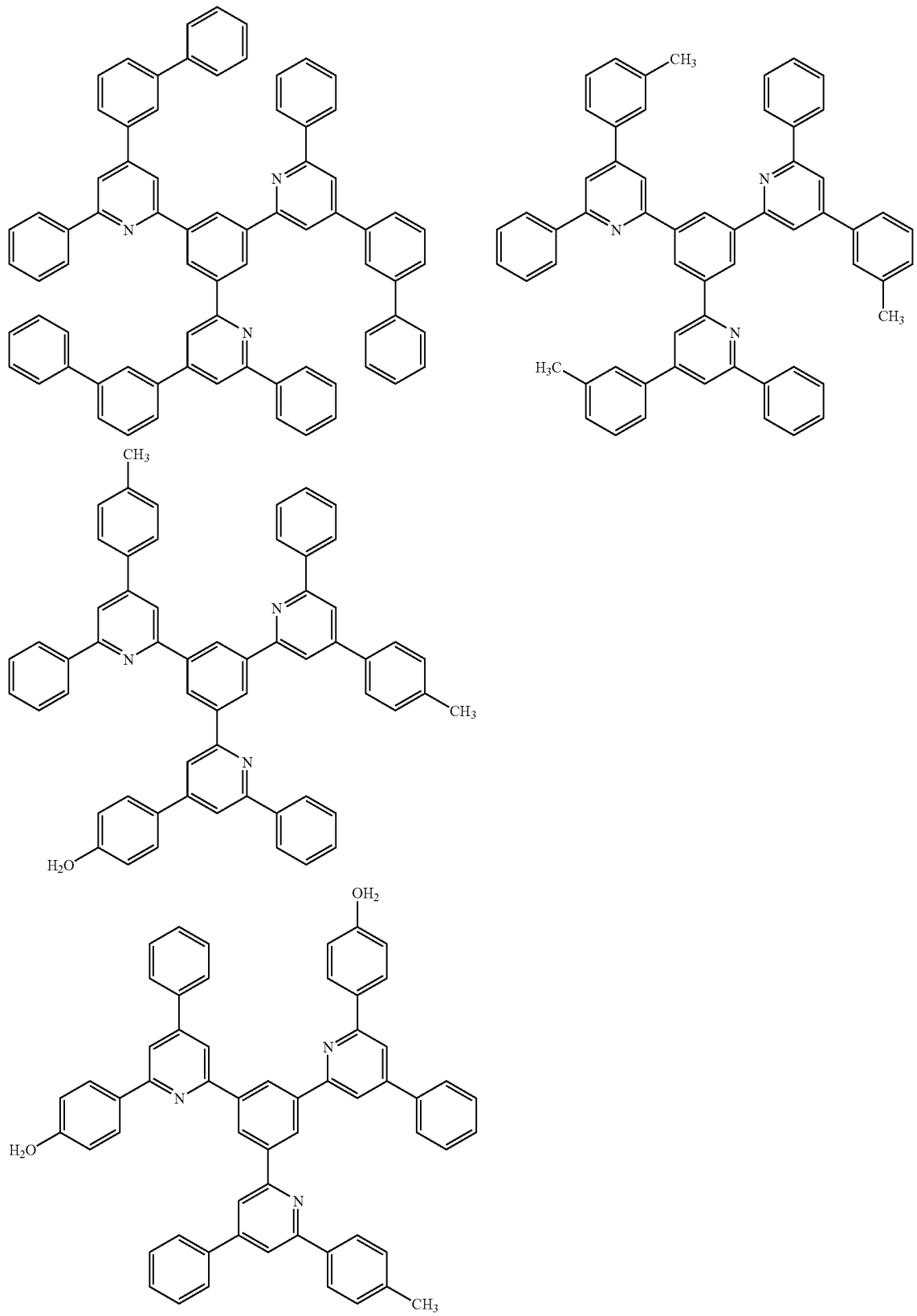

-continued
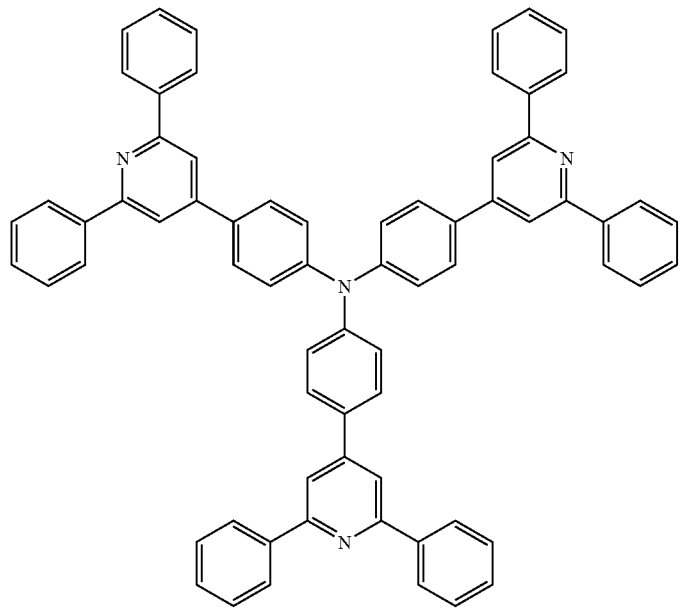
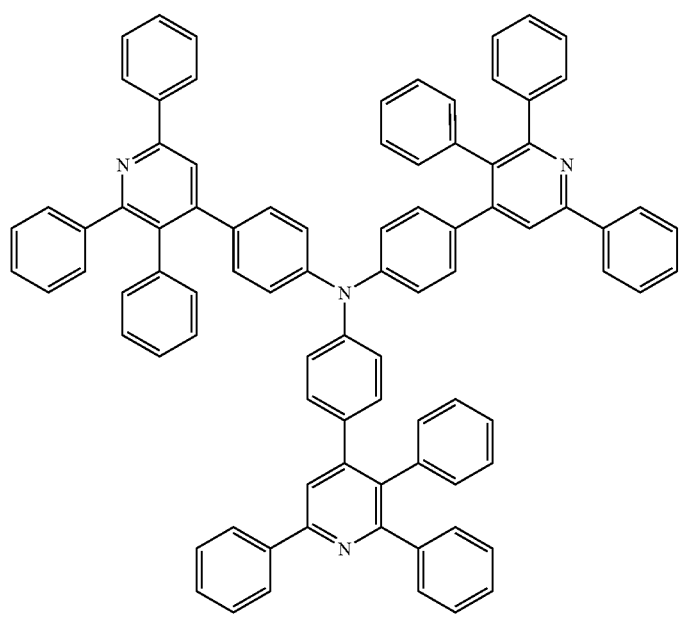

-continued
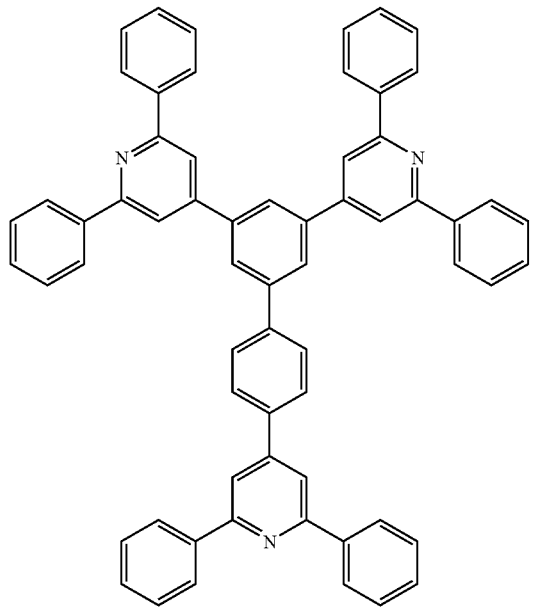
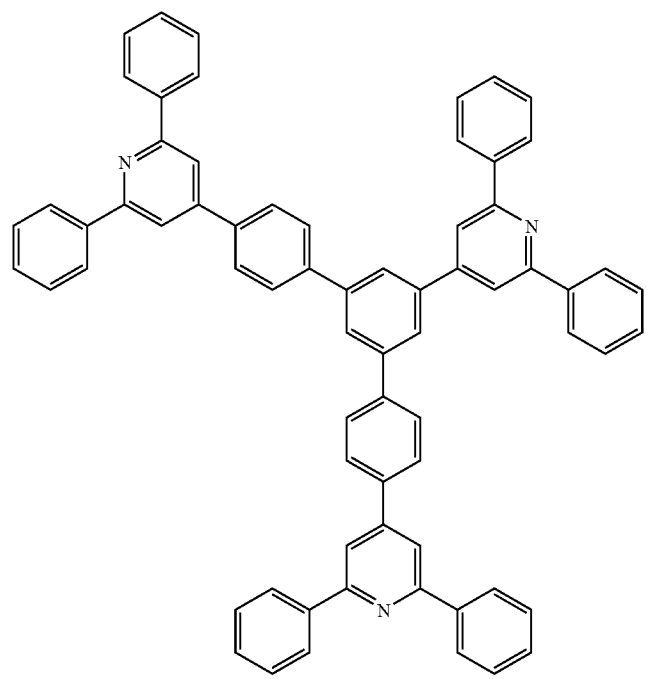

-continued
| 101 | 102 |
|---|---|
| 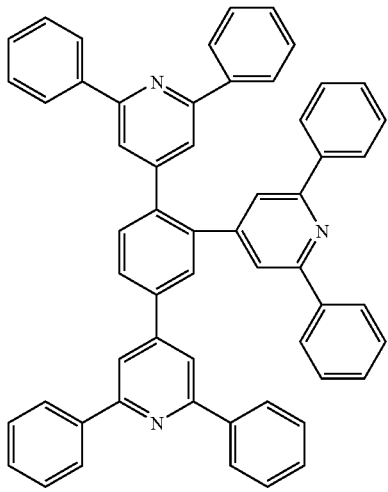 | 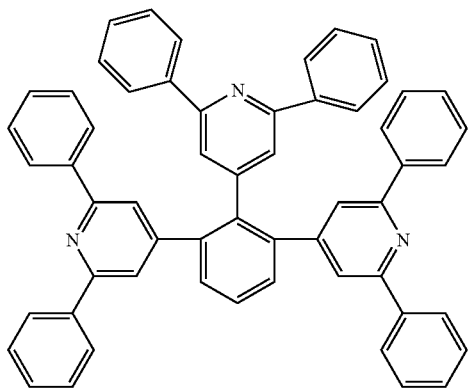 |
| 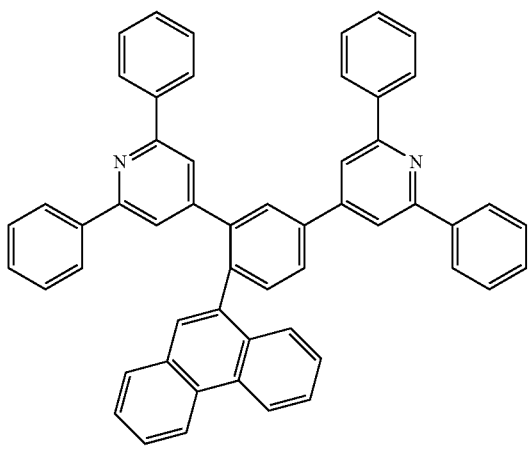 | 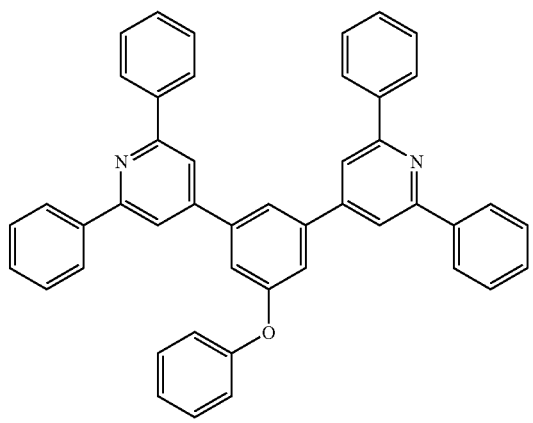 |
| 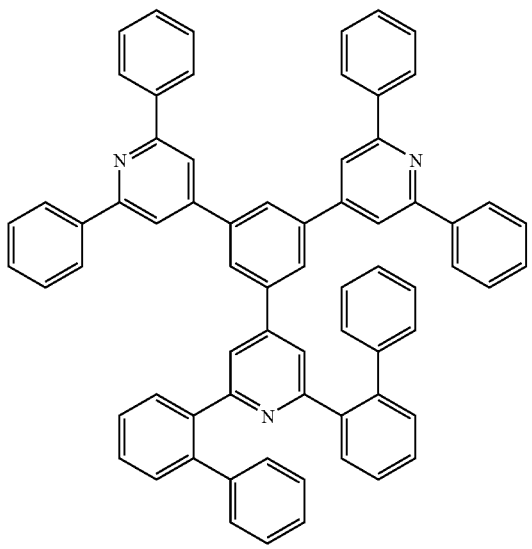 | 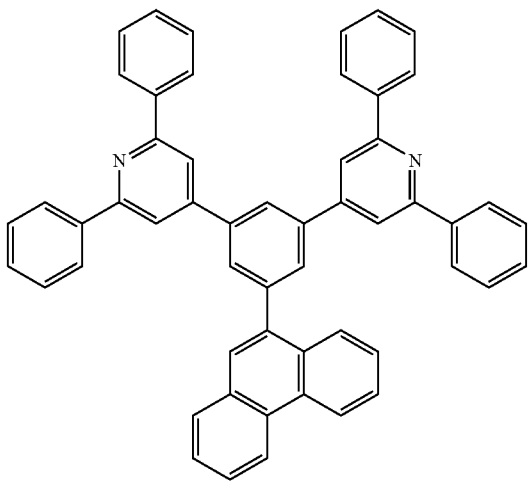 |

-continued
103
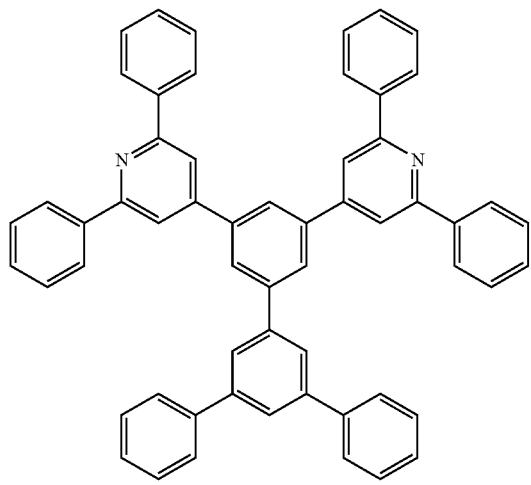
104
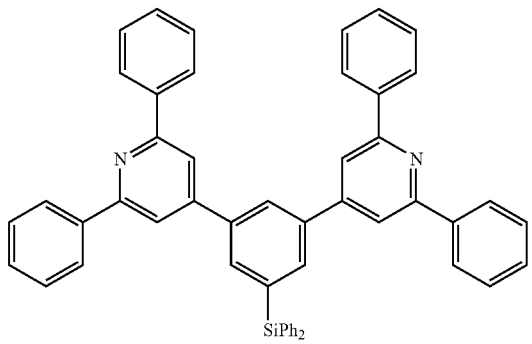
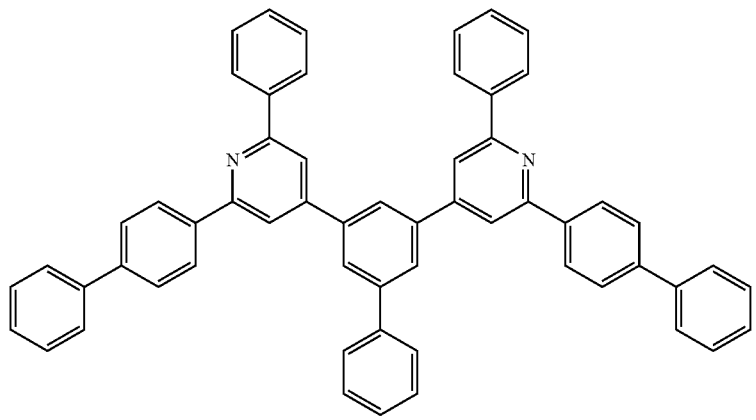
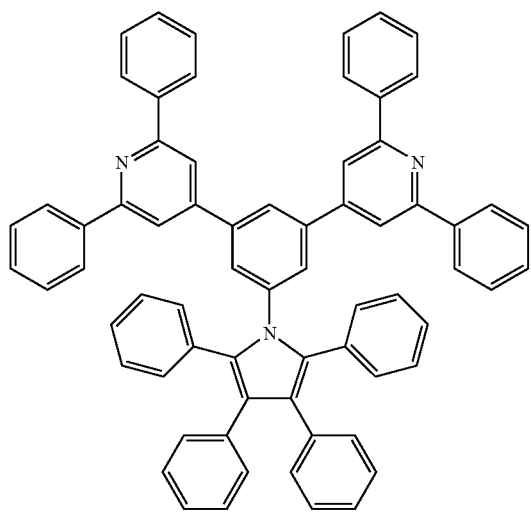

-continued
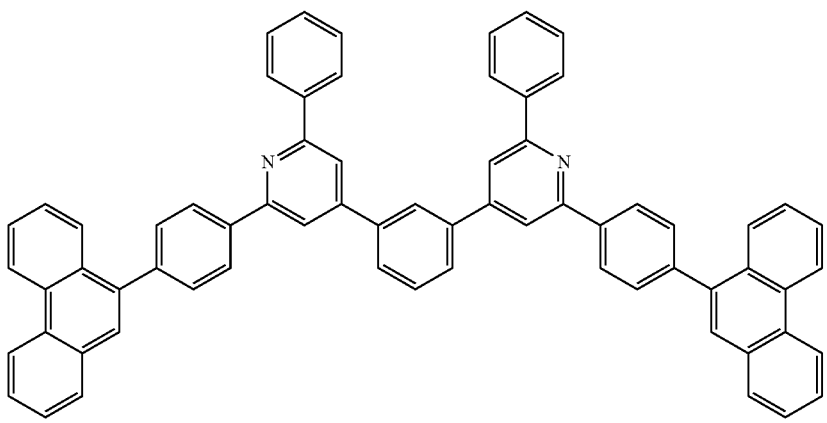
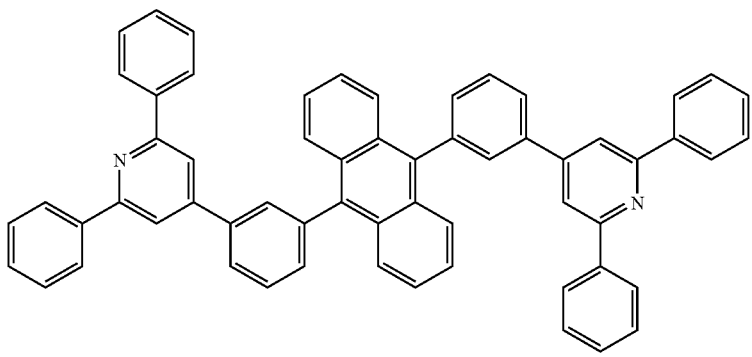
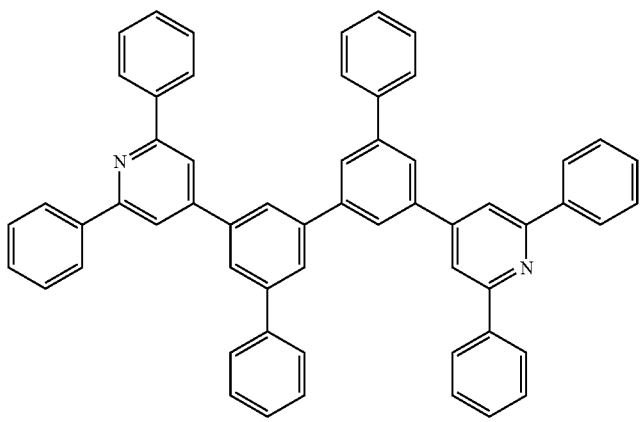
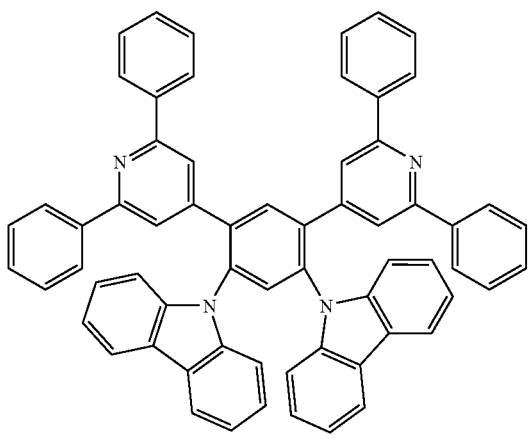

-continued
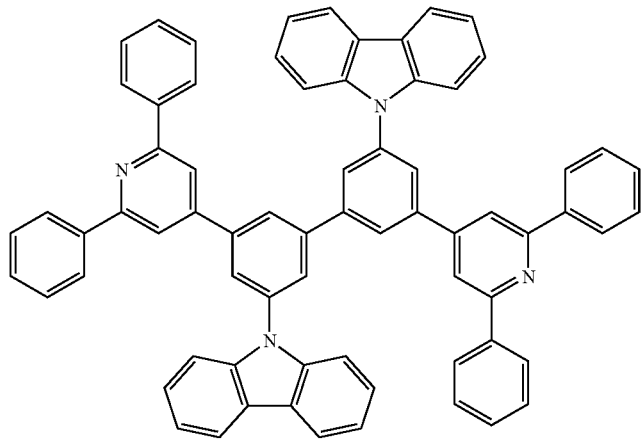
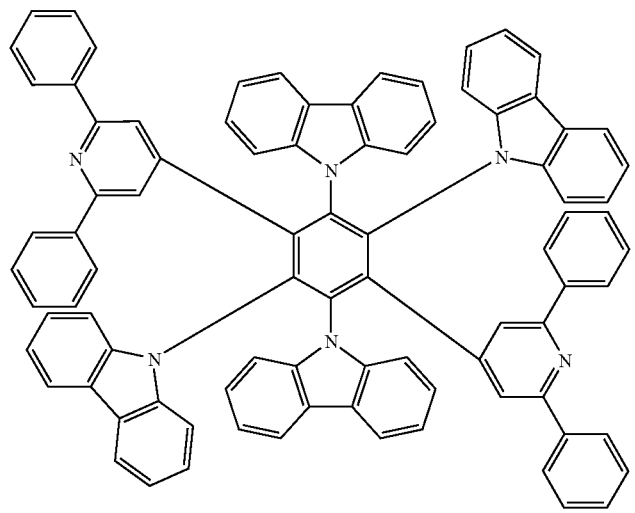
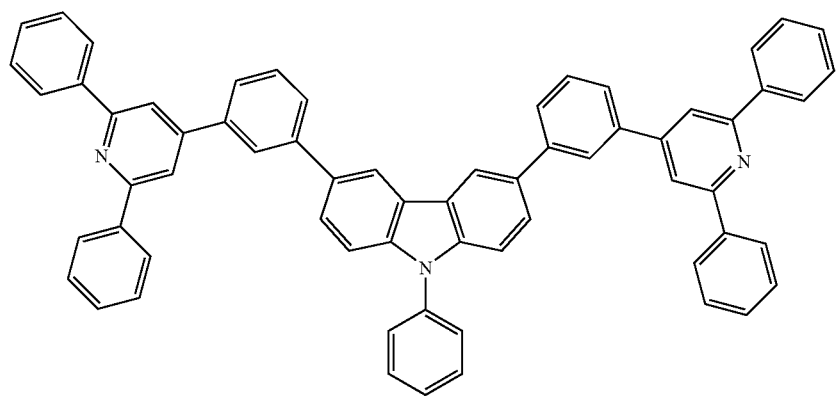

-continued
| 109 | 110 |
|---|---|
| 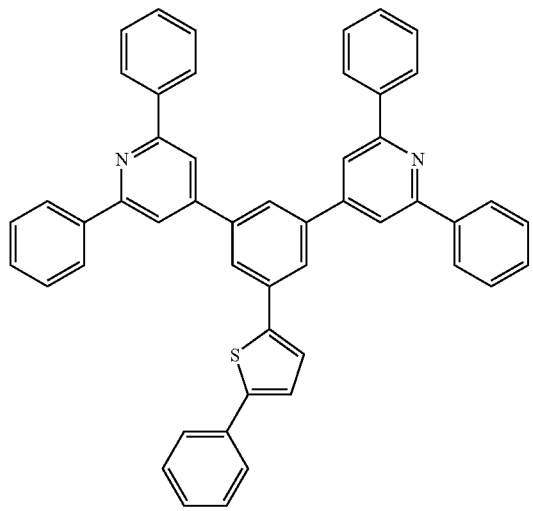 | 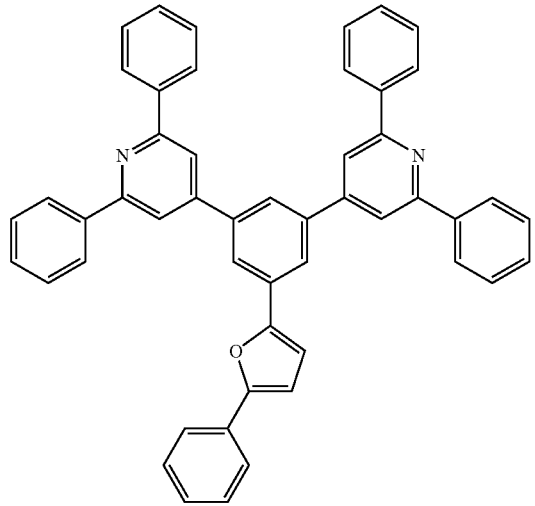 |
| 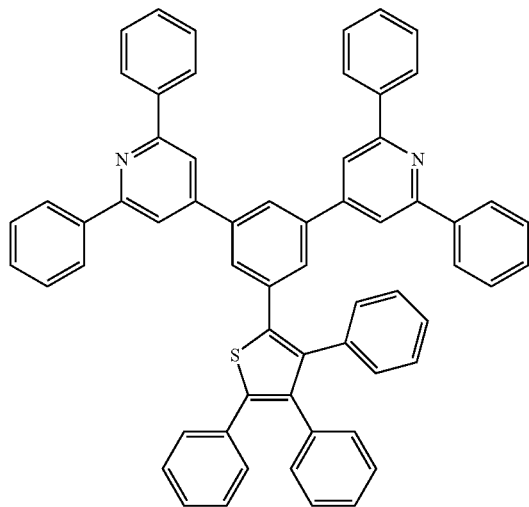 | 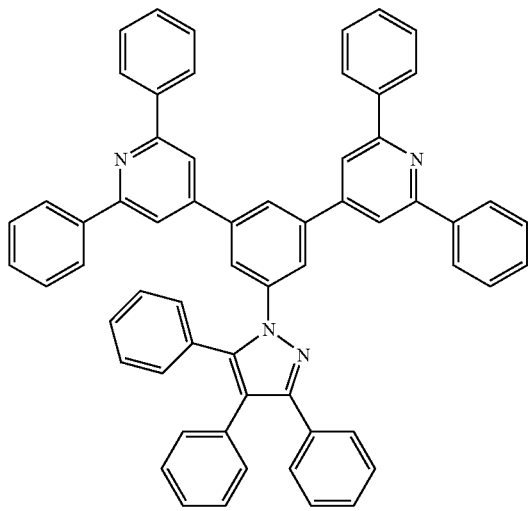 |
| 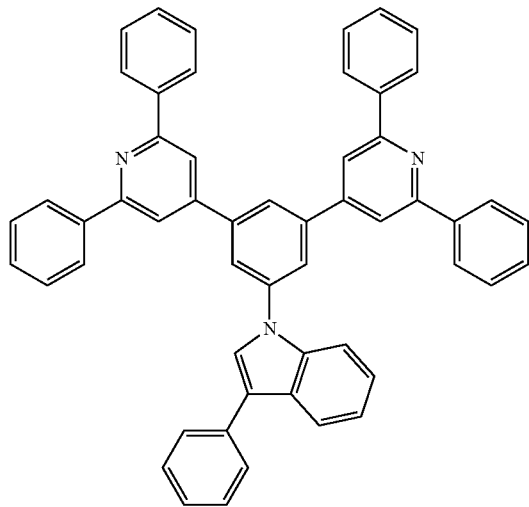 | 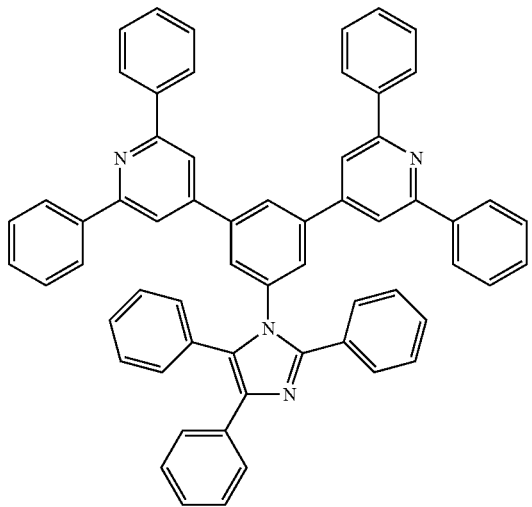 |

111 112
-continued
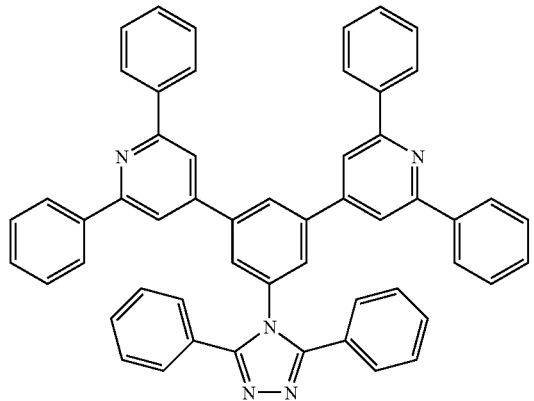
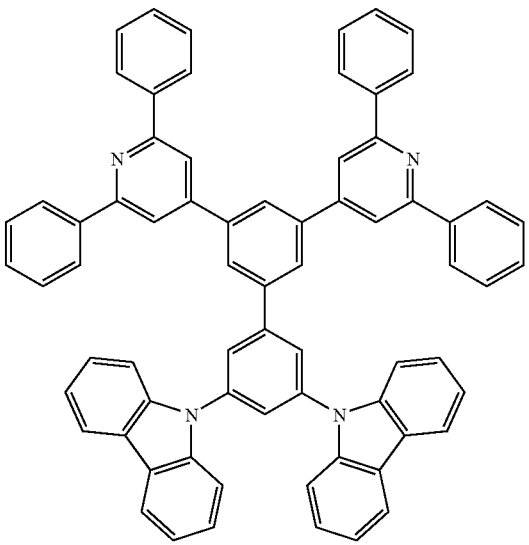
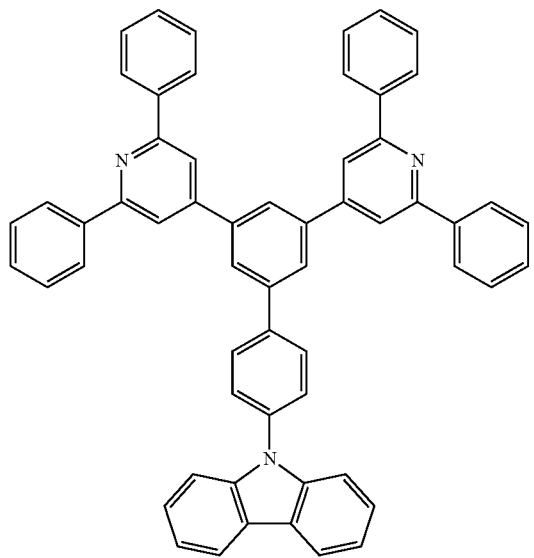
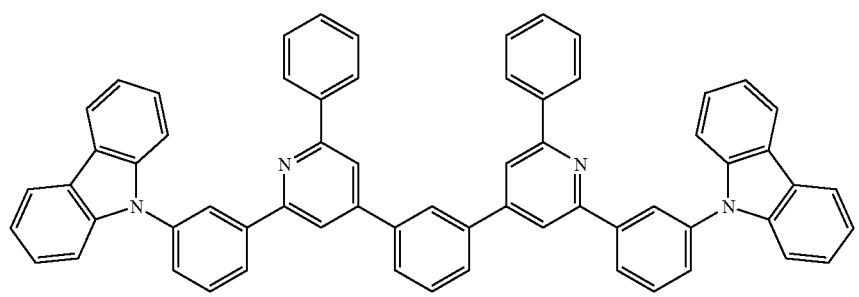

-continued
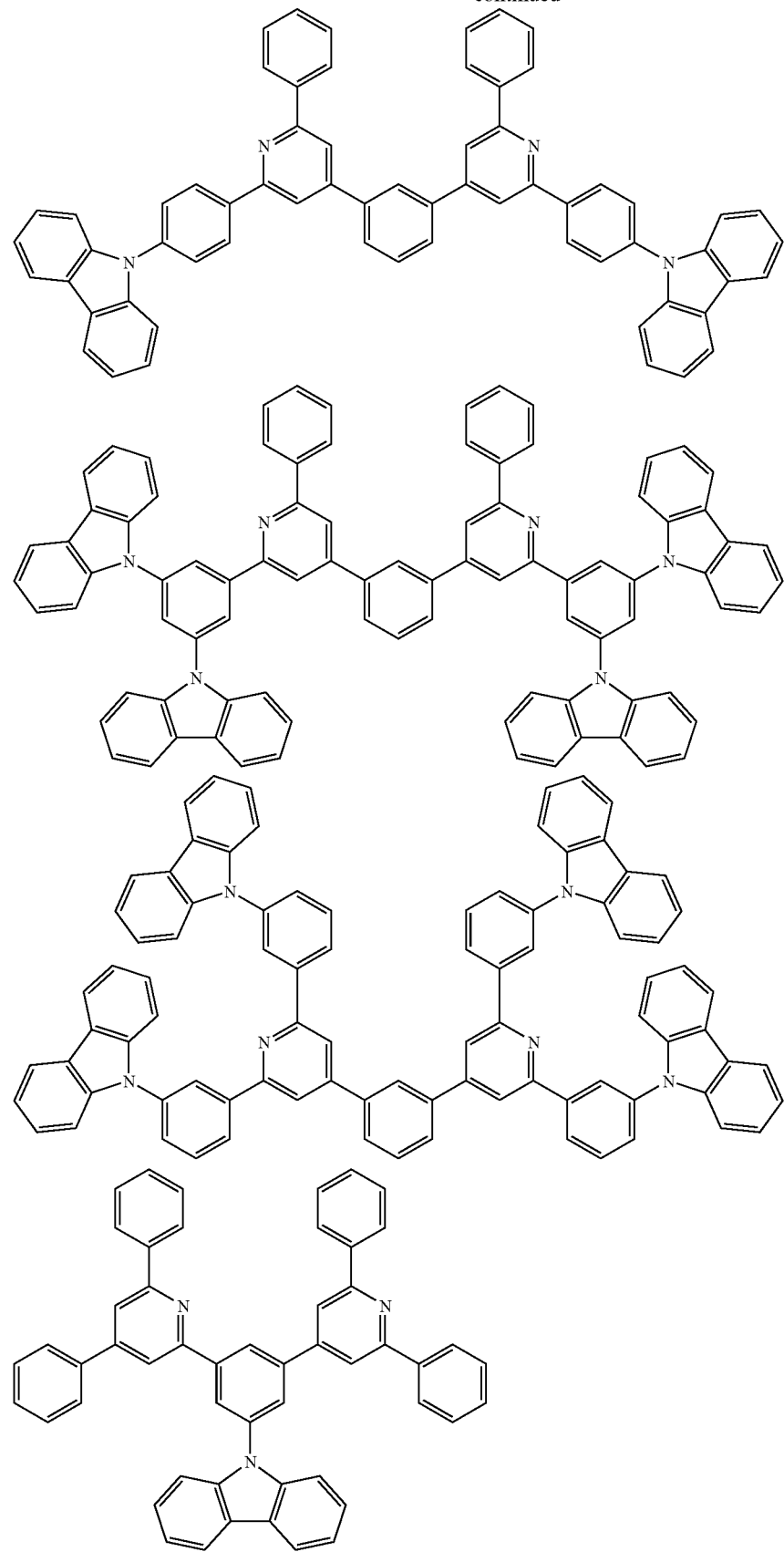

-continued
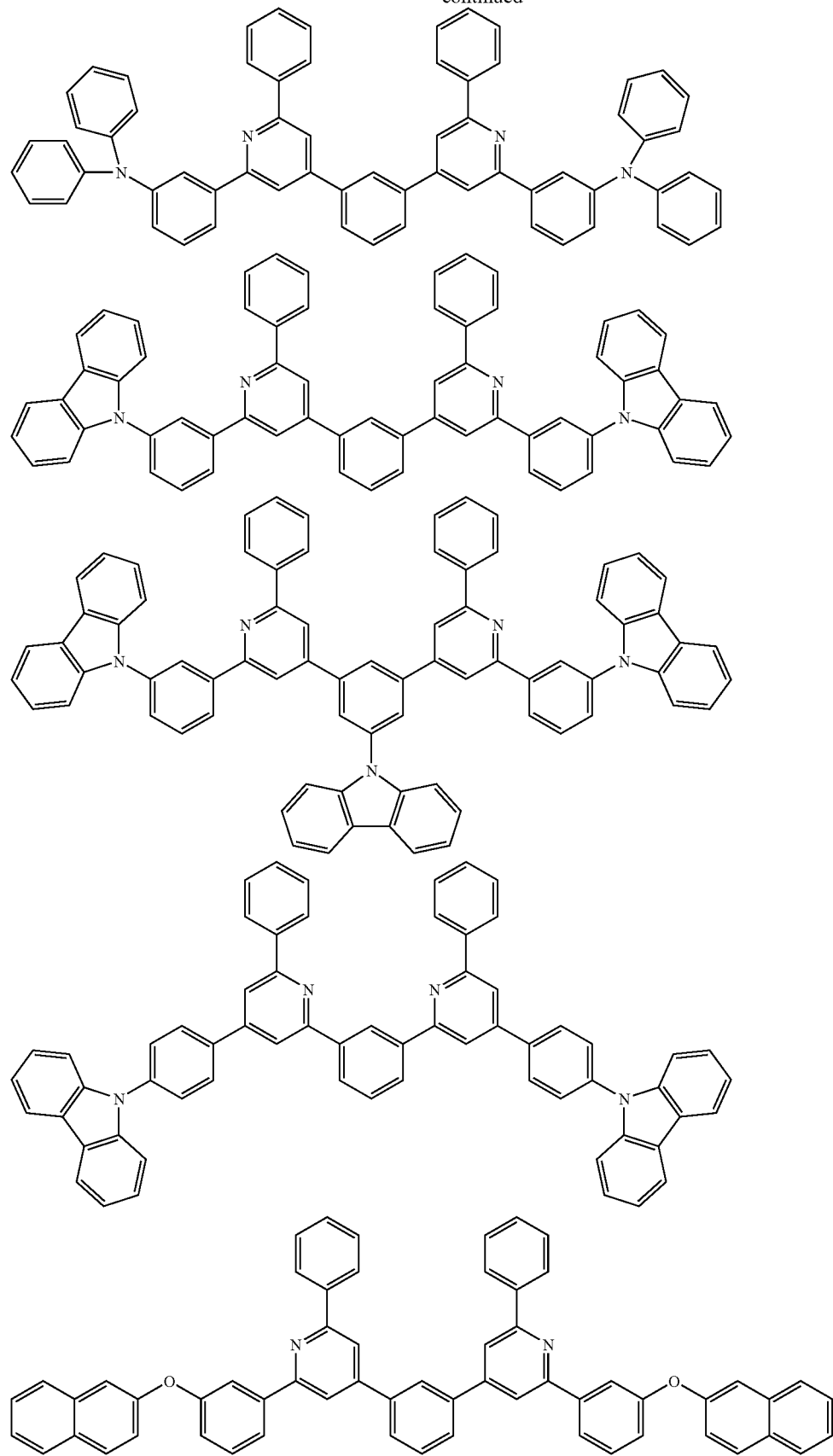

-continued
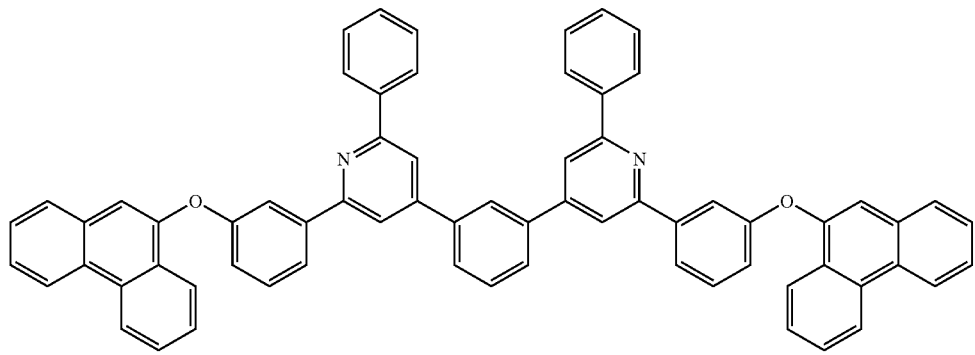
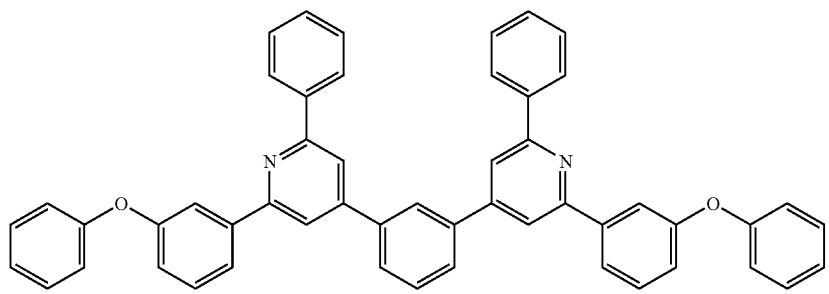
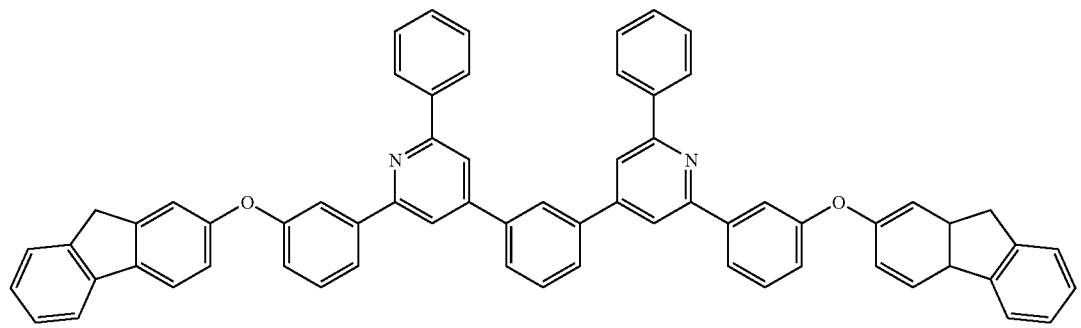
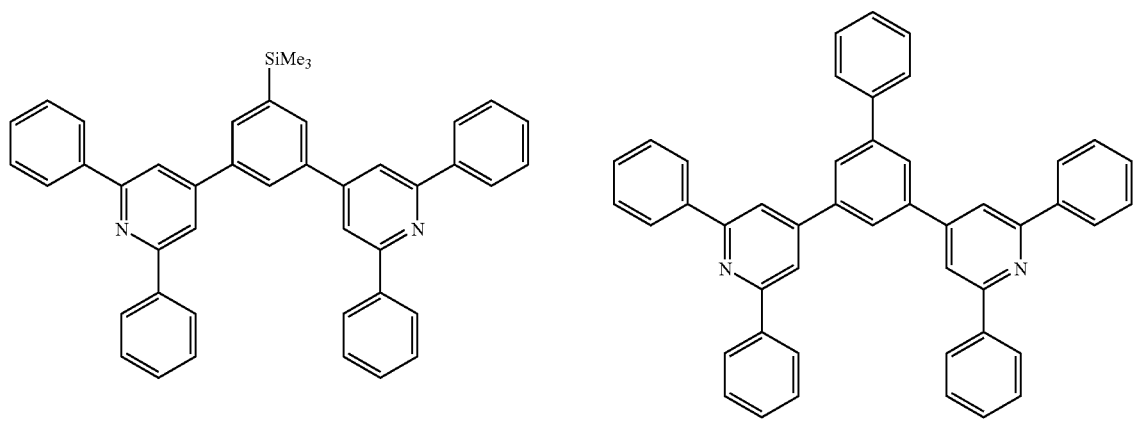

-continued
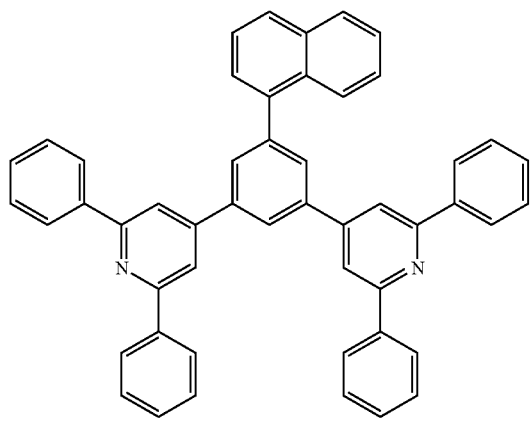
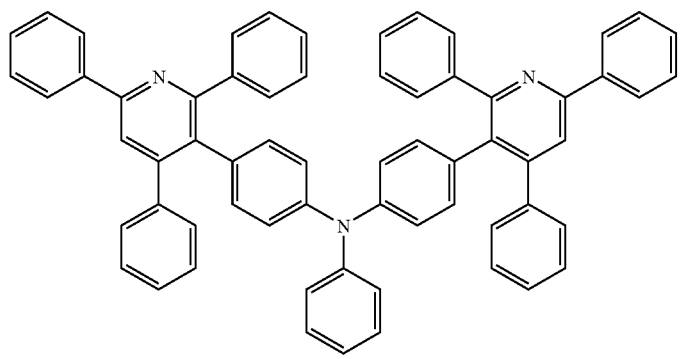
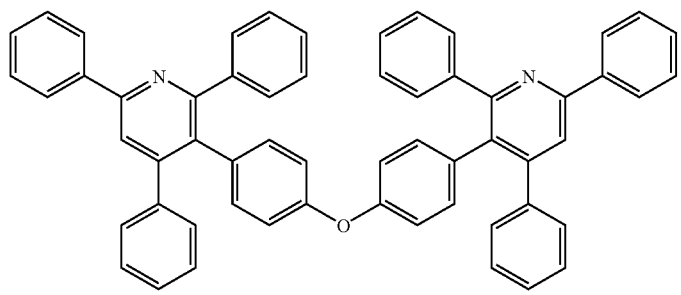
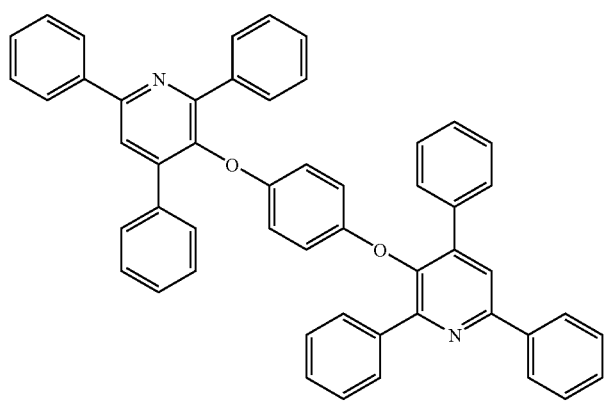

-continued

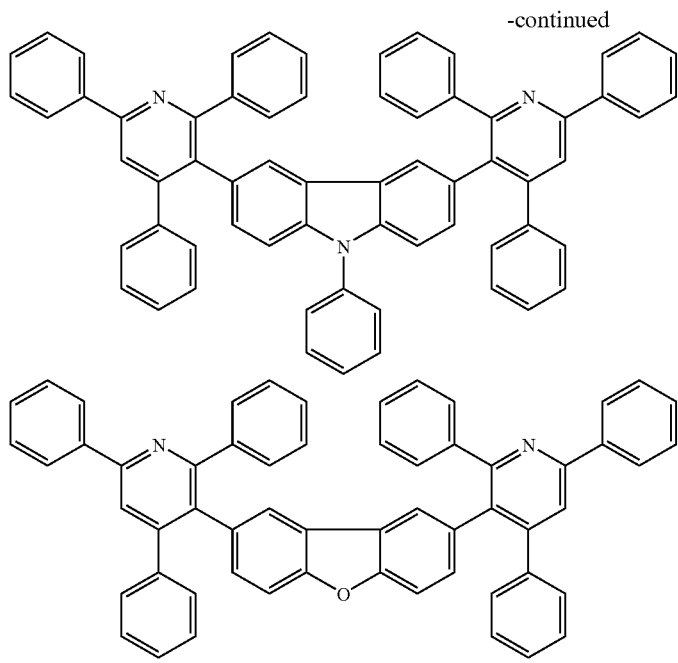

The compounds to be used as charge transporting materials of the invention can be synthesized by employing known processes with selecting starting materials according to the structure of an intended compound.

For example,

A) in the case of using Z—(CHO) as a starting material: there may be employed the following processes.

1) A process of synthesizing by stirring 1 equivalent of an aldehyde and 0.5 to 2 equivalents of an acetylide in the presence of a strong acid such as sulfuric acid in a single solvent of acetic acid, alcohol, nitrobenzene, chlorobenzene, dichlorobenzene or cyclohexane or in a mixed solvent thereof at room temperature for 1 to 10 hours or stirring them in the presence of a strong base such as sodium hydroxide in an alcohol and/or an aqueous solvent under heating condition for 1 to 10 hours to obtain an intermediate (—CH=CR—CO—), and acting thereon an acylpyridinium salt and ammonium acetate under heating condition in the presence of oxygen, as disclosed in Angew. Chem. Int. Ed. Engl. (1962), Synthesis (1976), 1-24, J. Heterocyclic Chem. (1977) 14, 147, Collect. Czech. Chem. Commun. 57(1992) 2, 385-392 and CS-262585.

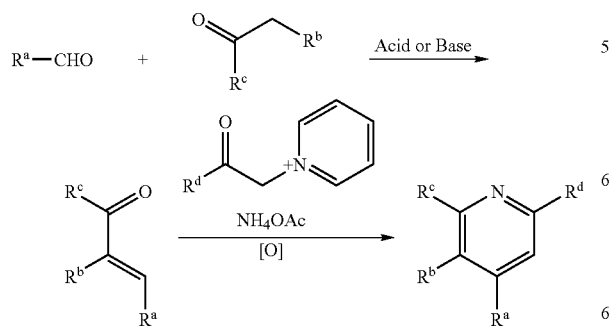

2) A process of reacting an aldehyde and an acetylide in the presence of an oxidizing agent such as boron trifluoride or perchloric acid under heating condition in a toluene solvent to produce a pyrylium salt, and reacting the product with ammonia in water or an alcohol solvent, as disclosed in Liebigs Ann. Chem. (1974), 1415-1422, J. Org. Chem. 38, (2002) 6, 830-832 and JP-A-2000-186066.

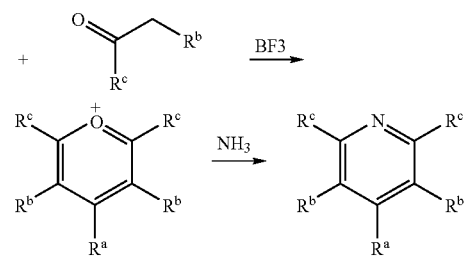

3) A process of synthesizing in one step from ammonium acetate, an aldehyde and an acetylide in a single solvent of acetic acid, alcohol, nitrobenzene, toluene, chlorobenzene, dichlorobenzene or cyclohexane or a mixed solvent thereof under heating, as disclosed in J. Am. Chem. Soc. (1952) 74,200.

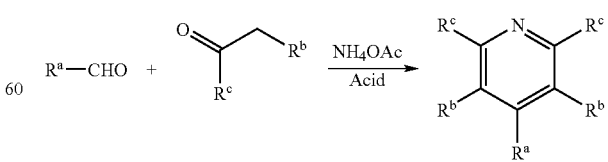

4) A process of synthesizing by grinding an aldehyde and 2 equivalents of an acetylide in the presence of a strong base such as sodium hydroxide and in the absence of a solvent using a mortar to produce an intermediate (diketone), and then acting thereon ammonium acetate in a single solvent of acetic acid, alcohol, nitrobenzene, toluene, chlorobenzene, dichlorobenzene or cyclohexane or a mixed solvent thereof under heating condition, as disclosed in Chem. Commun. (Cambridge) (2000) 22, 2199-2200.

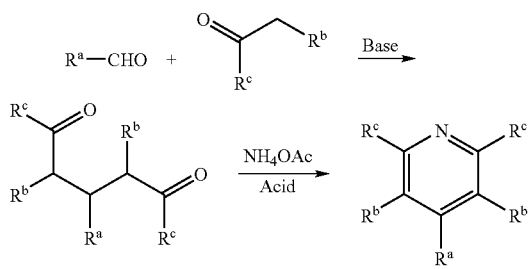

5) A process of synthesizing in one step from an aldehyde and ethylidenevinylamine, as disclosed in J. Org. Chem. (1988), 53, 5960.

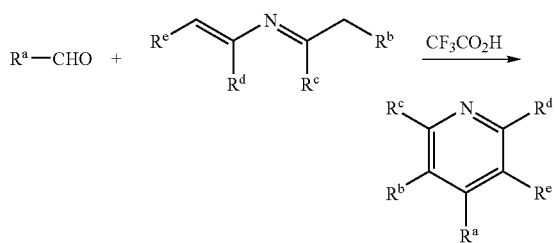

B) Use of a pyridine ring substituted by a halogen atom such as chlorine, bromine or iodine at least in one of 2-, 4- and 6-positions enables one to convert the halogen element to an arbitrary substituent.

There may be illustrated, for example, a process of synthesizing by acting zinc bromide or boric acid in the presence of a palladium catalyst under heating condition, as disclosed in Org. Lett. 3(2001) 26, 4263-4265.

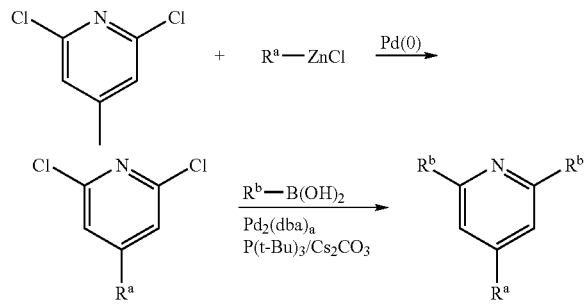

C) Besides, in introducing various substituents or forming the connector Z, any known technique may be employed as needed. For example, in the case when Z is a direct bond, there are illustrated:

1) a process of synthesizing pyridine having an aromatic group at 2- and 6-positions thereof by using paraformaldehyde as an aldehyde and an aromatic acyl compound as an acetylide, halogenating 4-position of the pyridine ring by using a halogenating agent such as N-bromosuccinimide to obtain a halide product, converting the halogen atom to —B(OH)$_2$ group, —ZnCl group or —MgBr group, and coupling this product with the halide product;

2) a process of converting the halide product to its lithio product with n-butyllithium, treating it with N,N-dimethylformamide to synthesize pyridine having an aromatic ring group at 2- and 6-positions thereof and having a CHO group at 4-position thereof, and then reacting the product with an acetylide to synthesize a second pyridine ring; and 3) a process of stirring 2,6-dichloro-4-iodopyridine described as a starting material in the foregoing B) in the presence of a base using a copper catalyst such as copper dust at 150 to 250° C. to synthesize 2,6,2',6'-tetrachloro-[4,4']bipyridyl, and treating this in the same manner as in the foregoing B.

Additionally, as the aldehyde (R$^a$—CHO) to be used upon synthesis, commonly available reagents may properly be utilized but, if necessary, it is possible to synthesize with ease according to the following processes:

1) a process of acting an alkyllithium such as butyllithium or a strong base such as sodium hydride, triethylamine, potassium tert-butoxide or sodium hydride (preferably alkyllithium such as butyllithium) on, for example, a halide (R$^a$—X) or a hydrocarbon compound having an active hydrogen (R$^a$—H), and then treating the product with N,N-dimethylformamide (Organic & Biomolecular Chemistry (2003) 1, 7, 1157-1170 or Tetrahedron Lett. 42(2001) 37, 6589-6592);

2) a process of reducing —CO$_2$R group (wherein R represents a hydrogen atom, a chlorine atom, an alkyl group, an aromatic group or an amino group) with lithium aluminum hydride or sodium boron hydride to produce an alcohol, and then oxidizing with pyridinium chlorochromate, manganese dioxide, iodoxybenzoic acid or peroxodisulfate, 2,3-dichloro-5,6-dicyano-1,4-benzoquinone to form a —CHO product (J. Med. Chem. (1990) 33, 2408-2412; Angew. Chem., Int. Ed. 40(2001)23, 4395-4397; J. Am. Chem. Soc. (2002) 124, 10, 2245-58; J. Am. Chem. Soc. (1993) 115, 9, 3752-3759; J. Chem. Res., Synop. (2001) 7, 274-276; Synthesis (2001) 15, 2273-2276; Bull. Korean Chem. Soc. 20 (1999) 11, 1373-1374; Arzneim. Forsch. 47 (1997) 1, 13-18; J. Org. Chem. 63 (1998) 16, 5658-5661; J. Chem. Soc. Sec. C; Organic (1968) 6, 630-632);

3) a process of reducing a —CO$_2$R group (wherein R represents a hydrogen atom, a chlorine atom, an alkyl group, an aromatic ring group or an amino group) with lithium tris(dialkylamino)aluminum hydride or sodium tris(dialkylamino)aluminum hydride to convert to —CHO in one step (Bull. Korean Chem. Soc., 13 (1992) 6, 670-676; Bull. Korean Chem. Soc., 12 (1991) 1, 7-8; Org. Prep. Proced. Int. 24 (1992) 3, 335-337);

4) a process of converting a —CO$_2$R group (wherein R represents a hydrogen atom, a chlorine atom, an alkyl group, an aromatic ring group or an amino group) to —CHO in one step (Chem. Ber. (1959) 92, 2532-2542; WO 00/12457; Bull. Chem. Soc. Jpn. (2001) 74, 1803-1815);

5) a process of reducing a —CN group with lithium tris(dialkylamino)aluminum hydride to convert to —CHO in one step (Bull. Korean Chem. Soc., 13 (1992) 6, 670-676);

6) a process of acting o-iodylbenzoic acid, Dess-Martin periodinane or acetoxyiodosylbenzoic acid on an Ar—CH$_3$ group (wherein Ar represents an aromatic group) to Ar—CHO (J. Am. Chem. Soc. (2002) 124, 10, 2245-58);

7) a process of converting an Ar—CH$_3$ group (wherein Ar represents an aromatic group) to Ar—CH$_2$OH via Ar—CH$_2$Br and Ar—CH$_2$OAcO, and oxidizing the product with pyridinium chlorochromate, manganese dioxide or iodoxybenzoic acid to convert to —CHO (J. Org. Chem. (1993) 58, 3582-3585);

8) a process of synthesizing an arylcarboxyaldehyde by acting a Vilsmeier reagent on 1-ethyl-1-arylallyl alcohol (Indial Journal of Chemistry (1988) 27B, 213-216);

9) a process of synthesizing an arylcarboxyaldehyde by acting a Vilsmeier reagent on a 1,4-cyclohexadiene (Synthesis (1987), 197-199; Synthesis (1985), 779-781);

10) a process of converting an Ar—$CH_3$ group (wherein Ar represents an aromatic ring group) to Ar—CHO by brominating the Ar—$CH_3$ group with bromine or N-bromosuccinimide to produce Ar—$CH_2Br$, then acting thereon a 2-nitropropane carboanion reagent or hexamethylenetetramine (Collect. Czech. Chem. Commun. (1996) 61, 1464-1472; Chem. Eur. J. (1996) 2, 12, 1585-1595; J. Chem. Research (S), (1999) 210-211);

11) a process of obtaining an arylaldehyde (e.g., 1,3,5-triformylbenzene) from a polymethinium salt (e.g., heptamethinium salt) (Collect. Czech. Chem. Commun. (1965) 30, 53-60);

12) a process of obtaining 1,3,5-triformylbenzene by self-condensation of triformylmethane (Collect. Czech. Chem. Commun. (1962) 27, 2464-2467); and 13) a process of converting an Ar—$CHBr_2$ group (wherein Ar represents an aromatic ring group) to ArCHO by using a dialkylamine (Bulletin de La Societe Chmique De France (1966) 9, 2966-2971).

As the ketone ($R^c$—CO—$CH_2$—$R^b$)) to be used upon synthesis of the compound, commonly available reagents may properly be utilized but, if necessary, it is possible to synthesize with ease according to the following processes:

1) a process of converting an $R^c$—$CO_2R$ group (wherein R represents a hydrogen atom, a chlorine atom, an alkyl group, an aromatic ring group or an amino group) to $R^c$—CO—$CH_2R^b$ by treating it with various alkylating agents (e.g., alkyllithium, dimethylsulfuric acid or dimethyl sulfoxide) (J. Am. Chem. Soc. (1959), 81, 935-939; J. Am. Chem. Soc. (1961) 83, 4668-; Tetrahedron Lett. (1967) 1073-; J. Chem. Soc., Perkin Trans. 1 (1977) 680; JP-5-5062039); and 2) a process of synthesizing acting an acylating agent such as an acid chloride in the presence of Lewis acid such as aluminum chloride (extremely popular Friedel-Crafts reaction).

The compound of the invention can be obtained by separating an end product from the reaction product according to a conventional manner by filtration or extraction and subsequent concentration and purifying, as needed, through such technique as recrystallization or column chromatography.

In the Case where the connectors $Z_1$ and $Z_2$, $Q_0$, and $R_1$ to $R_8$ are hetero rings, it is also possible to synthesize the end product by preparing the precursor thereof as a commonly available reagent or through synthesis employing synthesizing processes described or cited in Heterokan No Kagaku-Iyakuhin No Kiso (2002, Kunieda, et al., Kagakudojin-sha) and Heterocyclic Chemistry ($4^{th}$ ed., 2000, J. A. Joule and K. Mills, Blackwell Science Co.), and subjecting the resulting precursor to the afore-mentioned synthesizing processes or conducting coupling reaction between the rings as described or cited in Palladium in Heterocyclic Chemistry: A guide for the Synthetic Chemist ($2^{nd}$ ed., 2002, Jie Jack Li and Gordon W. Gribble, Pergamon Co.) and Senikinzoku Ga Hiraku Yuki-gousei—Sono Tasai Na Hannokeishiki To Saishin No Seika (1997, Jiro Tsuji, Kagakudojin-sha).

In the case of applying the charge transporting material of the invention to an organic electroluminescent element, use of an organometallic complex of a phosphorescence-emitting dye as a dopant in the light-emitting layer provides particularly excellent luminous efficiency and driving life. The effect is particularly remarkable when the organometallic complex is a complex wherein a 2-arylpyridine-based ligand and a metal element are connected to each other through carbon-to-metal sigma bond and nitrogen-to-metal coordination bond. Therefore, it is preferred for the organometallic complex to have a 2-arylpyridine-based ligand.

As a central metal, a metal which produces a complex whose light-emitting mechanism involves at least charge transfer from the ligand orbital to the metal atom orbital is preferred.

When the charge transporting material of the invention is applied to the same layer as the dopant (light-emitting layer) and/or a layer adjacent to the layer (hole blocking layer and/or electron transport layer), physicochemical similarity, electrochemical similarity and similarity of a triplet excitation level of the charge transporting material with a 2-arylpyridine-based ligand exert their effects and thereby improvement in the efficiency of re-coupling of the charge on the dopant, improvement in the efficiency of energy transfer from the host molecule to the dopant, and reduction in a exciton deactivation possibility between the light-emitting layer and the hole blocking layer are brought about.

The charge transporting material of the invention has such a high charge transporting ability that it can favorably be used as a charge transporting material in an electrophotographic photoreceptor, an organic electroluminescent element, a photoelectric conversion element, an organic solar cell and an organic rectification element. In particular, it is suitable as an electron transporting compound owing to its excellent electron transporting ability.

Also, use of the charge transporting material of the invention provides an organic electroluminescent element which has an excellent heat resistance and can stably operate (emit light) for a long period of time, and hence it is suitable as an organic electroluminescent element material.

Next, the organic electroluminescent element of the invention is described below.

The organic electroluminescent element of the invention has an anode, a cathode and an organic light-emitting layer (hereinafter in some cases referred to merely as "light-emitting layer") provided between the two electrodes, and is characterized in that it has a layer containing the charge transporting material of the invention. It suffices for the element of the invention to have at least an anode, a cathode and a light-emitting layer provided between the two electrodes.

Since the charge transporting material of the invention has a broad optical band gap and has an appropriate electron transporting ability, it is particularly effective to use the material in a layer provided in contact with the cathode side of the light-emitting layer (hereinafter referred to as "hole blocking layer).

Additionally, the charge transporting material of the invention can be used in any layer that constitutes the organic electroluminescent element. In particular, as has been described hereinbefore, it is preferred to use in an organic light-emitting layer (hereinafter in some cases merely referred to as "light-emitting layer") and an electron transport layer provided between the light-emitting layer and the cathode. In order to effectively utilize the characteristic properties of the compound to be used as the charge transporting material of the invention, it is preferred to use the compound as a material for the hole blocking layer which is not necessarily be provided in contact with the light-emitting layer. Additionally, a layer in contact with the cathode side interface of the light-emitting layer is usually called a hole blocking layer.

Also, in the case of using as a material for the light-emitting layer, particularly as a host material, an organic electroluminescent element showing a high luminous efficiency can be obtained, thus such case being preferred. Particularly, in the case of using the charge transporting material of the invention in the light-emitting layer, electrons are properly injected into the light-emitting layer because the material has an appropriate LUMO level derived from the pyridine ring, leading to effective recombination with holes injected from the hole transport layer. Thus, such light-emitting layer can be used as a light-emitting layer of an organic electroluminescent element which does not have a hole blocking layer.

Further, the charge transporting material of the invention may be used in plural layers, and it is particularly preferred to use it in both the light-emitting layer and the hole blocking layer. Use of the charge transporting material of the invention in both the light-emitting layer and the hole blocking layer serves to further prolong the lifetime of the element. It is also possible to use plural kinds of the charge transporting material of the invention in respective layers, or to use them in combination with other charge transporting materials than the charge transporting material of the invention.

In the case where the charge transporting materials of the invention are incorporated in two or more layers, the materials may be the same or different from each other.

Additionally, in the organic electroluminescent element of the invention, a layer between the cathode and the light-emitting layer is referred to as "electron transport layer" and, where two or more layers exist, a layer in contact with the cathode is referred to as electron injection layer" and other layer or layers are generically referred to as "electron transport layers". Of the layers provided between the cathode and the light-emitting layer, a layer in contact with the light-emitting layer is in some cases particularly referred to as "hole blocking layer".

Hereinafter, an embodiment of the organic electroluminescent element of the invention is described in detail by reference to the attached drawings taking for instance the case where the charge transporting material of the invention is contained in the hole blocking layer.

FIG. 1 is a cross-sectional view schematically showing an example of the structure of a general organic electroluminescent element to be employed in the invention wherein 1 designates a substrate, 2 an anode, 4 a hole transport layer, 5 a light-emitting layer, 6 a hole blocking layer, and 8 a cathode. The substrate 1 functions as a support in the organic electroluminescent element, and a plate of quartz or glass, a metal plate or metal foil, or a plastic film or sheet is used. In particular, a glass plate and a plate or film of transparent synthetic resin such as polyester, polymethacrylate, polycarbonate or polysulfone are preferred. In the case of using the synthetic resin substrate, care must be taken with respect to gas barrier properties. In case where the gas barrier properties are too small, the organic electroluminescent element might be deteriorated due to the air outside having passed through the substrate, thus small gas barrier properties not being preferred. Therefore, it is one preferred method to provide a dense silicon oxide film on at least one side of the synthetic resin substrate to thereby ensure sufficient gas barrier properties.

An anode 2 is provided on the substrate 1. The anode 2 functions to inject holes into a hole transport layer 4. The anode 2 is usually constituted by a metal such as aluminum, gold, silver, nickel, palladium or platinum, a metal oxide such as indium oxide and/or tin oxide, a metal halide such as copper iodide, carbon black, or a conductive polymer such as poly(3-methylthiophene), polypyrrole or polyaniline. The anode 2 is usually formed by a sputtering method or a vacuum deposition method. In the case of forming the anode 2 from fine particles of a metal such as silver, fine particles of copper iodide, carbon black, fine particles of a conductive metal oxide or fine particles of a conductive polymer, it can also be formed by dispersing in a suitable binder resin solution and coating the dispersion on the substrate 1. Further, in the case of forming the anode 2 from the conductive high polymer, it is also possible to directly form a polymerized thin film on the substrate 1 through electrolytic polymerization or form the anode 2 by coating conductive high polymer molecules on the substrate 1 (App. Phys. Lett., vol. 60, p. 2711, 1992).

The anode 2 is usually of a single-layer structure but, as needed, it may be of a laminated structure.

The thickness of the anode 2 varies depending upon required transparency. In the case of some transparency being required, the transmittance for visible light is adjusted to be usually 60% or more, preferably 80% or more In this case, the thickness is usually 5 nm or more, preferably 10 nm or more, and is usually 1,000 nm or less, preferably 500 nm or less. In the case where the anode may be opaque, the thickness of the anode 2 is arbitrary, and may be formed by a metal, as needed, so as to also function as the substrate 1.

In the element of the structure shown in FIG. 1, a hole transport layer 4 is provided on the anode 2. As a material of the hole transport layer, the material is required to show a high hole injecting efficiency from the anode and transport the injected holes with high efficiency. For satisfying the requirements, the material is required to have a small ionization potential, show a high transparency for a visible light, show a large hole mobility, have an excellent stability and difficultly generate impurities, which function as a trap, upon production or upon use. Also, since the hole transport layer is in contact with the light-emitting layer 5, the material is required not to reduce the luminous efficiency by quenching the light emitted from the light-emitting layer or by forming exciplex. In addition to the above-described general requirements, the element is required to have some heat resistance in consideration of application to an onboard display. Therefore, a material having a glass transition temperature Tg of 85° C. or more is desirable.

Examples of such hole transporting material include aromatic diamines containing two or more tertiary amines wherein the nitrogen atoms are substituted by two or more condensed aromatic rings, represented by 4,4'-bis[N-(1-naphthyl)-N-phenylamino]biphenyl (JP-A-5-234681); aromatic amine compounds having a star-burst structure such as 4,4',4"-tris(1-naphthylphenylamino)triphenylamine (J. Lumin., vol. 72-74, p. 985, 1997); aromatic amine compounds comprising a tetramer of triphenylamine (Chem. Commun., p. 2175, 1996); and spiro compounds such as 2,2',7,7'-tetrakis-(diphenylamino)-9,9'-spirobifluorene (Synth. Metals, vol. 91, p. 209, 1997). These compounds may be used independently or, as needed, a plurality of them may be mixed to use.

In addition to the above-mentioned compounds, there may be illustrated, as materials for the hole transport layer 4, high polymer materials such as polyvinylcarbazole, polyvinyltriphenylamine (JP-A-7-53953), and polyarylene ether sulfone containing tetraphenylbenzidine (Polym. Adv. Tech., vol. 7, p. 33, 1996). The hole transport layer 4 can be formed by a wet filming method such as a common coating method (e.g., a spraying method, a printing method, a spin coating method, a dip coating method or a die coating method) or a varying printing method (e.g., an ink jet method or a screen printing method) or a dry filming method such as a vacuum deposition method.

With the case of the coating method, one, two or more kinds of the hole transporting materials and, as needed, a binder resin or an additive such as a coating property-improving agent which does not function as a trap of holes are dissolved in a proper solvent to prepare a coating solution, and the solution is coated on the anode 2 according to the spin coating method or the like, followed by drying to form the hole transport layer 4. Examples of the binder resin include polycarbonate, polyarylate and polyester. When added in a large amount, the binder resin would reduce the hole mobility, and hence the amount is preferably small, with 50% by weight or less being usually preferred.

With the case of vacuum deposition method, the hole transporting material is placed in a crucible installed within a vacuum container and, after evacuating the vacuum container by means of a proper vacuum pump to a degree of about $10^{-4}$ Pa, the crucible is heated to evaporate the hole transporting material and form the hole transport layer 4 on the substrate 1 on which the anode 2 has been formed and which is placed facing the crucible.

The thickness of the hole transport layer 4 is usually 5 nm or more, preferably 10 nm or more, and is usually 300 nm or less, preferably 100 nm or less. In order to uniformly form such a thin film, the vacuum deposition method is generally often employed.

In the element shown in FIG. 1, a light-emitting layer 5 is provided on the hole transport layer 4. The light-emitting layer 5 is formed by a light-emitting compound which can emit a strong light when strongly excited in a space between energized electrodes by recombination of holes injected from the anode and having migrated through the hole transport layer and electrons injected from the cathode and having migrated through the hole blocking layer 6.

The light-emitting compound to be used in the light-emitting layer 5 is required to be a compound which shows a stable thin film form, shows a high light (fluorescence or phosphorescence)-emitting quantum yield in a solid state and can transport holes and/or electrons with a high efficiency. Further, the compound is required to be electrochemically and chemically stable and difficultly generate impurities functioning as a trap upon production or use thereof.

As a material which satisfies the requirements and forms an organic light-emitting layer capable of emitting fluorescence, there are illustrated metal complexes such as 8-hydroxyquinoline aluminum complex (JP-A-59-194393), metal complexes of 10 hydroxybenzo[h]quinoline (JP-A-6-322362), bisstyrylbenzene derivatives (JP-A-1-245087 and JP-A-2-222484), bisstyrylarylene derivatives (JP-A-2-247278), metal complexes of (2-hydroxyphenyl)benzothiazole (JP-A-8-315983), and silole derivatives. These materials for the light-emitting layer are laminated on the hole transport layer usually by the vacuum deposition method. Of the aforementioned hole transporting materials, aromatic amine-based compounds capable of emitting a light can also be used as materials for the light-emitting layer.

Additionally, the charge transporting material of the invention can also be used as a material for the light-emitting layer. In this case, it is preferred to select and use, as a material to be used in the hole blocking layer 6 or the electron transport layer 7, a material having an ionization potential larger than that of the charge transporting material of the invention by 0.1 eV or more, represented by the known materials described hereinbefore.

Further, in the organic electroluminescent element of the invention, the electron transporting material of the invention may be used in both the organic light-emitting layer (also referred to merely as "light-emitting layer") and a layer in contact with the cathode side interface of the organic light-emitting layer and, in view of driving life, such element is particularly preferred. The layer in contact with the cathode side interface is in many cases the hole blocking layer.

In the case where the light-emitting layer does not contain the dopant, it suffices to select a material having an ionization potential difference of 0.1 eV or more from among the charge transporting materials specified in the invention and use it in each of the light-emitting layer and the hole contains the dopant, it suffices to select a compound having an ionization potential larger than that of the dopant by 0.1 eV or more from among the charge transporting materials specified in the invention and use it in each of the light-emitting layer and the hole blocking layer.

For the purpose of improving luminous efficiency of the element and changing the color of emitted light, it has been conducted, for example, to dope a host material of 8-hydroxyquinoline aluminum complex with a fluorescent dye for laser such as coumarin (J. Appl. Phys., vol. 65, p. 3610, 1989). This doping technique can also be applied to the light-emitting layer 5 and, as the material for doping, various fluorescent dyes other than coumarin may be used as well.

Examples of fluorescent dyes giving a blue light emission include perylene, pyrene, anthracene, coumarin and the derivatives thereof. Examples of fluorescent dyes giving a green light emission include quinacridone derivatives and coumarin derivatives. Examples of fluorescent dyes giving a yellow light emission include rubrene and perimidone derivatives. Examples of fluorescent dyes giving a red light emission include DCM-based compounds, benzopyran derivatives, rhodamin derivatives, benzothioxanthene derivatives and azabenzothioxanthene.

In addition to the above-described fluorescent dyes for doping, fluorescent dyes illustrated in Laser Kenkyu, vol. 8, p. 694, p. 803, p. 958 (1980) and ibid., vol. 9, p. 85 (1981) may be used as a doping material for the light-emitting layer depending upon the kind of the host material.

The doping amount of the above-mentioned fluorescent dye for the host material is preferably $10^{-3}$% by weight or more, more preferably 0.1% by weight or more, and is preferably 10% by weight or less, more preferably 3% by weight or less. In case when the amount is less than the lower limit, the dopant might fail to contribute to improvement of luminous efficiency of the element whereas, in case when the amount exceeds the upper limit, there might result quenching of light, possibly leading to reduction in the luminous efficiency.

On the other hand, a light-emitting layer showing emission of phosphorescence is usually formed by incorporating a phosphorescent dopant and a host material. Examples of the phosphorescent dopant include organometallic complexes containing metals selected from metals belonging to the group 7 to group 11 of the periodic table, and it is preferred to use as a host material a charge transporting organic compound having a T1 (minimum excited triplet level) higher than that of the metal complex.

Preferred examples of the metal in the phosphorescent organometallic complex containing a metal selected from among metals belonging to the group 7 to group 11 of the periodic table include ruthenium, rhodium, palladium, silver, rhenium, osmium, iridium, platinum and gold. As these organometallic complexes, there are preferably illustrated compounds represented by the following formula (X) or (VI):

$$ML_{q-j}L'_{j} \qquad (X)$$

wherein M represents a metal, q represents a number of valence of the metal, L and L' each represents a bidentate ligand, and j represents 0 or 1 or 2:

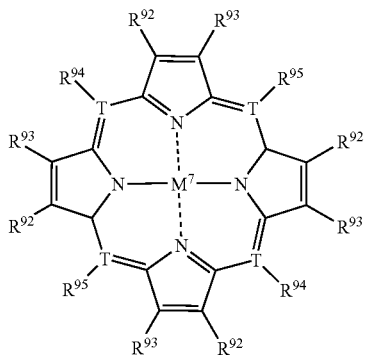

(VI)

wherein $M^7$ represents a metal, T represents carbon or nitrogen and, when T represents nitrogen, $R^{94}$ and $R^{95}$ are absent and, when T represents carbon, $R^{94}$ and $R^{95}$ each represents a hydrogen atom, a halogen atom, an alkyl group, an arylalkyl group, an alkenyl group, a cyano group, an amino group, an acyl group, an alkoxycarbonyl group, a carboxyl group, an alkoxy group, an alkylamino group, an arylalkylamino group, a haloalkyl group, a hydroxyl group, an aryloxy group, or an aromatic hydrocarbon group or aromatic heterocycle group which may have a substituent, $R^{92}$ and $R^{93}$ each represents a hydrogen atom, a halogen atom, an alkyl group, an arylalkyl group, an alkenyl group, a cyano group, an amino group, an acyl group, an alkoxycarbonyl group, a carboxyl group, an alkoxy group, an alkylamino group, an arylalkylamino group, a haloalkyl group, a hydroxyl group, an aryloxy group, or an aromatic hydrocarbon group or aromatic heterocycle group which may have a substituent, and may be connected to each other to form a ring.

The bidentate ligands L and L' in the formula (X) each represents a ligand having the following partial structure:

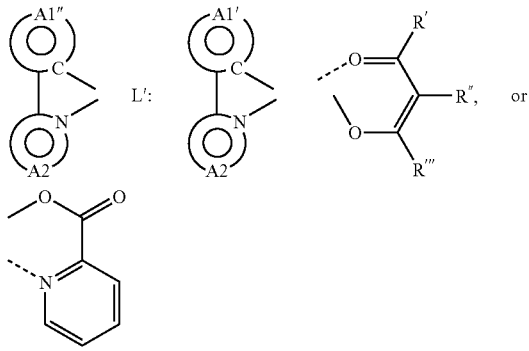

wherein ring A1" and ring A1' each independently represents an aromatic hydrocarbon group or an aromatic heterocycle group, which may have a substituent, ring A2 and ring A2' each represents a nitrogen-containing aromatic heterocycle group, which may have a substituent, and R', R" and R'" each represents a halogen atom, an alkyl group, an alkenyl group, an alkoxycarbonyl group, a methoxy group, an alkoxy group, an aryloxy group, a dialkylamino group, a diarylamino group, a carbazolyl group, an acyl group, a haloalkyl group or a cyano group.

As more preferred compounds represented by the formula (X), there are illustrated compounds represented by the following formulae (Va), (Vb) and (Vc):

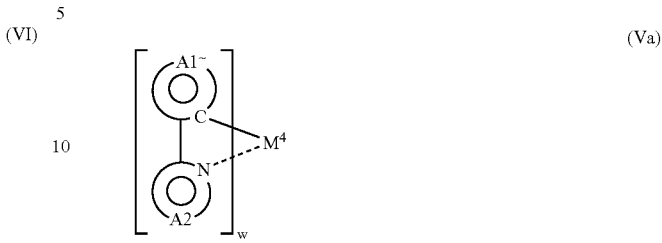

(Va)

wherein $M^4$ represents a metal, w represents a number of valence of the metal, ring A1" represents an aromatic hydrocarbon group which may have a substituent, and ring A2 represents a nitrogen-containing aromatic heterocycle group which may have a substituent;

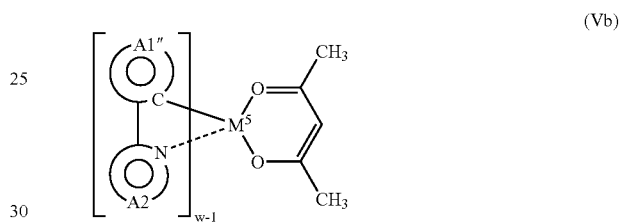

(Vb)

wherein $M^5$ represents a metal, w represents a number of valence of the metal, ring A1" represents an aromatic hydrocarbon group or an aromatic heterocycle group which may have a substituent, and ring A2 represents a nitrogen-containing aromatic heterocycle group which may have a substituent;

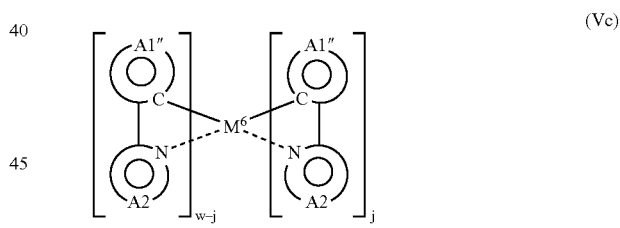

(Vc)

wherein $M^6$ represents a metal, w represents a number of valence of the metal, j represents 0, 1 or 2, ring A1" and ring A1' each independently represents an aromatic hydrocarbon group or an aromatic heterocycle group which may have a substituent, and ring A2 and ring A2' each independently represents a nitrogen-containing aromatic heterocycle group which may have a substituent.

Preferred examples of the ring A1 and ring A1' of the compounds represented by the formulae (Va), (Vb) and (Vc) include a phenyl group, a biphenyl group, a naphthyl group, an anthryl group, a thienyl group, a furyl group, a benzothienyl group, a benzofuryl group, a pyridyl group, a quinolyl group, an isoquinolyl group and a carbazolyl group.

Preferred examples of ring A2 and ring A2' include a pyridyl group, a pyrimidyl group, a pyrazyl group, a triazyl group, a benzothiazole group, a benzoxazole group, a benzimidazole group, a quinolyl group, an isoquinolyl group, a quinoxalyl group and a phenanthryl group.

Examples of the substituent which the compounds represented by the formulae (Va), (Vb) and (Vc) may have include a halogen atom such as a fluorine atom; an alkyl group containing from 1 to 6 carbon atoms such as a methyl group or an ethyl group; an alkenyl group containing from 2 to 6 carbon atoms such as a vinyl group; an alkoxycarbonyl group containing from 2 to 6 carbon atoms such as a methoxycarbonyl group or an ethoxycarbonyl group; an alkoxy group containing from 1 to 6 carbon atoms such as a methoxy group or an ethoxy group; an aryloxy group such as a phenoxy group or a benzyloxy group; a dialkylamino group such as a dimethylamino group or a diethylamino group; a carbazolyl group; an acyl group such as an acetyl group; a haloalkyl group such as a trifluoromethyl group; and a cyano group. These may be connected to each other to form a ring.

Additionally, the substituent which ring A1" has and the substituent which ring A2 has may be connected to each other to form one condensed ring, or the substituent which ring A1' has and the substituent which ring A2' has may be connected to each other to form one condensed ring. An example of such condensed ring is a 7, 8-benzoquinoline group. More preferred examples of the substituent in ring A1", ring A1', ring A2 and ring A2' include an alkyl group, an alkoxy group, an aromatic hydrocarbon group, a cyano group, a halogen atom, a haloalkyl group, a diarylamino group and a carbazolyl group.

Preferred examples of $M^4$ and $M^5$ in formulae (Va) and (Vb) include ruthenium, rhodium, palladium, silver, rhenium, osmium, iridium, platinum and gold. Preferred examples of $M^7$ in formula (VI) include ruthenium, rhodium, palladium, silver, rhenium, osmium, iridium, platinum and gold, with divalent metals such as platinum and palladium being particularly preferred.

Specific examples of the organometallic complexes represented by the foregoing general formulae (X), (Va), (Vb) and (Vc) are illustrated below. However, the complexes are not limited only to the following compounds

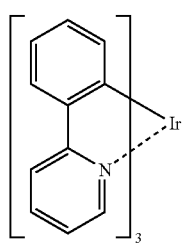
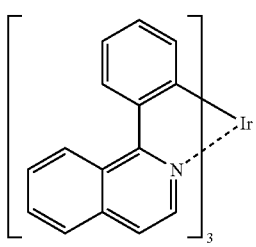
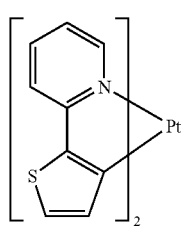

-continued

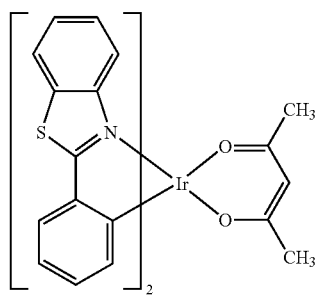
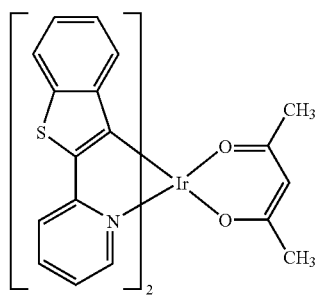
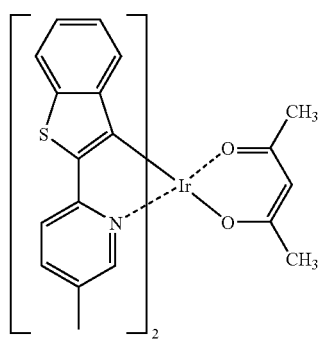
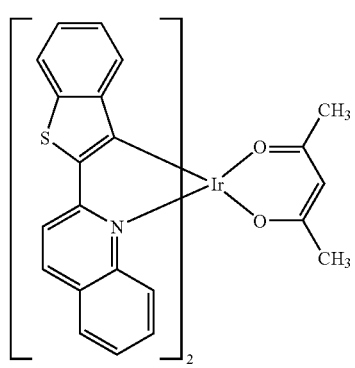
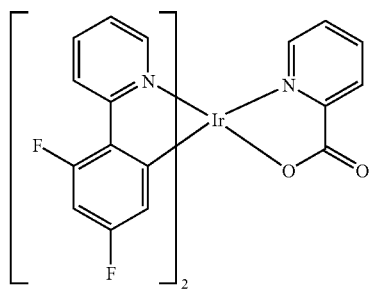

-continued
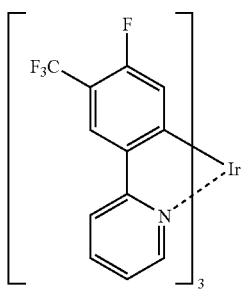
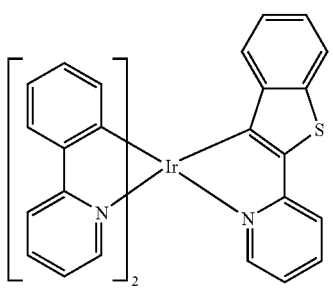
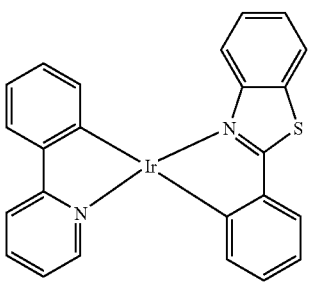
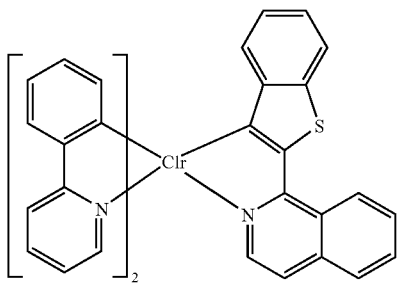
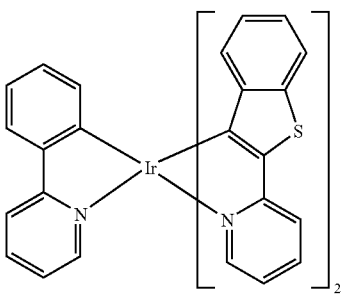
-continued
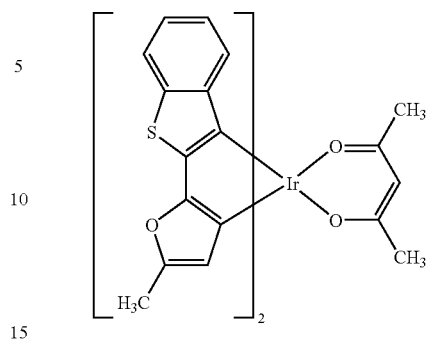
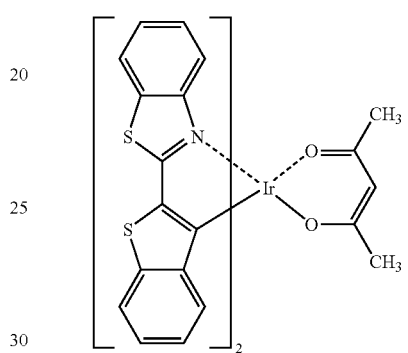
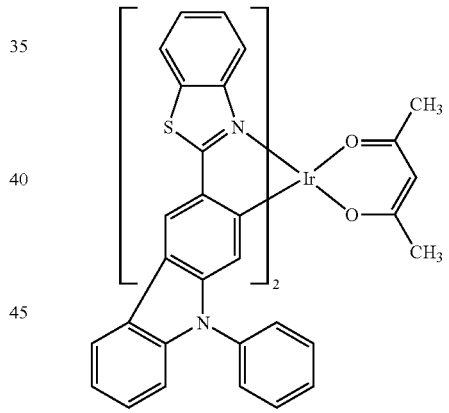
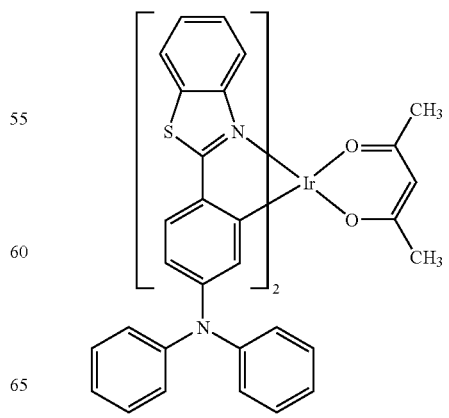

-continued

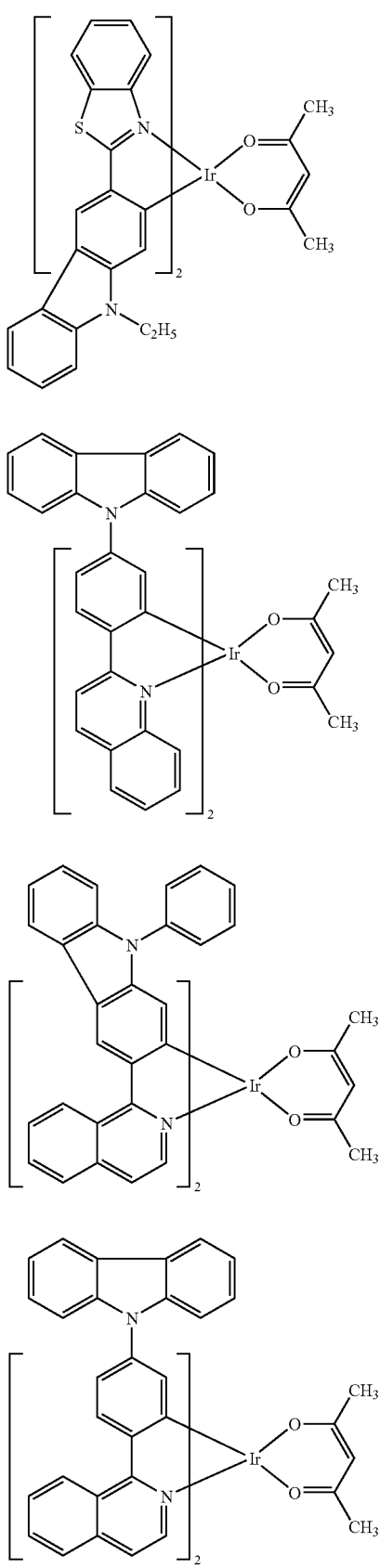

-continued

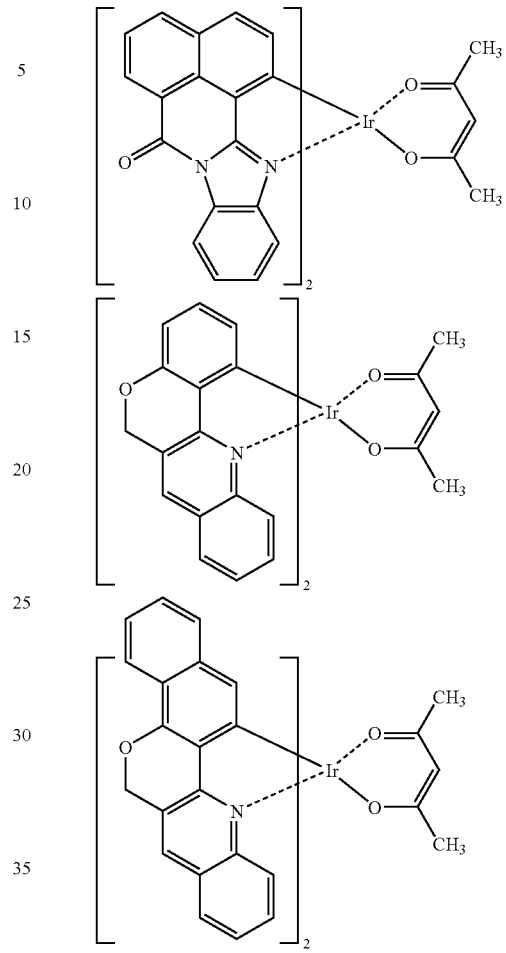

Of the organometallic complexes represented by the foregoing formulae (X), (Va), (Vb) and (Vc), those compounds are preferred which have a 2-arylpyridine-based ligand (2-arylpyridine, a 2-arylpyridine derivative having an arbitrary substituent or a 2-arylpyridine derivative having arbitrary groups forming a condensed system) as ligand L and/or L'.

Specific examples of the organometallic complexes represented by the foregoing formula (VI) are shown below which, however, are not limitative at all.

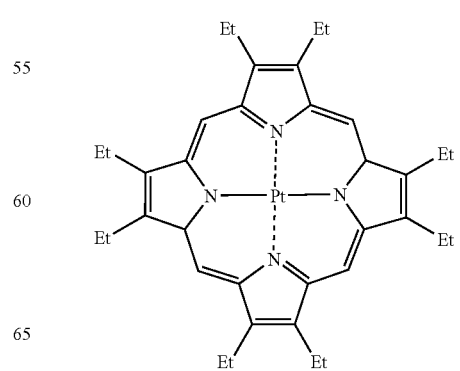

(T-1)

(T-10)
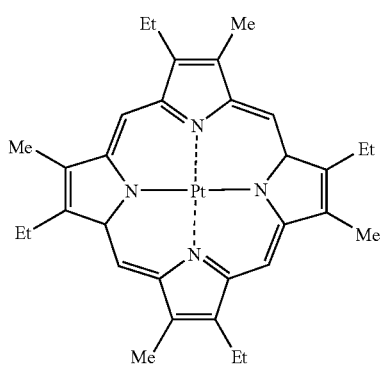

(T-11)
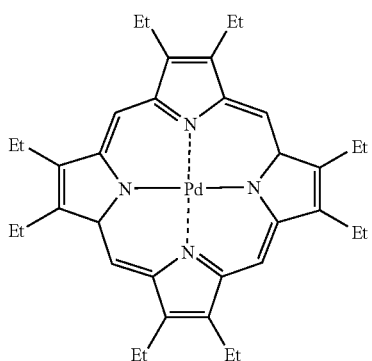

(T-12)
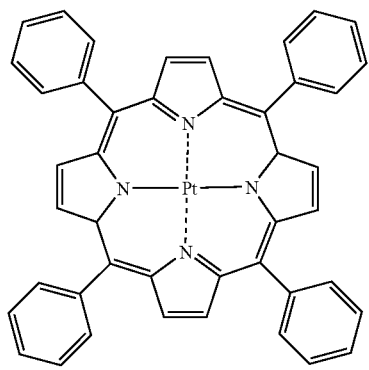

(T-13)
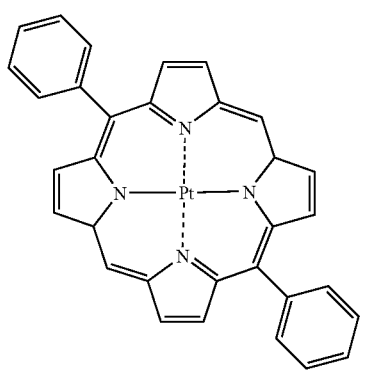

(T-14)
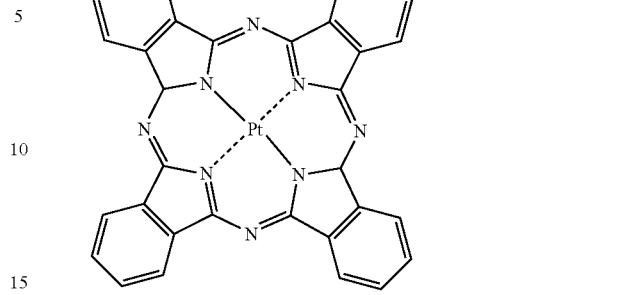

(T-15)
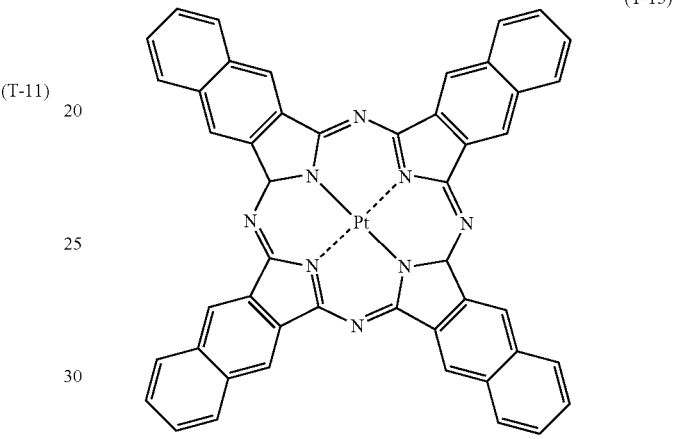

As the host material to be used in the light-emitting layer giving phosphorescent light, there are illustrated, in addition to the materials having been described as host materials to be used in the light-emitting layer giving fluorescent light (including the electron transporting materials of the invention), carbazole derivatives such as 4,4'-N,N'-dicarbazolebiphenyl (WO 00/70655), tris(8-hydroxyquinoline)aluminum (U.S. Pat. No. 6,303,238), 2,2',2"-(1,3,5-benzenetolyl)tris[1-phenyl-1H-benzimidazole] (Appl. Phys. Lett., vol. 78, p. 1622, 2001), and polyvinylcarbazole (JP-A-2001-257076).

As has been described hereinbefore, the charge transporting materials of the invention can be used as host materials.

Further, the light-emitting layer in the organic electroluminescent element of the invention may contain the aforesaid fluorescent dye together with the host material and the phosphorescent dopant.

The amount of the organometallic complex to be contained as a dopant in the light-emitting layer is preferably 0.1% by weight or more, and is preferably 30% by weight or less. In case when the amount is less than the lower limit, the complex might fail to contribute to the improvement of the luminous efficiency of the element whereas, in case when the complex exceeds the upper limit, there arises the possibility that concentration quenching takes place due to formation of a dimmer of the organometallic complex, leading to reduction of luminous efficiency.

There is a tendency that the amount of the phosphorescent dopant in the light-emitting layer showing phosphorescent light emission is preferably somewhat larger than the amount of the fluorescent dye (dopant) contained in the light-emitting layer in an element utilizing conventional fluorescence (singlet). Also, in the case where a fluorescent dye is contained in the light-emitting layer together with a phosphorescent dopant, the amount of the fluorescent dye is preferably 0.05% by weight or more, more preferably 0.1% by weight or more, and is preferably 10% by weight or less, more preferably 3% by weight or less.

The thickness of the light-emitting layer 5 is usually 3 nm or more, preferably 5 nm or more, and is usually 200 nm or less, preferably 100 nm or less.

The light-emitting layer can also be formed in the same manner as with the hole transport layer. A method of doping the above-mentioned fluorescent dye and/or the phosphorescent dye (phosphorescent dopant) in the host material of the light-emitting layer is described below.

In the case by coating, the aforesaid host material of the light-emitting layer, a dye for doping and, as needed, a binder resin which does not function as a trap of electrons or as a emitted light-quenching agent are added and dissolved to prepare a coating solution, and the coating solution is coated on the hole transport layer 4 by a spin coating method or the like, followed by drying to form the light-emitting layer 5. Examples of the binder resin include polycarbonate, polyarylate and polyester. When added in a large amount, the binder resin reduces the hole/electron mobility and, therefore, a smaller amount of the binder resin is desirable, with 50% by weight or less being preferred.

In the case by the vacuum deposition method, the aforementioned host material is placed in a crucible placed in a vacuum container, a doping dye is placed in a different crucible, and the inside of the vacuum container is evacuated to a degree of about $1.0 \times 10^{-4}$ Torr by means of a proper vacuum pump. Thereafter, the crucibles are heated at the same time to evaporate them and form a layer on the substrate which is placed facing the crucibles. As an alternative method, a mixture previously prepared by mixing the above-mentioned materials in a predetermined ratio may be evaporated using the same crucible.

In the case of introducing each dopant into the light-emitting layer, the dopant is uniformly distributed in the thickness direction of the light-emitting layer. However, there may be a concentration distribution of the dopant in the thickness direction. For example, doping may be conducted only in the vicinity of the interface with the hole transport layer or, reversely, may be conducted in the vicinity of the hole blocking layer.

The light-emitting layer can be formed in the same manner as with the hole transport layer but, usually, the vacuum deposition method is employed.

Additionally, the light-emitting layer 5 may contain other ingredients than are described above within a range of not spoiling the performance of the invention.

In the element shown in FIG. 1, the hole blocking layer 6 is laminated on the light-emitting layer 5 in contact with the cathode side interface of the light-emitting layer 5.

The hole blocking layer is preferably formed by a compound which functions to prevent holes migrating from the hole transport layer from reaching the cathode and which can effectively transport electrons injected from the cathode in the direction toward the light-emitting layer. Physical properties required for a material constituting the hole blocking layer include a high electron mobility and a low hole mobility the hole blocking layer 6 has the function of confining holes and electrons within the light-emitting layer to thereby improve luminous efficiency.

In this example, the charge transporting material of the invention is used for the hole blocking layer.

The charge transporting material of the invention may be used in the hole blocking layer independently or in combination of plural kinds thereof. Further, known hole blocking compounds may be used in combination within the scope of not spoiling the performance of the charge transporting material of the invention.

The ionization potential of the hole blocking layer to be employed in the invention is preferably larger than the ionization potential of the light-emitting layer (in the case where the light-emitting layer contains both a host material and a dopant, ionization potential of the dopant) by 0.1 eV or more (more preferably the ionization potential of the hole blocking layer is larger than the ionization potential of the host material by 0.1 eV or more).

The ionization potential is defined in terms of energy necessary to release an electron at HOMO (highest occupied molecular orbital) level of a substance to a vacuum level. The ionization potential can be directly defined by the photoelectron spectrometry or by correcting an electrochemically measured oxidation potential based on the standard electrode. In the latter method using, for example, saturated calomel electrode, the ionization potential is defined as:

$$\text{Ionization potential} = \text{oxidation potential(vs. SCE)} + 4.3 \text{ eV}$$

(Molecular Semiconductors, Springer-Verlag, 1985, p. 98)

Further, electron affinity (EA) of the hole blocking layer to be used in the invention is preferably the same as, or more than, electron affinity of the light-emitting layer (in the case where the light-emitting layer contains both a host material and a dopant, electron affinity of the host material). The electron affinity is defined in terms of energy released when an electron in a vacuum level falls to LUMO (lowest unoccupied molecular orbital) level to stabilize with taking the vacuum level as a standard as with the ionization potential. The electron affinity is similarly determined by subtracting an optical band gap from the above-mentioned ionization potential or from an electrochemical reduction potential according to the following formula:

$$\text{Electron affinity} = \text{reduction potential(vs. SCE)} + 4.3 \text{ eV}$$

Therefore, the hole blocking layer to be used in the invention can be expressed as follows using oxidation potential and reduction potential:

$$\text{(Oxidation potential of the hole blocking material)} - \text{(oxidation potential of the light-emitting material)} \geq 0.1 \text{V};$$

$$\text{(Reduction potential of the hole blocking material)} \geq \text{(reduction potential of the light-emitting material)}$$

Further, in an element having an electron transport layer to be described hereinafter, electron affinity of the hole blocking layer is preferably the same as, or more than, electron affinity of the electron transport layer.

$$\text{(Reduction potential of the electron transport material)} \geq \text{(reduction potential of the hole blocking material)} \geq \text{(reduction potential of the light-emitting material)}$$

The thickness of the hole blocking layer 6 is usually 0.3 nm or more, more preferably 0.5 nm or more, and is usually 100 nm or less, more preferably 50 nm or less. The hole blocking layer can also be formed in the same manner as the hole transport layer, with the vacuum deposition method being usually employed.

The cathode 8 functions to inject electrons into the light-emitting layer 5 through the hole blocking layer 6. As the material to be used as the cathode 8, those materials which are used for the cathode 2 may be employed but, in order to inject electrons with a high efficiency, metals having a low work function are preferred. Thus, suitable metals such as tin, magnesium, indium, calcium, aluminum and silver or the alloys thereof are used. Specific examples thereof include electrodes of alloys having a low work function, such as magnesium-silver alloy, magnesium-indium alloy and aluminum-lithium alloy. Further, in order to improve efficiency of the element, it is also an effective technique to insert an extremely thin insulating film of LiF, $MgF_2$ or $Li_2O$ into the interface between the cathode and the light-emitting layer or the electron transport layer (Appl. Phys. Lett., vol. 70, p. 152, 1997; JP-A-10-74586; and IEEE Trans. Electron. Devices, vol. 44, p. 1245, 1997). The thickness of the cathode 8 is usually the same as the thickness of the anode 2. To further laminate thereon a metal layer having a low work function and stable in the atmosphere for the purpose of protecting the cathode comprising the metal having a low work function serves to enhance stability. For this purpose, metals such as aluminum, silver, copper, nickel, chromium, gold and platinum are used.

Figure 2:
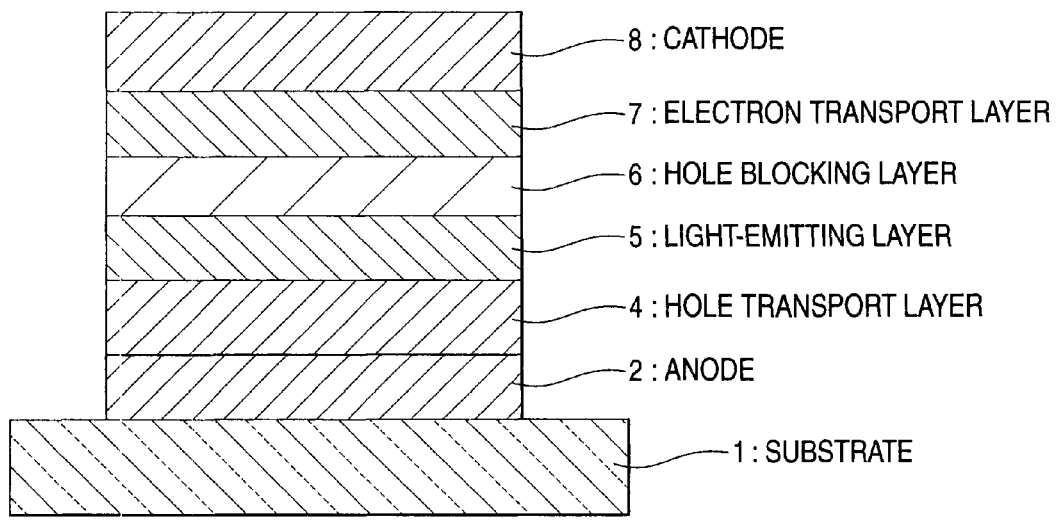
FIG. 2 is a schematic cross-sectional view showing another example of the organic electroluminescent element.
Figure 3:
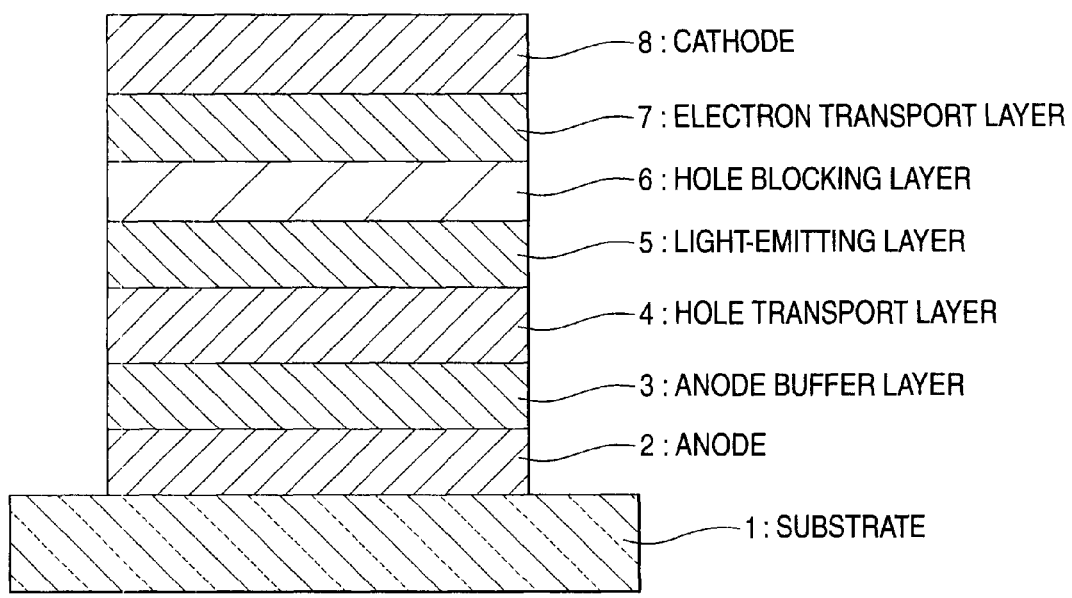
FIG. 3 is a schematic cross-sectional view showing the other example of the organic electroluminescent element.

For the purpose of further improving luminous efficiency of the element, an electron transport layer 7 may be provided between the hole blocking layer 6 and the cathode 8 as shown in FIGS. 2 and 3. The electron transport layer 7 is formed from a compound which can transport, with a good efficiency, electrons injected from the cathode toward the hole blocking layer 6 between the energized electrodes.

Examples of the material satisfying such requirements include metal complexes such as aluminum complex of 8-hydroxyquinoline (JP-A-59-194393); a metal complex of 10-hydroxybenzo[h]quinoline; an oxadiazole derivative; a distyrylbiphenyl derivative; a silole derivative; a metal complex of 3- or 5-hydroxyflavone; a metal complex of benzoxazole; a metal complex of benzothiazole; trisbenzimidazolylbenzene (U.S. Pat. No. 5,645,948), a quinoxaline compound (JP-A-6-207169); a phenanthroline derivative (JP-A-5-331459); 2-t-butyl-9,10-N,N'-dicyanoanthraquinonediimine; n-type hydrogenated amorphous silicon carbide; n-type zinc sulfide; and n-type zinc selenide.

It is preferred to dope the electron transporting material described above with an alkali metal (described in, e.g., JP-A-10-270171, Japanese Patent Application Nos. 2000-285656 and 2000-285657) since it serves to improve the electron transporting ability.

The electron transport layer 7 is formed on the hole blocking layer 6 by the coating method or the vacuum deposition method to laminate in the same manner as with the hole transport layer 4. Usually, the vacuum deposition method is employed.

Additionally, the charge transporting material of the invention may be used in this electron transport layer 7. In such case, the electron transport layer 7 may be formed by using only the compound of the invention or by using it in combination with various known materials having been described hereinbefore.

In the case of using the charge transporting material of the invention in the electron transport layer 7, the charge transporting material may also be used in the aforesaid hole blocking layer 6, or the charge transporting material of the invention may be used only in the electron transport layer 7, with other known hole blocking material being used in the hole blocking layer 6.

The thickness of the electron transport layer 6 is usually 5 nm or more, more preferably 10 nm or more, and is usually 200 nm or less, more-preferably 100 nm or less.

The electron transport layer 7 is formed on the hole blocking layer 6 by the coating method or the vacuum deposition method to laminate in the same manner as with the hole transport layer 4. Usually, the vacuum deposition method is employed.

For the purpose of more improving efficiency of injecting holes and improving adhesion of the whole organic layers onto the anode, it is also conducted to insert an anode buffer layer 3 between the hole transport layer 4 and the anode 2 (see, FIG. 3). Insertion of the anode buffer layer 3 serves to provide the effect of reducing the initial driving voltage of the element and, at the same time, depressing an increase in voltage upon continuously driving the element at a constant current. As to requirements for materials to be used in the anode buffer layer, the materials are required to have a good contact with the anode, form a uniform thin film, and be thermally stable, i.e., and have a high melting point and a high glass transition temperature, with the melting point being preferably 300° C. or more, and the glass transition temperature being 100° C. or more. Further, the materials are required to have an enough low ionization potential to facilitate injection of holes from the anode and have a large hole mobility.

For this purpose, there have been reported, as the materials for the anode buffer layer 3, organic compounds such as porphyrin derivatives or phthalocyanine derivatives (JP-A-63-295695), hydrazone compounds, alkoxy-substituted aromatic diamine derivatives, p-(9-anthryl)-N,N'-di-p-tolylaniline, polythienylenevinylene or poly-p-phenylenevinylene, polyaniline (Appl. Phys. Lett., vol. 64, p. 1245, 1994), polythiophene (Optical Materials, vol. 9, p. 125, 1998) and starburst type aromatic triamines (JP-A-4-308688); sputtered carbon film (Synth. Met., vol. 91, p. 73, 1997); and metal oxides such as vanadium oxide, ruthenium oxide and molybdenum oxide (J. Phys. D, vol. 29, p. 2750, 1996).

There may also be illustrated a layer containing a hole injecting and transporting, low-molecular organic compound and an electron acceptive compound (described in, for example, JP-A-11-251067 and JP-A-2000-159221), a layer comprising an aromatic amino group-containing, non-conjugated high-molecular compound doped with, as needed, an electron acceptive compound (e.g., JP-A-11-135262, JP-A-11-283750, JP-A-2000-36390, JP-A-2000-150168, JP-A-2001-223084 and WO97/33193) and a layer containing a conductive polymer such as polythiophene (JP-A-10-92584) which, however, are not limitative.

As materials for the anode buffer layer, either of low-molecular compounds and high-molecular compounds may be used.

Of the low-molecular compounds, porphine compounds and phthalocyanine compounds are popularly used. These compounds may have a central metal or may be metal-free. Preferred examples of these compounds include the following: porphine;
5,10,15,20-tetraphenyl-21H,23H-porphine;
5,10,15,20-tetraphenyl-21H,23H-porphine cobalt(II);
5,10,15,20-tetraphenyl-21H,23H-porphine copper(II);
5,10,15,20-tetraphenyl-21H,23H-porphine zinc(II);
5,10,15,20-tetraphenyl-21H,23H-porphine vanadium(IV) oxide;
5,10,15,20-tetra(4-pyridyl)-21H,23H-porphine;
29H,31H-phthalocyanine;
copper(II) phthalocyanine;
zinc(II) phthalocyanine;
titanium phthalocyanine oxide;
magnesium phthalocyanine;
lead phthalocyanine; and
copper(II) 4,4',4",4'''-tetraza-29H,31H-phthalocyanine.

In the case of the anode buffer layer, too, the thin film can be formed similarly with the hole transport layer and, in the case of using an inorganic material, a sputtering method, an electron beam deposition method or a plasma CVD method may further be employed.

As to the thickness of the thus-formed anode buffer layer 3, the lower limit is usually abut 3 nm, preferably about 10 nm, and the upper limit is usually about 100 nm, preferably about 50 nm in the case of using the low-molecular compound.

When the polymer compound is used, the aforesaid polymer compound, the electron acceptive compound and, as needed, a binder resin or an additive such as a coating property-improving agent (e.g., a leveling agent) which does not function as a trap of holes, for example, are added and dissolved to prepare a coating solution, and the solution is coated on the anode 2 according to a common coating method such as a spray coating method, a printing method, a spin coating method, a dip coating method or a die coating method or by an ink jet method, followed by drying to form the anode buffer layer 3. Examples of the binder resin include polycarbonate, polyarylate and polyester. When added in a large amount, the binder resin might reduce the hole mobility, and hence the amount is preferably smaller, with 50% by weight or less in terms of content in the anode buffer layer 3 being usually preferred.

It is also possible to previously form a thin film on a medium such as a film a supporting substrate or a roll according to the aforementioned thin film-forming method and transferring the thin film on the medium onto the anode 2 by applying heat or pressure to thereby form a thin film.

The lower limit of the film thickness of the anode buffer layer 3 formed as described hereinbefore is usually about 5 nm, preferably about 10 nm, and the upper limit is usually about 1,000 nm, preferably about 500 nm.

As to the layer structure of the organic electroluminescent element of the invention, a reverse structure to that shown in FIG. 1, i.e., a structure wherein the cathode 8, the hole blocking layer 6, the light-emitting layer 5, the hole transport layer 4 and the anode 2 are laminated in this order on the substrate may also be employed. And, as has been already described, it is possible to provide the organic electroluminescent element of the invention between two substrates at least one of which has a high transparency. Likewise, it is possible to laminate in the reverse order to each of the layer structures shown in FIGS. 2 and 3. Also, in any of the layer structures shown in FIGS. 1 to 3, other optional layer than the above-described layers may be provided within the range of not departing from the spirit of the invention, or a proper variation such as a variation of providing a layer having the functions of a plurality of the layers to thereby simplify the layer structure is possible.

Further, it is possible to employ a top emission structure or to use transparent electrodes as the cathode and the anode to prepare a transparent element or, further, to employ a layer structure wherein a plurality of the layer structures shown in FIG. 1 are stacked (a structure wherein a plurality of the light-emitting units are stacked). In such occasion, use of, for example, $V_2O_5$ as a charge generating layer (CGL) in place of the interface layers (in the case where ITO and Al are used as the anode and the cathode, respectively, the two layers of the anode and the cathode) between the units (light-emitting units) serves to reduce barrier between the units, thus being more preferred in view of luminous efficiency and driving voltage.

The invention can be applied to any of a structure wherein the organic electroluminescent element comprises a single element, a structure which comprises elements provided in an array form, and a structure wherein the anode and the cathode are disposed in an X-Y matrix pattern.

According to the organic electroluminescent element of the invention, there can be obtained an element having a high luminous efficiency, emitting a light having a high color purity and having a largely improved driving stability by incorporating the compound having the specific skeleton as a charge transporting material. In particular, with a blue (fluorescent) light-emitting element or a phosphorescent light-emitting element with which formation of the hole blocking layer has been difficult due to difficulty in selecting proper materials, an excellent luminous efficiency, an excellent emitted light purity and an excellent driving stability can be obtained, and hence the element can exhibit excellent performance when applied to full-color or multi-color panels.

Next, of the charge transporting materials of the invention, novel compounds are described below. Of the charge transporting materials of the invention, compounds represented by the following formula (II) and not forming a plane structure in an optimized geometry, and compounds represented by the following formula (II) and forming a plane structure in an optimized geometry, with p being 0, are novel compounds.

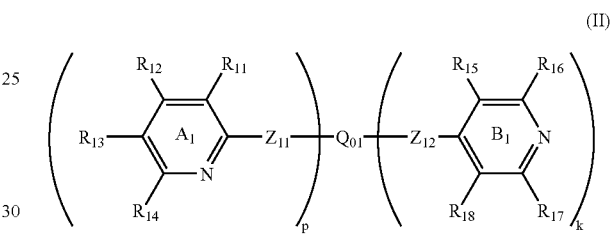

(II)

In the above formula, $R_{11}$, $R_{13}$, $R_{15}$ and $R_{18}$ each independently represents a hydrogen atom or an arbitrary substituent. $R_{12}$, $R_{14}$, $R_{16}$ and $R_{17}$ each independently represents an arbitrary substituent. $Z_{11}$ represents a direct bond or a divalent connector having electrons capable of conjugating the ring $A_1$. $Z_{12}$ represents a direct bond or a divalent connector having electrons capable of conjugating the ring $B_1$. $Q_{01}$ represents a (p+k)-valent aromatic hydrocarbon group or aromatic heterocycle group which makes conjugation between any two members selected from the group consisting of the rings $A_1$ and rings $B_1$ contained within the molecule substantially impossible. p represents an integer of from 0 to 8. k represents an integer of from 0 to 8. The sum of p and k is an integer of from 2 to 8.

Additionally, when p and/or k represents 2 or more, plural $R_{11}$s to $R_{18}$s contained within the molecule may be the same or different from each other, and plural $Z_{11}$s and $Z_{12}$s contained within the molecule may be the same or different from each other. The molecular weight of the compound represented by the above formula (II) is usually 4,000 or less, preferably 3,000 or less, more preferably 2,000 or less, and is usually 200 or more, preferably 300 or more, more preferably 400 or more.

In case when the molecular weight exceeds the upper limit, there might result seriously reduced sublimation properties which can cause troubles when a vacuum deposition method is employed for preparing an electroluminescent element or might result a decreased solubility in an organic solvent which makes it difficult to conduct high purification (removal of substances causing deterioration) with an increase in the amount of impurities formed in the synthesizing steps. Also, in case when the molecular weight is less than the lower limit, there results a reduced glass transition temperature, reduced melting point and reduced gasification temperature, which seriously spoils heat resistance.

The melting point of the compound represented by the above formula (II) is usually 100° C. or more, preferably 120° C. or more, and is usually 600° C. or less, preferably 500° C. or less. In case when the melting point exceeds the upper limit, there might results a reduced sublimation properties and reduced solubility, thus such melting point not being preferred. In case when it is lower than the lower limit, there might result a reduced heat resistance as an element, thus such melting point not being preferred.

The glass transition point of the compound represented by the above formula (II) is usually 50° C. or more, preferably 60° C. or more. In case when it is lower than the lower limit, there might result a reduced heat resistance as an element, thus such glass transition point not being preferred.

The oxidation potential of the compound represented by the above formula (II) is usually +1.3 V or more, preferably +1.5 or more, and is usually +2.5 V or less, preferably +2.0 V for less. In case when the oxidation potential exceeds the upper limit, there might result an increase in driving voltage as an element, thus such oxidation potential not being preferred and, in case when the oxidation potential is lower than the lower limit, there might result reduced hole blocking properties and reduced luminous efficiency, thus such oxidation potential not being preferred.

Additionally, reversibility in the electrode oxidation reaction is not particularly required, and the reaction may be irreversible or reversible. In the case of applying to the use of transporting positive charge, however, it is desirable for the compound to clear the standard with respect to reversibility described in the invention.

The reduction potential of the compound represented by the above formula (II) is usually −1.6 to −2.6 V, preferably −1.8 to −2.4 V. In case when the reduction potential exceeds the upper limit, there results a reduced electron transporting ability, thus such reduction potential not being preferred whereas, in case when it is lower than the lower limit, there might result troubles in transferring electrons to the light-emitting material (phosphorescent dye), thus such reduction potential not being preferred.

Additionally, reversibility in the electrode reduction reaction is an important factor, and it is of importance that standards with respect to reversibility described in the invention be cleared.

($Z_{11}$, $Z_{12}$)

It suffices that $Z_{11}$ is a direct bond or a divalent connector having electrons capable of conjugating the ring $A_1$, and that $Z_{12}$ is a direct bond or a divalent connector having electrons capable of conjugating the ring $B_1$. In particular, those which can appropriately delocalize the charge within the molecule by partly accepting charge which is liable to be localized on the ring(s) $A_1$ and the ring(s) $B_1$ or by further transporting the charge to other substituent are preferred.

Specific examples of $Z_{11}$ and $Z_{12}$ are the same as are described in the foregoing descriptions in foregoing ($Z_1$, $Z_2$).

As $Z_{11}$ and $Z_{12}$ to be used in the compound of the invention, direct bond or a divalent aromatic hydrocarbon group which may have a substituent is preferred in the point of a high triplet excitation level and oxidation-reduction potential difference, with Z-1 (direct bond) being particularly preferred.

Also, the substituents which $Z_{11}$ and $Z_{12}$ may have are the same as the aforesaid substituents which $Z_1$ and $Z_2$ may have.

The molecular weights of $Z_{11}$ and $Z_{12}$ including the molecular weight of the substituent are preferably 400 or less, more preferably 250 or less.

($Q_{01}$)

It suffices that $Q_{01}$ is a (p+k)-valent connector which makes it substantially impossible for any two members selected from the group consisting of the ring(s) $A_1$ and the ring(s) $B_1$ contained in the molecule to conjugate each other. In particular, those which have the property of reducing the difference in charge by partly accepting the charge which is liable to be localized on the ring(s) $A_1$ and the ring(s) $B_1$ are preferred.

Specific examples thereof are the same as are described in the description of foregoing ($Q_0$). Of the specific examples, Q-1 and Q-35 are preferred as $Q_{01}$ to be used in the compound of the invention.

Also, the substituents which $Q_{01}$ may have are the same as the substituents which $Q_0$ may have.

The molecular weight of $Q_{01}$ including the molecular weight of the substituent are preferably 400 or less, more preferably 250 or less.

($R_{11}$ to $R_{18}$)

$R_{11}$, $R_{13}$, $R_{15}$ and $R_{18}$ each independently represents a hydrogen atom or an arbitrary substituent, and $R_{12}$, $R_{14}$, $R_{16}$ and $R_{17}$ each independently represents an arbitrary substituent.

The arbitrary substituent to be used in $R_{11}$ to $R_{18}$ is the same as that described in foregoing (substituents for $R_1$ to $R_8$), and preferred specific examples are also the same as described there.

Also, specific examples of $R_{11}$ to $R_{18}$ are the same as those described in foregoing ($R_1$ to $R_8$) and preferred specific examples are also the same as described there.

The molecular weight of each of $R_{11}$ to $R_{18}$ including the molecular weight of the substituent are preferably 400 or less, more preferably 250 or less.

With compounds represented by the foregoing formula (II) and not forming a plane structure in an optimized geometry, $R_{12}$, $R_{14}$, $R_{16}$ and $R_{17}$ are preferably aromatic hydrocarbon groups or aromatic heterocycle groups which may have a substituent in view of improving durability against oxidation and reduction and improving heat resistance.

(Case of not Forming a Plane Structure)

Of the compounds represented by the above formula (II), those which do not form a substantially single plane structure as an optimized geometry of the molecule have a molecular structure with which substantially single plane structure is impossible as a molecular structure. Therefore, the structure serves to depress Π-Π stacking interaction between molecules and provide excellent amorphousness, solubility and sublimation properties.

Further, when formed into a film which is an aggregate of molecules, the compounds of the structure can depress the phenomenon of increase in wavelength of absorption maximum and wavelength of fluorescence maximum in comparison with a solution state (wherein molecules are dispersed). Still further, it is considered that the compounds can depress the phenomenon of reduction in triplet excitation level or the phenomenon of reduction in electric oxidation-reduction potential difference.

Thus, they are compounds which can store a large energy (of, for example, light, electricity or heat) and effectively release the stored energy (as light, electricity or heat).

Also, the compounds are useful not only as electron transporting materials but as materials for emitting light, materials for solar cells, materials for battery (e.g., electrolytic solution, electrode, separating membrane or stabilizer), materials for medical use, materials for paints, coating materials, materials for organic semi-conductors, materials for toiletries, antistatic materials, and materials for thermocouple.

The term "optimized geometry of a compound" as used herein in the invention means a structure obtained by introducing the optimized geometry of the compound of the invention by employing the common MM2 calculation method (see, for example, M. J. Dudek & J. W. Ponder, J. Comput. Chem., 16, 791-816 (1995)).

Compounds which do not form a plane structure when in an optimized geometry, i.e., compounds which cannot form a substantially single plane structure when in an optimized geometry are described below.

To describe by reference to examples thereof, compounds wherein any two adjacent aromatic rings constituting the molecule have about the same non-plane properties as 2-methylbiphenyl (FIG. D) are compounds which do not form a plane structure.

FIG. D

More specifically, compounds wherein the plane angle between any two adjacent aromatic rings constituting the molecule is strictly 15° or more, more strictly 20° or more, still more strictly 30° or more can be said not to form a plane structure.

Further, it is preferred that an arbitrary aromatic ring (referred to as Ar2) bound to at least one aromatic ring (referred to as Ar1) within the molecule and an arbitrary substituent (referred to as Rr) are desirably present at adjacent substitution positions. Rr may be connected to Ar1 or other substituent to form a ring.

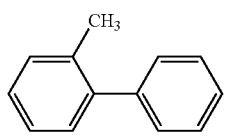

Examples thereof are those which are illustrated below.

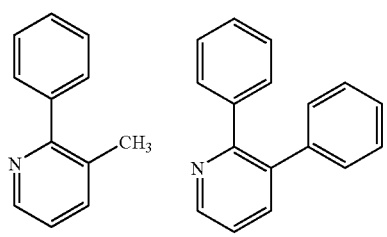

-continued

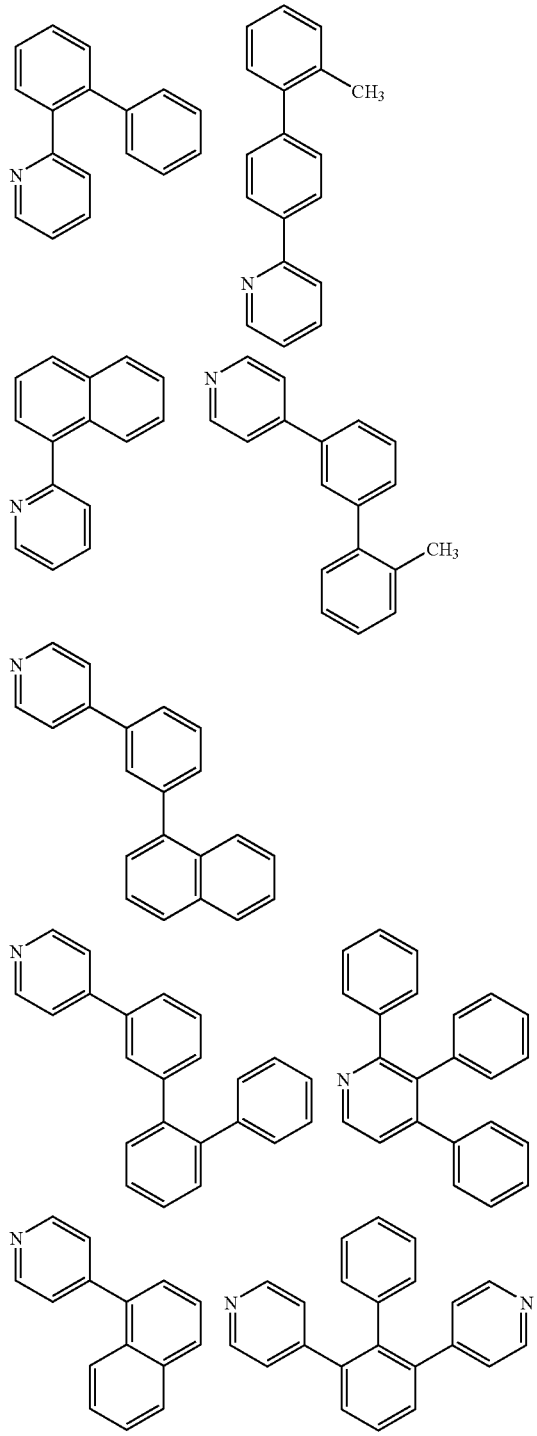

Preferred Example 1

Of the compounds represented by the foregoing formula (II), those compounds wherein plural skeletons of skeleton A(s) comprising ring $A_1$ and $Z_{11}$ connected thereto and skeleton B(s) comprising ring. $B_1$ and $Z_{12}$ connected thereto are substantially on the same plane as the connector $Q_{01}$ are preferred in view of obtaining excellent durability against electric oxidation and reduction and not damaging the excellent charge transporting ability.

As examples of the rings $A_1$ and $B_1$ which are on substantially the same place as the connector $Q_{01}$, there are illustrated the following:

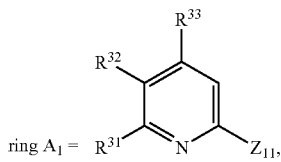

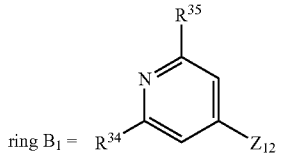

wherein $R^{31}$ and $R^{33}$ to $R^{35}$ each represents an arbitrary aromatic group, and $R^{32}$ represents a hydrogen atom or an arbitrary substituent. Preferred examples of $Z_{11}$ and $Z_{12}$ in the rings are as described hereinafter.

Preferred Example 2

Of the compounds represented by the foregoing formula (II), those compounds wherein arbitrary ring $A_1$ (or ring $B_1$) is not substantially on the same plane as the connector $Z_{11}$ (or $Z_{12}$) and/or the connector $Q_{01}$ are preferred in view of obtaining broad electric oxidation-reduction potential difference and high triplet excitation level.

As examples of the arbitrary ring $A_1$ (or ring $B_1$) of "arbitrary ring $A_1$ (or ring $B_1$) is not substantially on the same plane as the connector $Z_{11}$ (or $Z_{12}$) and/or the connector $Q_{01}$", there are illustrated the following:

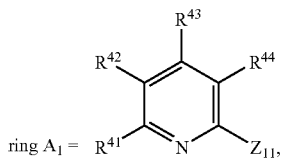

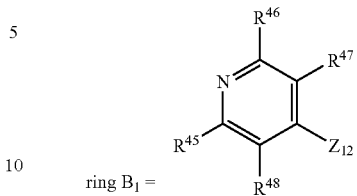

wherein $R^{41}$, $R^{43}$, $R^{45}$ and $R^{46}$ each represents an arbitrary aromatic group, and $R^{42}$, $R^{44}$, $R^{47}$ and $R^{48}$ each represents a hydrogen atom or an arbitrary substituent. Preferred examples of $Z_{11}$ and $Z_{12}$ in the rings are as described below.

($Z_{11}$, $Z_{12}$ and $Q_{01}$ in the Preferred Examples 1 and 2)

In order to constitute the structure as in the preferred example 1), $Z_{11}$ and $Z_{12}$ are preferably Z-1 (direct bond), Z-3, 12, 16, 19, 20 to 30, 37 to 39, 41, 42, 45, 46, 48, 49, 52, 53 and 58 to 60 described hereinbefore, more preferably Z-1 (direct bond), Z-3, 12, 16, 19, 20 and 21, still more preferably Z-1 (direct bond) and Z-3, most preferably Z-1 (direct bond).

With the case of the preferred example 2), $Z_{11}$ and $Z_{12}$ are preferably Z-1 (direct bond), Z-2 to 21, 28, 29, 31 to 35, 48 to 52, and 56 to 60, more preferably Z-1 (direct bond), Z-2, 3, 4, 5, 8, 10, 12, 15, 16, 17, 19, 28, 29, 31, 33, 34, 52, and 56 to 58, still more preferably Z-1 (direct bond), Z-2, 5, 8, 12, 19, 28 and 29, most preferably Z-1 (direct bond) and Z-2.

In the case of the preferred example 1), $Q_{01}$ is preferably Q-1, 23, 29, 34, 35, 45, and 58 to 61 described hereinbefore, more preferably Q-1, 23, 29, 35, 45, 58 and 61, still more preferably Q-1, 35 and 45, most preferably Q-1 and 35.

In the case of the preferred example 2), $Q_{01}$ is preferably Q-1, 2, 19 to 23, 29 to 43, 45, 51 to 53, and 58 to 61 described hereinbefore, more preferably Q-1, 2, 19 to 23, 29, 33, 35 to 42 and 45, still more preferably Q-1, 2, 19 to 23, 35 to 42 and 45, most preferably Q-1, 2, 23 and 35.

Specific examples thereof are illustrated below which, however, are not limitative at all.

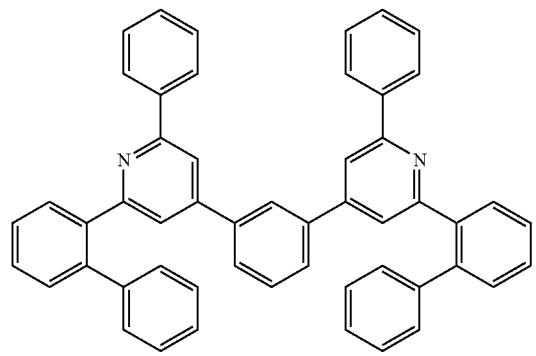

-continued
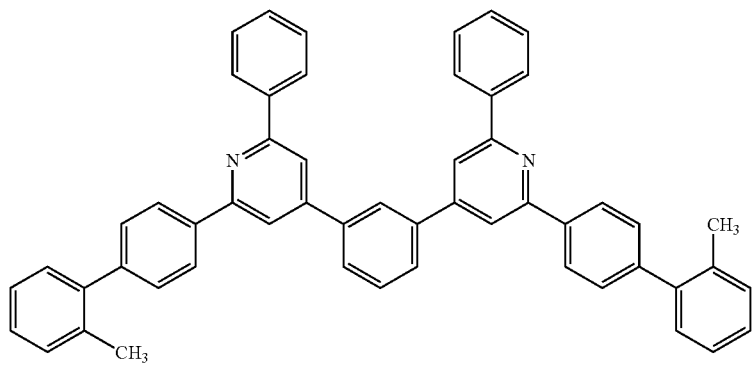
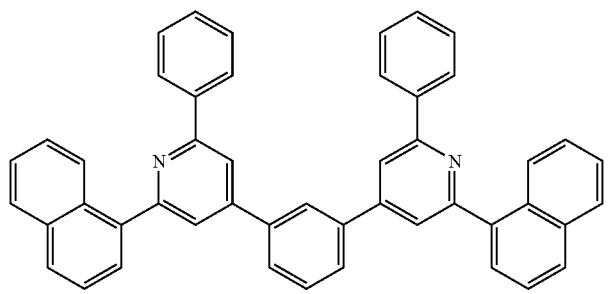
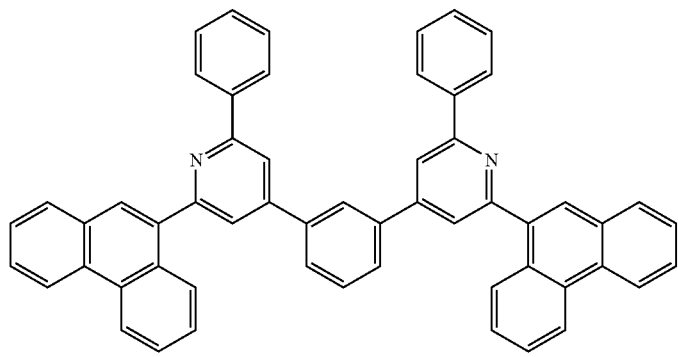
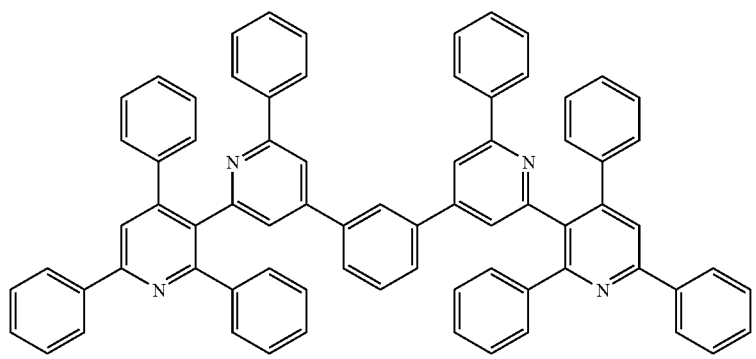

-continued
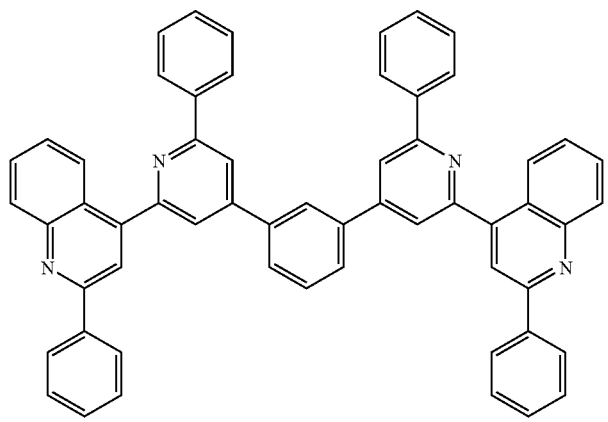
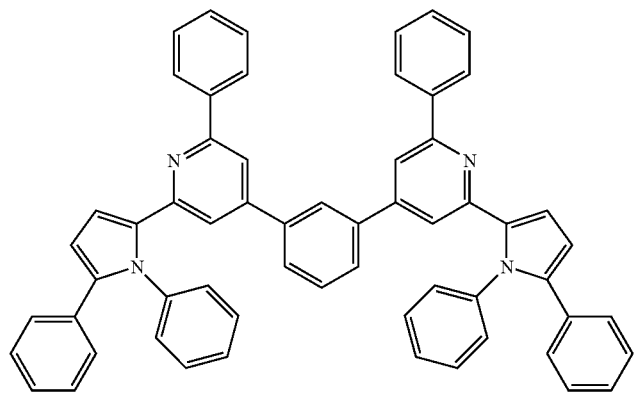
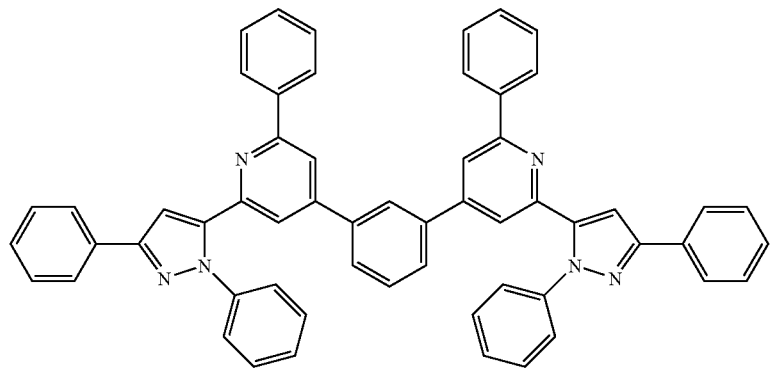
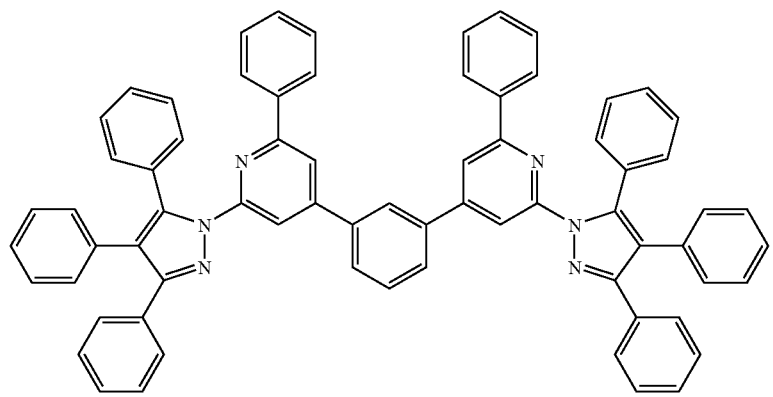

-continued
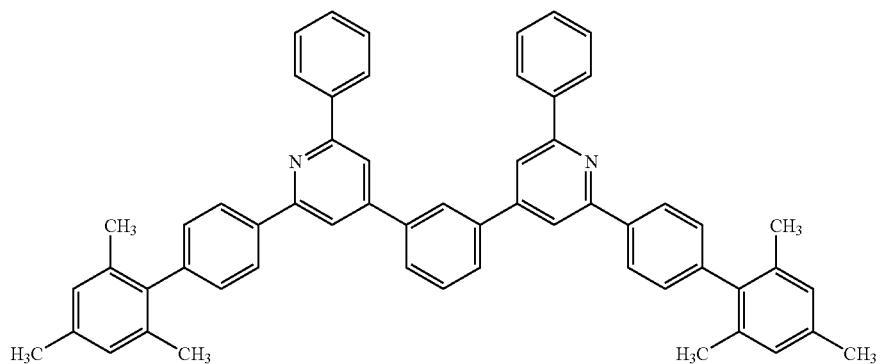
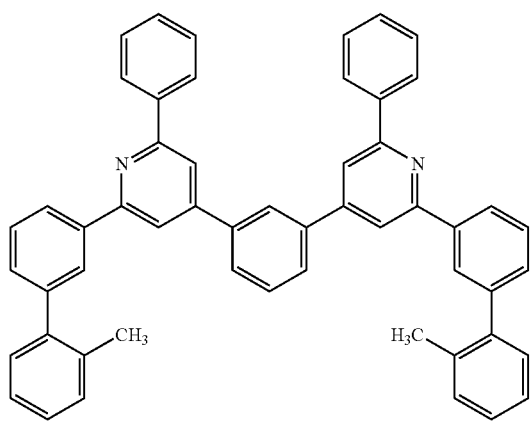
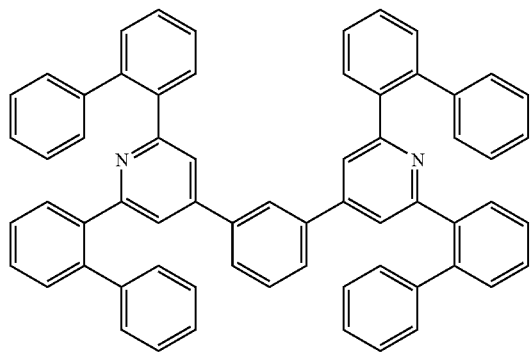
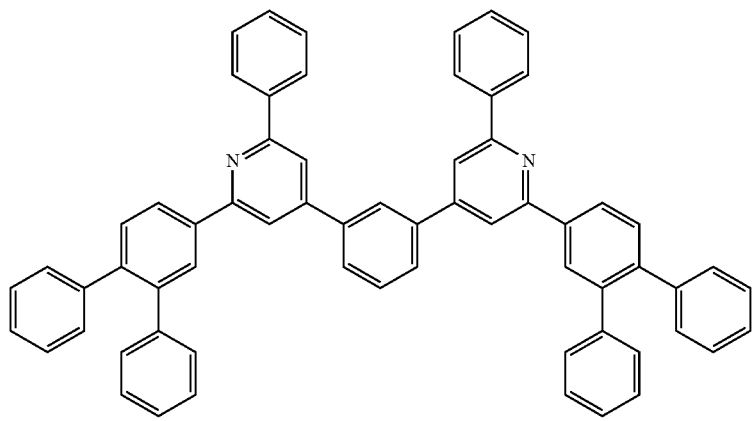

-continued
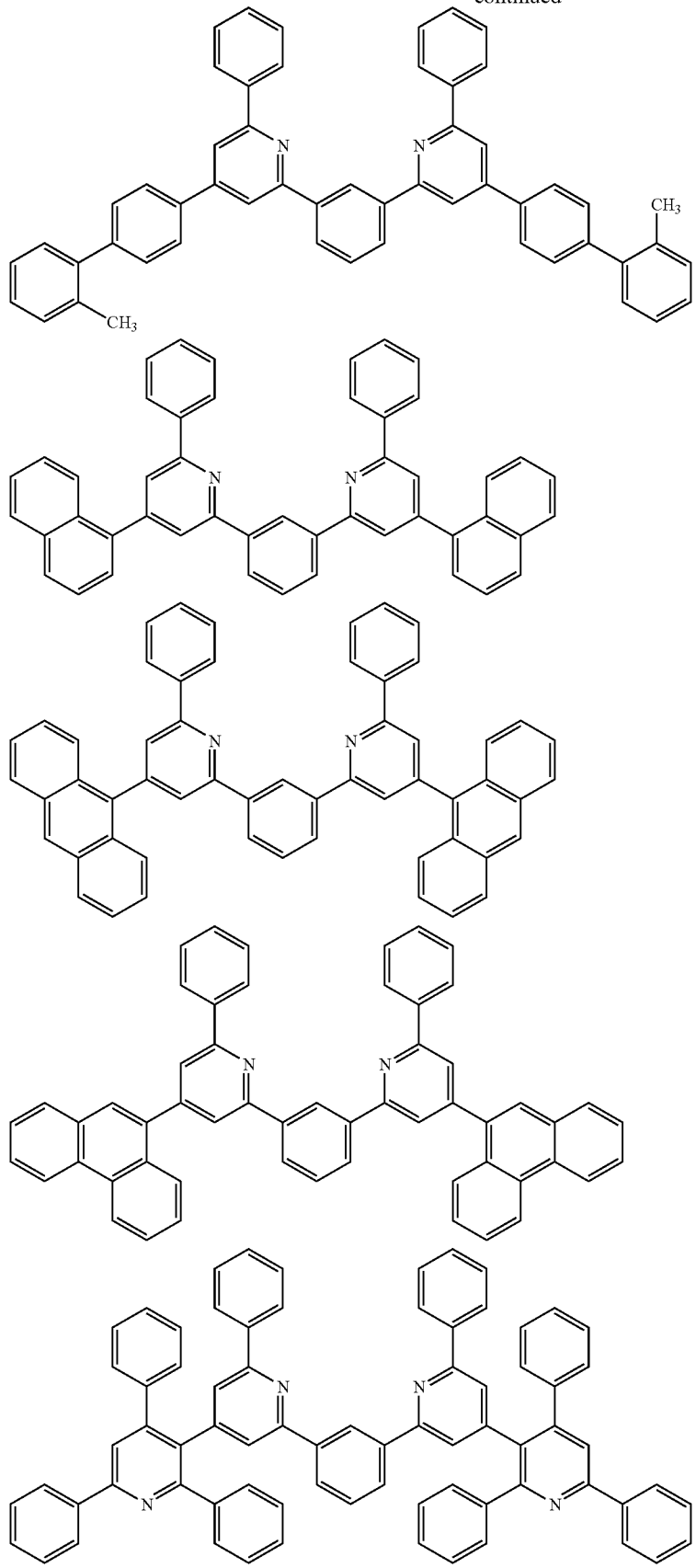

-continued
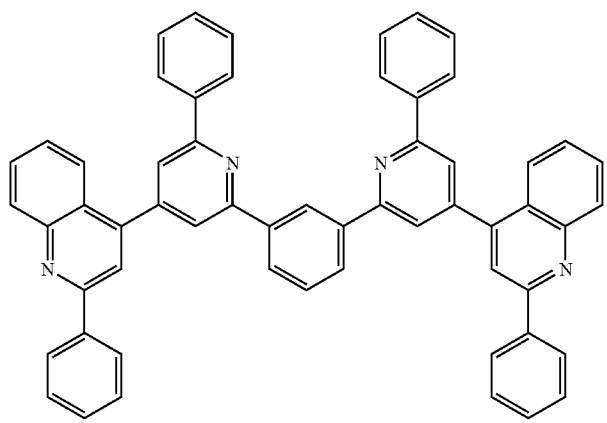
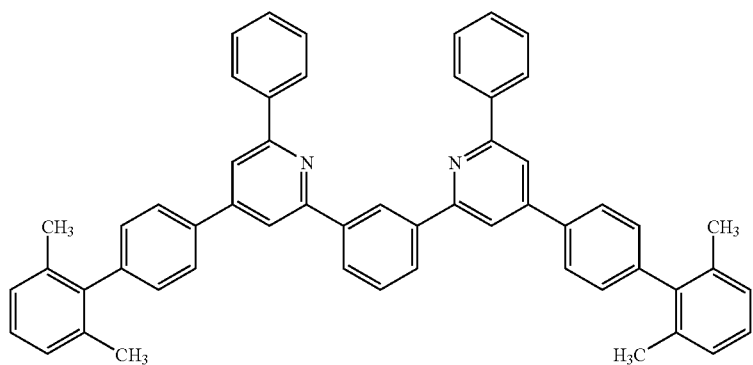
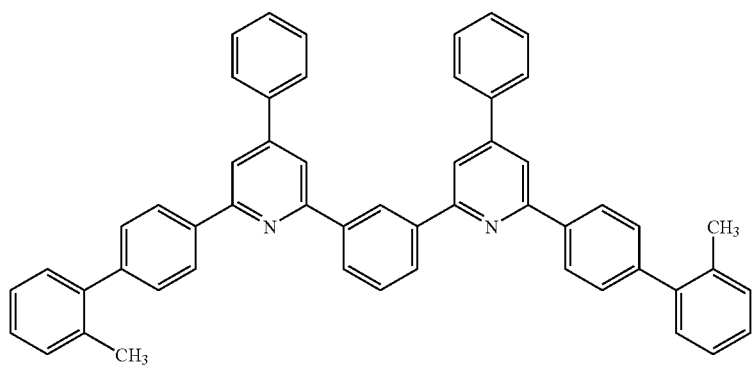
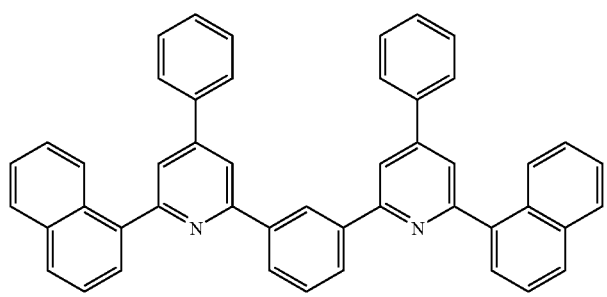

-continued
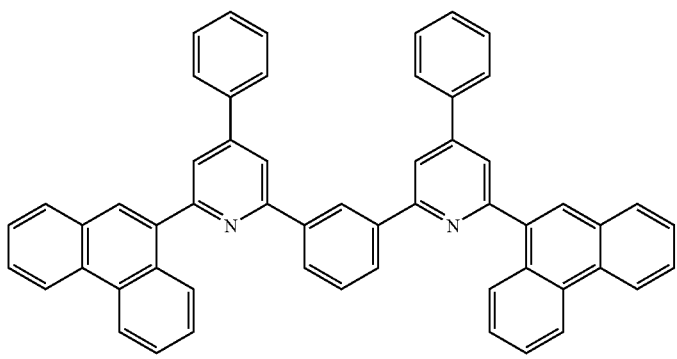
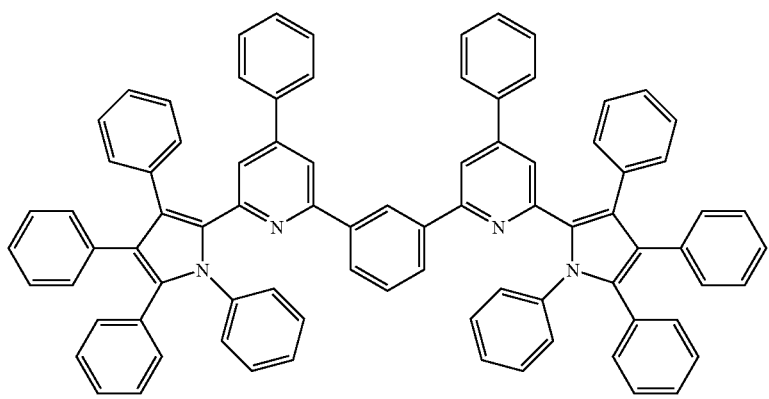
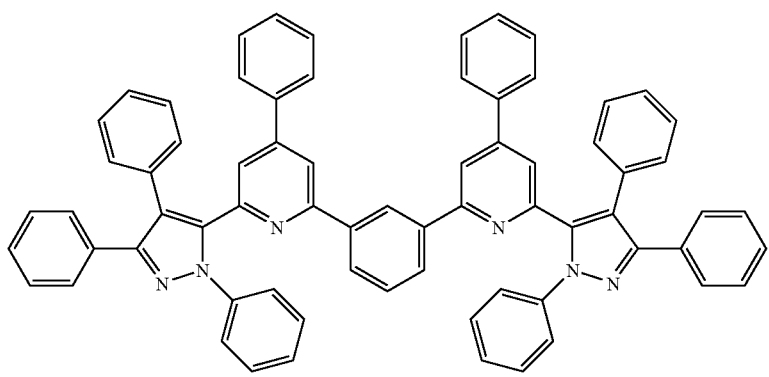
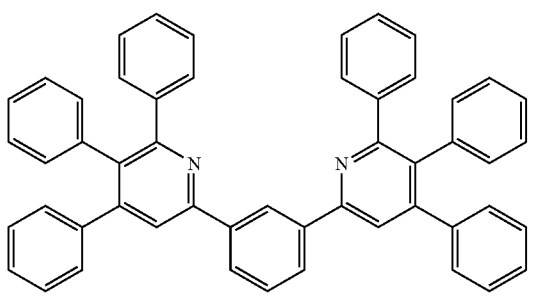

-continued
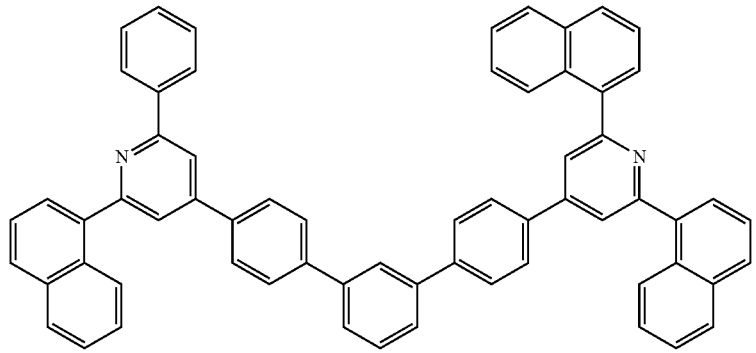
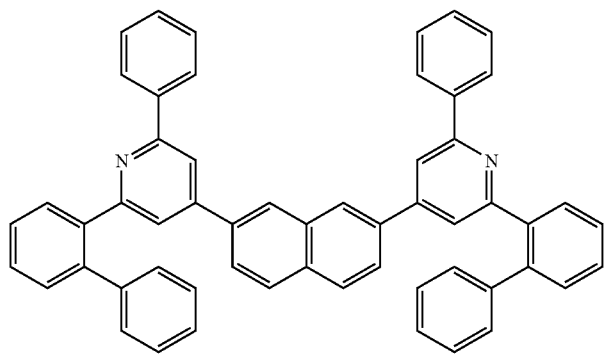
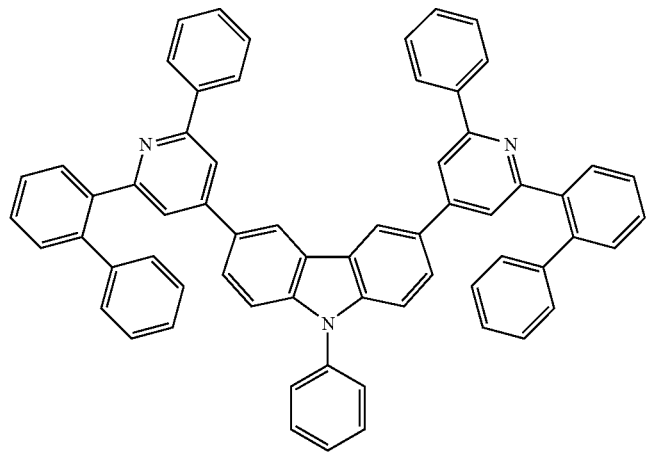

-continued
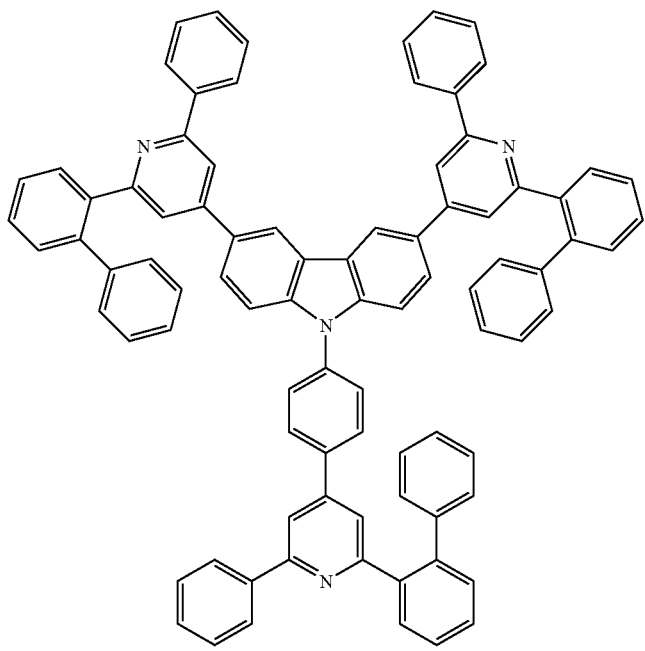
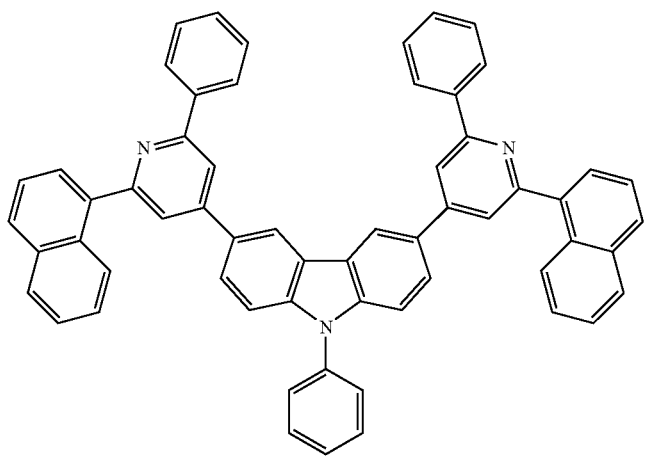
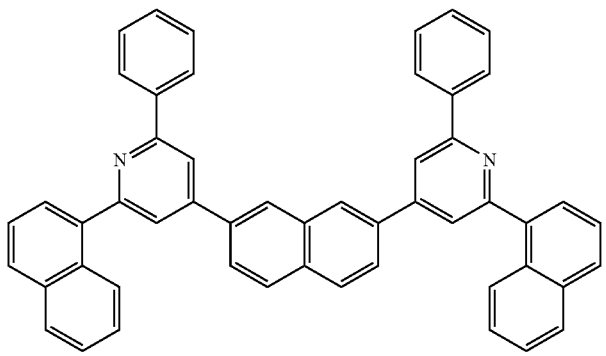

-continued
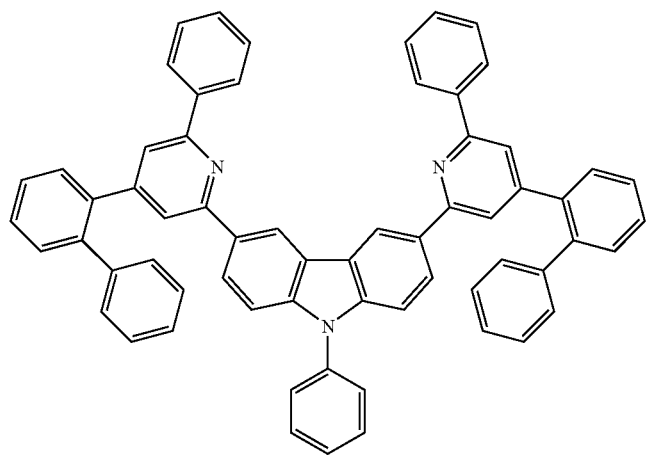
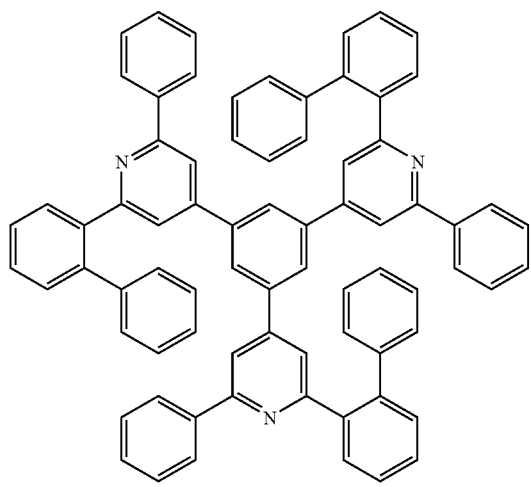
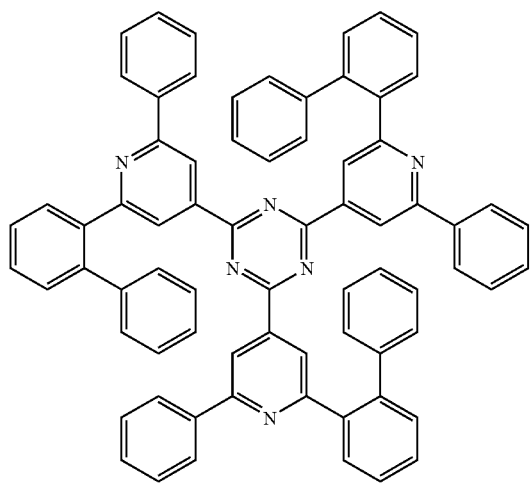

-continued
171
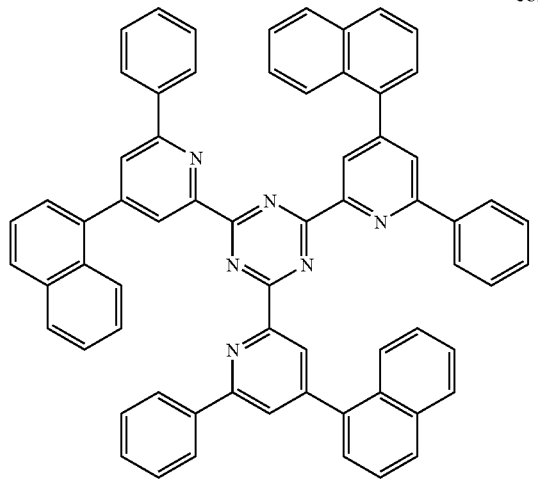
172
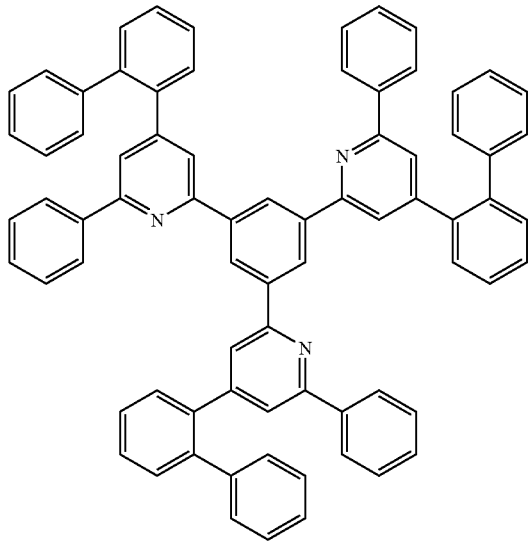
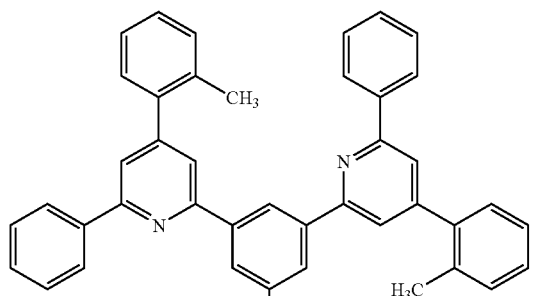
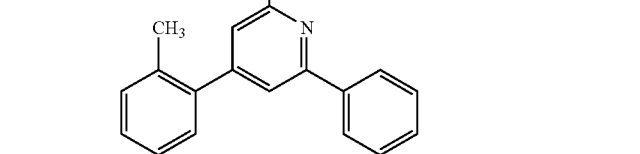
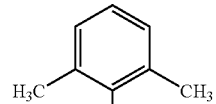
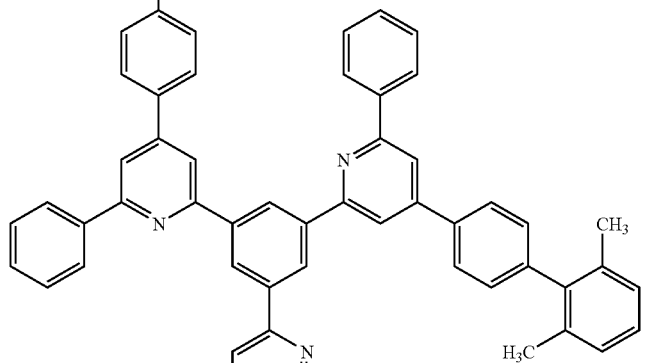
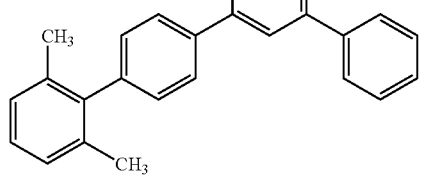

-continued
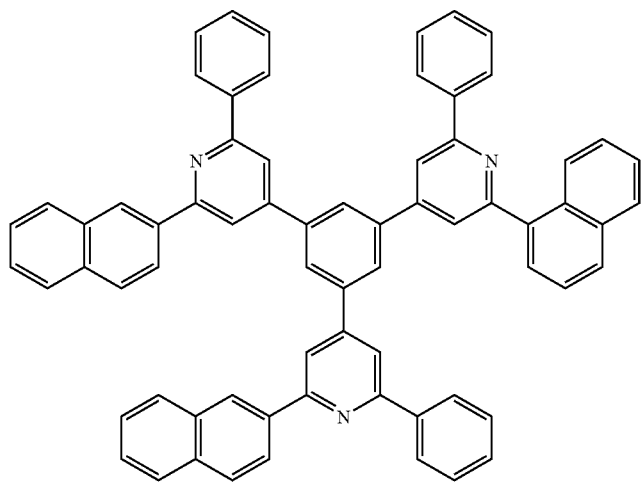

-continued
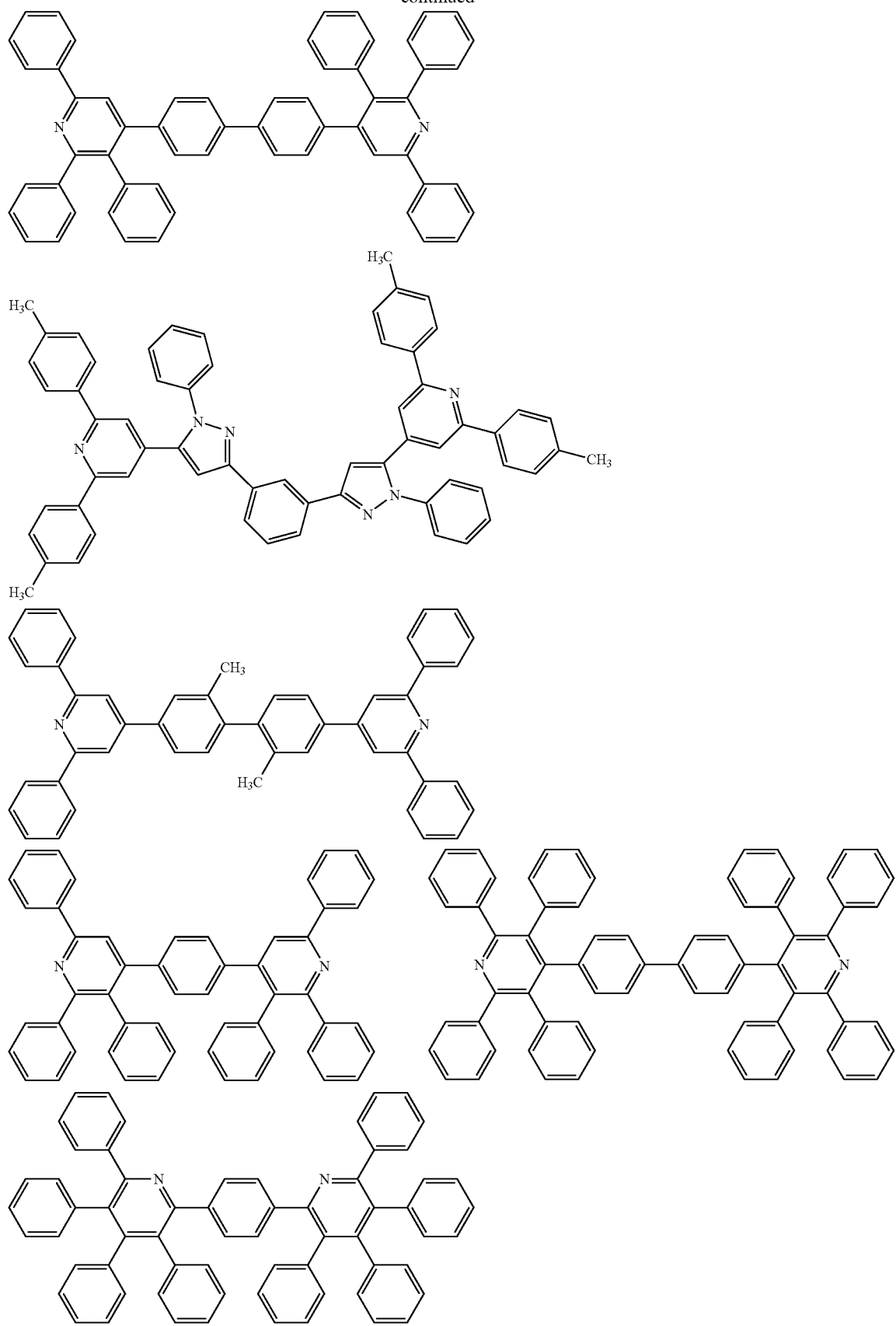

-continued
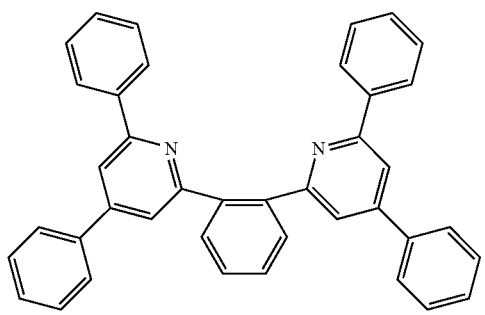
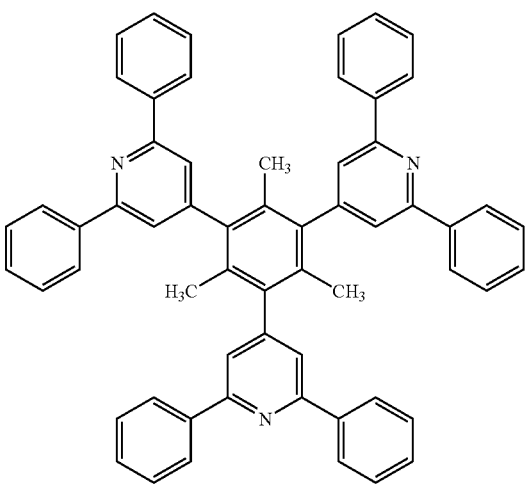
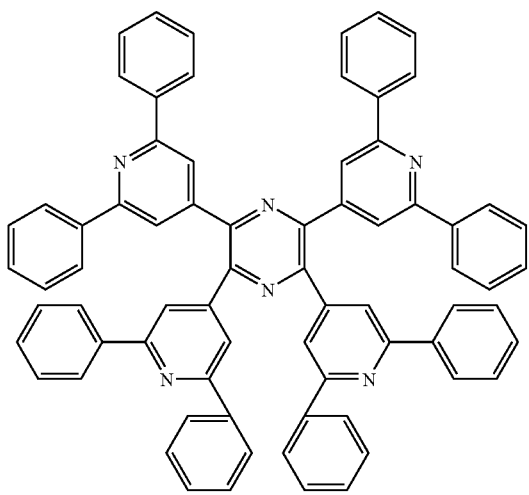
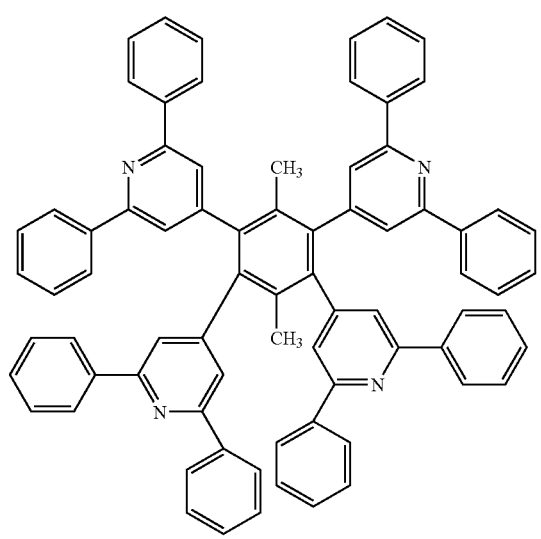
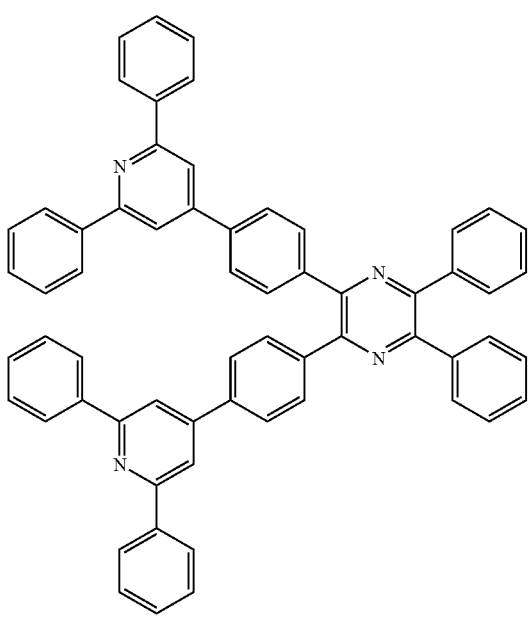

-continued
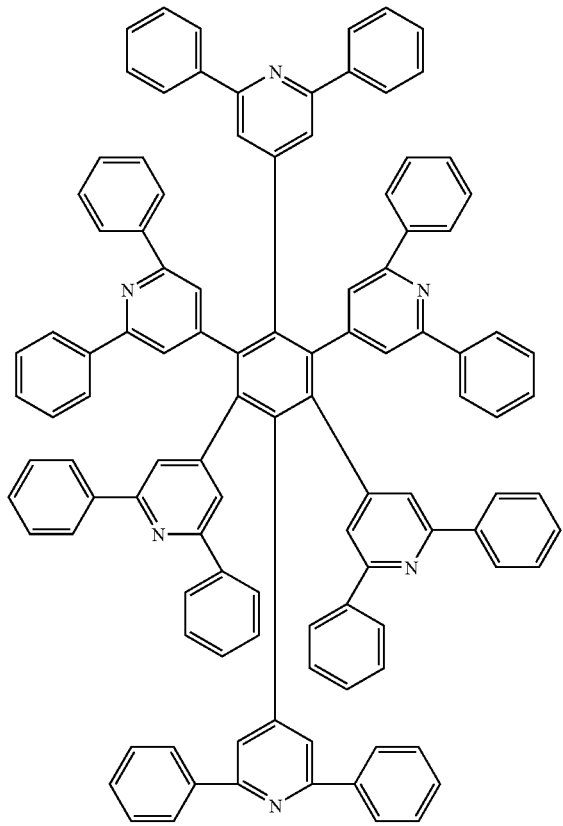
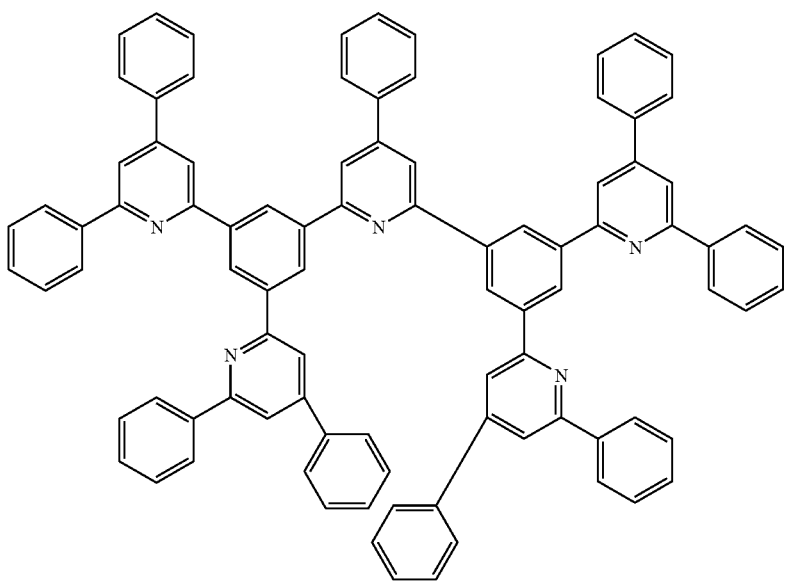

-continued
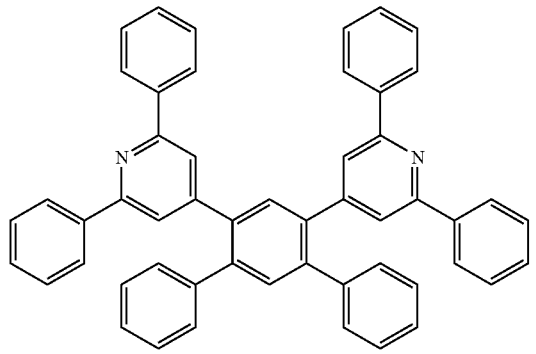
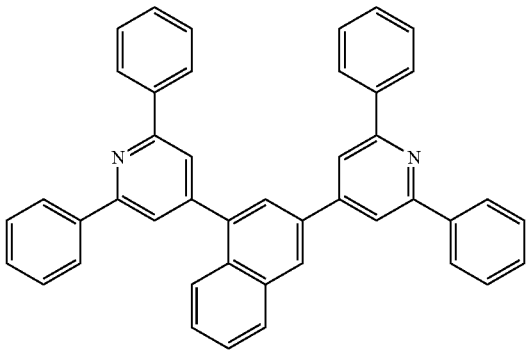
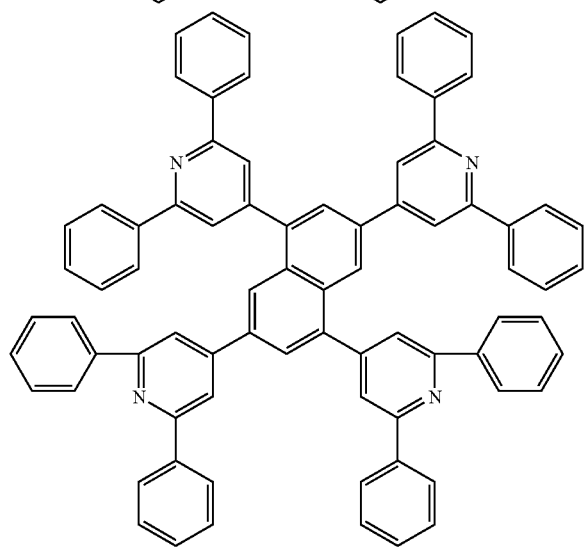
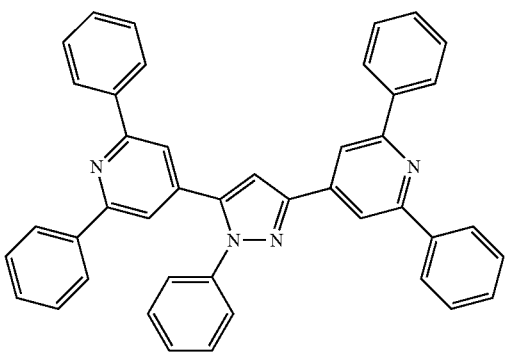
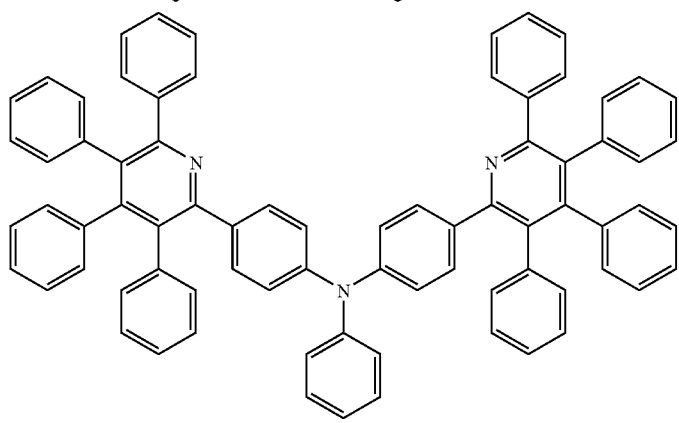
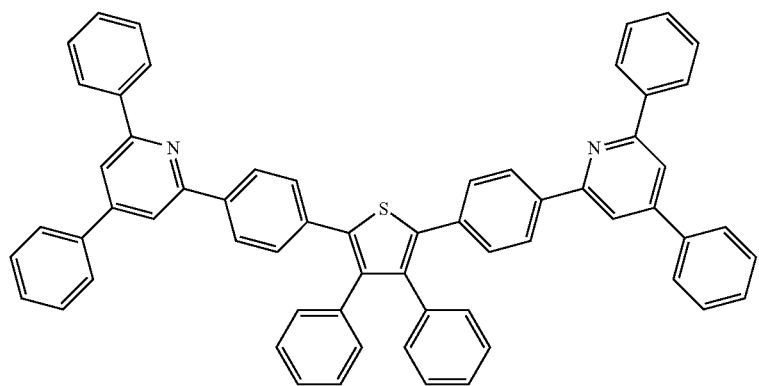

-continued
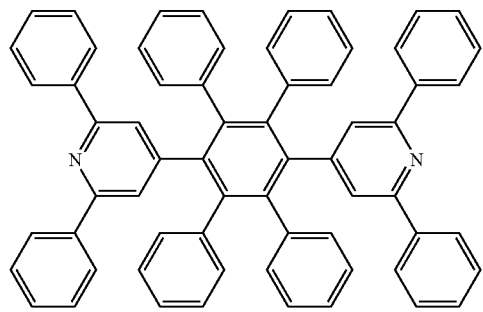
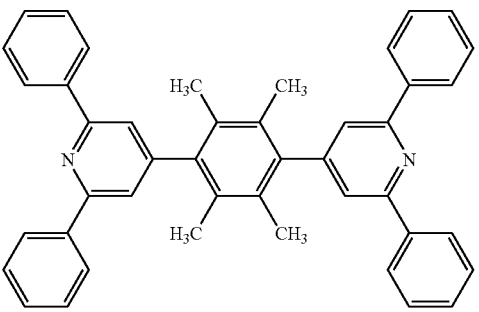
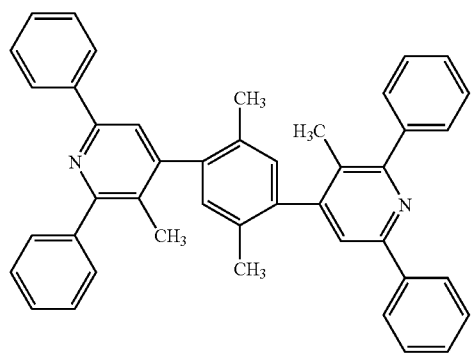
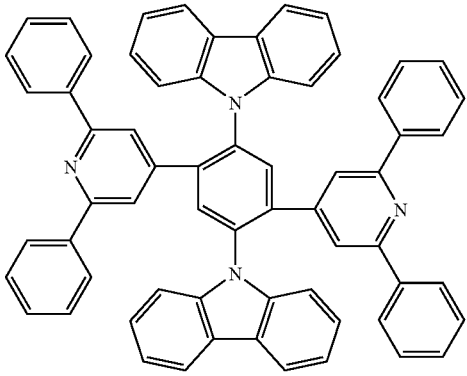
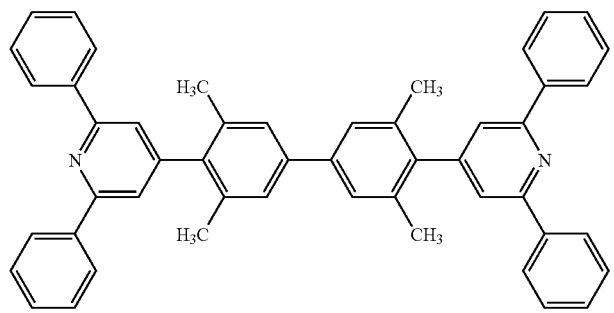
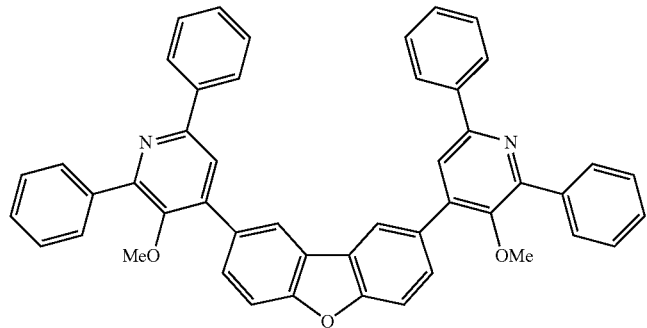
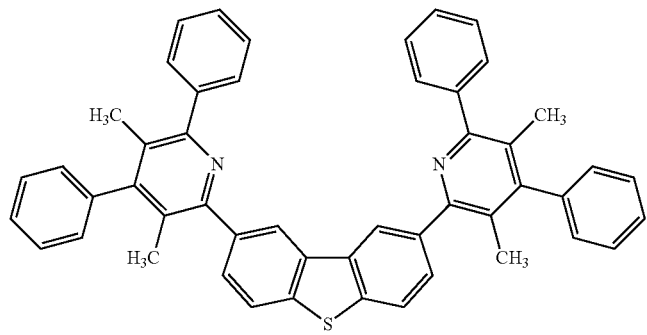

-continued
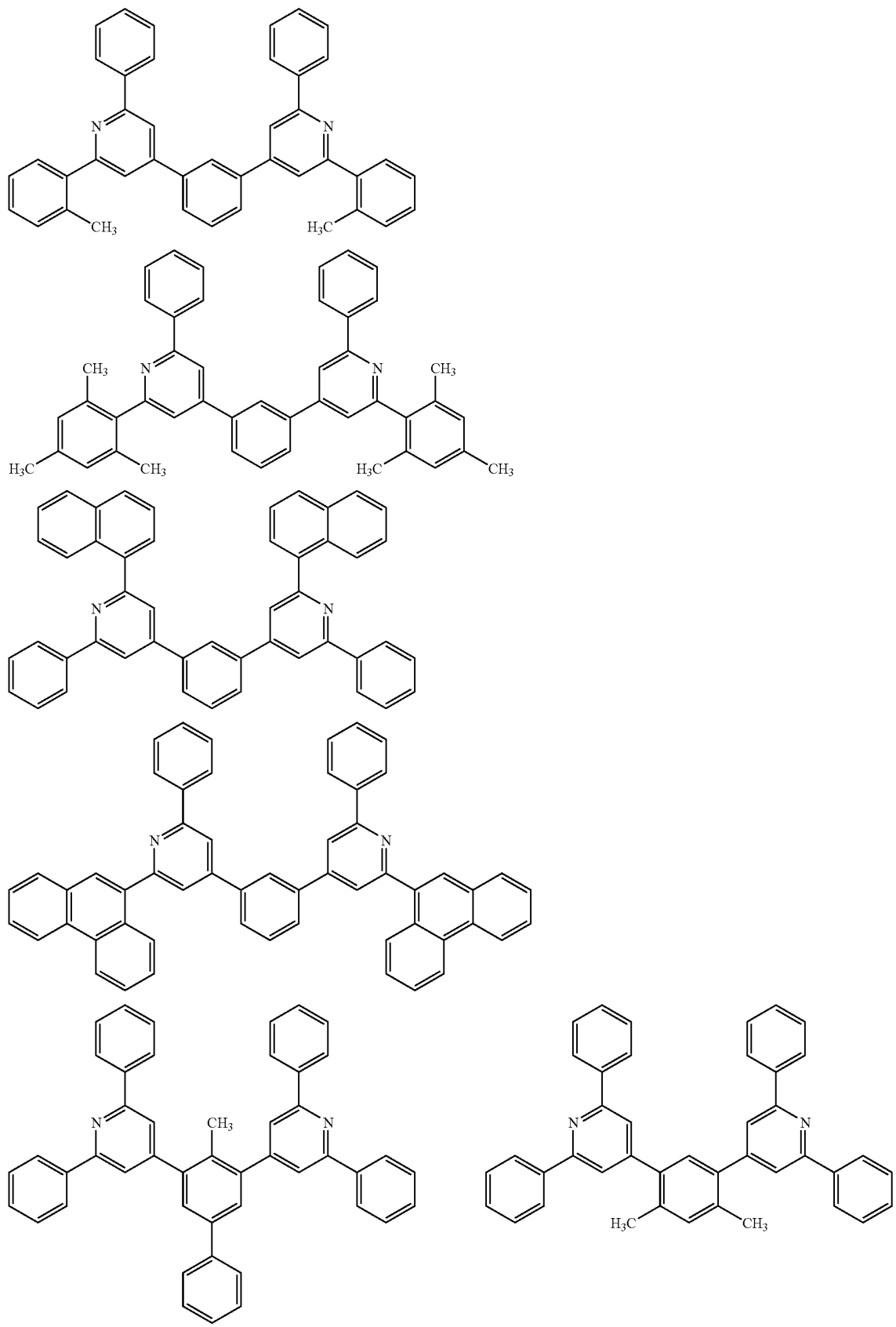

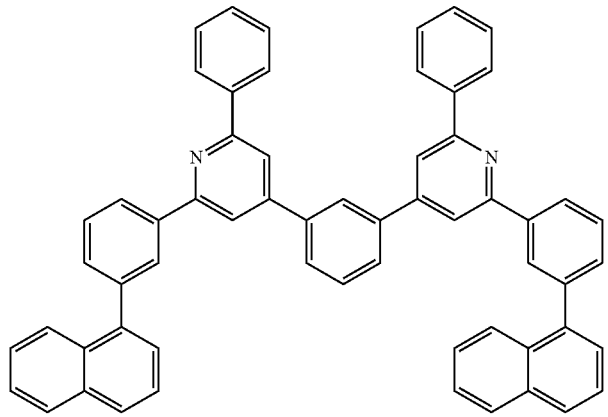
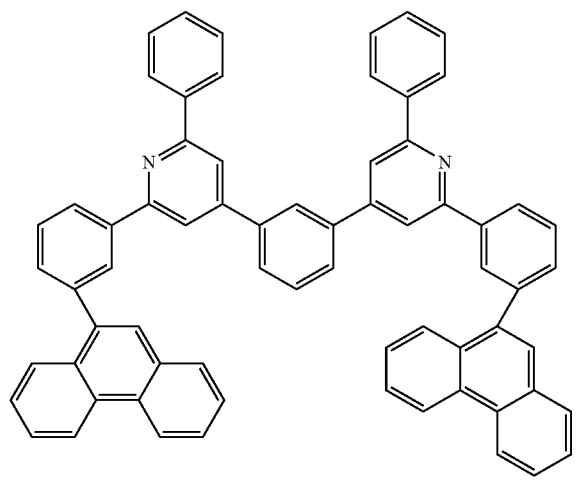
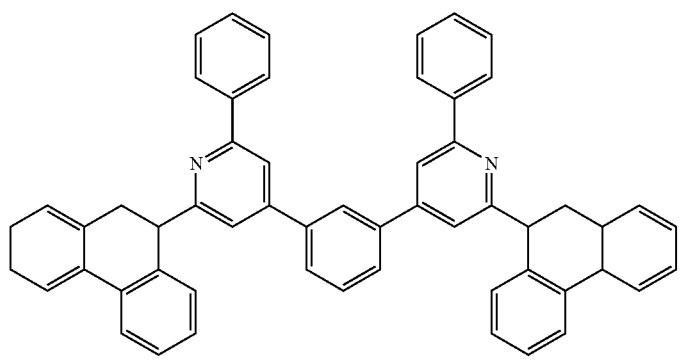

189 190
-continued
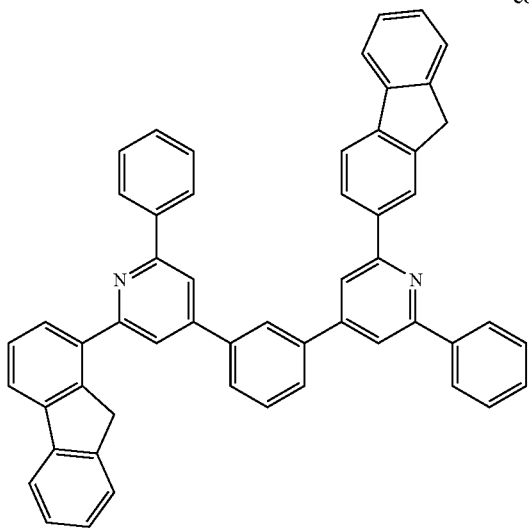
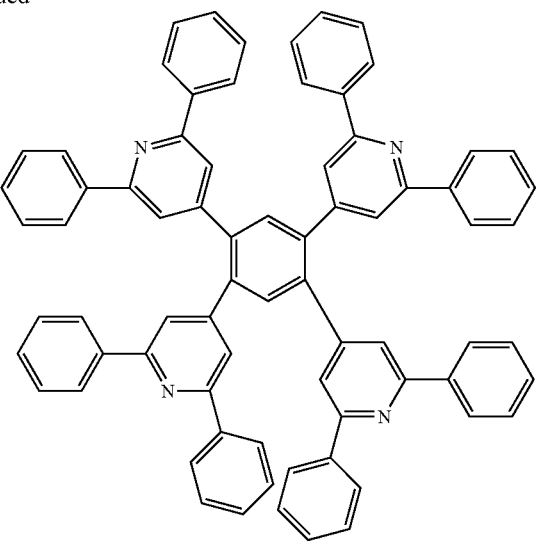
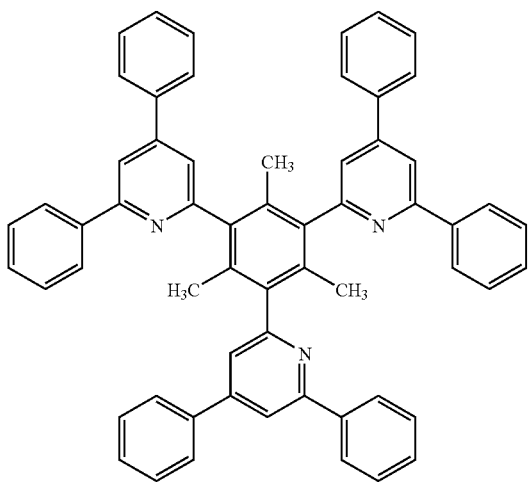
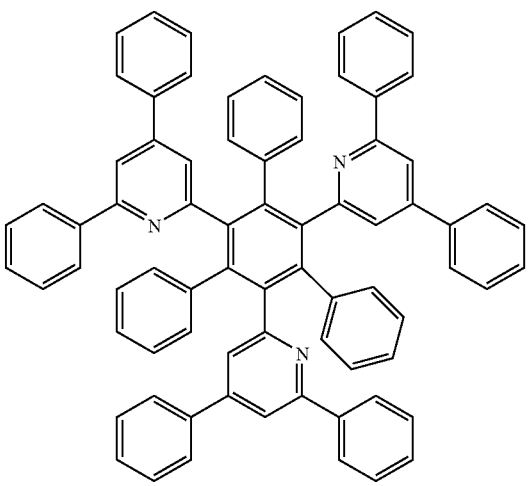
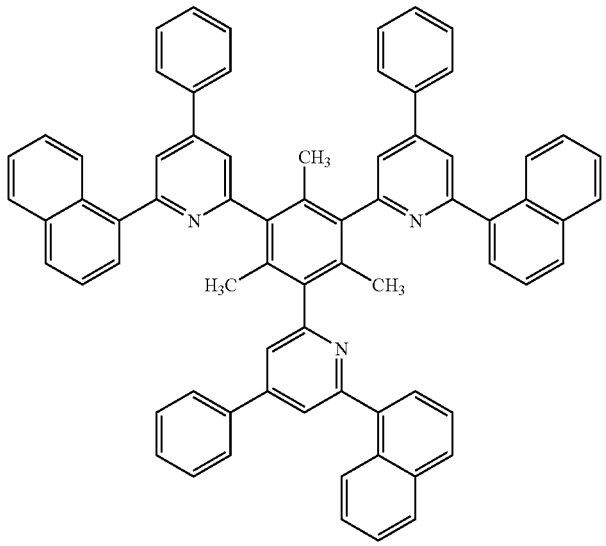

-continued
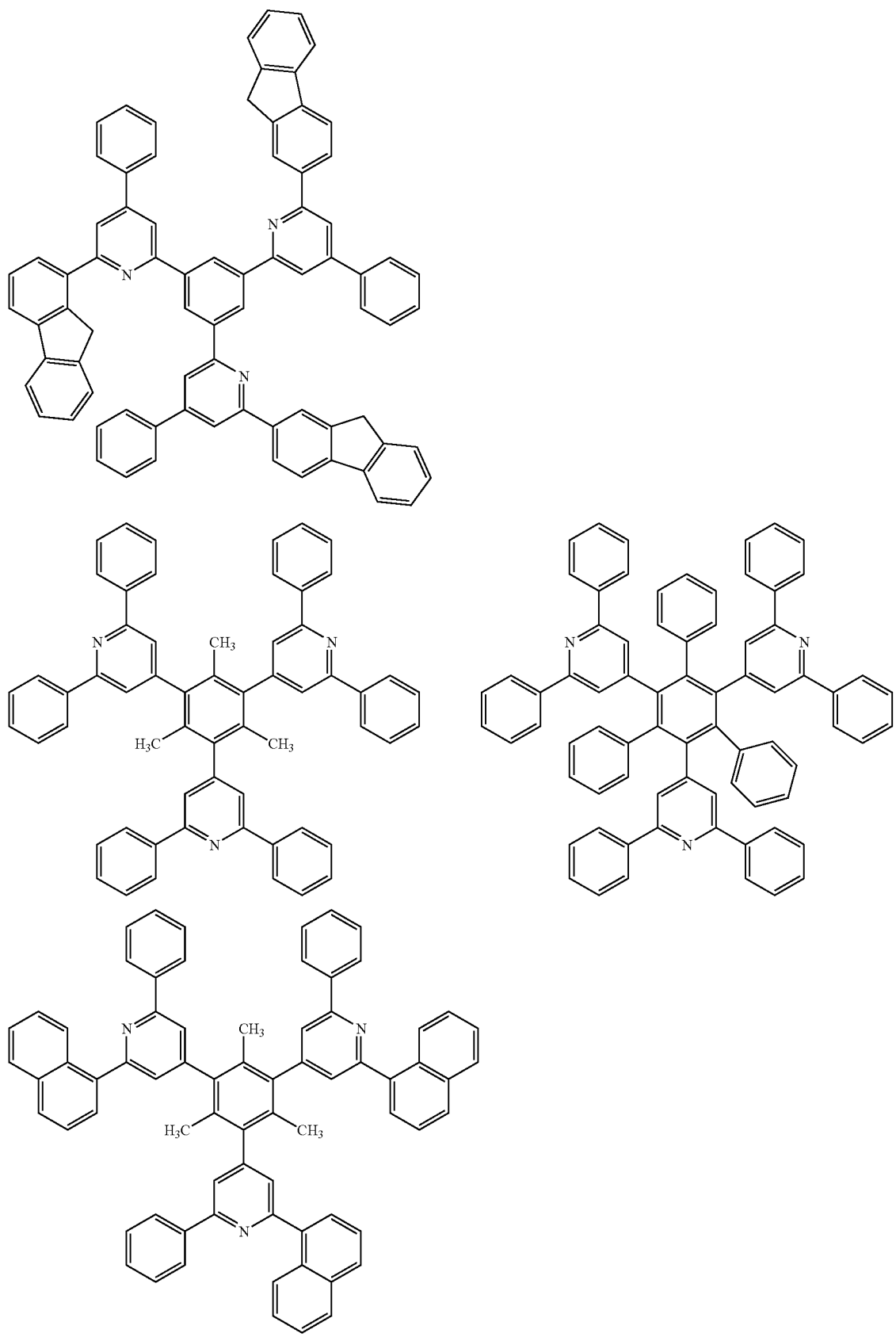

-continued
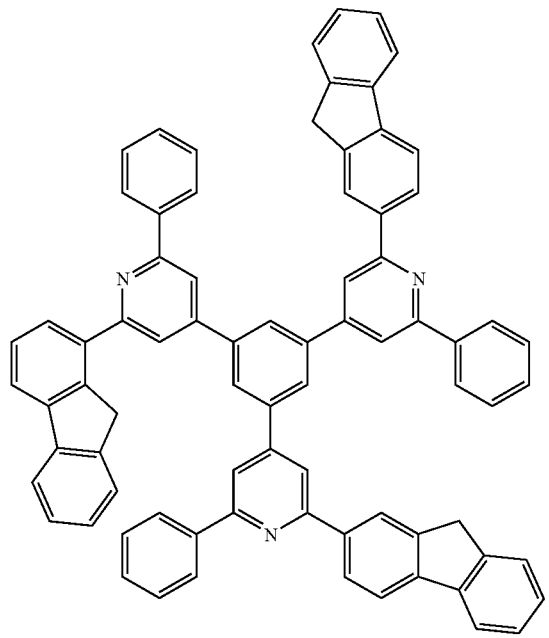
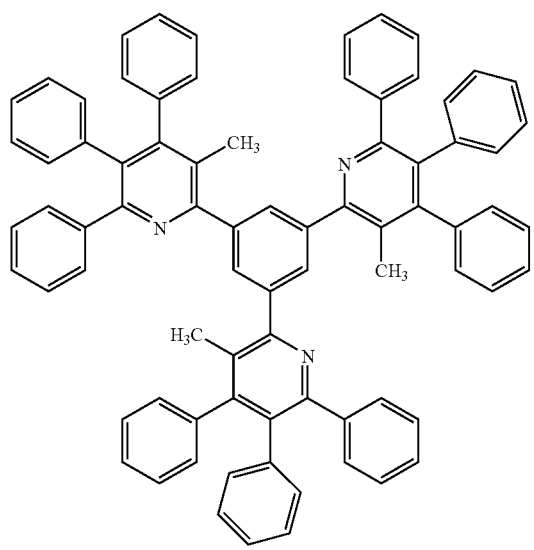

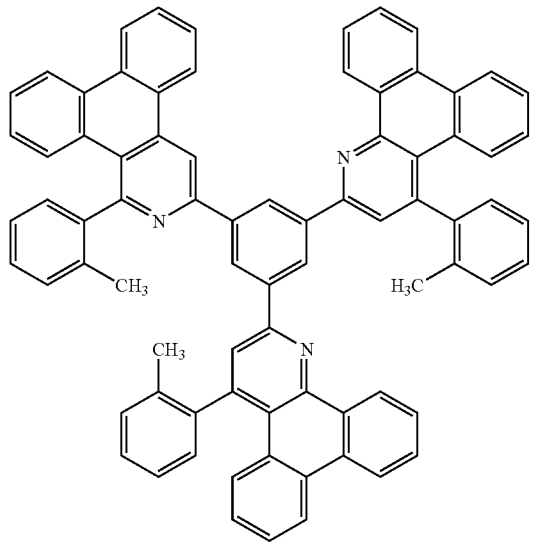

(In the Case of Forming a Plane Structure)

Of the compounds represented by the above formula (II) which form a plane structure when in an optimized geometry, those wherein p=0, i.e., compounds comprising a 4-pyridyl group have an extremely high durability against repeated oxidation.

Here, to form a plane structure when a compound is in an optimized geometry means the reverse of what has been described with respect to the compound which does not form the plane structure.

To describe by reference to examples, compounds wherein any arbitrary two aromatic rings constituting the molecule have about the same plane properties as biphenyl (FIG. C) are said to have a plane structure.

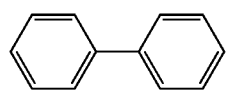

FIG. C

Of the compounds represented by the above formula (II) which form a plane structure when in an optimized geometry and wherein p=0, those compounds which are represented by the following formula (III) and wherein pyridine rings are connected to each other through a m-phenylene group have a large oxidation-reduction potential difference and a particularly excellent reversibility since the lone pairs on the pyridine rings do not directly conjugate each other and a conjugation structure is formed between the m-phenylene group and the pyridine group.

Also, the compounds have excellent amorphousness and excellent solubility into an organic solvent due to destroyed symmetricalness of the pyridine rings. Therefore, they show a stable filming property without crystallization when formed into a film.

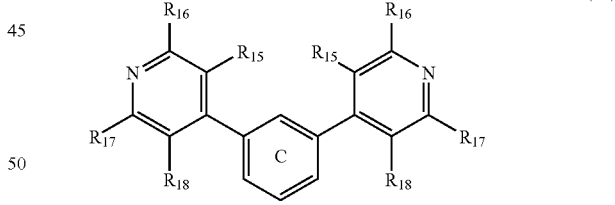

(III)

Here, $R_{15}$ to $R_{18}$ are the same as defined in the above formula (II). The ring C may have a substituent. Also, two $R_{15}$s to two $R_{18}$s in the formula (III) may be the same or different from each other.

Additionally, the molecular weight of the compound represented by the formula (III) is usually 200 or more, preferably 400 or more, and is usually 4,000 or less, preferably 1,000 or less. In case when the molecular weight is too large, there results a reduction in ease of purification operation whereas, in case when the molecular weight is lower than the lower limit, a stable filming property cannot be obtained, and there might result an insufficient durability due to reduction in glass transition temperature and gasification temperature and an increased crystallinity.

The glass transition temperature (Tg) of the compound represented by the above formula (III) is preferably 70° C. or more, more preferably 100° C. or more.

As to the oxidation-reduction potential difference of the compound represented by the above formula (III), the oxidation potential electrochemically measured versus the standard electrode is usually 1.3 V vs SCE or more, and the reduction potential is −1.7 V vs SCE or less. The oxidation potential is preferably 1.5 V vs SCE or more, and the reduction potential is preferably −1.9 V vs SCE or less. Particularly preferably, the oxidation potential is 1.7 V vs SCE or more, and the reduction potential is −2.0 V vs SCE or less.

Of the compounds represented by the above formula (II) which form a plane structure when in an optimized geometry, compounds wherein p=0 and $Q_{01}$ is a benzene ring-derived group represented by the following formula (V) whose 1-, 3- and 5-positions are all connected to $Z_{11}$ or $Z_{12}$ (1,3,5-substituted phenylene group). Such compound has a structure wherein the lone pair electrons on the nitrogen atoms cannot directly conjugate each other and a conjugation structure is formed between the 1,3,5-substituted phenylene group and the pyridine ring, and hence the compound has a large oxidation-reduction potential difference and is particularly excellent in reversibility.

In addition, electron transporting ability and heat resistance are more improved by introducing 3 heterocyclic rings having electron transporting properties. Further, since the compound has such an excellent amorphousness and an excellent solubility in an organic solvent that it shows a stable film-forming property without showing crystallinity and has an excellent heat resistance and an excellent durability due to the high glass transition temperature (Tg).

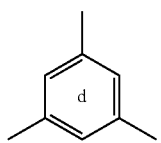
(V)

Among them, compounds represented by the following formula (IV) are preferred.

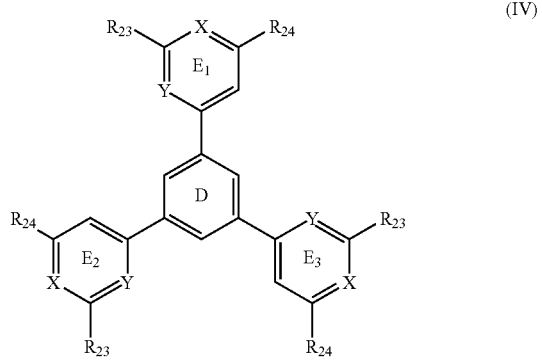
(IV)

In the formula (IV), X and Y each represents —CH═ or —N═. $R_{23}$ and $R_{24}$ each independently represents an arbitrary substituent. Rings $E_1$ to $E_3$ may have a substituent in addition to $R_{23}$ and $R_{24}$.

Plural $R_{23}$s and $R_{24}$s in the formula (IV) may be the same or different from each other. The ring D may have a substituent.

($R_{23}$ and $R_{24}$)

As $R_{23}$ and $R_{24}$, those which have been illustrated as ($R_1$ to $R_8$) may be employed. $R_{23}$ and $R_{24}$ may have a substituent and, as such substituent, those which have been illustrated as substituents for ($R_1$ to $R_8$) may be employed.

As $R_{23}$ and $R_{24}$, an aromatic hydrocarbon group optionally having a substituent is preferred in view of improving durability against electric oxidation and reduction and enlarging the oxidation-reduction potential difference.

Particularly preferred examples thereof include a phenyl group optionally having a substituent (in the case where a substituent exists, the substituent being preferably an alkyl group such as a methyl group, a phenyl group or a substituted aryl group such as a tolyl group or a mesityl group).

As the substituent which the rings $E_1$ to $E_3$ may have in addition to $R_{23}$ and $R_{24}$, there may be applied those which have been illustrated as the foregoing ($R_1$ to $R_8$).

Preferred are a hydrogen atom, an alkyl group and an aryl group, more preferred are a hydrogen atom and a phenyl group which may have a substituent (in the case where a substituent exists, the substituent being preferably an alkyl group such as a methyl group, a phenyl group or a substituted aryl group such as a tolyl group or a mesityl group) in view of not spoiling luminous efficiency by restricting molecular oscillation.

The molecular weights of $R_{23}$ and $R_{24}$ are the same as those of $R_{11}$ to $R_{18}$.

The molecular weight of the compound represented by the above formula (IV) is usually 300 or more, preferably 400 or more, and is usually 4,000 or less, preferably 1,500 or less. In case when the molecular weight exceeds the upper limit, there results a reduction in ease of purification operation whereas, in case when the molecular weight is lower than the lower limit, a stable filming property cannot be obtained, and there might result an insufficient durability due to reduction in glass transition temperature and gasification temperature and an increased crystallinity.

The glass transition temperature (Tg) of the compound represented by the above formula (IV) is preferably 90° C. or more, more preferably 100° C. or more.

As to the oxidation-reduction potential difference of the compound represented by the above formula (III), the oxidation potential electrochemically measured versus the standard electrode is usually 1.3 V vs SCE or more, and the reduction potential is −1.7 V vs SCE or less. The oxidation potential is preferably 1.5 V vs SCE or more, and the reduction potential is preferably −1.9 V vs SCE or less. Particularly preferably, the oxidation potential is 1.7 V vs SCE or more, and the reduction potential is −2.0 V vs SCE or less.

Specific examples are illustrated below, but the following specific examples are not limitative at all.

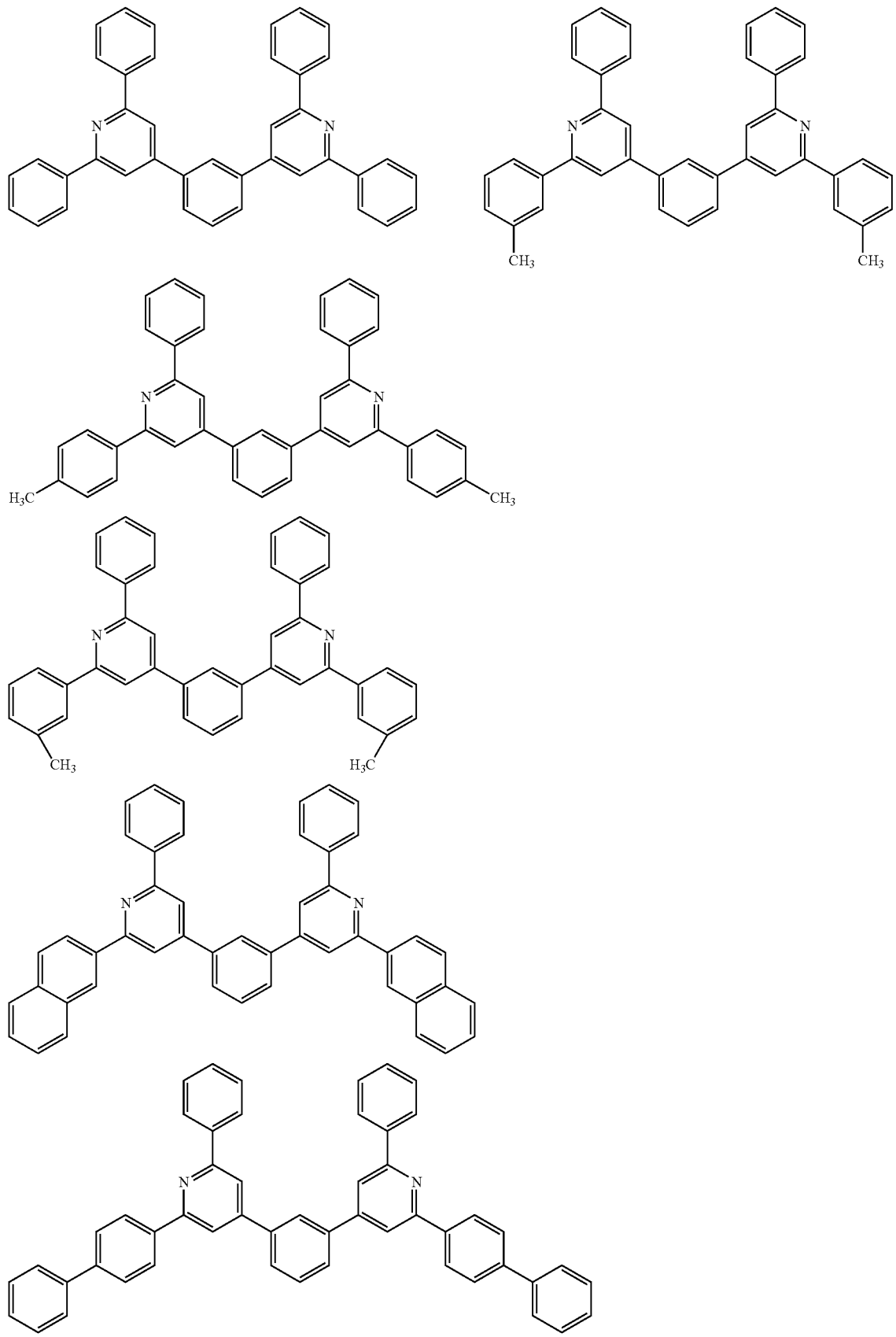

-continued
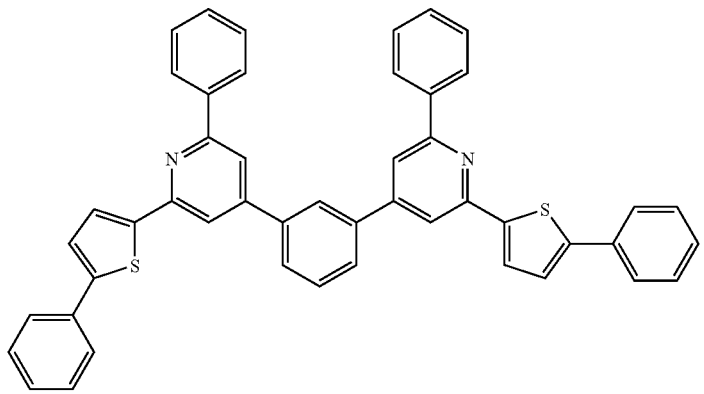
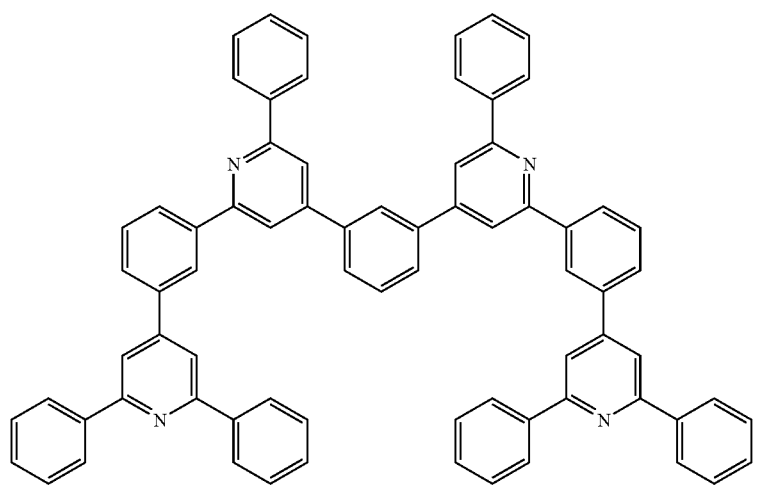
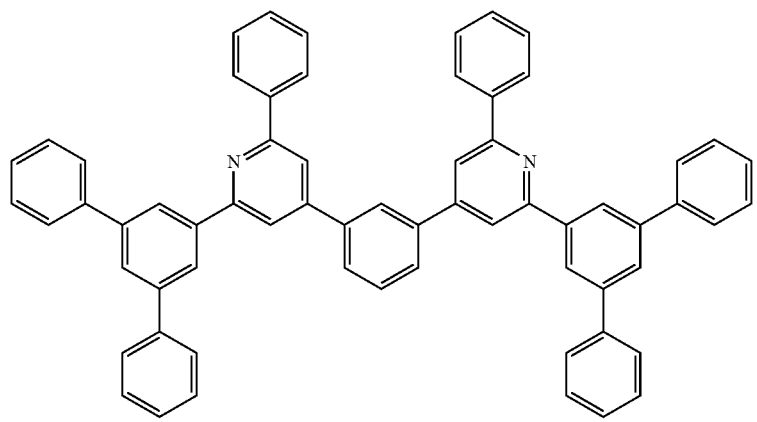

-continued
203
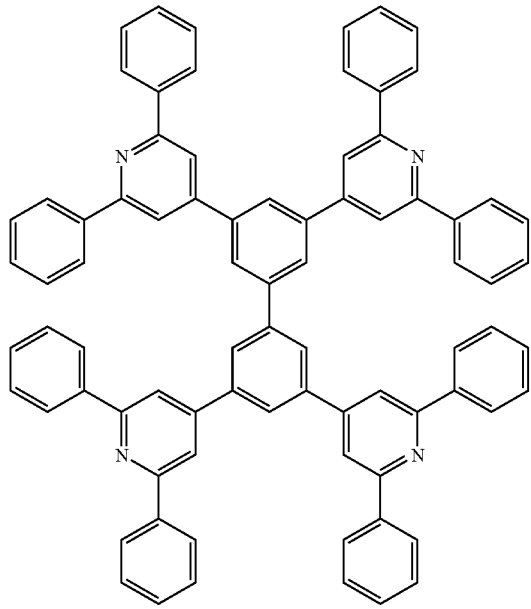
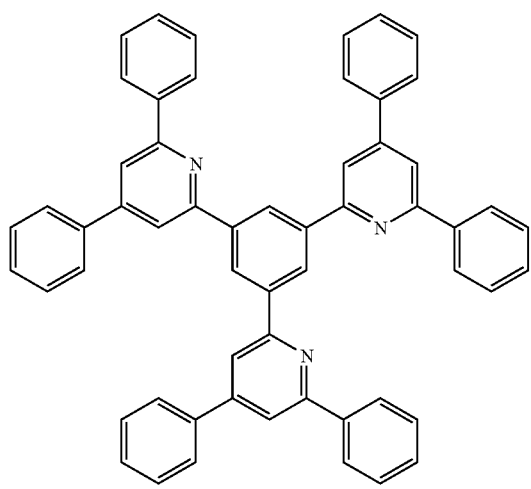
204
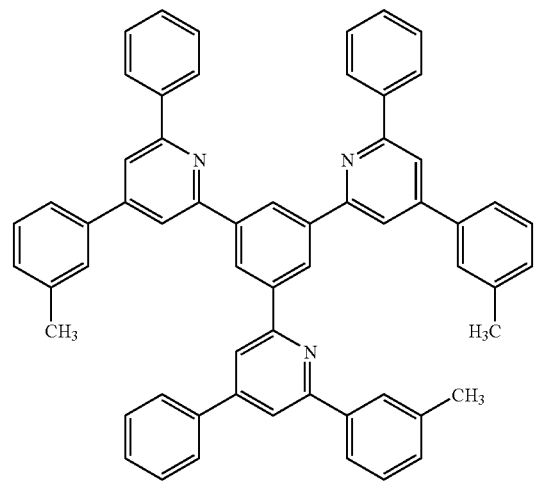

-continued
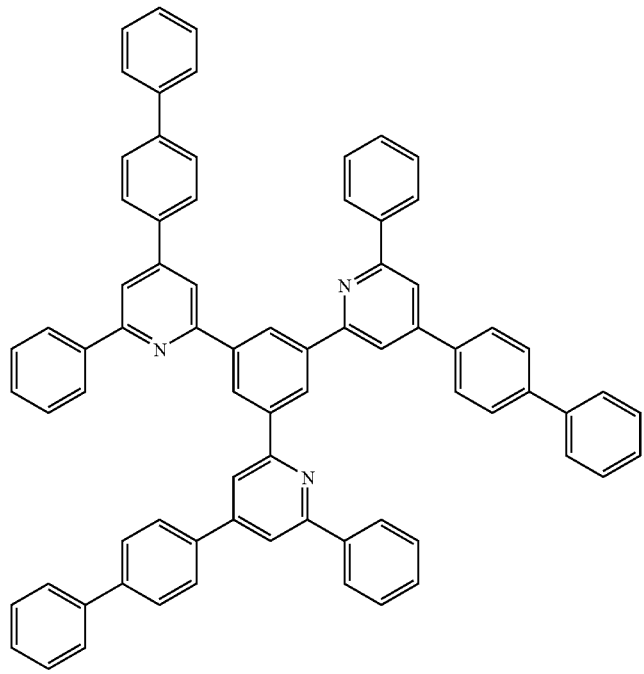
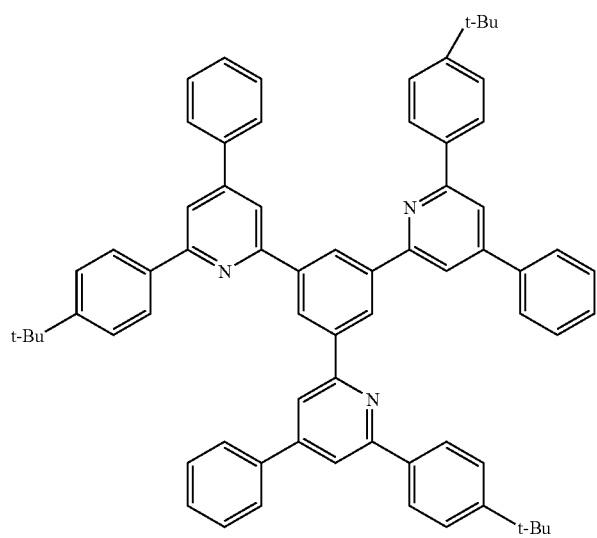

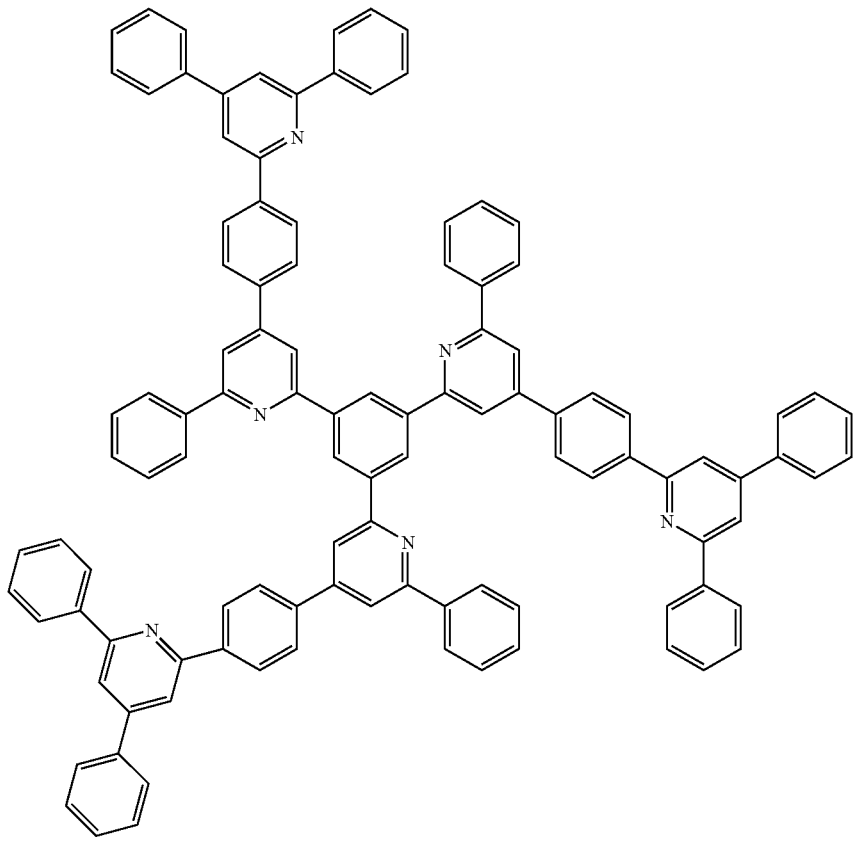
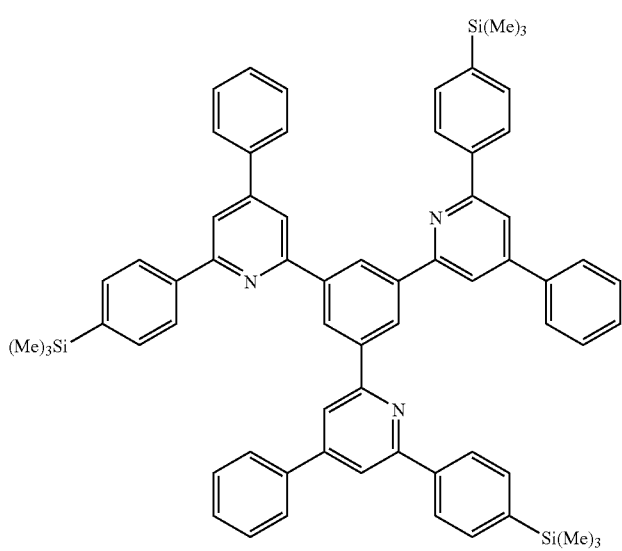

-continued
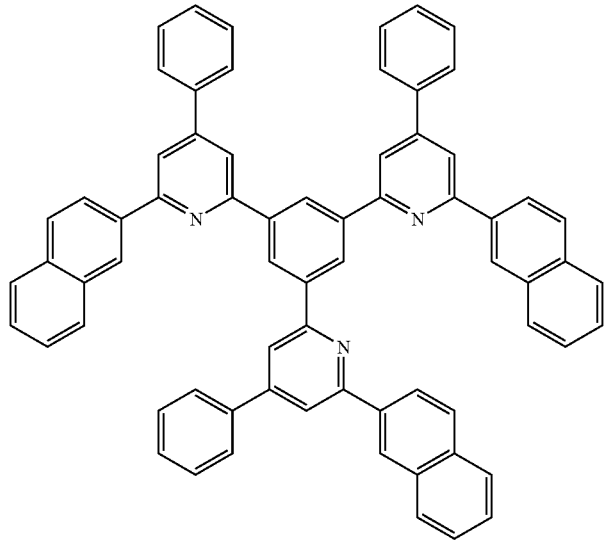
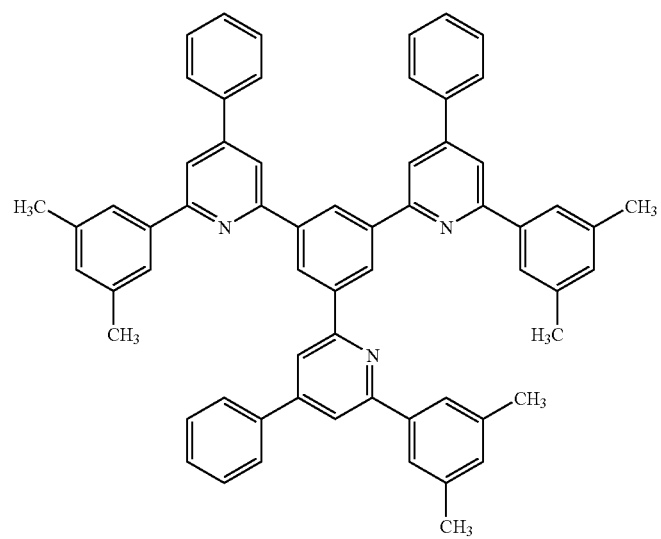

-continued
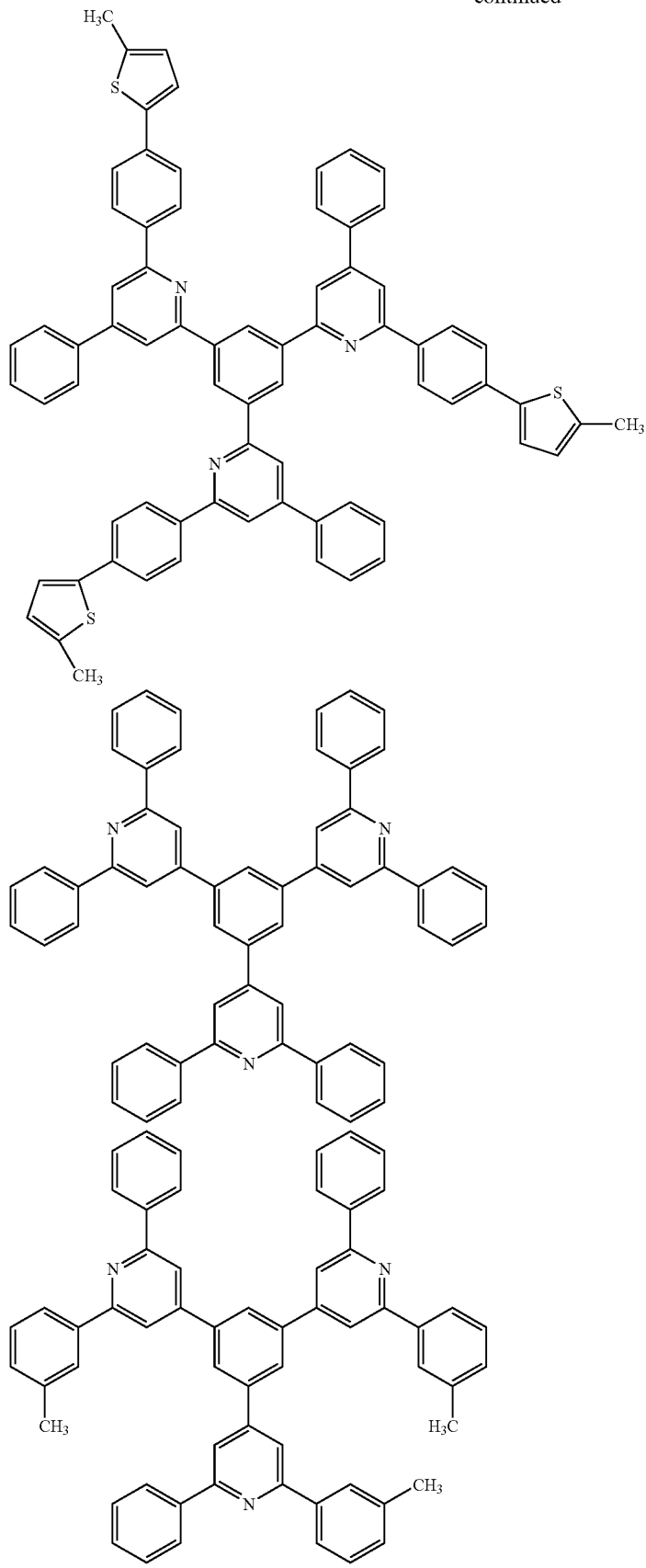

-continued
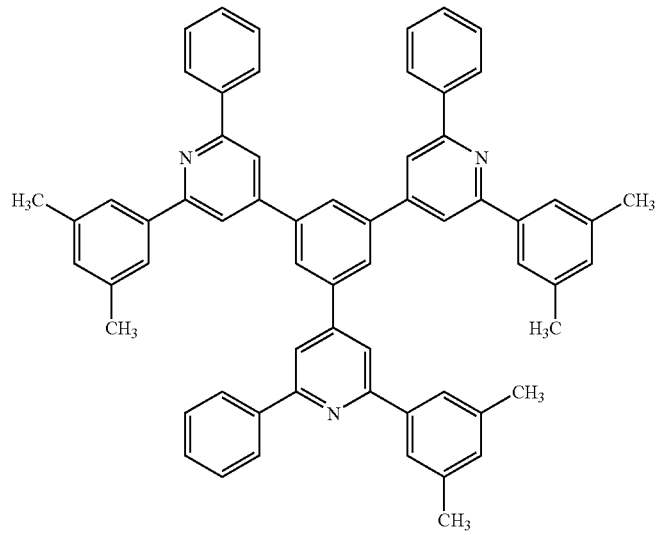
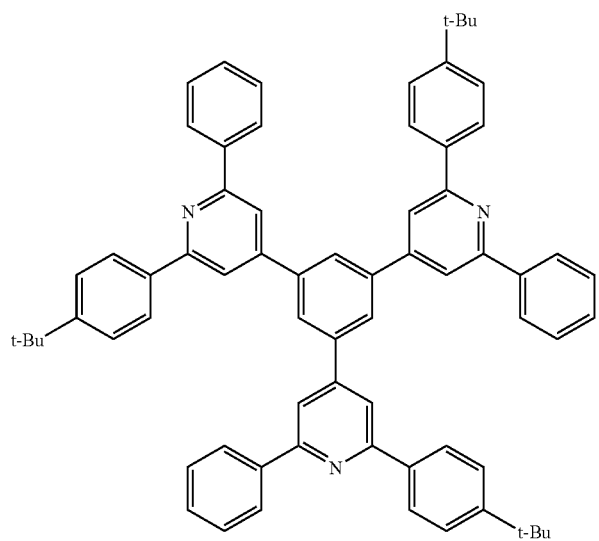

-continued
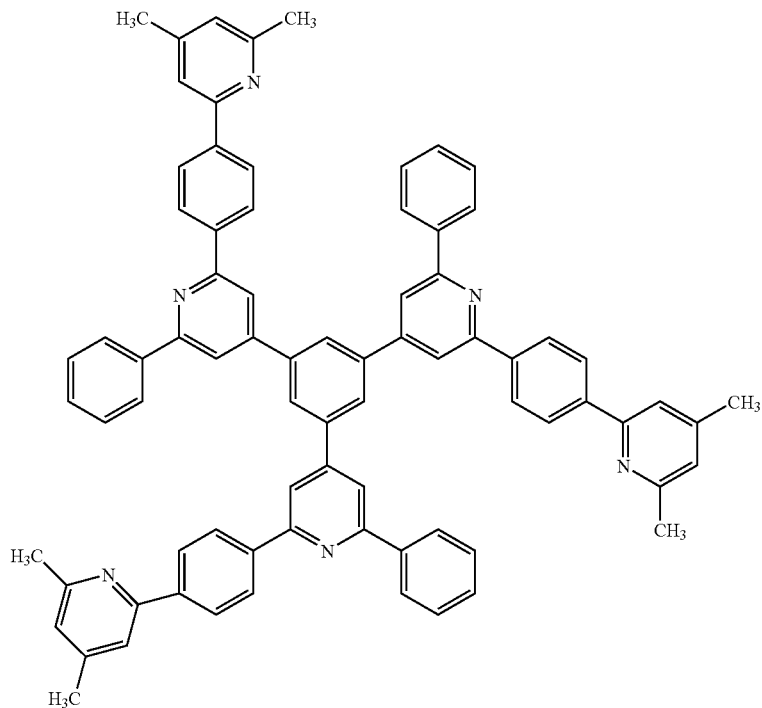
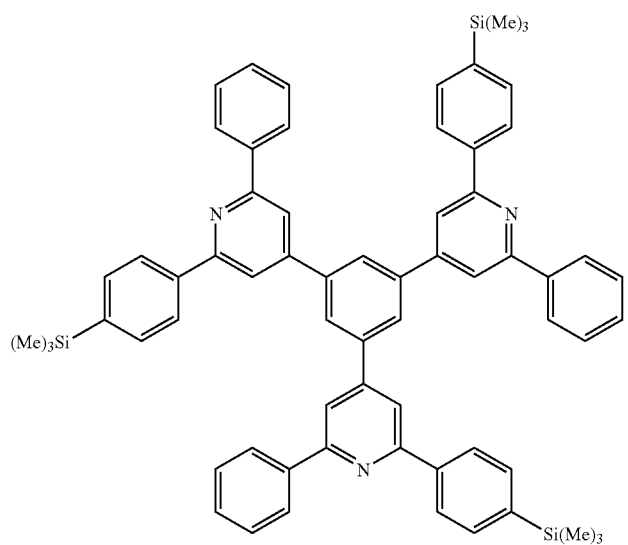

-continued
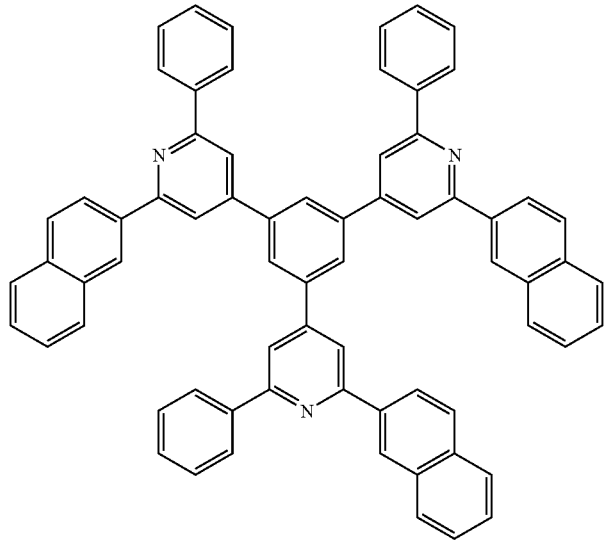
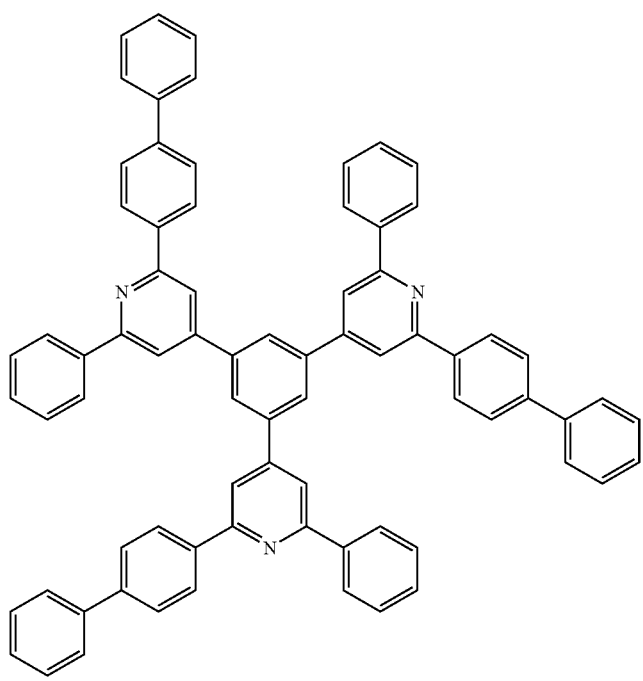

-continued
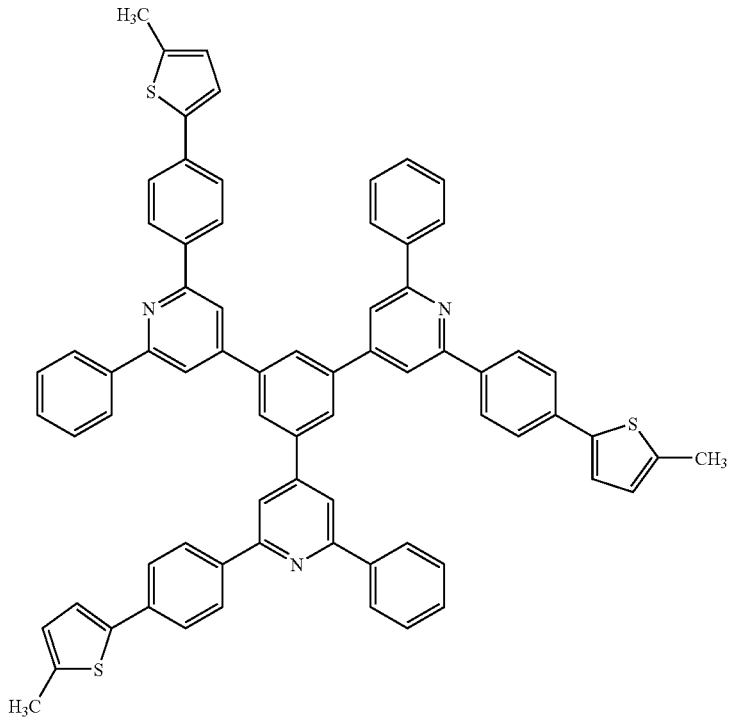
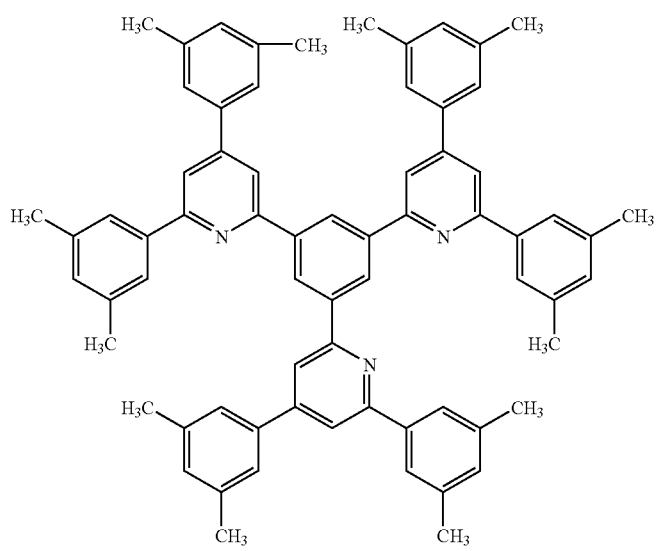

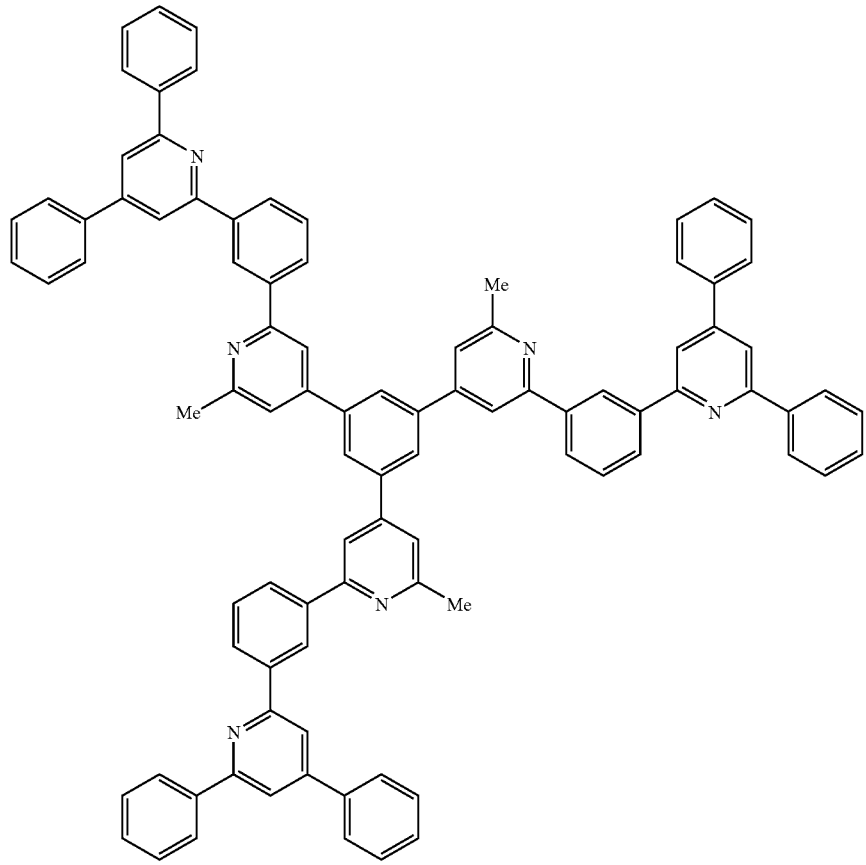
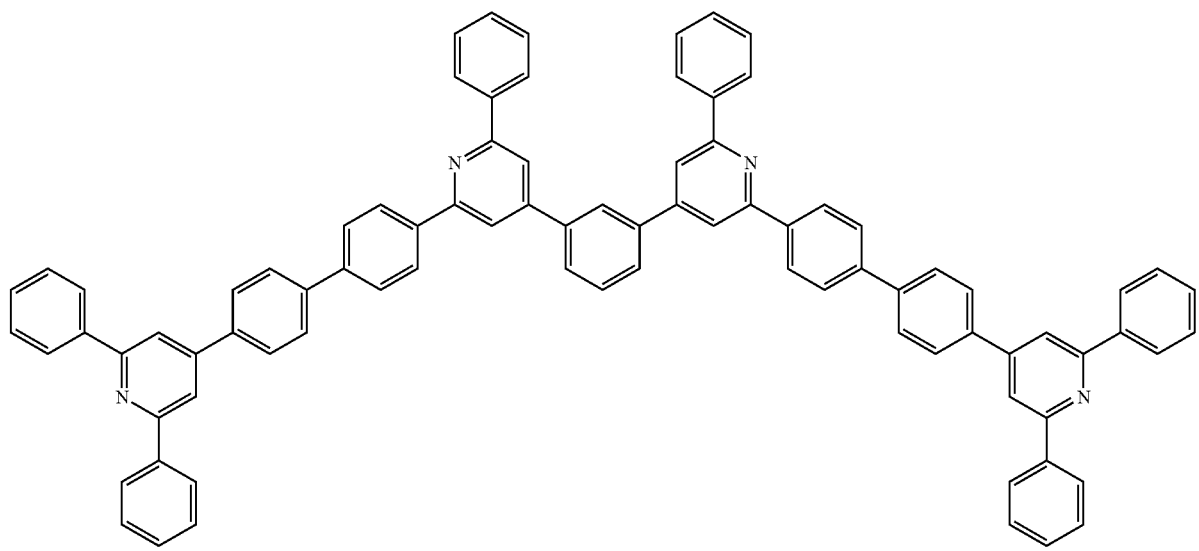

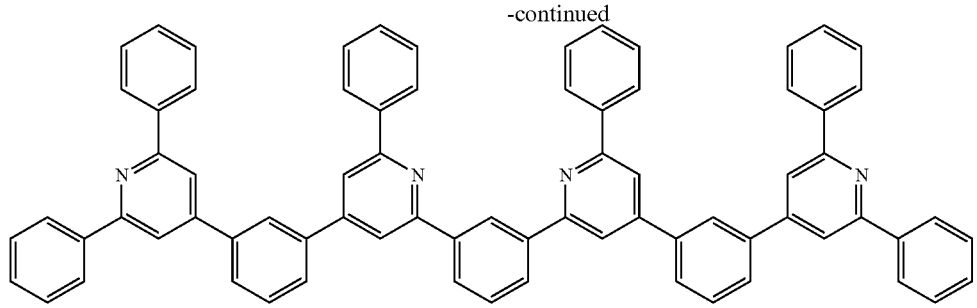

The process for synthesizing the compound of the invention is as has been described hereinbefore. The compound of the invention is useful as a charge transporting material. Also, the compound of the invention is usefully utilized in an electrophotographic photoreceptor as well as the organic electroluminescent element since it has an essentially excellent oxidation-reduction stability.

Further, the compound of the invention has excellent amorphousness, solubility, heat resistance and durability in addition to the high performance the charge transporting material of the invention has. Therefore, it is useful not only as a charge transporting material but as a material for light emission, a material for solar cell, a material for battery (e.g., an electrolytic solution, an electrode, a separation membrane or a stabilizer), a material for medical use, a material for paint, a material for coating, a material for organic semi-conductor, a material for toiletries, a material for antistatic material and a material for thermoelectric element.

EXAMPLES

Next, the invention is more specifically described by reference to Examples. However, the invention is not limited to the following Examples as long as the gist of the invention is not exceeded.

Synthesis Examples

Synthesis examples of compounds of the invention and compounds to be used as charge transporting materials of the invention are shown below as Synthesis Examples 1 to 26. The glass transition temperature was determined by DSC measurement, the gasification temperature was determined by Tg-DTA measurement, and the melting point was determined by DSC measurement or Tg-DTA measurement.

Synthesis Example 1

End Product 1 to End Product 2

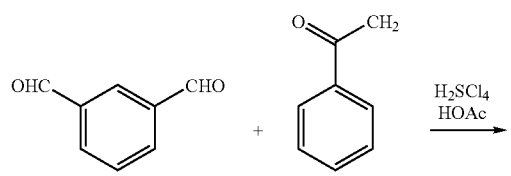

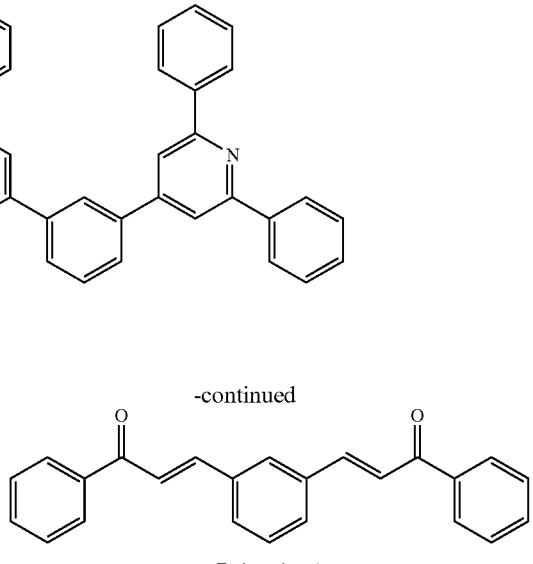

End product 1

Sulfuric acid (8.0 ml) was added to a mixture of isophthalaldehyde (2.7 g), acetophenone (9.6 g) and acetic acid (57 ml) in the atmosphere at room temperature, followed by stirring at room temperature for 6 hours. After adding methanol (50 ml) to the thus-obtained solution and stirring, a precipitate was collected by filtration and washed with methanol to obtain end product 1 (2.6 g).

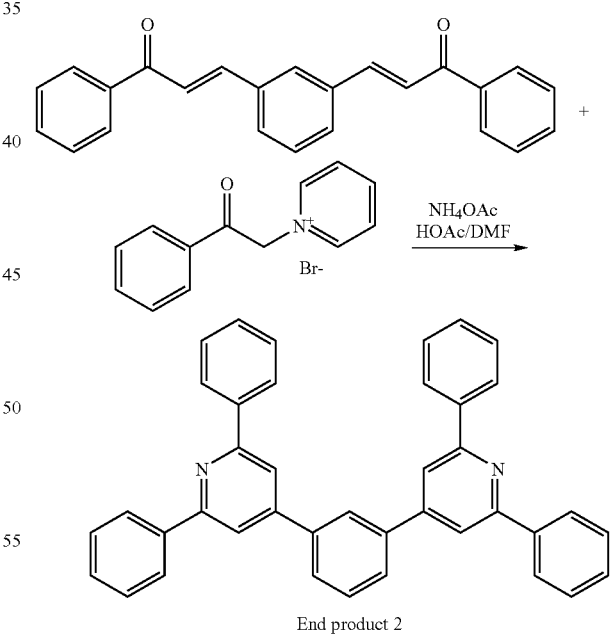

End product 2

End product 1 (2.6 g), 1-phenacylpyridinium bromide (6.3 g), ammonium acetate (29 g), acetic acid (130 ml) and N,N-dimethylformamide (130 ml) were stirred in a nitrogen stream for 8.5 hours while heating under reflux, and water (80 ml) and methanol (80 ml) were added to the thus-obtained solution, followed by stirring. The precipitate formed was collected by filtration and, after washing with methanol, the filtrate was recrystallized from toluene-ethanol to purify. Thus, end product 2 (1.7 g) was obtained. The product was identified as end product 2 through EI-MS (m/z=536(M+)) and 1H-NMR.

$^1$H-NMR (270 MHz, CDCl3), 8.25-8.21 (m, 8H), 8.06 (t, 1H), 7.96 (s, 4H), 7.87-7.83 (dd, 2H), 7.73-7.68 (dd, 1H), 7.56-7.43 (m, 12H)

This compound had a glass transition temperature of 79° C., a melting point of 205° C., and a gasification temperature of 414° C.

Synthesis Example 2

End Products 3 and 4

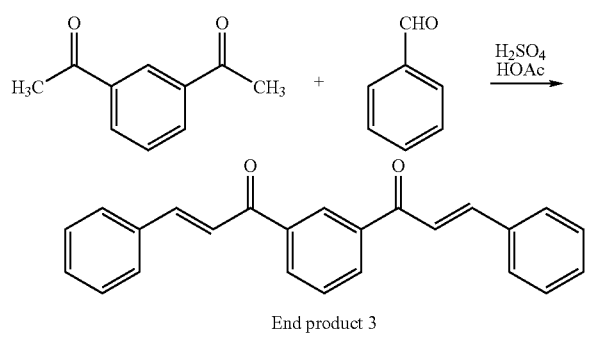

To a mixture of 1,3-diacetylbenzene (3.2 g), benzaldehyde (9.6 g) and acetic acid (57 ml) was added concentrated sulfuric acid (8.0 ml) in the atmosphere, and the mixture was stirred for 7 hours at room temperature. Water (10 ml) and methanol (50 ml) were added to the thus-obtained solution and, after stirring, a precipitate was collected by filtration and washed with methanol to obtain an end product 3 (6.0 g).

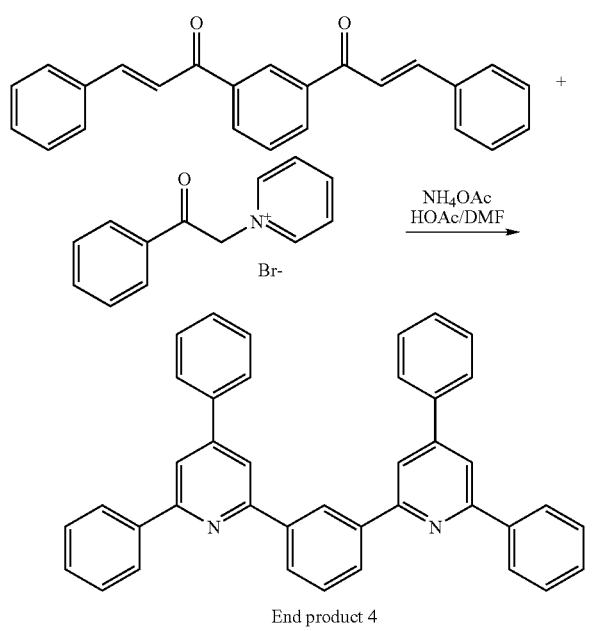

End product 4

End product 3 (3.4 g), 1-phenacylpyridinium bromide (8.3 g), ammonium acetate (39 g), acetic acid (150 ml) and N,N-dimethylformamide (150 ml) were stirred in a nitrogen stream for 5.7 hours while heating under reflux, and water (200 ml) and methanol (100 ml) were added to the thus-obtained solution, followed by stirring. A precipitate formed was collected by filtration and, after washing with methanol, the filtrate was recrystallized from toluene-ethanol to purify. Thus, end product 4 (3.9 g) was obtained. The product was identified as end product 4 through DEI-MS (m/z=536 (M+)) and 1H-NMR.

$^1$H-NMR (270 MHz, CDCl3), 9.01 (s, 1H), 8.32-8.25 (m, 6H), 8.019-8.015 (d, 2H), 7.95-7.94 (d, 2H), 7.81-7.78 (m, 4H), 7.71-7.65 (t, 1H), 7.59-7.46 (m, 12H)

This compound had a glass transition temperature of 71° C., a melting point of 233° C., and a gasification temperature of 449° C.

Synthesis Example 3

End Products 5 and 6

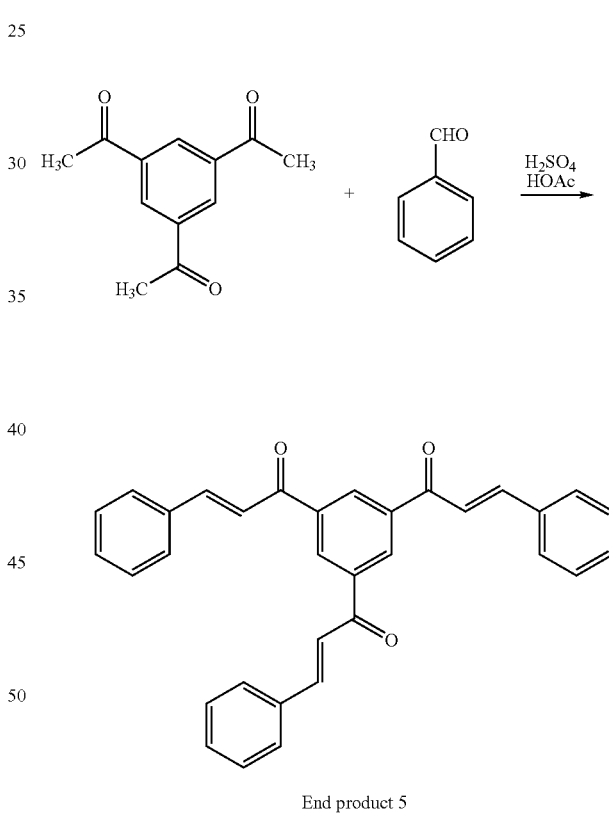

End product 5

To a mixture of 1,3,5-triacetylbenzene (3.1 g), benzaldehyde (8.0 g) and acetic acid (43 ml) was added concentrated sulfuric acid (6.0 ml) in the atmosphere at room temperature, and the mixture was stirred for 21 hours at room temperature. Water (100 ml) was added to the thus-obtained solution and, after stirring, a precipitate was collected by filtration and washed with water and methanol to obtain an end product 5 (3.5 g).

Synthesis Example 4

End Products 7 and 8

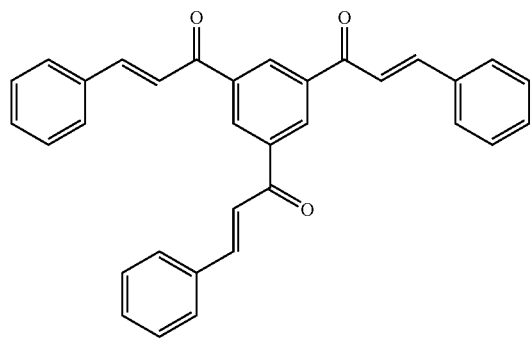

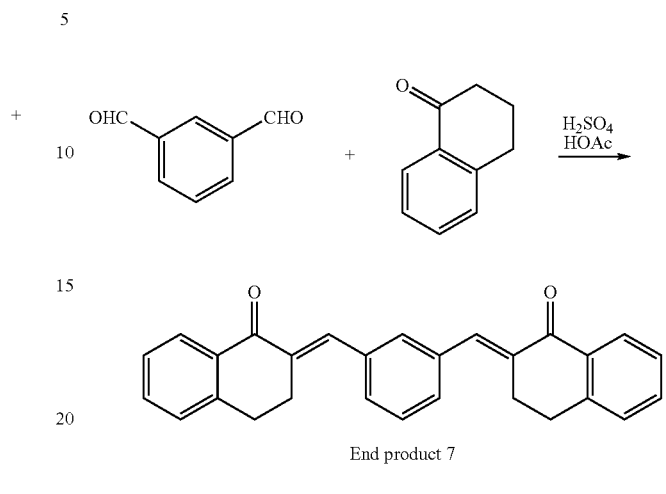

End product 7

To a mixture of isophthalaldehyde (2.7 g), α-tetralone (8.8 g) and acetic acid (57 ml) was added concentrated sulfuric acid (6.4 ml) in the atmosphere at room temperature, and the mixture was stirred for 6.5 hours at room temperature. Water (100 ml) and ethanol (100 ml) were added to the thus-obtained solution and, after stirring, a precipitate was collected by filtration and washed with methanol to obtain an end prouct 7 (6.5 g).

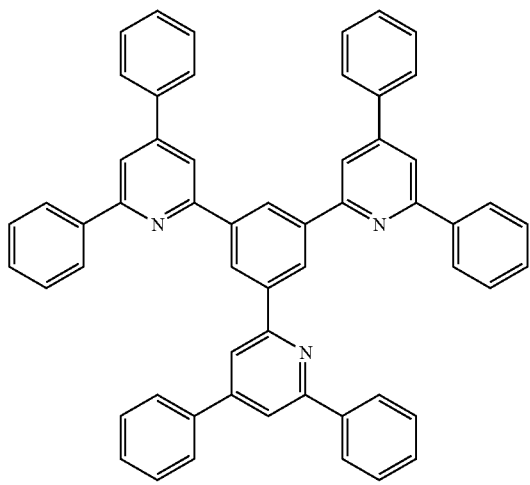

End product 6

The end product 5 (0.47 g), 1-phenacylpyridinium bromide (1.3 g), ammonium acetate (5.8 g), acetic acid (37 ml) and N,N-dimethylformamide (37 ml) were stirred in a nitrogen stream for 6 hours while heating under reflux, and water (100 ml) was added to the thus-obtained solution, followed by stirring. A precipitate formed was collected by filtration and, after washing with water, the precipitate was purified by washing in a suspended state in chloroform-ethanol under heating to obtain an end product 6 (0.38 g). The product was identified as end product 6 through DEI-MS (m/z=765(M+)) and 1H-NMR.

$^{1}$H-NMR (270 MHz, CDCl3), 9.11 (s, 3H), 8.34-8.31 (d, 6H), 8.133-8.128 (d, 3H), 7.993-7.998 (d, 3H), 7.84-7.82 (d, 6H), 7.57-7.48 (m, 18H)

This compound had a melting point of 384° C., a gasification temperature of 523° C., and a glass transition temperature Tg of 225° C.

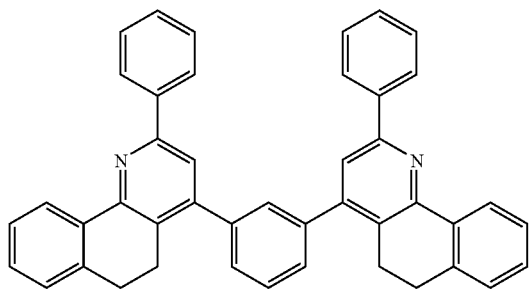

End product 8

The end product 7 (6.5 g), 1-phenacylpyridinium bromide (14 g), ammonium acetate (65 g), acetic acid (240 ml) and N,N-dimethylformamide (240 ml) were stirred in a nitrogen stream for 18 hours while heating under reflux, and the thus-obtained solution was allowed to cool. A precipitate formed was collected by filtration and, after washing with ethanol, the precipitate was purified by washing in a suspended state in ethanol under heating, followed by recrystallization from toluene-pyridine-ethanol, thereby obtaining an end product 8 (2.0 g). The product was identified as end product 8 through EI-MS (m/z=588(M+)) and 1H-NMR.

$^1$H-NMR (270 MHz, CDCl3), 8.60-8.57 (dd, 2H), 8.21-8.18 (td, 4H), 7.66 (s, 2H), 7.64-7.61 (d, H), 7.53-7.32 (m, 13H), 7.27-7.16 (m, 2H), 3.05-2.89 (m, 8H)

Synthesis Example 5

End Products 9 to 10

Isophthalaldehyde (4.0 g), 1-acetonaphthene (15.3 g), concentrated sulfuric acid (9.6 ml) and acetic acid (86 ml) were stirred in the atmosphere at room temperature for 6 hours. To the thus-obtained solution were added, under stirring, water (100 ml) and methanol (50 ml), and an oily product precipitated was dissolved by adding toluene. After extracting, the toluene layer was washed with successive, an aqueous solution of sodium bicarbonate, a solution of sodium chloride and water. After concentrating the toluene layer, the concentrate was purified by silica gel column chromatography to obtain an oily end product 9 (13 g).

The end product 9 (5.0 g), 1-phenacylpyridinium bromide (9.5 g), ammonium acetate (43.9 g), acetic acid (110 ml) and N,N-dimethylformamide (110 ml) were stirred for 8 hours while heating under reflux, and the thus-obtained solution was poured into water (250 ml). A precipitate formed was collected by filtration and, after washing with methanol (300

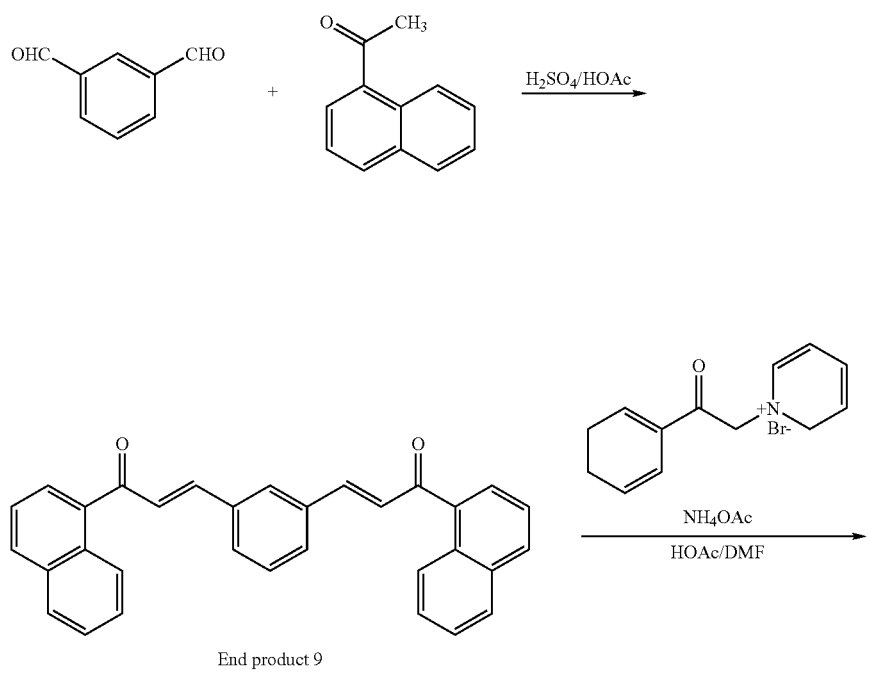

End product 9

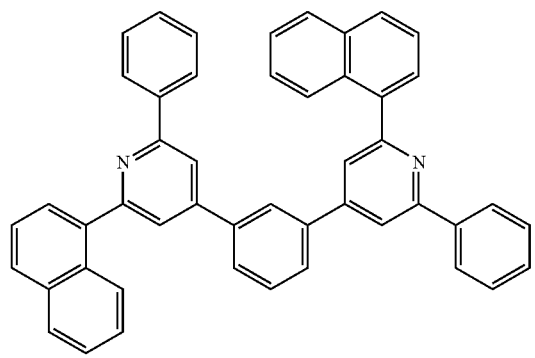

End product 10 ml), the precipitate was purified by silica gel column chromatography, thereby obtaining an end product 10 (1.75 g).
The product was identified as end product 10 through DEI-MS (m/z=636(M+)).
This compound had a gasification temperature of 486° C., and a glass transition temperature Tg of 106° C.
Synthesis Example 6
End Products 11 to 13
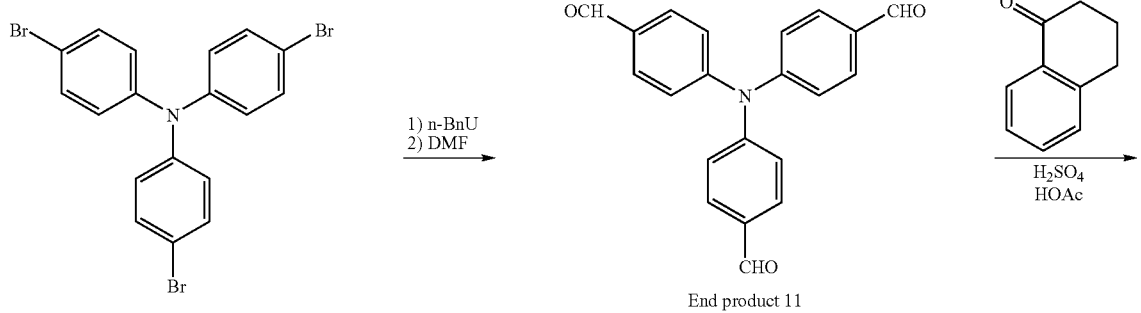
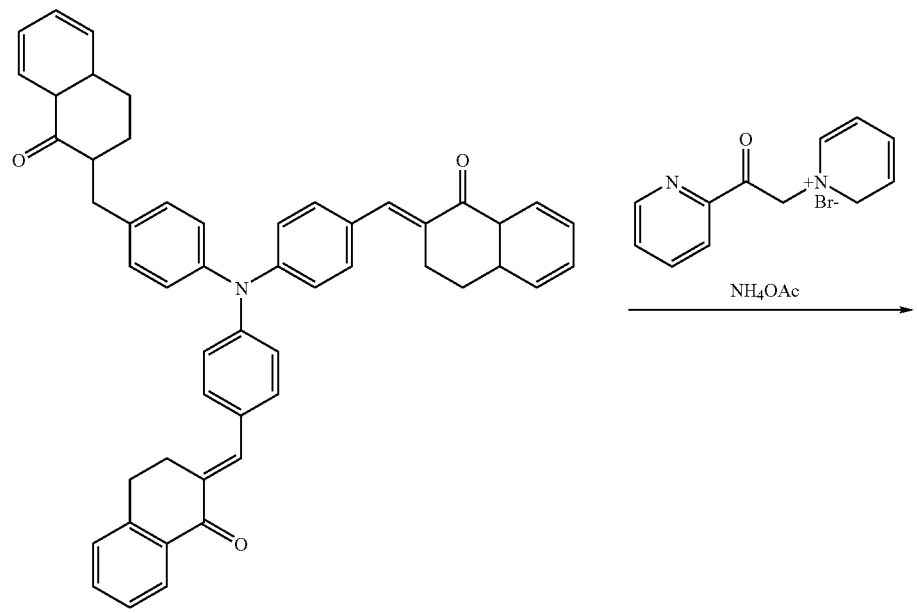

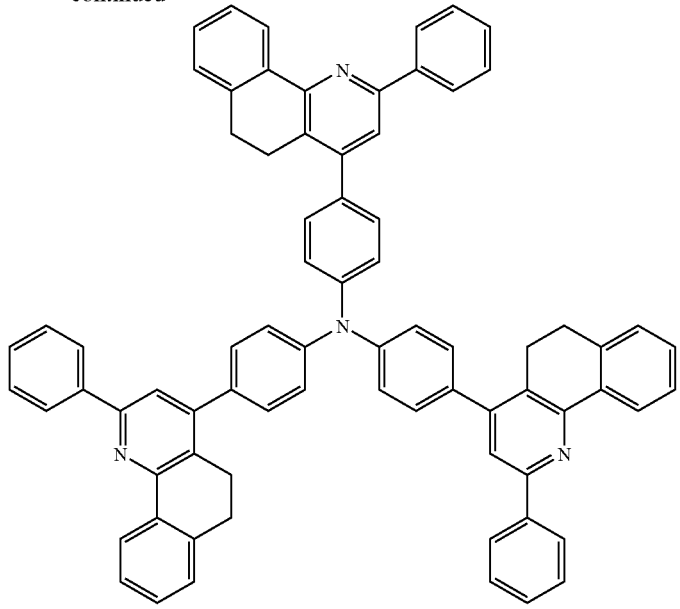

End product 13

To a solution of tris(4-bromophenyl)amine (4.8 g) in anhydrous tetrahydrofuran (160 ml) was dropwise added a solution of n-butyllithium (1.58M n-hexane solution; 21 ml) in anhydrous tetrahydrofuran (15 ml) over 15 minutes in a nitrogen atmosphere at −78° C., followed by stirring the solution for 70 minutes. Thereafter, anhydrous N,N-dimethylformamide (7.7 ml) was dropwise added thereto over 5 minutes, and the resulting solution was further stirred for 3.3 hours at room temperature for 30 minutes at 78° C. After adding ethyl acetate (10 ml) and methanol (100 ml) to the thus-obtained solution, the solvent was distilled off, and the residue was extracted with methylene chloride (150 ml), and washed with water (150 ml). The thus-obtained mixture was purified by silica gel chromatography to obtain an end product 11 (1.3 g). The product was identified as end product 11 through FAB-MS (m/z 329(M+), 330(M+H+)).

To a mixture of the end product 11 (1.3 g), α-tetralone (2.6 g) and acetic acid (22 ml) was added concentrated sulfuric acid (1.9 ml) in the atmosphere at room temperature, and the mixture was stirred for 7 hours at room temperature. Water (150 ml) and methanol (50 ml) were added to the thus-obtained solution and, after stirring, a precipitate was collected by filtration and washed with methanol to obtain an end product 12 (2.5 g).

The end product 12 (1.4 g), 1-phenacylpyridinium bromide (2.5 g), ammonium acetate (11.6 g), acetic acid (46 ml) and N,N-dimethylformamide (46 ml) were stirred in a nitrogen stream for 8 hours while heating under reflux, and water (50 ml) and methanol (50 ml) were added to the thus-obtained solution, followed by stirring. A precipitate formed was collected by filtration and, after washing with water, the precipitate was purified by washing in a suspended state in methanol (80 ml). Further, after recrystallization from chloroform-methanol, part of the product was purified by GPC, thereby obtaining an end product 13 (0.1 g). The product was identified as end product 13 through EEI-MS (m/z=1010(M+)) and 1H-NMR.

$^1$H-NMR (270 MHz, CDCl3), 8.60-8.57 (d, 3H), 8.22-8.19 (d, 6H), 7.68-7.65 (m, 3H), 7.56-7.25 (m, 30H)

Synthesis 7

End Products 14 and 15

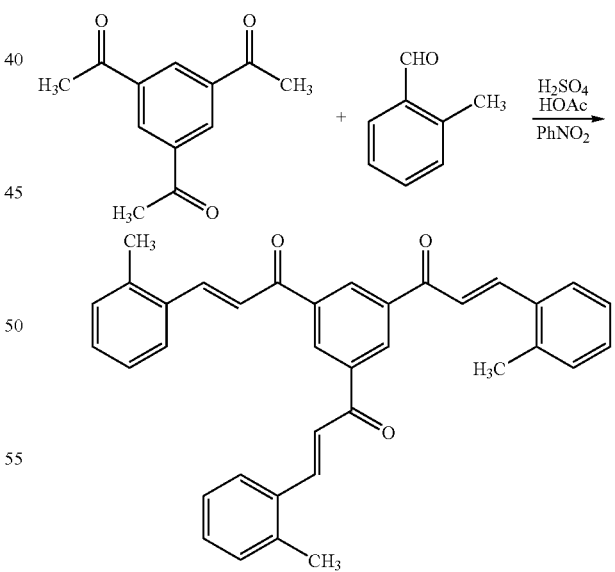

End product 14

To a mixture of 1,3,5-triacetylbenzene (5.2 g), o-tolualdehyde (18.5 g) and acetic acid (71 ml) was added concentrated sulfuric acid (16 ml) in the atmosphere at room temperature, and the mixture was stirred for 6.7 hours at room temperature. Water (100 ml) and methanol (50 ml) were added to the thus-obtained solution and, after stirring, a precipitate was collected by filtration and washed with methanol, then washed in a suspended state in methanol (150 ml), and collected by filtration and washed with methanol, thereby obtaining a mixture containing an end product 14. To a mixture of the resulting mixture, o-tolualdehyde (9.0 g), acetic acid (70 ml) and nitrobenzene (20 ml) was added concentrated sulfuric acid (8.0 ml) in the atmosphere at room temperature, and the mixture was stirred for 5 hours at room temperature. Water (100 ml) and ethanol (80 ml) were added to the thus-obtained solution and, after irradiating with ultrasonic wave for 10 minutes, a precipitate was collected by filtration and washed in a suspended state in a mixed solvent of ethanol (200 ml)-methanol (100 ml), and collected by filtration and washed with ethanol, thereby obtaining an end product 14 (12.2 g).

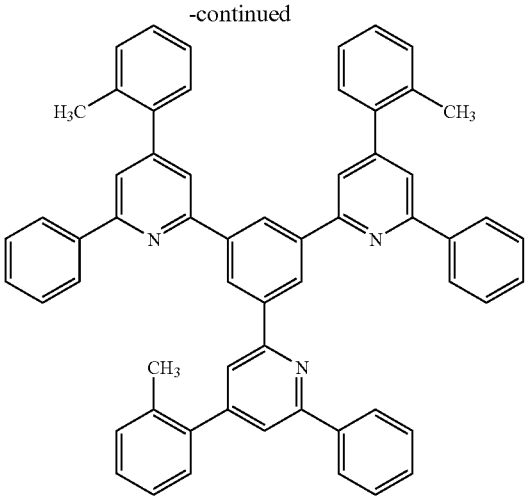

End product 15

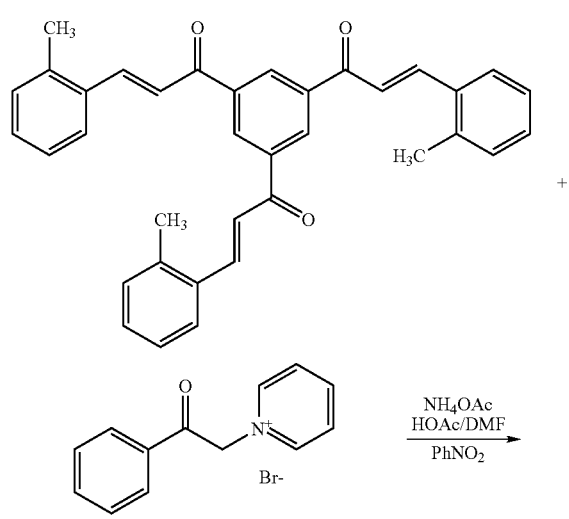

The end product 14 (12.2 g), 1-phenacylpyridinium bromide (29.9 g), ammonium acetate (166 g), acetic acid (280 ml), N,N-dimethylformamide (250 ml) and nitrobenzene (70 ml) were stirred for 10.5 hours while heating under reflux, and water (200 ml) and ethanol (100 ml) were added to the thus-obtained solution, followed by stirring. A precipitate formed was collected by filtration and, after washing with ethanol, the precipitate was purified by washing in a suspended state in ethanol (500 ml) under heating (for 2 hours), then washing in a suspended state in chloroform (200 ml)-toluene (250 ml) under heating (for 1.5 hours) to obtain an end product 15 (8.9 g). The product was identified as end product 15 through DEI-MS (m/z=807(M+)) and 1H-NMR. This compound had a glass transition temperature of 105° C., a melting point of 280° C., and a gasification temperature of 507° C.

Synthesis Example 8

End Products 16 to 18

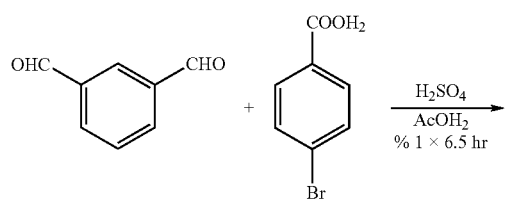

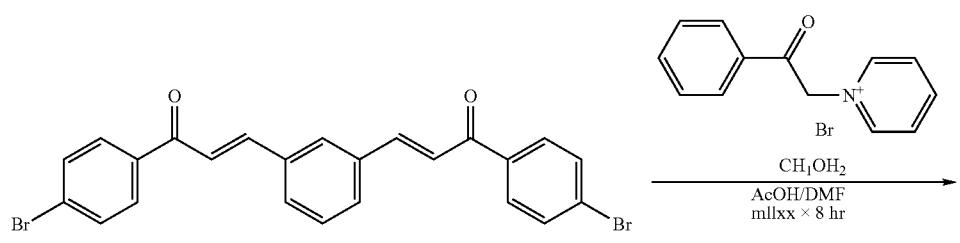

End product 16

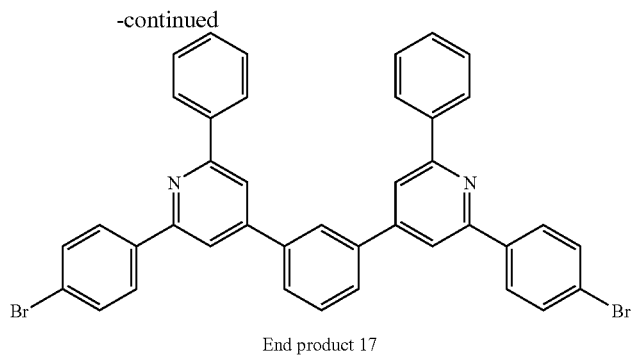

End product 17

To a solution obtained by stirring isophthalaldehyde (4.0 g), 4-bromoacetophenone (17.9 g), concentrated sulfuric acid (9.6 ml) and acetic acid (86 ml) at room temperature in the atmosphere for 6.5 hours were added water (100 ml) and methanol. (50 ml) under stirring, and crystals precipitated were collected by filtration. Then, the crystals were washed in a suspended state in 100 ml of methanol to obtain an end product 16 (13.04 g).

The end product 16 (10 g), 1-phenacylpyridinium bromide (16.8 g), ammonium acetate (77.8 g) acetic acid (280 ml) and N,N-dimethylformamide (430 ml) were stirred for 8 hours while heating under reflux, and the thus-obtained solution was poured into water (300 ml) and ethanol (80 ml). A precipitate formed was collected by filtration and, after washing with methanol (300 ml), dissolved in 50 ml of methylene chloride, then reprecipitated in 250 ml of methanol to obtain an end product 17 (11.34 g).

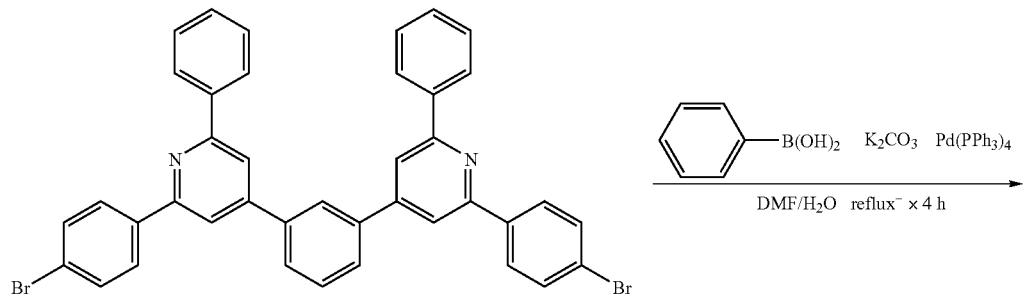

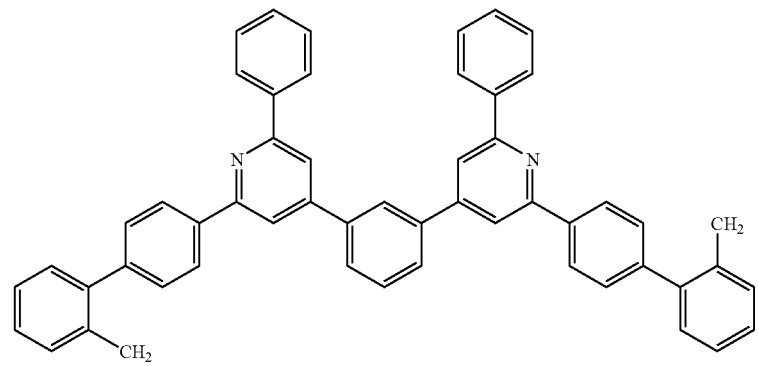

End product 18

The end product 17 (5 g), phenylboric acid (2.25 g), potassium carbonate (3.97 g), ethylene glycol dimethyl ether (70 ml) and water (23 ml) were heated to 80° C. in a nitrogen stream, and tetrakis(triphenylphosphine)palladium (0.416 g) was added thereto, followed by reacting at 80° C. for 4 hours. After the reaction, the reaction solution was extracted with water/chloroform to obtain an organic layer. This was purified by silica gel column chromatography to obtain an end product 18 (2.97 g). The product was identified as end product 18 through DEI-MS (m/z=719). This compound had a gasification temperature of 495° C. and a glass transition temperature Tg of 109° C.

Synthesis Example 9

End Products 19 and 20

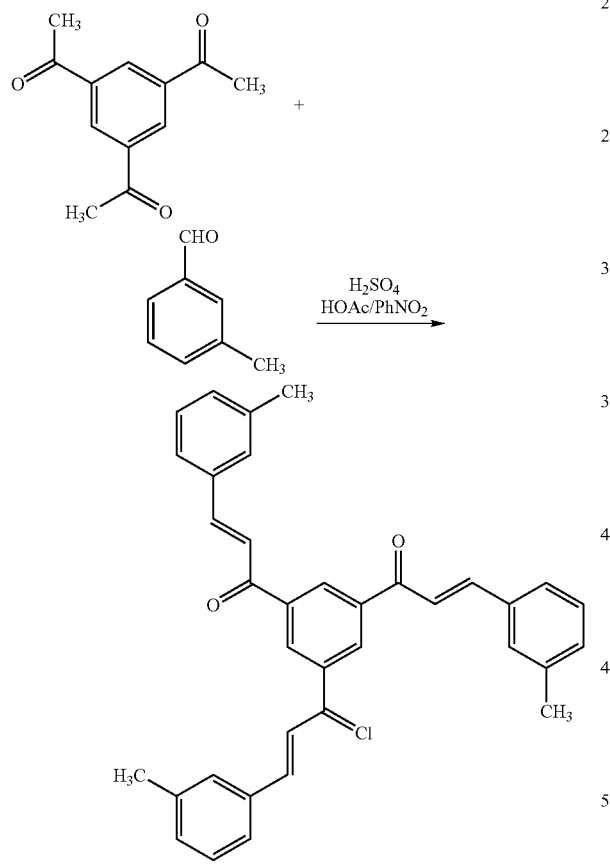

End product 19

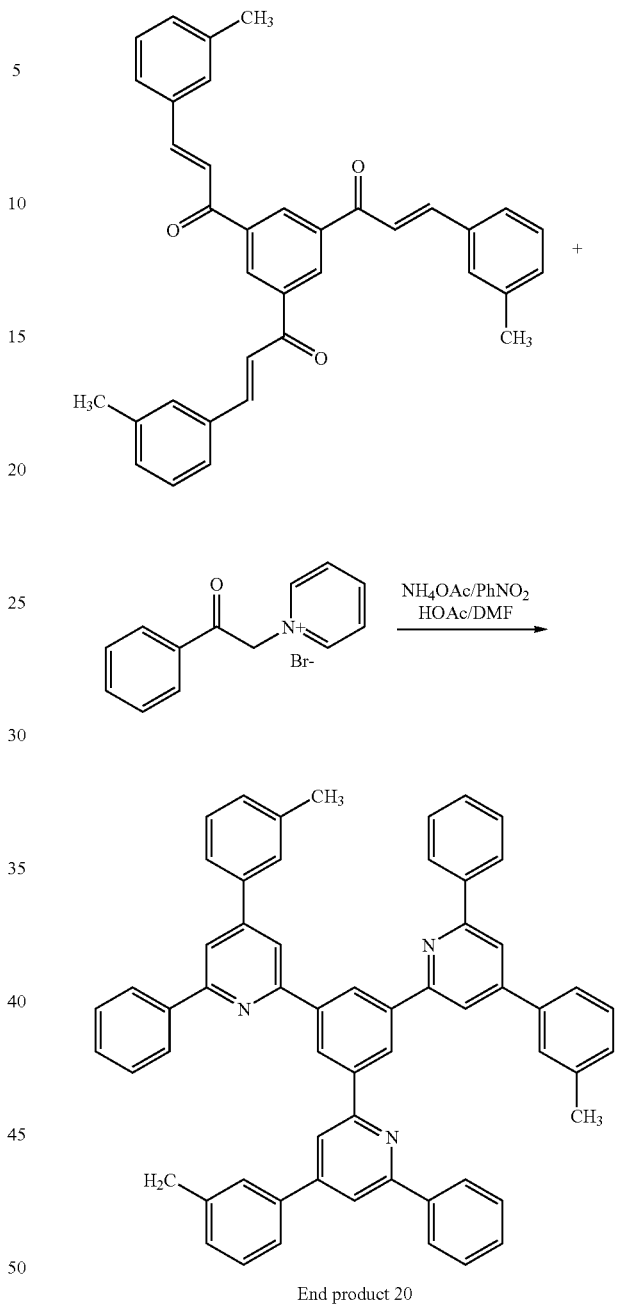

End product 20

To a mixture of 1,3,5-triacetylbenzene (1.03 g), m-tolualdehyde (3.63 g), acetic acid (14 ml) and nitrobenzene (8 ml) was added concentrated sulfuric acid (3.2 ml) in the air at room temperature, and the mixture was stirred for 6 hours at 43 to 45° C. Methanol (70 ml) was added to the thus-obtained solution, then water (30 ml) was added thereto and, after stirring and irradiating with ultrasonic waves, a precipitate was collected by filtration and washed by pouring methanol thereto. The thus-obtained residue was purified by washing in a suspended state in methanol (50 ml), and washing in a suspended state in ethanol (100 ml) while heating under reflux, thereby obtaining an end product 19 (2.23 g).

The end product 19 (2.21 g), 1-phenacylpyridinium bromide (5.41 g), ammonium acetate (30.0 g), acetic acid (49 ml), N,N-dimethylformamide (40 ml) and nitrobenzene (20 ml) were stirred for 7.5 hours while heating under reflux, and methanol (70 ml) was added to the thus-obtained solution, then water (30 ml) was added thereto, followed by stirring and irradiation with ultrasonic waves. A precipitate formed was collected by filtration and, after washing with ethanol, the precipitate was purified by recrystallization from chloroform-methanol to obtain an end product 20 (2.00 g). The product was identified as end product 20 through DEI-MS (m/z 807 (M+)). This compound had a glass transition temperature of 216° C., and a melting point of 304° C.

Synthesis Example 10

End Products 21 to 23

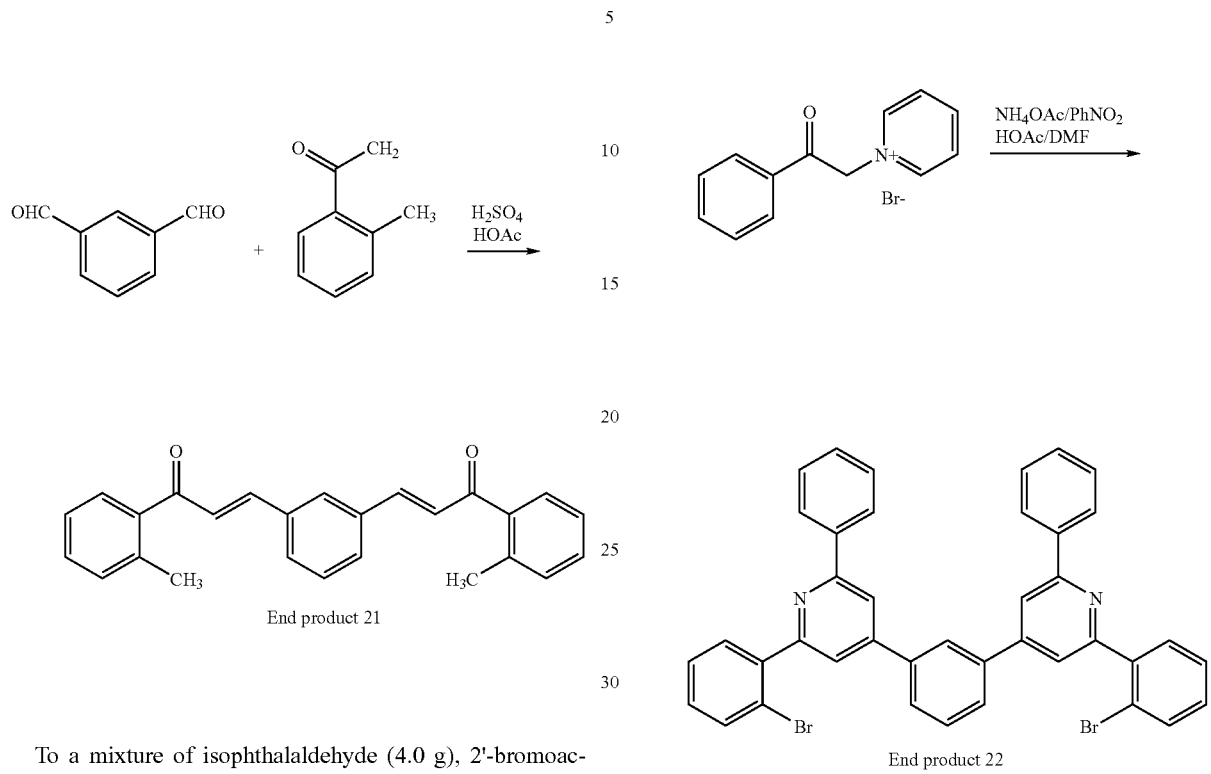

End product 21

End product 22

To a mixture of isophthalaldehyde (4.0 g), 2'-bromoacetophenone (17.9 g) and acetic acid (86 ml) was added concentrated sulfuric acid (14.7 ml) in the air at room temperature, and the mixture was stirred for 6.5 hours at room temperature. Water (50 ml) and ethanol (150 ml) were added to the thus-obtained solution and, after stirring, a precipitate was collected by filtration and purified by washing with ethanol then by washing in a suspended state in ethanol (350 ml) to obtain an end product 21 (10.0 g).

The end product 21 (10.0 g), 1-phenacylpyridinium bromide (16.9 g), ammonium acetate-(77.8 g), acetic acid (230 ml), N,N-dimethylformamide (200 ml) and nitrobenzene (70 ml) were stirred for 6.5 hours while heating under reflux, and water (150 ml) and methanol (100 ml) were added to the thus-obtained solution, followed by stirring. A precipitate formed was collected by filtration and, after washing with methanol, the precipitate was purified by washing in a suspended state in a mixed solvent of methanol (100 ml)-ethanol (100 ml), thereby obtaining an end product 22 (10.5 g).

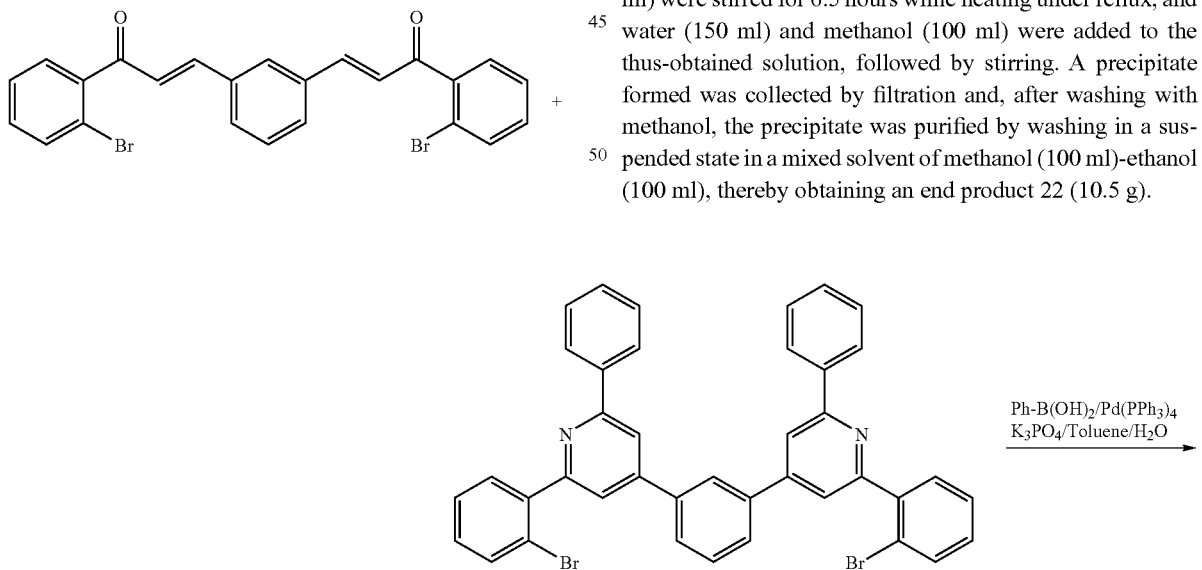

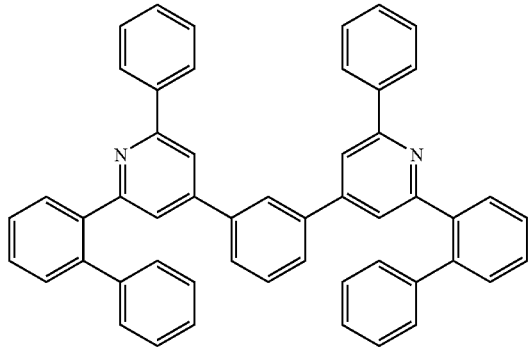

End product 23

A mixture of the end product 22 (10.5 g), phenylboric acid (5.5 g), tetrakis(triphenylphosphine)pallasium (1.4 g), tripotassium phosphate (12.8 g), toluene (200 ml) and ion-exchanged water (30 ml) was stirred for 5.5 hours while heating under reflux, then toluene (50 ml) and water (120 ml) were added thereto, followed by well mixing. Only an organic layer was taken out and, after further washing with water (100 ml), dried over anhydrous magnesium sulfate, and filtered. The filtrate was concentrated and purified by silica gel column chromatography to obtain an end product 23 (2.9 g). The product was identified as end product 23 through DEI-MS (m/z=688 (M+)) This compound had a glass transition temperature of 102° C. and a gasification of 466° C., but had no detectable melting point.

Synthesis Example 11

End Products 24 and 25

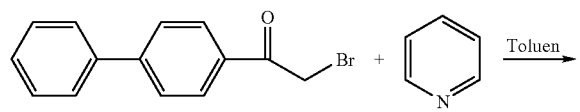

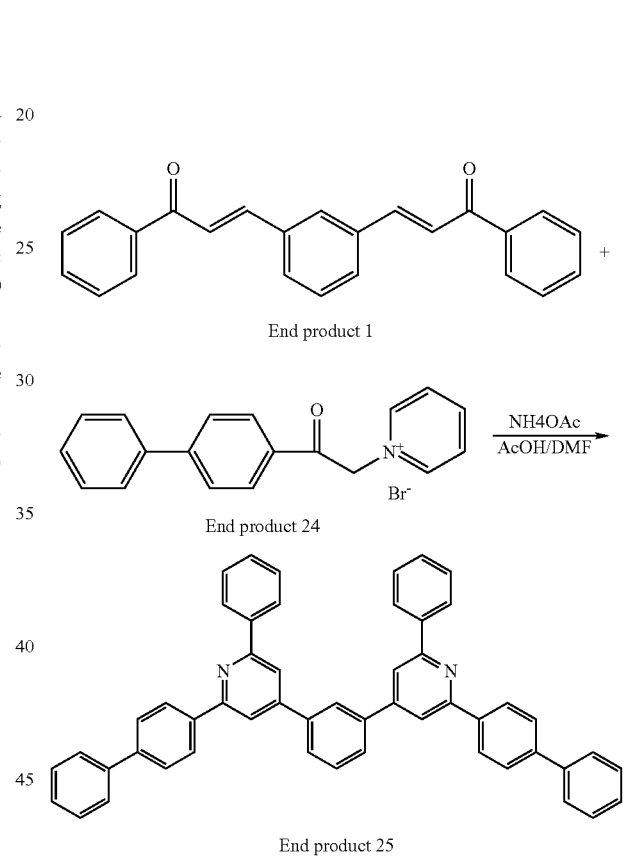

2-Bromo-4'-phenylacetophenone (13.7 g) was dissolved in toluene (85 ml) under heating at 70° C., followed by adding thereto pyridine (7.9 g). Simultaneously with the dropwise addition, crystals separated out. After completion of the dropwise addition, the temperature was raised, and the mixture was stirred at a reflux temperature. After 1 hour, the reaction mixture was allowed to cool. After filtration, crystals were washed in toluene (250 ml) in a suspended state, further in n-hexane (250 ml) in a suspended state. After drying, there was obtained an end product 24 (17.3 g).

To a solution obtained by stirring the end product 1 of Example 1 (3.0 g), the above-obtained end product 24 (9.45 g), ammonium sulfate (34.2 g), acetic acid (127 ml), N,N-dimethylformamide (100 ml) for 7 hours while heating under reflux was added ethanol (80 ml) and, after stirring, the mixture was poured into water (160 ml). A precipitate formed was collected by filtration. The crystals thus obtained were washed by refluxing in ethanol (150 ml) under heating. Recrystallization from toluene (50 ml) and methanol (20 ml) was conducted and, further, the thus-obtained crystals were recrystallized from chloroform (40 ml) and methanol (20 ml) to obtain an end product 25 (1.5 g).

The product was identified as end product 25 through DEI-MS (m/z=688(M+)). This compound had a gasification temperature of 515.5° C. and a glass transition temperature Tg of 111° C.

Synthesis Example 12

End Products 26 to 29

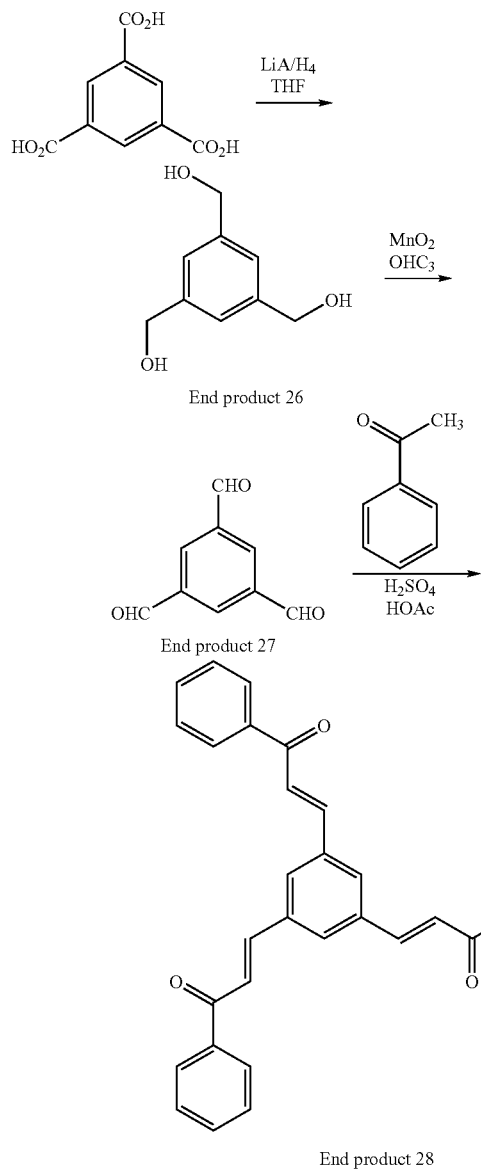

End product 26

End product 27

End product 28

A solution of 5.8 g of trimesic acid in 100 ml of tetrahydrofuran (dehydrated) was dropwise added, under stirring, to a mixture of a solution of lithium aluminum hydride in tetrahydrofuran (1 mol/L) 100 ml and tetrahydrofuran (dehydrated) 100 ml over 17 minutes under cooling with ice in a nitrogen stream, followed by stirring for 27 minutes at room temperature, for 20 minutes while refluxing under heating, further for 3.5 hours at room temperature. To the thus-obtained solution were added ethyl acetate and ice-water to destroy excess lithium aluminum hydride, followed by filtration and washing by pouring ethanol. The thus-obtained solid was dispersed in 250 ml of methylene chloride to extract an organic product, followed by filtration. The thus-obtained filtrate was concentrated to obtain an end product 26 (1.8 g).

The end product 26 (1.8 g), manganese dioxide (activated, 11.3 g) and chloroform (100 ml) were stirred for 8.3 hours in a dry air while heating under reflux, then filtered. The thus-obtained filtrate was concentrated and purified by silica gel column chromatography to obtain an end product 27 (0.6 g). Production of the end product 27 was confirmed through DEI-MS (m/z=162(M$^+$)).

Concentrated sulfuric acid (1.6 ml) was dropwise added to the end product 27 (0.53 g), acetophenone (1.8 g) and acetic acid (14 ml) in a dry air, followed by stirring at 35° C. for 11 hours. Ethanol and water were added thereto to form a precipitate. The precipitate was collected by filtration, and the solid thus obtained was purified by washing in ethanol in a suspended state to obtain an end product 28 (0.63 g).

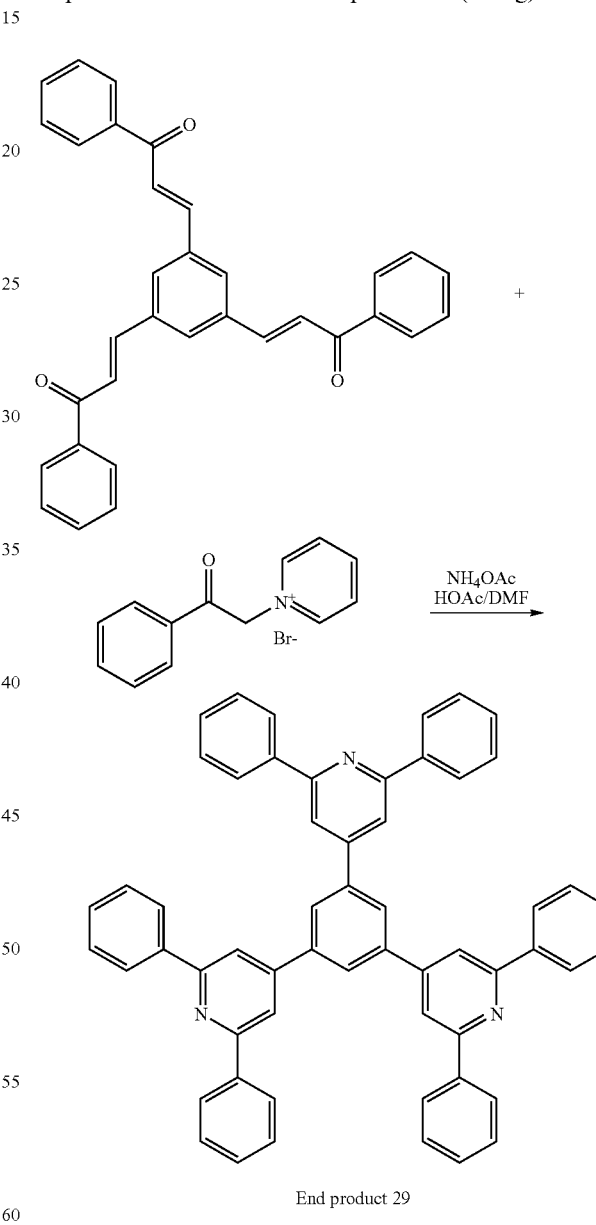

End product 29

The end product 28 (0.47 g), 1-phenacylpyridinium bromide (1.26 g), ammonium acetate (7.1 g), acetic acid (25 ml) and N,N-dimethylformamide (25 ml) were stirred for 6.5 hours while heating under reflux. Methanol and water were added to the thus-obtained mixture to form a precipitate. The precipitate was filtered off, and the filtrate was concentrated.

The thus-obtained residue was purified by silica gel column chromatography, thereby obtaining an end product 29 (0.17 g) The product was identified as end product 29 through MALDI-TOF-MS (m/z=766(M+)). This compound had a melting point of 344° C., a glass transition temperature of 299° C. and a gasification of 524° C.

Synthesis Example 13

End Products 30 to 33

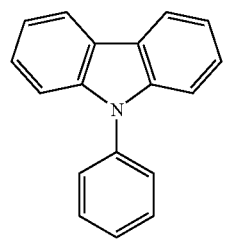

End product 30

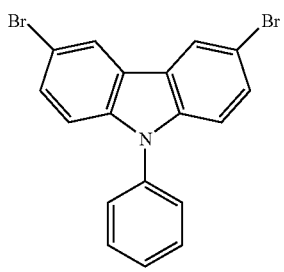

End product 30

A solution of N-bromosuccinimide (15.3 g) in N,N-dimethylformamide (70 ml) was dropwise added to a solution of N-phenylcarbazole (10.2 g) in N,N-dimethylformamide (80 ml) in a nitrogen stream under cooling with ice, followed by stirring at room temperature for 7 hours. 50 ml of water and 100 ml of methanol were added to the thus-obtained solution to form a precipitate. The precipitate was collected by filtration and purified by washing with methanol to obtain an end product 30 (14.8 g).

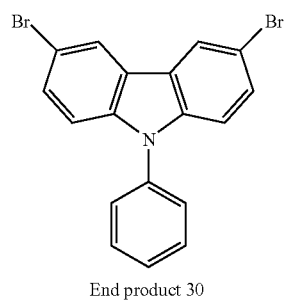

End product 30

-continued

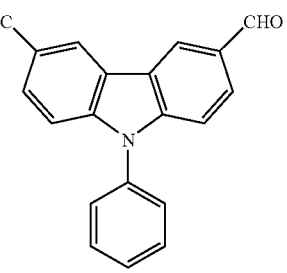

End product 31

A solution of 1.6 M of n-butyllithium in hexane (30.2 ml) was dropwise added to a solution of an end product 30 (8.0 g) in tetrahydrofuran (100 ml) at −70° C. in a nitrogen stream over a period of 15 minutes and stirred for 1 hour. After dropwise adding thereto N,N-dimethylformamide (15.5 ml) at −60° C., the solution was stirred at room temperature for 2 hours. A precipitate thus formed was filtered and extracted with dichloromethane. A solid obtained by concentration was washed in methanol in a suspended state and collected by filtration to obtain an end product 31 (2.28 g). Water was added to the finally obtained filtrate, and a solid precipitated was collected by filtration to further obtain the end product 31 (1.01 g; total 3.29 g).

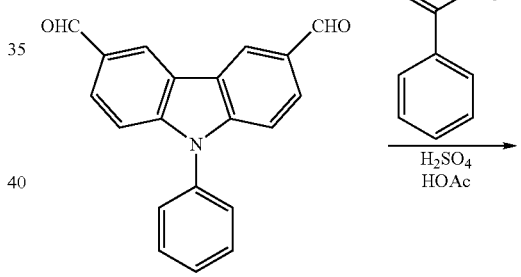

End product 31

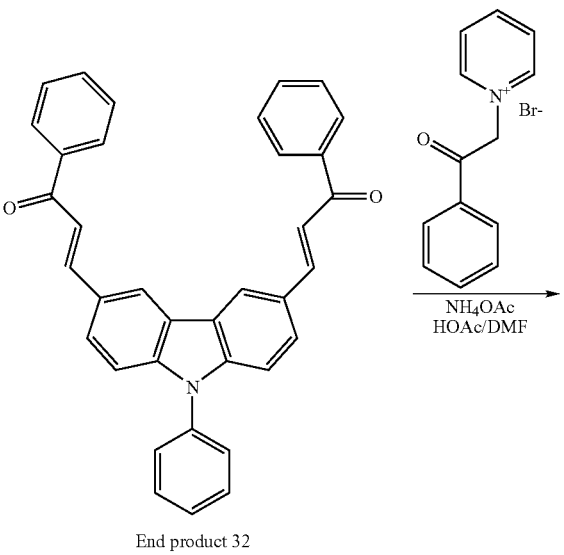

End product 32

-continued

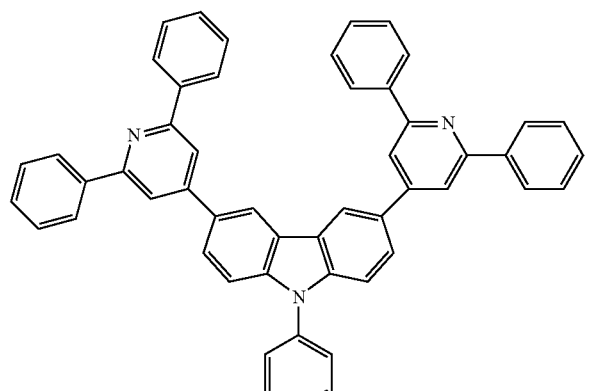

End product 33

Concentrated sulfuric acid (1.3 ml) was added to the end product 31 (1.20 g), acetophenone (1.44 g) and acetic acid (23 ml) in a dry air, followed by stirring at 35 to 40° C. for 8.5 hours. Methanol (20 ml) and water (50 ml) were added thereto to form a precipitate. The precipitate was collected by filtration and washed with methanol. This was washed in methanol by applying ultrasonic waves to obtain an end product 32 (1.90 g).

The end product 32 (1.81 g), 1-phenacylpyridinium bromide (3.00 g), ammonium acetate (14.0 g), acetic acid (62 ml) and N,N-dimethylformamide (62 ml) were stirred for 5 hours while heating under reflux. Thereafter, methanol (20 ml) and water (100 ml) were added thereto. A precipitate thus formed was collected by filtration and washed with methanol. The thus-obtained solid was purified by silica gel column chromatography to obtain an end product 33 (0.26 g).

The product was identified as end product 33 through DEI-MS (m/z=701(M+)). This compound had a melting point of 285° C. and a gasification of 523° C.

Synthesis Example 14

End Product 34

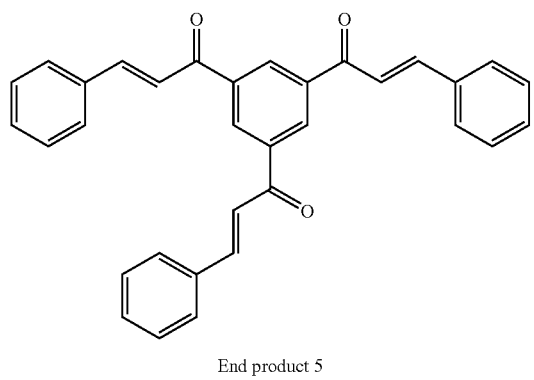

End product 5

-continued

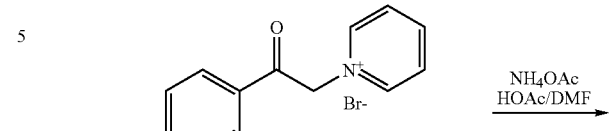

End product 24

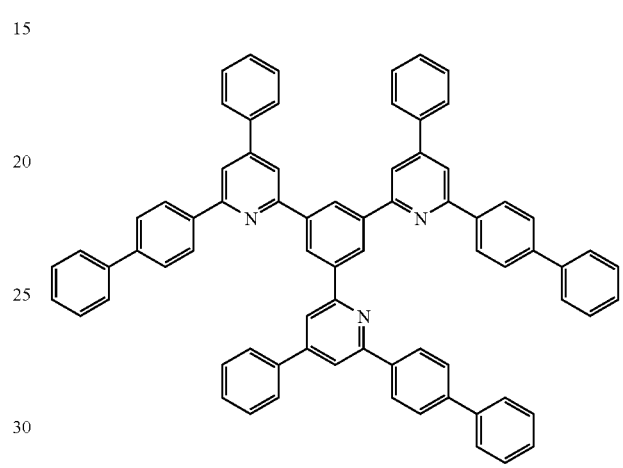

End product 34

The end product 5 (0.70 g), the end product 24 (2.39 g), ammonium sulfate (8.78 g), acetic acid (43 ml) and N,N-dimethylformamide (43 ml) were stirred for 10 hours while heating under reflux in the atmosphere, and methanol (20 ml) was added to the resulting solution, followed by stirring. A precipitate formed was collected by filtration and purified by silica gel column chromatography to obtain an end product 34 (0.52 g).

The product was identified as end product 34 through MALDI-TOF-MS (m/z=994(M+)([M+H]$^+$). This compound had a glass transition temperature of 138° C., a melting point of 340° C., and a gasification temperature of 571° C.

Synthesis Example 15

End Products 35 to 38

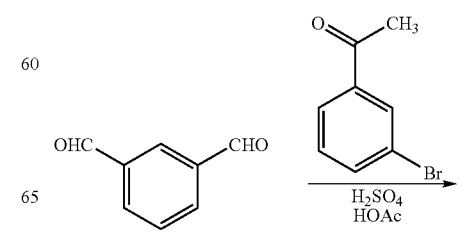

-continued

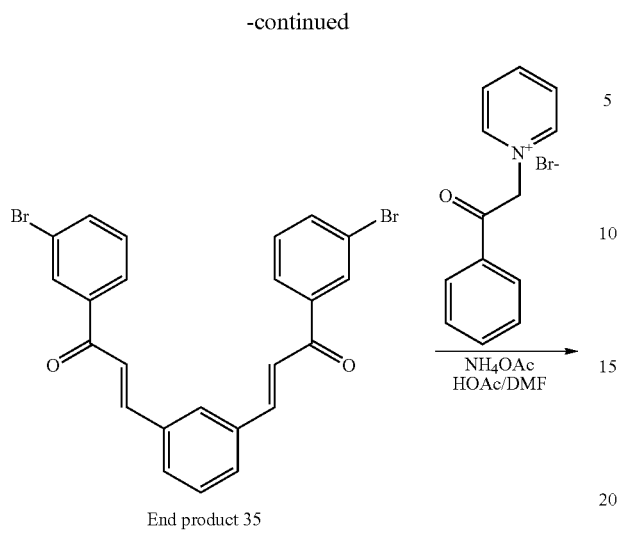

End product 35

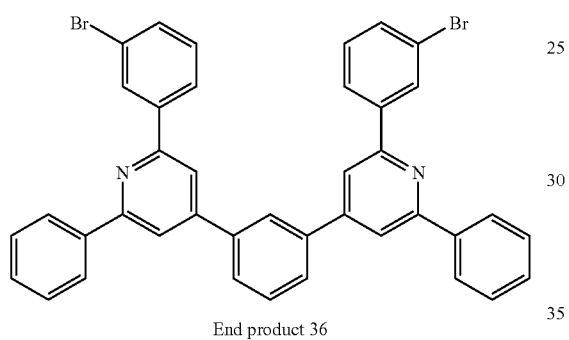

End product 36

To a mixed solution of isophthalaldehyde (6.71 g), 3-bromoacetophenone (20.9 g) and acetic acid (215 ml) was added concentrated sulfuric acid (16.1 ml) in a dry air, and stirred for 9 hours at 35° C. Then, ethanol (70 ml) and water (150 ml) were added thereto, and a precipitated formed was collected by filtration, and washed with methanol. This was purified by washing in methanol while applying ultrasonic waves, thereby obtaining an end product 35 (15.5 g).

The end product 35 (9.92 g), 1-phenacylpyridinium bromide (16.7 g), ammonium acetate (78 g), acetic acid (350 ml) and N,N-dimethylformamide (350 ml) were stirred for 7.5 hours while heating under reflux, and the thus-obtained solution was poured into water (700 ml). A precipitate formed was collected by filtration and purified by washing with methanol to obtain an end product 36 (11.3 g).

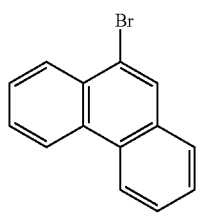

+

-continued

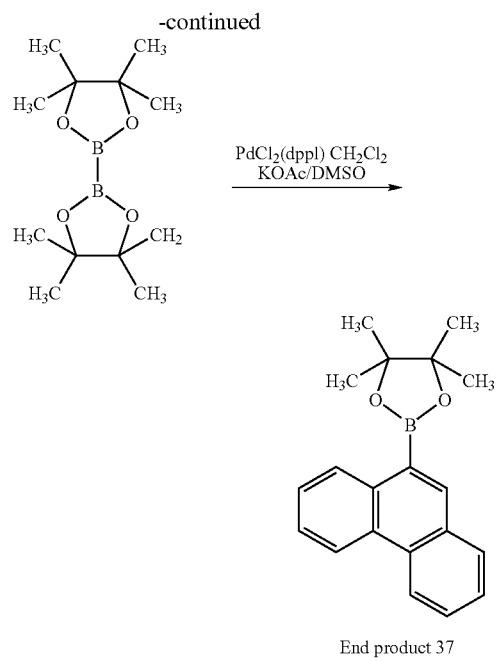

End product 37

To a mixed solution of 9-bromophenanthrene (18.4 g), bis(pinacolato)diboron (20.0 g), potassium acetate (23.9 g) and dimethylsulfoxide (420 ml) was added [1,1'-bis(diphenylphosphino)ferrocene]dichloropalladium (II) dichloromethane complex (1:1) (1.75 g) in a nitrogen stream at 60° C., followed by stirring at 80° C. for 8.2 hours. The thus-obtained solution was poured into 1 L of water to form a precipitate. After removing the supernatant, the resulting solid was purified by silica gel column chromatography to obtain an end product 37 (13.3 g).

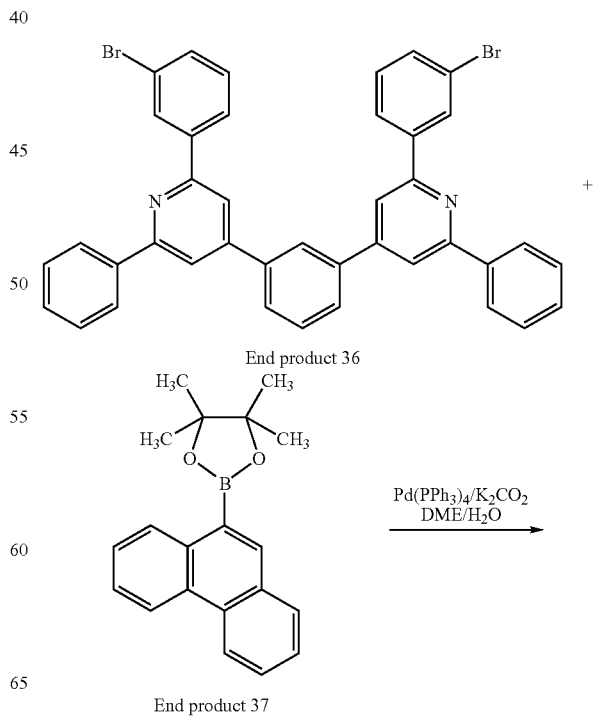

End product 37

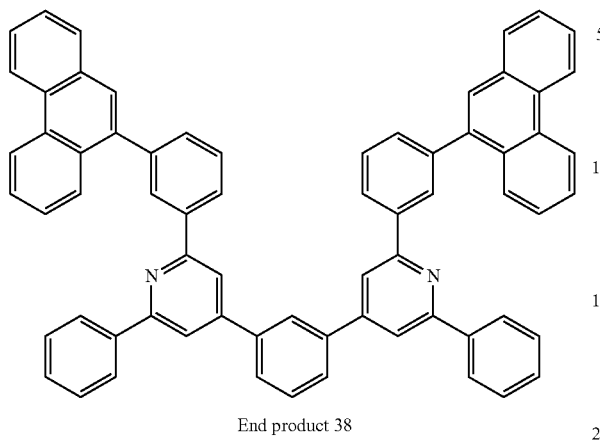

End product 38

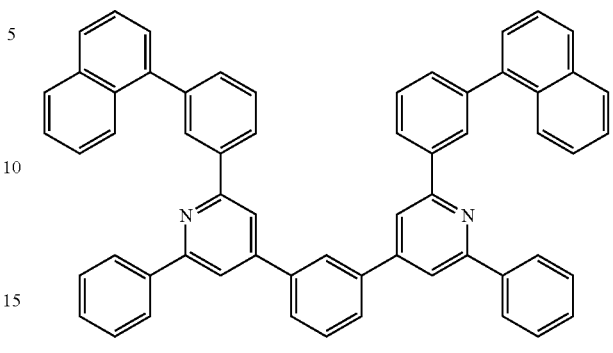

End product 39

To a mixture of the end product 36 (3.47 g), the end product 37 (4.26 g) and dimethoxyethane (50 ml) were successively added tetrakis(triphenylphosphine)palladium (0.46 g) and a 2M potassium carbonate aqueous solution (10 ml), followed by stirring for 5.5 hours while heating under reflux. This was extracted with dichloromethane (100 ml), and the extract was washed with salt water (50 ml), dried over magnesium sulfate, filtered, and concentrated. The thus-obtained solid was purified by silica gel column chromatography to obtain an end product 38 (3.59 g).

The product was identified as end product 38 through DEI-MS (m/Z=888(M+)). This compound had a glass transition temperature of 148° C. and a gasification temperature of 558° C., and did not have a detectable melting point.

Synthesis Example 16

End Product 39

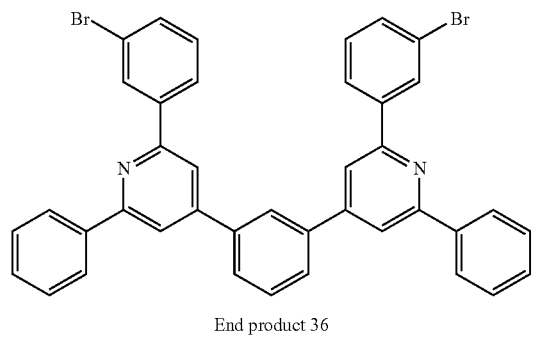

End product 36

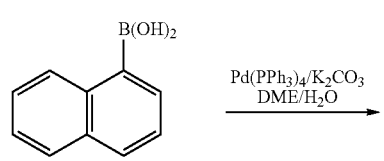

To a mixture of the end product 36 (2.78 g), 1-naphthylboric acid (1.79 g) and dimethoxyethane (40 ml) were successively added tetrakis(triphenylphosphine)palladium (0.37 g) and a 2M potassium carbonate aqueous solution (8 ml), followed by stirring for 6.3 hours while heating under reflux. This was extracted with dichloromethane, and the extract was washed with salt water (50 ml), dried over magnesium sulfate and filtered. The filtrate was concentrated. The thus-obtained solid was purified by silica gel column chromatography to obtain an end product 39 (2.66 g).

The product was identified as end product 39 through DEI-MS (m/Z=788(M+)). This compound had a glass transition temperature of 113° C. and a gasification temperature of 530° C., and did not have a detectable melting point.

Synthesis Example 17

End Products 40 to 43

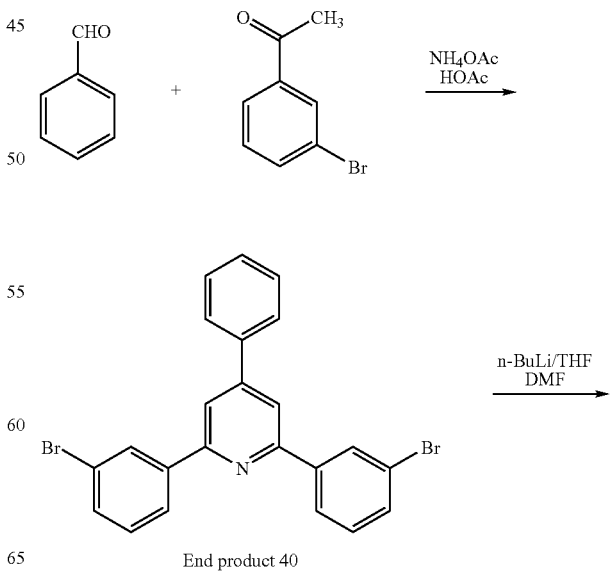

End product 40

-continued

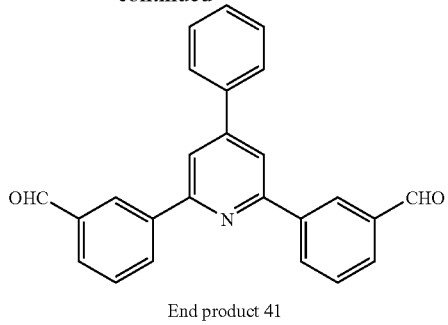
End product 41

A mixed solution of 3-bromoacetophenone (11.9 g), benzaldehyde (3.18 g), ammonium acetate (30.0 g) and acetic acid (75 ml) was stirred for 55 minutes while heating under reflux and bubbling thereinto a dry air. After allowing the thus-obtained solution to cool, a precipitate was collected by filtration, washed with acetic acid/water (7/3; 100 ml) and further washed in methanol in a suspended state, followed by purifying by recrystallization from toluene-ethanol to obtain an end product 40 (3.20 g).

To a mixed solution of the end product 40 (3.19 g), diethyl ether (160 ml) and tetrahydrofuran (115 ml) was added a 1.58 M n-butyllithium hexane solution (15.0 ml) over a period of 10 minutes in a nitrogen stream at −77° C. After further stirring for 4.7 hours, N,N-dimethylformamide (5.3 ml) was added thereto, followed by stirring for 2.8 hours at room temperature. A 1 N hydrochloric acid aqueous solution (24 ml) was added to the thus-obtained solution to neutralize, then the organic solvent was distilled away under reduced pressure. Methanol (100 ml) was added to the residue, and a precipitate was collected by filtration and washed with methanol to purify. Thus, there was obtained an end product 41 (1.80 g).

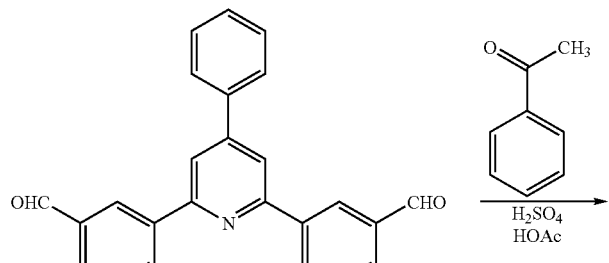
End product 41

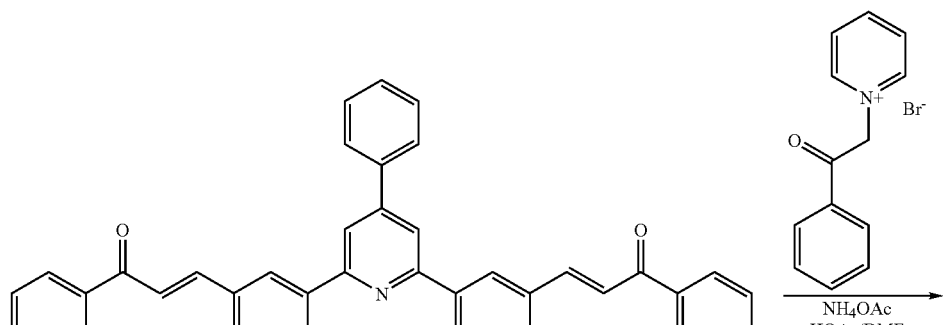
End product 42

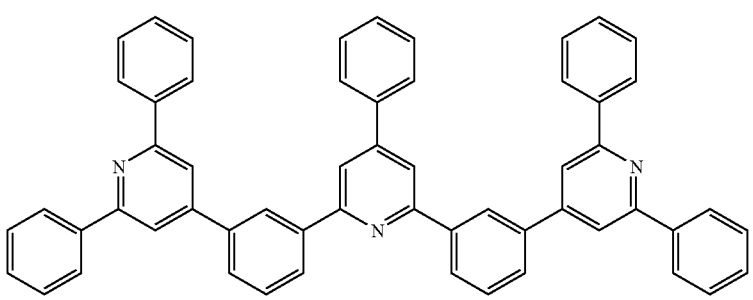
End product 43

To a mixed solution of the end product 41 (1.80 g), acetophenone (1.25 g) and acetic acid (20 ml) was added concentrated sulfuric acid (1.6 ml) in a dry air. After stirring at 35° C. for 9.5 hours, methanol (10 ml) and water (40 ml) were added thereto, and a supernatant was removed by decantation. The thus-obtained solid was purified by recrystallization from chloroform-methanol to obtain an end product 42 (1.78 g).

The end product 42 (1.78 g), 1-phenacylpyridinium bromide (2.62 g), ammonium acetate (12.1 g), acetic acid (75 ml) and N,N-dimethylformamide (75 ml) were stirred for 5 hours while bubbling thereinto a dry air and heating under reflux. 50 ml of methanol and 50 ml of water were added thereto, and a precipitate formed was collected by filtration and purified by silica gel chromatography and recrystallization from chloroform-methanol to obtain an end product 43 (0.87 g).

The product was identified as end product 43 through DEI-MS (m/Z=765(M+)).

This compound had a glass transition temperature of 111° C., a melting point of 266° C., and a gasification temperature of 528° C.

Synthesis Example 18

End Products 44 to 46

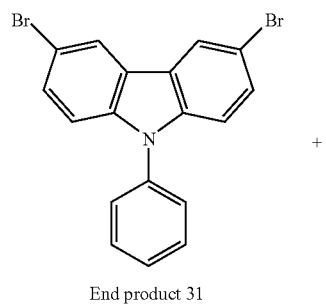

End product 31

+

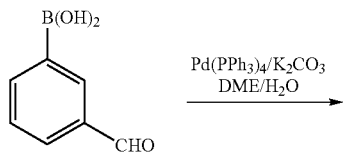

$Pd(PPh_3)_4/K_2CO_3$
$DME/H_2O$

-continued

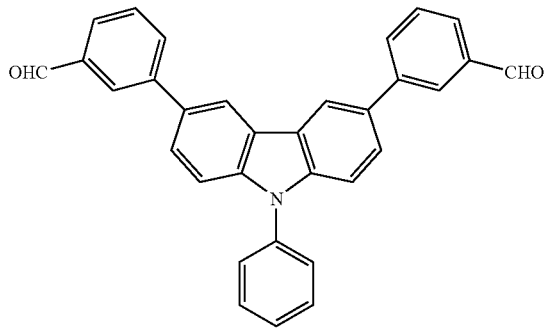

End product 44

To a mixture of the end product 31 (4.01 g), 3-carboxyphenylboric acid (3.90 g) and dimethoxyethane (100 ml) were successively added tetrakis(triphenylphosphine)palladium (0.92 g) and a 2 M potassium carbonate aqueous solution (20 ml), and the mixture was stirred for 7.5 hours while heating under reflux. Removal of the supernatant by decantation gave a solid. The solid was purified by silica gel column chromatography to obtain an end product 44 (3.70 g).

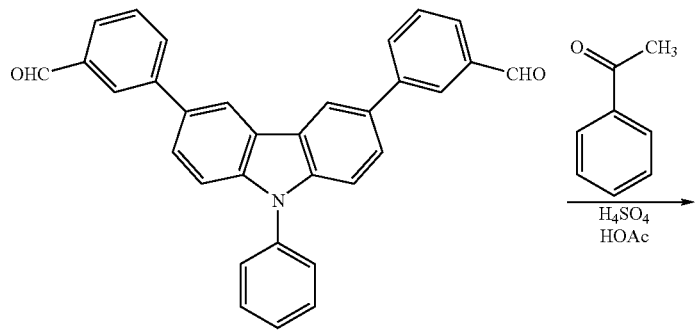

End product 44

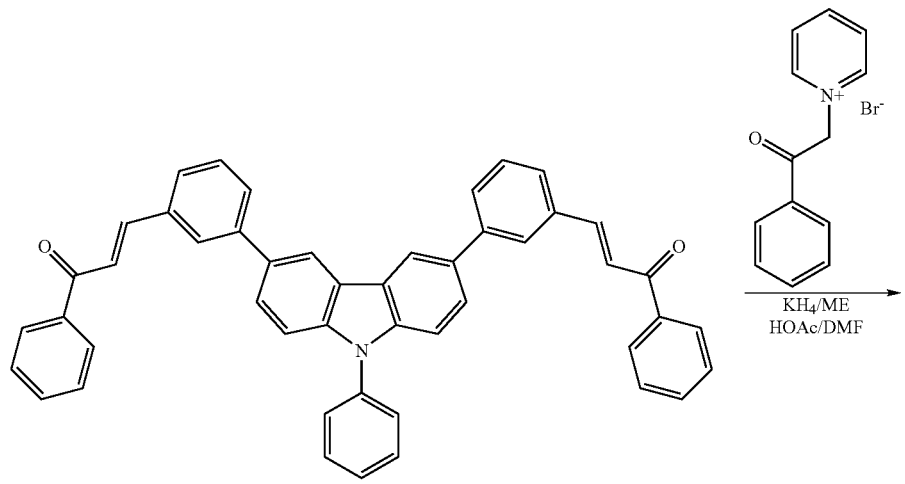

End product 45

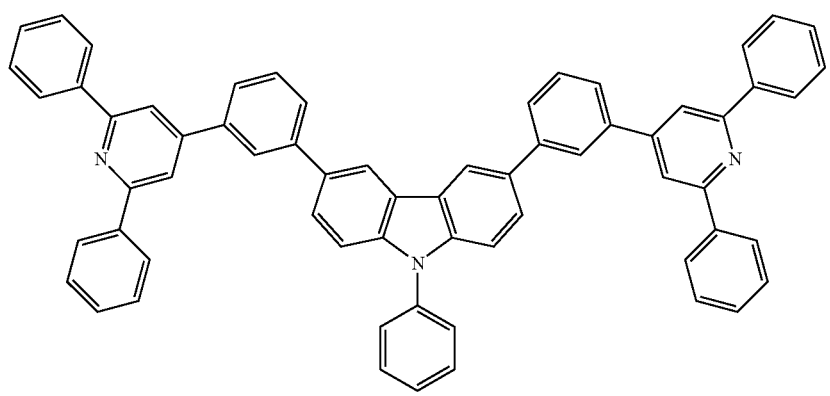

End product 46

To a mixed solution of the end product 44 (3.70 g), acetophenone (2.07 g) and acetic acid (52 ml) was added concentrated sulfuric acid (2.6 ml). After stirring at 35° C. for 9 hours, methanol (30 ml) was added thereto. Removal of the supernatant by decantation gave a solid. The solid was purified by silica gel column chromatography to obtain an end product 45 (1.56 g).

The end product 45 (1.56 g), 1-phenacylpyridinium bromide (1.99 g), ammonium acetate (9.2 g), acetic acid (57 ml) and N,N-dimethylformamide (57 ml) were stirred for 6.9 hours while heating under reflux, and 50 ml of methanol and 50 ml of water were added thereto. A precipitate formed was collected by filtration and purified by silica gel column chromatography to obtain an end product 46 (0.65 g).

The product was identified as end product 46 through DEI-MS (m/z=853(M+)). This compound did not have a detectable melting point and had a glass transition temperature of 140° C., and a gasification temperature of 553° C.

Synthesis Example 19

End Products 47 to 50

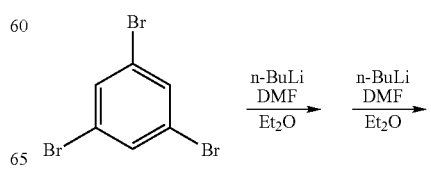

-continued

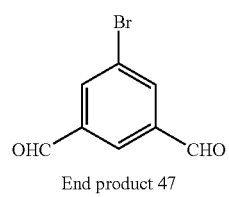
End product 47

A solution of 11.6 g of 1,3,5-tribromobenzene in dehydrated diethyl ether (240 mL) was cooled to −78° C. in a nitrogen atmosphere, and 23 mL of a 1.6 M n-butyllithium hexane solution was dropwise added thereto. Stirring was conducted for 1 hour at −78° C. and, subsequently, 2.9 mL of dimethylformamide was added thereto taking care so that the temperature was not increased, followed by stirring for 1 hour. Further, 25 mL of a 1.6 M n-butyllithium hexane solution was gradually added thereto and, after stirring for 1 hour, 9.1 mL of dimethylformamide was added thereto, and the mixture was stirred for further 2 hours at −78° C. Thereafter, the temperature of the reaction solution was increased to 0° C., and 200 mL of 3N hydrochloric acid was added thereto, followed by extracting with 400 mL of diethyl ether. The organic layer was treated with magnesium sulfate, and the solvent was distilled off under reduced pressure. Hexane was added to the thus-obtained crude product, and recrystallization was conducted to obtain 4.9 g of a product as a white solid. The product was identified as an end product 47 from the results of measurement of mass spectrum.

M/e: 212 (M+: EI-MS)

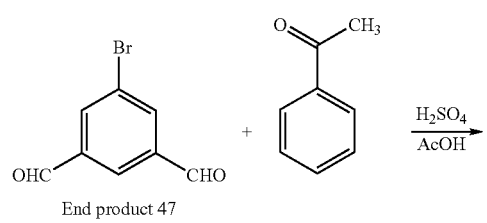
End product 47

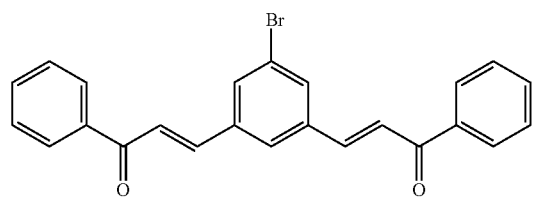
End product 48

3.3 g of acetophenone and 3.5 mL of sulfuric acid were added to a solution of the end product 47 (2.4 g) in acetic acid (30 mL), and the mixture was stirred for 9.5 hours in the air. Thereafter, 100 mL of water and 30 mL of methanol were added to the reaction system and, after stirring, filtration was conducted. A crude product thus obtained was washed with methanol to obtain 4.5 g of a product as an ocher solid.

The thus-obtained compound was identified as an end product 48 from the results of measurement of mass spectrum.

M/e: 416 (M+: EI-MS)

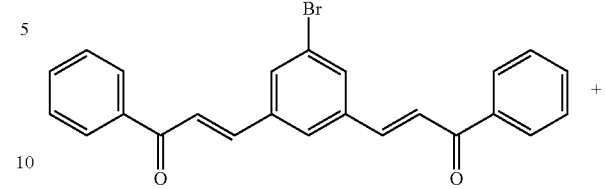
End product 48

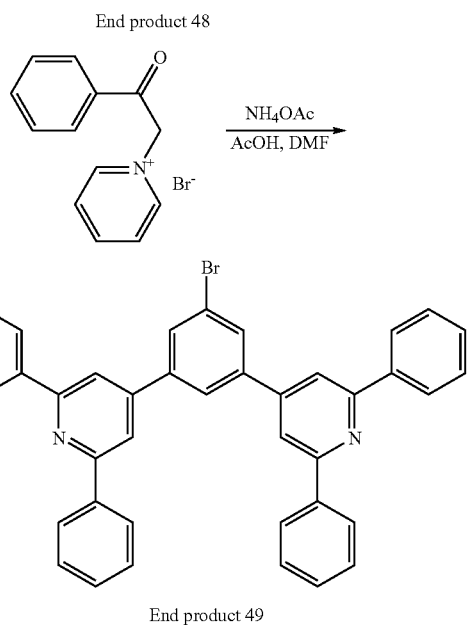
End product 49

120 mL of acetic acid and 60 mL of dimethylformamide were added to the end product 48 (4.16 g), 1-phenacylpyridinium bromide (8.34 g) and anhydrous ammonium acetate (46 g), and heated for 8.5 hours under reflux in the air. Thereafter, 100 mL of water was added to the reaction solution, and a precipitate was collected by filtration and washed with methanol. The thus-obtained crude product was purified by column chromatography to obtain 4.5 g of a product as an ocher solid. The thus-obtained compound was identified as an end product 49 from the results of measurement of mass spectrum.

M/e: 614 (M+;EI-MS)

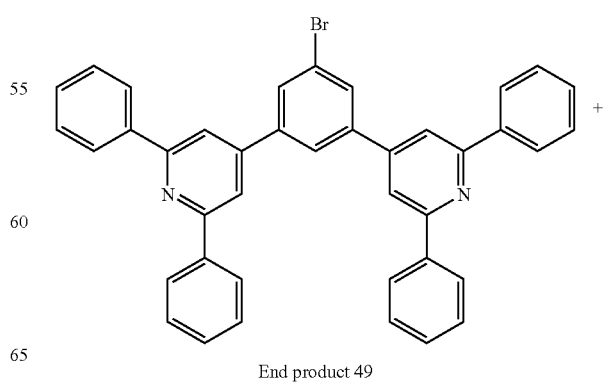
End product 49

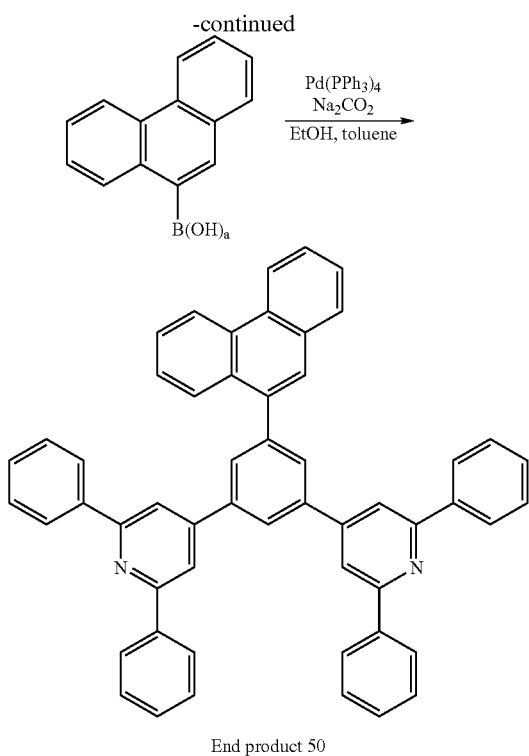

End product 50

To the end product 49 (468 mg) and 9-phenanthrylboric acid (444 mg) were added 20 mL of toluene, 1.5 mL of ethanol and 1.5 mL of a 2N sodium carbonate aqueous solution and, after stirring for 30 minutes at room temperature under nitrogen, 40 mg of tetrakistriphenylphosphine-palladium(0) was added thereto, followed by heating for 7 hours under reflux. Thereafter, 50 mL of water was added to the reaction solution, and several times extracted with methylene chloride. To the extract was added potassium carbonate to dry, the solvent was distilled off under reduced pressure. Then, the thus-obtained precipitate was purified by column chromatography to obtain a yellowish white solid (462 mg).

The thus-obtained compound was identified as an end product 50 from the results of measurement of mass spectrum.

M/e: 712 (M+: EI-MS)

This compound had a glass-transition temperature of 136° C., a melting point of 278° C., and a gasification temperature of 507° C.

Synthesis Example 20

End Products 51 to 53

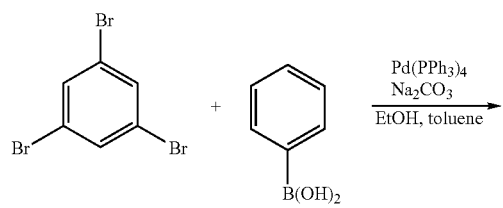

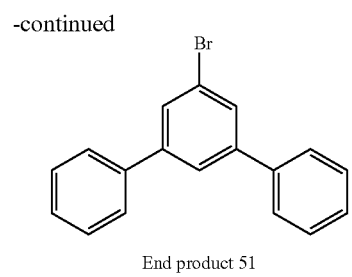

End product 51

To 1,3,5-tribromobenzene (15.7 g) and phenylboric acid (12.1 g) were added 750 mL of toluene, 150 mL of ethanol and 100 mL of a 2N sodium carbonate aqueous solution and, after stirring for 30 minutes at room temperature under nitrogen, 40 mg of tetrakistriphenylphosphinepalladium(0) was added thereto, followed by heating for 4 hours under reflux. After cooling to room temperature, 50 mL of water was added to the reaction solution, and several times extracted with methylene chloride. To the extract was added potassium carbonate to dry, the solvent was distilled off under reduced pressure. Then, the thus-obtained precipitate was purified by column chromatography to obtain a white solid (7.3 g). The thus-obtained compound was identified as an end product 51 from the results of measurement of mass spectrum.

M/e: 308 (M+: EI-MS)

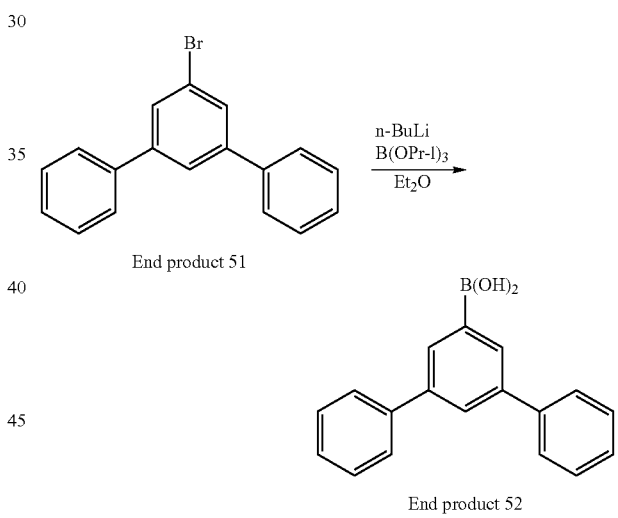

A solution of the end product 51 (3.04 g) in dehydrated tetrahydrofuran (25 mL) was cooled to −78° C. in a nitrogen atmosphere, and 13.8 mL of a 1.6M n-butyllithium hexane solution was dropwise added thereto gradually. Stirring was conducted for 45 minutes at −78° C. and, subsequently, tri-isopropoxyborane (4.1 g) was added thereto at once. After stirring for 30 minutes at −78° C., the temperature of the reaction solution was raised to room temperature, followed by stirring for further 1 hour. 100 mL of 3N hydrochloric acid was added to the thus-obtained reaction solution, followed by extracting with 200 mL of diethyl ether. The organic layer was washed with 50 mL of water, and then treated with sodium sulfate, and the solvent was distilled off under reduced pressure.

Diethyl ether was added to the thus-obtained crude product, and reprecipitation was conducted to obtain 1.97 g of a white solid (end product 52).

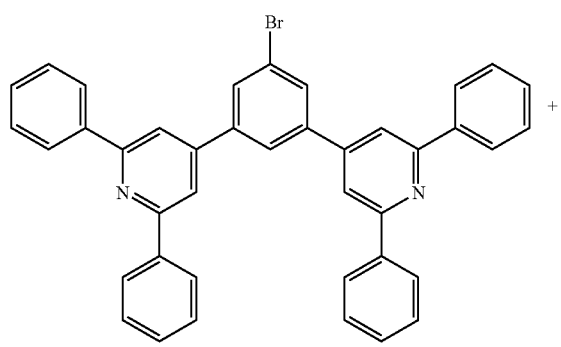

End product 49

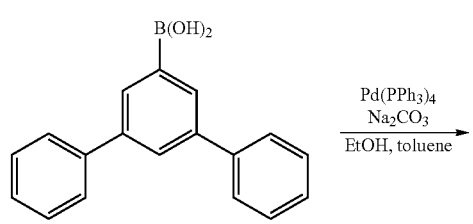

End product 52

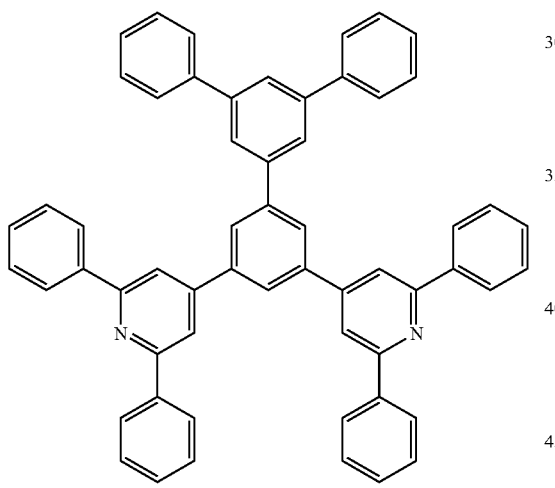

End product 53

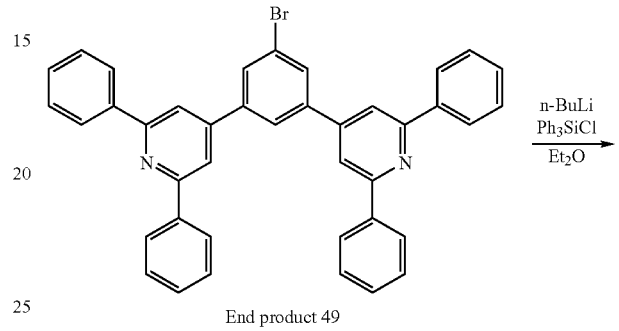

End product 49

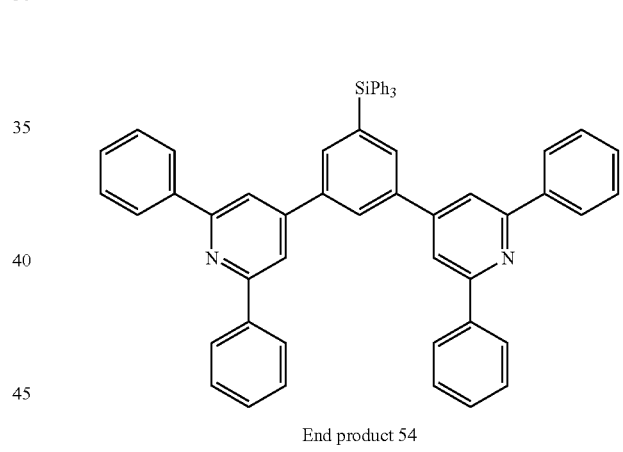

End product 54

M/e: 764 (M+:DEI-MS)

This compound did not have a detectable glass transition temperature, and had a melting point of 284° C., and a gasification temperature of 524° C.

Synthesis Example 21

End Product 54

To the end product 49 (936 mg) and the end product 52 (685 mg) were added 40 mL of toluene, 3.0 mL of ethanol and 3.0 mL of a 2N sodium carbonate aqueous solution and, after stirring for 30 minutes at room temperature under nitrogen, 40 mg of tetrakistriphenylphosphinepalladium(0) was added thereto, followed by heating for 4 hours under reflux. After further adding thereto 400 mg of the end product 52, heating was conducted under reflux for 1.5 hours. Thereafter, 50 mL of water was added to the reaction solution, and the solution was several times extracted with ethyl acetate. To the extract was added potassium carbonate to dry, the solvent was distilled off under reduced pressure. Then, the thus-obtained precipitate was purified by column chromatography to obtain a yellowish white solid (685 mg). The thus-obtained compound was identified as an end product 53 from the results of measurement of mass spectrum.

A solution of the end product 49 (936 mg) in dehydrated tetrahydrofuran (25 mL) was cooled to −78° C. in a nitrogen atmosphere, and 2.6 mL of a 1.6M n-butyllithium hexane solution was dropwise added thereto gradually, and stirring was conducted for 15 minutes at −78° C. Subsequently, triphenylchlorosilane (885 mg) was added thereto at once, and the temperature of the reaction solution was raised to room temperature, followed by stirring for 3 hour. After distilling off the solvent under reduced pressure, purification by column chromatography and GPC yielded 700 mg of a white solid. The thus-obtained compound was identified as an end product 54 from the results of measurement of mass spectrum.

M/e: 794 (M+: DEI-MS)

This compound had a glass transition temperature of 110° C., a melting point of 228° C., and a gasification temperature of 494° C.

Synthesis Example 22

End Products 55 to 56

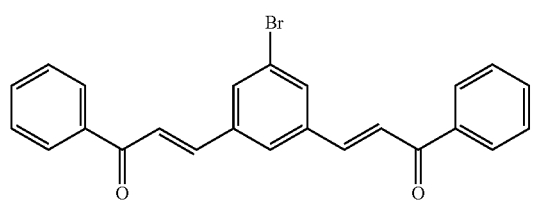

End product 48

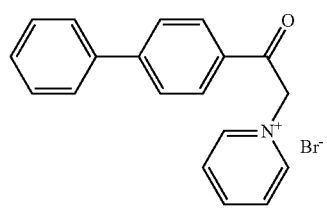

End product 24

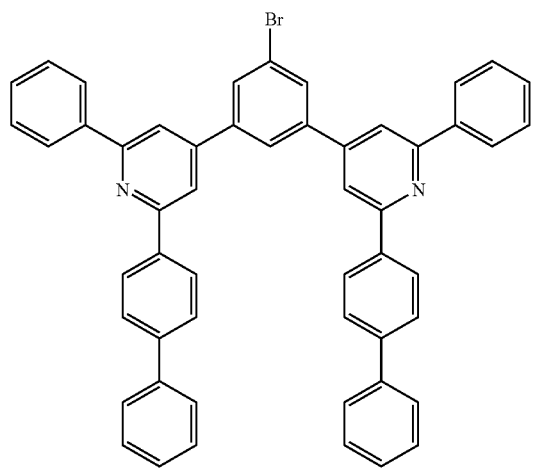

End product 55

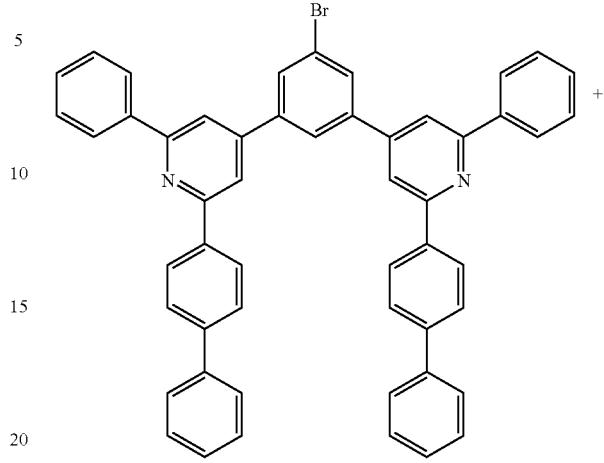

End product 55

M/e: 766 (M+: DEI-MS)

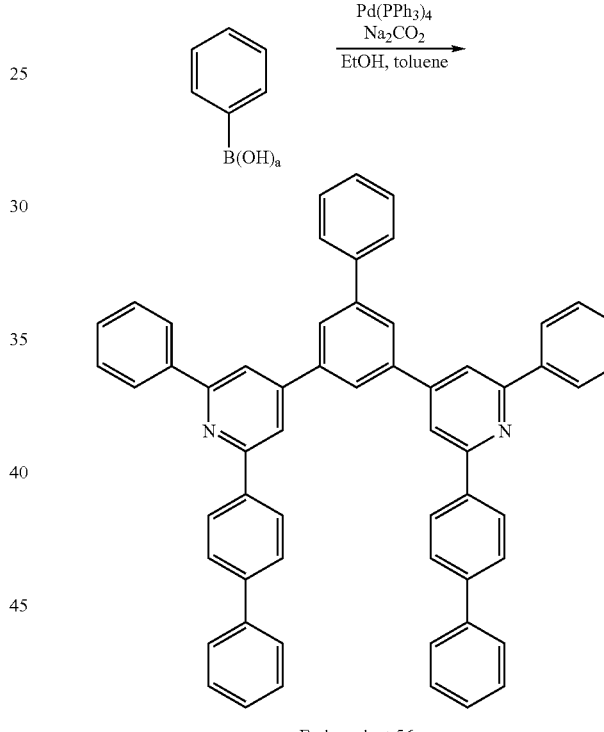

End product 56

To the end product 48 (1.07 g), the end product 24 (2.7 g) and anhydrous ammonium acetate (11.8 g) were added 30 mL of acetic acid and 15 mL of dimethylformamide, followed by heating for 8 hours under reflux in the air. Thereafter, 50 mL of water and 20 mL of methanol were added to the reaction solution, and the precipitate was collected by filtration and washed with methanol to obtain 1.4 g of an ocher solid.

The thus-obtained compound was identified as an end product 55 from the results of measurement of mass spectrum.

To the end product 55 (977 mg) and phenylboric acid (242 mg) were added 30 mL of toluene, 2.0 mL of ethanol and 2.0 mL of a 2N sodium carbonate aqueous solution and, after stirring for 30 minutes at room temperature under nitrogen, 40 mg of tetrakistriphenylphosphinepalladium(0) was added thereto, followed by heating for 5 hours under reflux. Thereafter, 50 mL of water was added to the reaction solution, and the solution was several times extracted with chloroform. To the extract was added potassium carbonate to dry, the solvent was distilled off under reduced pressure. Then, the thus-obtained precipitate was purified by column chromatography to obtain a yellowish white solid (823 mg). The thus-obtained compound was identified as an end product 56 from the results of measurement of mass spectrum.

M/e: 764 (M+: DEI-MS)

This compound had a glass transition temperature of 125° C., a melting point of 268° C., and a gasification temperature of 528° C.

Synthesis Example 23

End Product 57

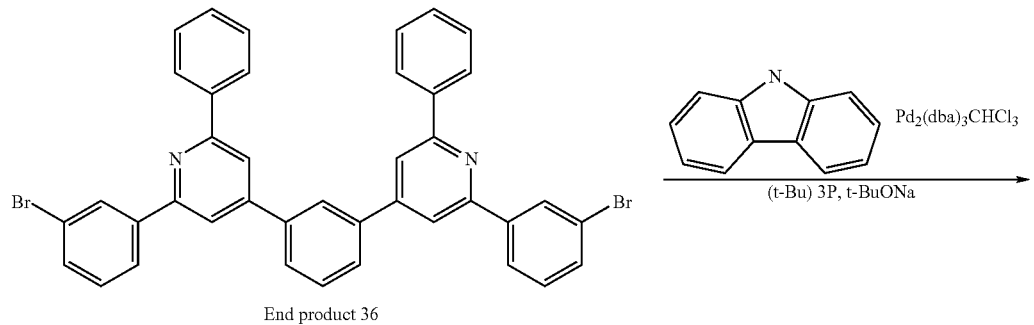

End product 36

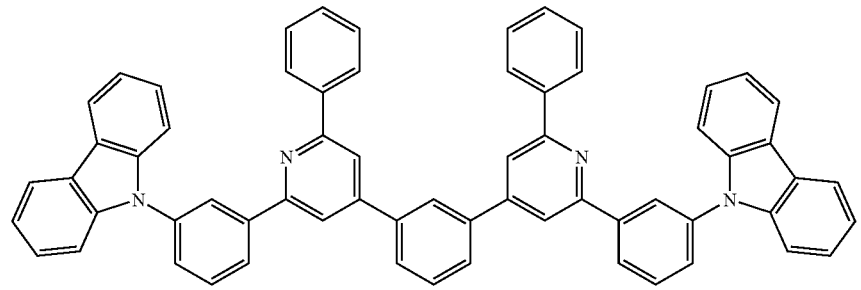

End product 57

The end product 36 (3.0 g), carbazole (1.73 g), sodium t-butoxide (1.8 g) and toluene (80 ml) were heated to 60° C. under stirring, and a solution of tris(dibenzylideneacetone)dipalladium (0.16 g) and tri-t-butylphosphine (0.16 g) in 5 ml of toluene was added thereto. Thereafter, the mixture was stirred for 8.5 hours while heating under reflux and, after cooling, poured into methanol (400 ml) to obtain crude crystals. Then, they were stirred in methanol (400 ml) under heating, and purified by silica gel column chromatography to obtain 3.43 g of an end product.

The product was identified as the end product 57 through DEI-MS (m/z=866). This had a gasification temperature of 554° C. and a glass transition temperature of 142° C.

Synthesis Example 24

End Product 58

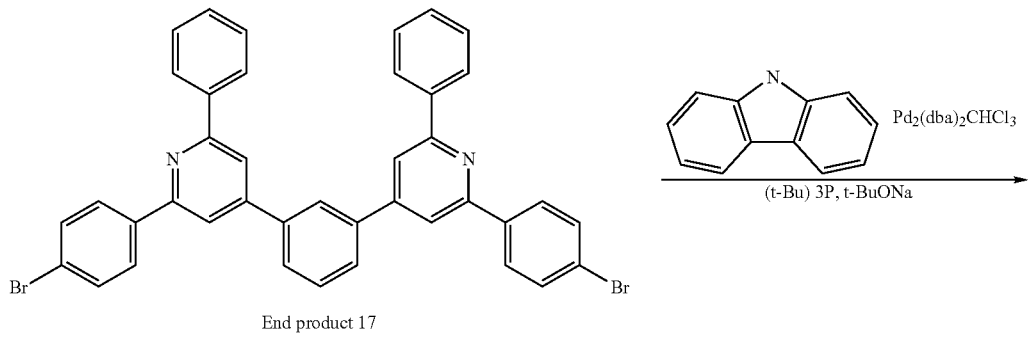

End product 17

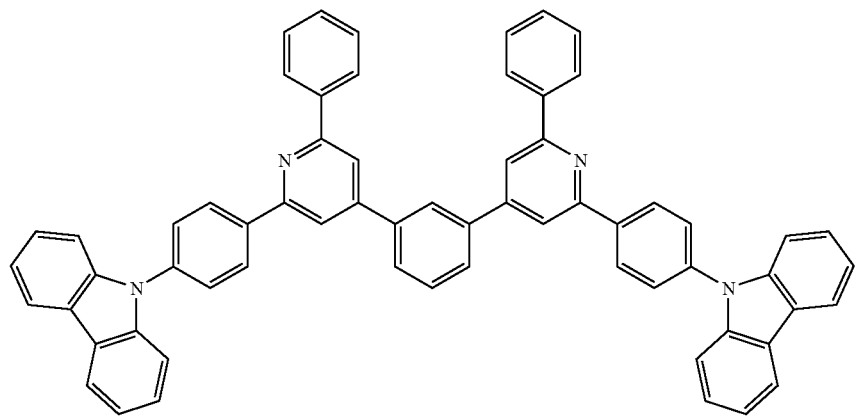

End product 58

The end product 17 (3.0 g), carbazole (1.73 g), sodium t-butoxide (1.8 g) and toluene (80 ml) were heated to 60° C. under stirring, and a solution of tris(dibenzylideneacetone)dipalladium (0.16 g) and tri-t-butylphosphine (0.2 g) in 5 ml of toluene was added thereto.

Thereafter, the mixture was stirred for 5.5 hours while heating under reflux and, after cooling, crystals formed were collected by filtration and stirred in methanol (400 ml) under heating, thereby obtaining a crude product. Then, the crude product was purified by silica gel column chromatography to obtain 2.27 g of an end product.

The product was identified as the end product 58 through DEI-MS (m/z=866). This had a gasification temperature of 556° C., a melting point of 317° C. and a glass transition temperature of 154° C.

Synthesis Example 25

End Product 59

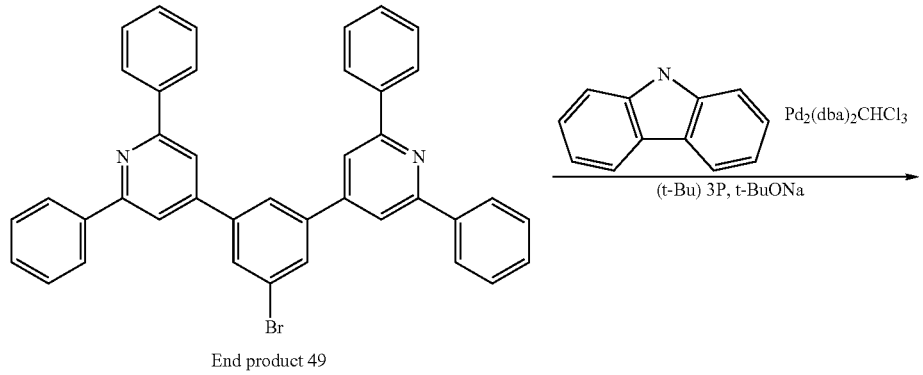

End product 49

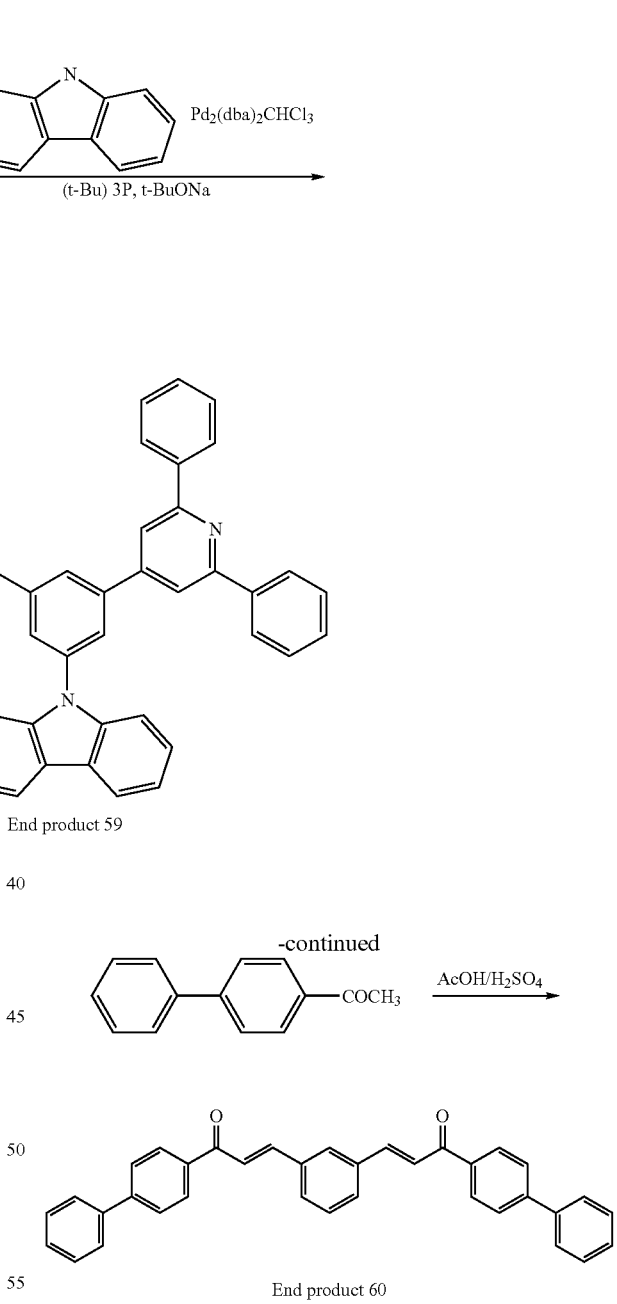

End product 59

The end product 49 (2.0 g), carbazole (0.65 g), sodium t-butoxide (0.68 g) and toluene (30 ml) were heated to 60° C. under stirring, and a solution of tris(dibenzylideneacetone) dipalladium (0.06 g) and tri-t-butylphosphine (0.03 g) in 5 ml of toluene was added thereto. Thereafter, the mixture was stirred for 7.5 hours while heating under reflux and, after cooling, crystals formed were collected by filtration, washed by stirring in methanol and stirred in methanol (400 ml) under heating, thereby obtaining crystals. Recrystallization of the crystals yielded 0.45 g of an end product.

The product was identified as the end product 59 through DEI-MS (m/z=701). This had a gasification temperature of 507° C., a melting point of 360° C. and a glass transition temperature of 130° C.

Synthesis Example 26

End Products 60 to 62

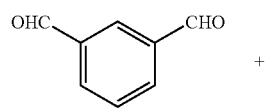

+

-continued

End product 60

Isophthalaldehyde (2.73 g), 4-acetylbiphenyl (7.98 g), concentrated sulfuric acid (6.54 ml) and acetic acid (58 ml) were stirred for 6.5 hours in the atmosphere at 50° C. Thereafter, ethanol (60 ml) and water (60 ml) were added thereto, and crystals precipitated were collected by filtration. Then, the crystals were stirred in 150 ml of ethanol while heating under reflux and, after collecting by filtration, purified by column chromatography to obtain 1.8 g of an end product 60.

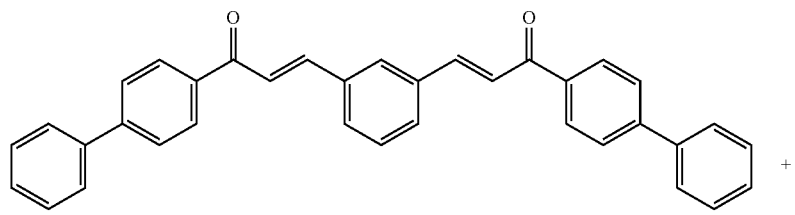

End product 61

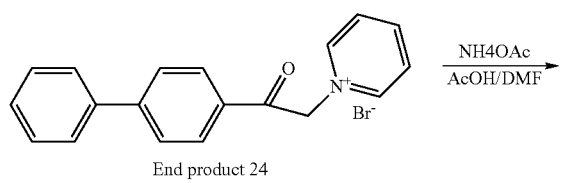

End product 24

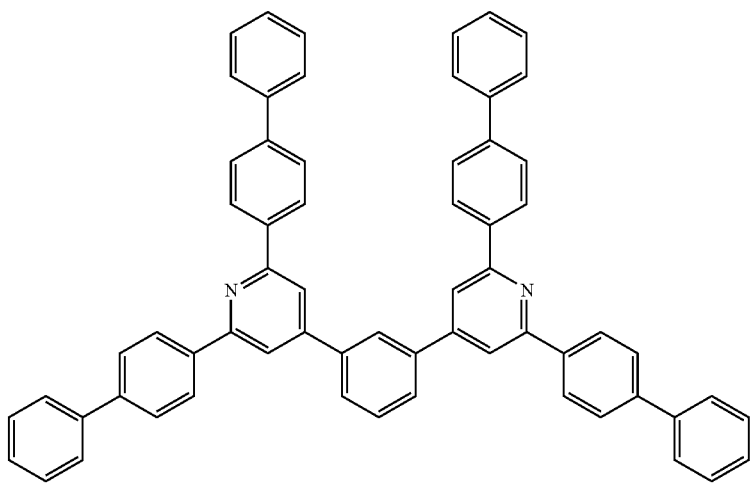

End product 62

50 ml of ethanol was added to a solution obtained by stirring the end product 60 (1.2 g), the end product 24 (2.5 g), ammonium acetate (9.4 g), acetic acid (36.63 g) and N,N-dimethylformamide (40 ml) for 7.5 hours while heating under reflux, and crystals obtained were collected by filtration. The crystals were twice stirred in 50 ml of ethanol under heating to obtain the end product 62 (0.97 g).

The product was identified as the end product 62 through DEI-MS (m/z=840). This had a melting point of 319° C. and a glass transition temperature of 142° C.

Examples

Example 1

Evaluation of Compounds

Example 1-1

Measurement of Oxidation and Reduction Potentials

Measurement of oxidation and reduction potentials was conducted on the end product 2 (HB-1), the end product 6

(HB-3) and the end product 15 (HB-5), obtained in the above Synthesis Examples. Measuring conditions are as follows. Results obtained by converting the obtained potentials employing a saturated calomel electrode (SCE) as a standard electrode are shown in Table 1-1.
Reference electrode: silver wire (using ferrocene as an internal standard substance)
Action electrode: glassy carbon
Counter electrode: platinum wire
Solvent for measurement: 0.1 ml/L tetra(n-butyl)ammonium perchlorate methylene chloride solution (acetonitrile solution)
Sweep speed: 100 ml/sec
Sample concentration: 1 mmol/L Comparative Example 1-1

Measurement of Oxidation and Reduction Potentials

Measurement of oxidation and reduction potentials was conducted in the same manner as in Example 1-1 on a comparative compound of the following structure (HB-6) wherein nitrogen atoms on pyridine rings are conjugately connected to each other. The results are shown in Table 1-1-1.

TABLE 1-1-1

HB-6

| | Oxidation Potential (V) | Reduction Potential (V) |
|---|---|---|
| End product 2 (HB-1) | 1.76 | −2.03 |
| End product 6 (HB-3) | 1.94 | −2.06 |
| End product 15 (HB-5) | 1.90 | −2.11 |
| HB-6 | 1.78 | −1.86 |

Table 1-1-1 shows that, because of their structures wherein connection is of non-conjugation type, the compounds of the invention have a larger oxidation-reduction potential difference than that of the compound having the structure wherein conjugation connection exists.

Example 1-2

Wavelength of Maximum Light Emission Peak of the Compound

Thin film (50 nm in thickness) of each of the end product 18 and the end product 15 which are included in the compounds of the invention represented by the formula (II) which do not form a plane structure in an optimized geometry (hereinafter referred to as "compounds II") was formed on a glass substrate by the vacuum deposition method.

The thus-obtained films were transparent amorphous films. Wavelength of maximum light emission peak in the fluorescence emission spectrum obtained by exciting each of the resulting films with light of maximum absorption wavelength of each of the resulting film is shown in Table 1-2.

Comparative Example 1-2

Wavelength of Maximum Light Emission Peak of the Comparative Compound

Thin film of each of the end product 6 and the end product (HB-8) 25 which are not included in the compounds of the invention represented by the formula (II) and are not compounds which do not form a plane structure in an optimized geometry was prepared in the same manner as in (Example 1-2). The thus-obtained films were transparent amorphous films. Wavelength of maximum light emission peak in the fluorescence emission spectrum obtained by exciting each of the resulting films with light of maximum absorption wavelength of each of the resulting film is shown in Table 1-1-2.

TABLE 1-1-2

| Compound | Compound II | Wavelength of Maximum Light Emission Peak (nm) |
|---|---|---|
| End compound 18 | included | 379 |
| End compound 15 | included | 366 |
| End compound 6 | not included | 390 |
| End compound25 | not included | 390 |

It is clear from the results that the compounds of the formula (II) (compounds II) show a restricted intramolecular mutual action in a film state.

Example 2

Preparation of Elements 1 to 8 and Light-Emitting Characteristics

Example 2-1

Preparation of Element 1

An organic electroluminescent element having a structure shown in FIG. 3 was prepared according to the following method.

An indium-tin oxide (ITO) transparent conductive film 2 formed in a thickness of 150 nm on a glass substrate 1 (sputtered film; sheet resistance: 15Ω) was patterned in a 2-mm width stripe pattern using the common photolithography technique and etching with hydrochloric acid, thereby forming an anode. The thus patterned ITO substrate was washed by applying ultrasonic waves in acetone, washed with pure water, then washed by applying ultrasonic waves in isopropyl alcohol, followed by drying using a nitrogen blow and washing by applying UV rays and ozone.

As a material for the anode buffer layer 3, non-conjugation type polymer compound (PB-1) of the following structural formula having aryl amino groups:

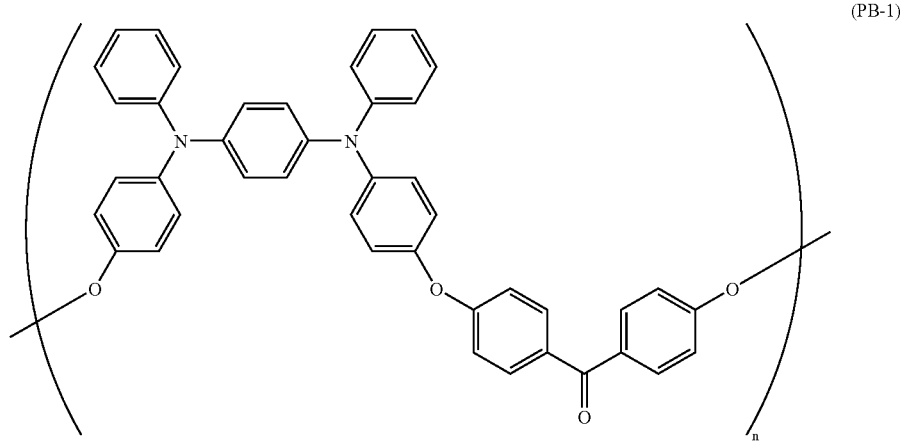

weight-average molecular weight: 29,400
number-average molecular weight: 12,600 was spin-coated together with an electron acceptor (A-1):

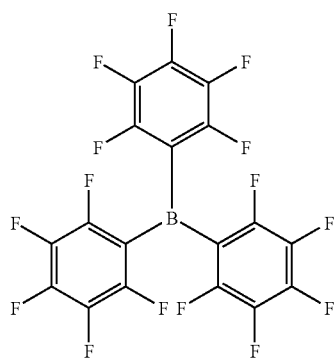

under the following conditions:
Solvent: ethyl benzoate;
Concentration of coating solution: 2 [wt %];
PB-1:A-1=10:1;
Rotation number of spinner: 1,500 [rpm];
Rotation time of spinner: 30 [sec]; and
Drying condition: 100° C., 1 hour.

A uniform thin film of 30 nm in film thickness was formed by the above-described spin coating.

Next, the substrate having formed thereon the anode buffer layer was placed in a vacuum deposition apparatus. After roughly evacuating the apparatus by means of an oil rotary pump, the inside of the apparatus was evacuated till a vacuum degree became $1.1 \times 10^{-6}$ Torr (about $1.5 \times 10^{-4}$ Pa) or less by employing an oil diffusion pump.

An arylamine compound (H-1) shown below and placed in a ceramic crucible placed within the apparatus:

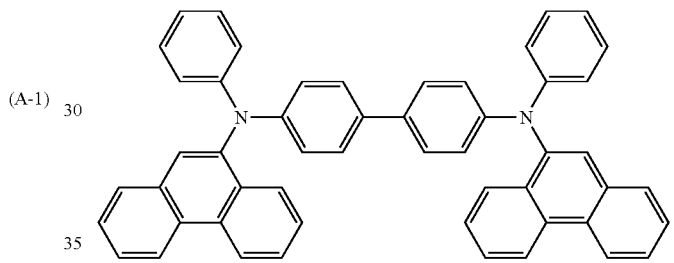

was heated through a tantalum wire heater disposed around the crucible to conduct vacuum deposition. The temperature of the crucible in this occasion was controlled in the range of from 318 to 334° C. The vacuum degree upon vacuum deposition was $1.1 \times 10^{-6}$ Torr (about $1.4 \times 10^{-4}$ Pa), and vacuum deposition rate was 0.15 nm/sec. Thus, there was obtained a 60-nm thick hole transport layer 4.

Subsequently, a carbazole derivative (E-1) shown below to be used as a major component (host material) of the light-emitting layer 5 and an organic iridium complex (D-1) to be used as a minor component (dopant) were placed in different ceramic crucibles, and filming was conducted by the simultaneous binary vacuum deposition method.

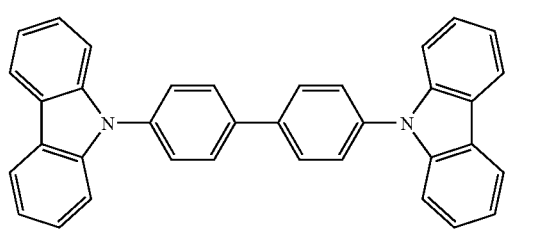

-continued

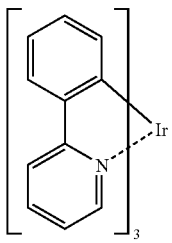
(D-1)

The crucible temperature for the compound (E-1) was controlled to be 184 to 196° C., and vacuum deposition rate was controlled to be 0.11 nm/sec, while the crucible temperature for the compound (D-1) was controlled to be 245 to 246° C. Thus, the 30-nm thick light-emitting layer 5 containing 6% by weight of the compound (d-1) was laminated on the hole transport layer 4. The vacuum degree upon vacuum deposition was $1.0 \times 10^{-6}$ Torr (about $1.3 \times 10^{-4}$ Pa).

Further, the end product 2 (HB-1) synthesized in the foregoing Synthesis Example 1:

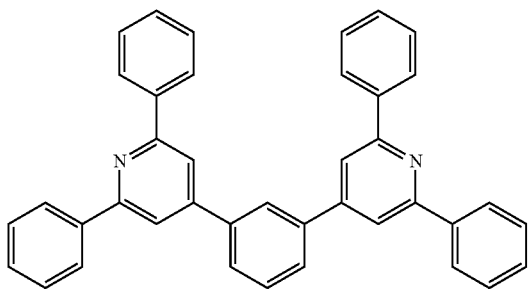
(HB-1)

was laminated as the hole blocking layer 6 in a thickness of 10 nm with controlling the temperature of the crucible to be 190 to 196° C. and the vacuum deposition rate to be 0.13 nm/sec. The vacuum degree upon vacuum deposition was $0.7 \times 10^{-6}$ Torr (about $0.9 \times 10^{-4}$ Pa).

On the hole blocking layer 6 was deposited, as the electron transport layer 7, the following aluminum 8-hydroxyquinoline complex (ET-1):

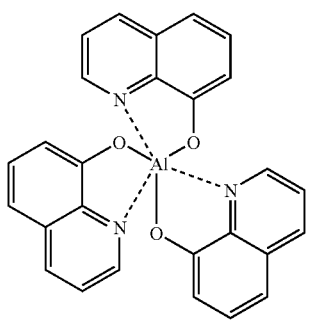
(ET-1)

in the same manner. The temperature of the crucible for the aluminum 8-hydroxyquinoline complex in this occasion was controlled within the range of from 250 to 262° C. The vacuum degree upon vacuum deposition was controlled to be $0.7 \times 10^{-6}$ Torr (about $0.9 \times 10^{-4}$ Pa), the vacuum deposition rate 0.21 nm/sec, and the film thickness 35 nm.

The temperature of the substrate upon vacuum deposition of the hole transport layer, the light-emitting layer and the electron transport layer was kept at room temperature.

Here, the element which has been subjected to vacuum deposition up to the electron transport layer 6 was once taken out of the vacuum deposition apparatus into the atmosphere. A 2-mm width striped shadow mask was closely contacted with the element as a mask for vacuum deposition of a cathode so as to cross at right angles to the ITO stripe of the anode 2, and the element was placed in a different vacuum deposition apparatus. The apparatus was evacuated to a vacuum degree within the apparatus of $2.7 \times 10^{-6}$ Torr (about $2.0 \times 10^{-4}$ Pa) or less in the same manner as with the organic layers. As the cathode 8, first, lithium fluoride (LiF) was laminated in a thickness of 0.5 nm on the electron transport layer 7 at a vacuum deposition rate of 0.01 nm/sec and a vacuum degree of $3.0 \times 10^{-6}$ Torr (about $4.0 \times 10^{-4}$ Pa) using a molybdenum boat. Subsequently, aluminum was heated in a molybdenum boat in the same manner to form a 80-nm thick aluminum layer at a vacuum deposition rate of 0.48 nm/sec and a vacuum degree of $8.5 \times 10^{-6}$ Torr (about $1.1 \times 10^{-3}$ Pa), thus the cathode 8 being completed. The substrate temperature during vacuum deposition of the two-layer type cathode 8 was kept at room temperature.

Thus, there was obtained an organic electroluminescent element (element 1) having a 2 mm×2 mm-sized light-emitting area portion.

Light-emitting characteristics of this element are shown in Table 2.

In Table 2, the maximum light emission luminance is a value at a current density of 0.25 A/cm², and luminous efficiency, luminance/current, and voltage are values at a luminance of 100 cd/m².

The emission maxima of the element 1 was 510 nm, and was identified to be from the organic iridium complex (D-1). Chromaticity was CIE(x, y)=(0.28, 0.62).

Example 2-2

Preparation of Element 2

An element 2 was prepared in the same manner as in (Example 2-1) except for using, as the minor component (dopant) of the light-emitting layer 5, the mixed ligand complex (D-2) shown below in place of the organic iridium complex (D-1).

Light-emitting characteristics of the element 2 are shown in Table 2.

The emission maxima of the element 2 was 626 nm, and chromaticity was CIE(x, y)=(0.68, 0.32), which was identified to be from the organic iridium complex (D-2).

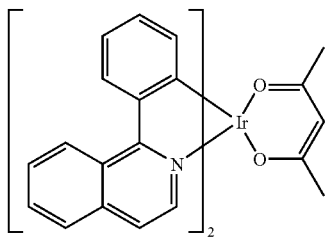
(D-2)

Example 2-3

Preparation of Element 3

An element 3 was prepared in the same manner as in (Example 2-1) except for using, as the minor component (dopant) of the light-emitting layer 5, the mixed ligand complex (D-3) shown below in place of the organic iridium complex (D-1).

Light-emitting characteristics of the element 3 are shown in Table 2. The emission maxima of the element was 471 nm, and chromaticity was CIE(x, y)=(0.16, 0.35), which was identified to be from the organic iridium complex (D-3).

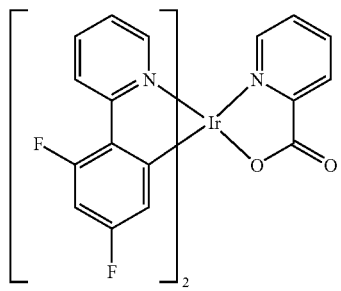

(D-3)

Example 2-4

Preparation of Element 4

An element 4 was prepared in the same manner as in (Example 2-1) except for using the end product 6 (HB-3) obtained in Synthesis Example 3 and shown below in place of the end product 2 (HB-1) in the hole blocking layer.

Light-emitting characteristics of the element 4 are shown in Table 2. The emission maxima of the element was 512 nm, and chromaticity was CIE(x, y)=(0.28, 0.63), which was identified to be from the organic iridium complex (D-1).

Initial light-emitting characteristics thereof were more efficient than that of element 1.

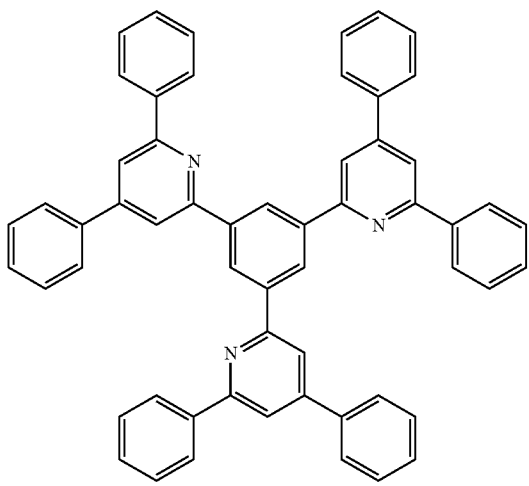

(HB-3)

Example 2-5

Preparation of Element 5

An element 5 was prepared in the same manner as in (Example 2-1) except for using the end product 10 (HB-4) obtained in Synthesis Example 5 and shown below in place of the end product 2 (HB-1) in the hole blocking layer.

Light-emitting characteristics of the element 5 are shown in Table 2. The emission maxima of the element was 512 nm, and chromaticity was CIE(x, y)=(0.28, 0.62), which was identified to be from the organic iridium complex (D-1). Initial light-emitting characteristic thereof was about the same as that of element 1.

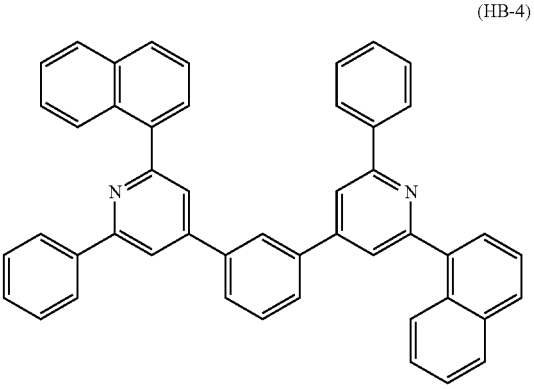

(HB-4)

Example 2-6

Preparation of Element 6

An element 6 was prepared in the same manner as in (Example 2-1) except for using the end product 15 (HB-5) obtained in Synthesis Example 7 and shown below in place of the end product 2 (HB-1) in the hole blocking layer.

Light-emitting characteristics of the element 6 are shown in Table 2. The emission maxima of the element was 512 nm, and chromaticity was CIE(x, y)=(0.29, 0.61), which was identified to be from the organic iridium complex (D-1). Initial light-emitting characteristics thereof were more efficient than that of element 1.

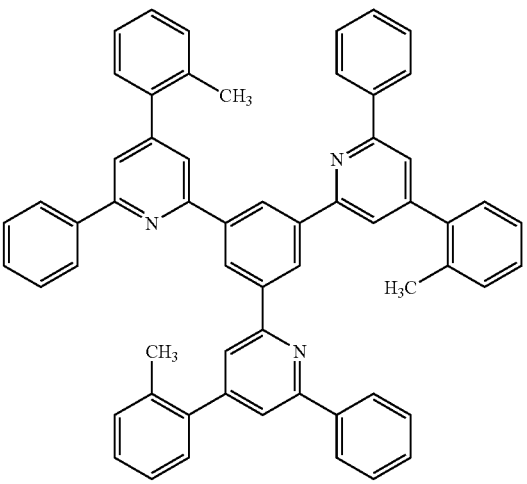

(HB-5)

Example 2-7

Preparation of Element 7

An element 7 was prepared in the same manner as in (Example 2-1) except for using the end product 18 (HB-6) obtained in Synthesis Example 8 and shown below in place of the end product 2 (HB-1) in the hole blocking layer.

Light-emitting characteristics of the element 7 are shown in Table 2. The maximum wavelength of light-emitting spectrum of the element was 512 nm, and chromaticity was CIE(x, y)=(0.29, 0.62), which was identified to be from the organic iridium complex (D-1). Initial light-emitting characteristics thereof were more efficient than that of element 1.

(HB-6)

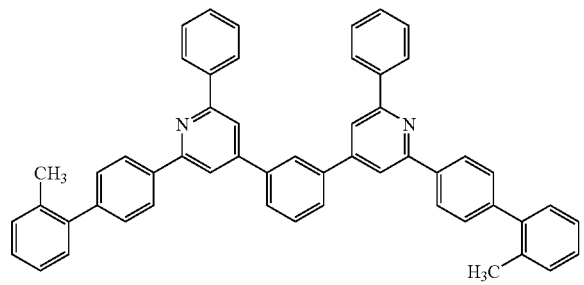

Example 2-8

Preparation of Element 8

An element 8 was prepared in the same manner as in (Example 2-1) except for using the end product 25 (HB-8) shown below in place of the end product 2 (HB-1) in the hole blocking layer.

Light-emitting characteristics of the element 8 are shown in Table 2. The emission maxima of the element was 510 nm, and chromaticity was CIE(x, y)=(0.28, 0.60), which was identified to be from the organic iridium complex (D-1).

(HB-8)

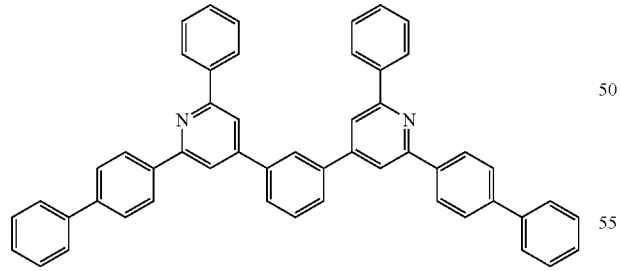

Example 2-9

Preparation of Element 11

An element 11 was prepared in the same manner as in (Example 2-1) except for using the end product 4 (HB-9) obtained in Synthesis Example 2 and shown below in place of the end product 2 (HB-1) in the hole blocking layer.

Light-emitting characteristics of the element 11 are shown in Table 2. The emission maxima of the element was 509 nm, and chromaticity was CIE(x, y)=(0.27, 0.58), which was identified to be from the organic iridium complex (D-1).

(HB-9)

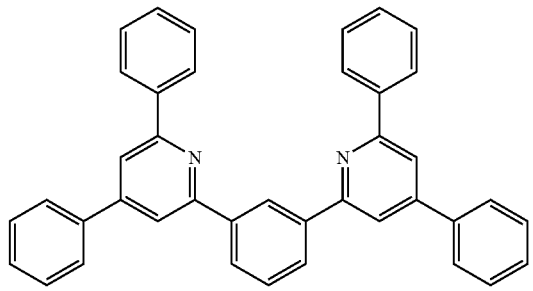

Example 2-10

Preparation of Element 12

An element 12 was prepared in the same manner as in (Example 2-1) except for using the end product 50 obtained in Synthesis Example 19 and shown below in place of the end product 2 (HB-1) in the hole blocking layer.

Light-emitting characteristics of the element 12 are shown in Table 2. The emission maxima of the element was 512 nm, and chromaticity was CIE(x, y)=(0.29, 0.61), which was identified to be from the organic iridium complex (D-1). Initial light-emitting characteristics thereof were more efficient than that of element 1.

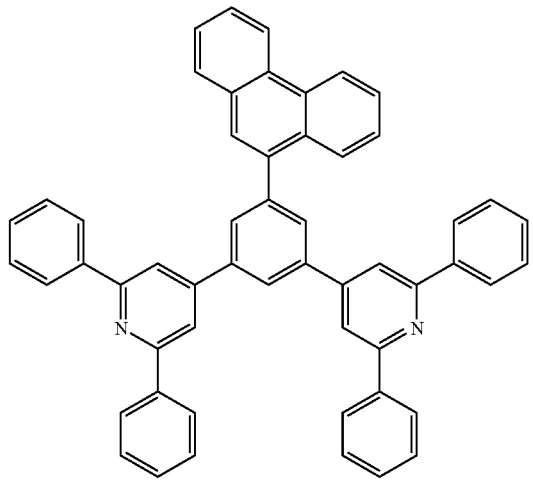

Example 2-11

Preparation of Element 13

An element 13 was prepared in the same manner as in (Example 2-1) except for using, as a material for the anode buffer layer 3, a material comprising a non-conjugation type polymer compound (PB-1) of the structural formula shown below having an aromatic amino group and an electron acceptive compound (A-2) and changing the thickness of the organic low molecular layer (layers from the hole transport layer 4 to the electron transport layer 7) as shown below.

Non-Conjugation Type Polymer Compound (PB-1) Having Aryl Amino Group:

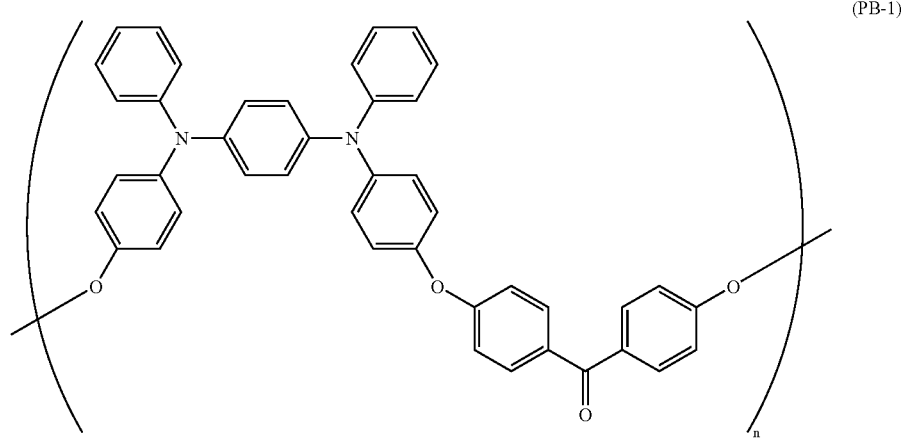

(PB-1)

weight-average molecular weight: 29,400
number-average molecular weight: 12,600

Electron acceptor (A-2): an ion compound of No. A-1 described in Table in Paragraph 0059 of Japanese Patent Application No. 2004-68958
Spin coating conditions:
Solvent: ethyl benzoate;
Concentration of coating solution: 2 [wt %];
PB-1:A-2=10:2;
Rotation number of spinner: 1,500 [rpm];
Rotation time of spinner: 30 [sec];
Drying conditions: 230° C.; 15 minutes.
A 30-nm thick uniform thin film was formed by the above-mentioned spin coating.

Organic Low Molecular Layers:

| | |
|---|---|
| Hole transport layer 4: arylamine compound (H-1) | 40 nm |
| Light-emitting layer 5: host material: carbazole derivative (E-1) dopant: organic iridium complex (D-1) 6 wt % | 30 nm |
| Hole blocking layer: end product 2 (HB-1) synthesized in Synthesis Example 1 | 5 nm |
| Electron transport layer 7: Al 8-hydroxyquinoline complex (ET-1) | 30 nm |

Light-emitting characteristics of the element 13 are shown in Table 2. The emission maxima of the element 13 was 512 nm, and chromaticity was CIE(x, y)=(0.30, 0.59), which was identified to be from the organic iridium complex (D-1).

Example 2-12

Preparation of Element 14

An element 14 was prepared in the same manner as in (Example 2-11) except for using the end product 38 obtained in Synthesis Example 15 and shown below in place of the end product 2 (HB-1) in the hole blocking layer.

Light-emitting characteristics of the element 14 are shown in Table 2. The emission maxima of the element was 513 nm, and chromaticity was CIE(x, y)=(0.30, 0.59), which was identified to be from the organic iridium complex (D-1).

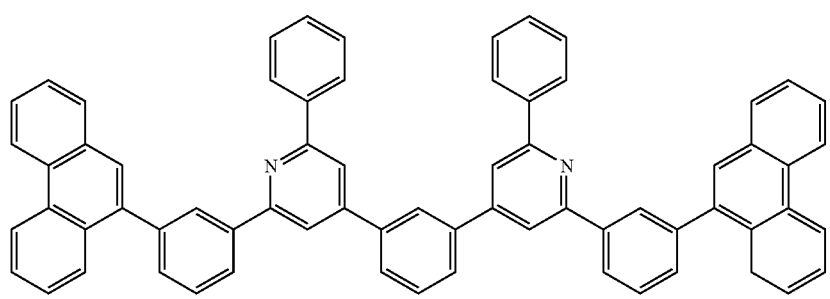

Example 2-13

Preparation of Element 15

An element 15 was prepared in the same manner as in (Example 2-11) except for using the end product 39 obtained in Synthesis Example 16 and shown below in place of the end product 2 (HB-1) in the hole blocking layer. Light-emitting characteristics of the element 15 are shown in Table 2.

The emission maxima of the element was 512 nm, and chromaticity was CIE(x, y)=(0.29, 0.58), which was identified to be from the organic iridium complex (D-1).

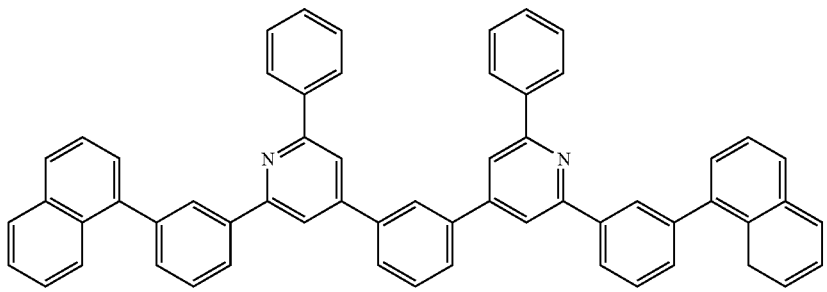

Comparative Example 2

Preparation of Comparative Elements 1 to 3 and Light-Emitting Characteristics Thereof

Comparative Example 2-1

Preparation of Comparative Element 1

A comparative element 1 was prepared in the same manner as in (Example 2-1) except for using the mixed ligand complex (HB-2) shown below in place of the end product 2 (HB-1) in the hole blocking layer. Light-emitting characteristics of the comparative element 1 are shown in Table 2. The emission maxima of the element was 510 nm, and chromaticity was CIE (x, y)=(0.28, 0.62), which was identified to be from the organic iridium complex (D-1). Initial light-emitting characteristics were the same as that of the element 1.

(HB-2)

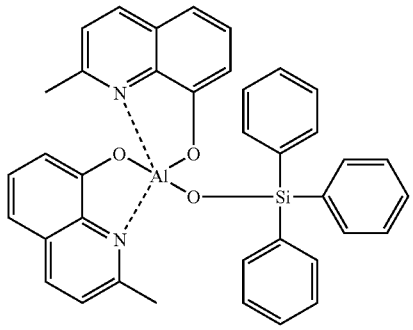

Comparative Example 2-2

Preparation of Comparative Element 2

A comparative element 2 was prepared in the same manner as in (Example 2-2) except for using the above-mentioned mixed ligand complex (HB-2) in place of the end product 2 (HB-1) in the hole blocking layer.

Light-emitting characteristics of the comparative element 2 are shown in Table 2. The emission maxima of the element was 626 nm, and chromaticity was CIE(x, y)=(0.67, 0.32), which was identified to be from the organic iridium complex (D-1) Initial light-emitting characteristics were the same as that of the element 2.

Comparative Example 2-3

Preparation of Comparative Element 3

A comparative element 3 was prepared in the same manner as in (Example 2-3) except for using the above-mentioned mixed ligand complex (HB-2) in place of the end product 2 (HB-1) in the hole blocking layer.

Light-emitting characteristics of the comparative element 3 are shown in Table 2. The emission maxima of the element was 472 nm, and chromaticity was CIE(x, y)=(0.17, 0.37), which was identified to be from the organic iridium complex (D-3). As to initial light-emitting characteristics, luminous efficiency and luminescence per electric current were lower than those of the element 3.

TABLE 2(A)

| | Hote Blocking Layer | Dopant in Light-emitting Layer | Electron Acceptor in Anode Buffer Layer | Turn on Voltage [V] @1 cd/m$^2$ | Maximum Light Emission Luminance [cd/m$^2$] @0.25 A/cm$^2$ | Luminous efficiency [lm/W] @100 cd/m$^2$ | Current Efficiency [cd/A] @100 cd/m$^2$ | Voltage [V] @100 cd/m$^2$ |
|---|---|---|---|---|---|---|---|---|
| Example 2-1 (Element 1) | End product 2 | D-1 | A-1 | 4.1 | 36,100 | 16.1 | 31.5 | 6.2 |
| Example 2-2 (Element 2) | End product 2 | D-2 | A-1 | 4.1 | 13,400 | 3.8 | 8.0 | 6.8 |
| Example 2-3 (Element 3) | End product 2 | D-3 | A-1 | 5.1 | 14,500 | 5.9 | 13.8 | 7.4 |
| Example 2-4 (Element 4) | End product 6 | D-1 | A-1 | 3.1 | 49,500 | 24.8 | 38.7 | 4.9 |
| Example 2-5 (Element 5) | End product 10 | D-1 | A-1 | 4.1 | 38,900 | 17.1 | 31.5 | 5.8 |
| Example 2-6 (Element 6) | End product 15 | D-1 | A-1 | 3.1 | 41,000 | 27.4 | 40.4 | 4.7 |
| Example 2-7 (Element 7) | End product 18 | D-1 | A-1 | 3.5 | 43,600 | 30.4 | 48.5 | 5.0 |
| Example 2-8 (Element 8) | End product 25 | D-1 | A-1 | 4.1 | 31,500 | 16.4 | 29.8 | 5.8 |
| Example 2-9 (Element 11) | End product 4 | D-1 | A-1 | 3.5 | 31,880 | 17.3 | 28.4 | 5.2 |
| Example 2-10 (Element 12) | End product 50 | D-1 | A-1 | 4.1 | 36,060 | 17.0 | 32.8 | 6.1 |
| Example 2-11 (Element 13) | End product 2 | D-1 | A-2 | 3.0 | 38,620 | 27.9 | 36.6 | 4.3 |
| Example 2-12 (Element 14) | End product 38 | D-1 | A-2 | 3.1 | 39,520 | 24.1 | 32.4 | 4.3 |
| Example 2-13 (Element 15) | End product 39 | D-1 | A-2 | 3.4 | 32,030 | 15.9 | 25.4 | 5.0 |
| Comparative Example 2-1 (Comparative element 1) | HB-2 | D-1 | A-1 | 4.1 | 40,200 | 16.1 | 29.3 | 5.7 |
| Comparative Example 2-2 (Comparative element 2) | HB-2 | D-2 | A-1 | 3.8 | 12,700 | 4.0 | 7.6 | 6.1 |
| Comparative Example 2-3 (Comparative element 3) | HB-2 | D-3 | A-1 | 5.0 | 13,100 | 3.6 | 8.2 | 7.1 |

Example 3

Evaluation of Elements

Example 3-1

Luminance Lifetime Test 1

The elements 1, 6, 7, 8 and 12 were subjected to driving life test under the following conditions.
Temperature: room temperature
Initial luminance: 5,000 cd/m$^2$
Driving method: direct current driving (DC driving)

Driving characteristics of the element 1 are shown in Table 3-1. The lifetime and increase in voltage are shown in terms of a relative time taking operating time of the comparative element 1 at the point where luminance/initial luminance=0.8 as 1.0. It is seen that the elements 1, 6, 7, 8 and 12 showed a longer life than that of the comparative element 1.

Comparative Example 3-1

The comparative element 1 was subjected to the luminance lifetime test in the same manner as in Example 3-1, and the results are shown in Table 3-1.

TABLE 3-1

| | Initial Luminance [cd/m$^2$] | Driving Current Density [mA/cm$^2$] | Relative Time @L/L0 = 0.8 |
|---|---|---|---|
| Element 1 | 5,000 | 30.3 | 1.92 |
| Element 6 | 5,000 | 22.0 | 1.65 |
| Element 7 | 5,000 | 19.4 | 1.85 |
| Element 8 | 5,000 | 34.1 | 1.56 |
| Element 12 | 5,000 | 29.4 | 1.67 |
| Comparative Element 1 | 5,000 | 25.3 | 1.00 |

Example 3-2

Luminance Lifetime Test 2

The elements 4 and 5 were subjected to luminance lifetime test under the following conditions.
Temperature: room temperature
Initial luminance: 1,000 cd/m$^2$
Driving method: direct current driving (DC driving)
Driving time: 100 hours Driving characteristics of the elements are shown in Table 3-2. The luminance/initial luminance (L/L0) and an increase in voltage (=voltage−initial voltage) after 100 hours are shown therein.

Comparative Example 3-2

The comparative element 1 was subjected to the luminance lifetime test in the same manner as in Example 3-2, and the results are shown in Table 3-2.

The elements 4 and 5 showed a larger L/L0 after 100 hours than that of the comparative element 1, thus having a longer life.

TABLE 3-2

| Element Prepared | Initial Luminance [cd/m$^2$] | Driving Current Density [mA/cm$^2$] | L/L0 @ 100 hr | Increase in Voltage [V] @ 100 hr |
|---|---|---|---|---|
| Element 4 | 1,000 | 3.3 | 0.92 | 0.52 |
| Element 5 | 1,000 | 4.1 | 0.94 | 0.70 |
| Comparative Element 1 | 1,000 | 4.9 | 0.84 | 0.75 |

Example 3-3

Luminance Lifetime Test 3

The elements 1, 8 and 11 were subjected to luminance lifetime test under the following conditions.
Temperature: room temperature
Initial luminance: 2,000 cd/m$^2$
Driving method: direct current driving (DC driving)

Each element was allowed to continuously emit light by supplying a constant current, and a time required for luminance to decrease by 40% (L/L0=0.6) was determined to compare. Relative times of the elements of Examples are shown in Table 3-3 taking the time for the element of Comparative Example 1 as 1.00. It is seen that the elements 1, 8 and T11 showed a longer life than that of the comparative element 1.

Comparative Example 3-3

The comparative element 1 was subjected to the luminance lifetime test in the same manner as in Example 3-3, and results are shown in Table 3-3.

TABLE 3-3

| | Initial Luminance [cd/m$^2$] | Driving Current Density [mA/cm$^2$] | Relative Time @ L/L0 = 0.6 |
|---|---|---|---|
| Element 1 | 2,000 | 13.0 | 2.19 |
| Element 8 | 2,000 | 11.3 | 2.26 |
| Element 11 | 2,000 | 11.9 | 1.46 |
| Comparative element 1 | 2,000 | 9.1 | 1.00 |

Example 3-4

Luminance Lifetime Test 4

The elements 13 and 14 were subjected to luminance lifetime test under the following conditions.
Temperature: room temperature
Initial luminance: 5,000 cd/m$^2$
Driving method: direct current driving (DC driving)

Each element was allowed to continuously emit light by supplying a constant current, and a time required for luminance to decrease to a half (L/L0=0.5) was determined to compare. Driving lifetimes of the elements 13 and 14 are the same.

TABLE 3-4

| | Initial Luminance [cd/m$^2$] | Driving Current Density [mA/cm$^2$] | Half Luminance Life Period [hour] |
|---|---|---|---|
| Element 13 | 5,000 | 24.6 | 396 |
| Element 14 | 5,000 | 24.4 | 402 |

Example 4

Preparation of Element Wherein the Charge Transporting Material of the Invention is Used in Both the Light-Emitting Layer and the Hole Blocking Layer Example 4-1

Preparation of Element 9

An element 9 was prepared in the same manner as in Example 2-1 except for using the end product 2 (HB-1) in place of the carbazole derivative (E-1) as a major component (host material) of the light-emitting layer 5.

Light-emitting characteristics of the element 9 are shown in Table 5.

The maximum wavelength of light-emitting spectrum of the element was 512 nm, and chromaticity was CIE(x, y)= (0.29, 0.62), which was identified to be from the organic iridium complex (D-1).

Example 4-2

Preparation of Element 10

An element 10 was prepared in the same manner as in Example 2-1 except for using the end product 6 (HB-3) in place of the carbazole derivative (E-1) as a major component (host material) of the light-emitting layer 5.

Light-emitting characteristics of the element 10 are shown in Table 5.

The emission maxima of the element 10 was 514 nm, and chromaticity was CIE(x, y)=(0.30, 0.62), which was identified to be from the organic iridium complex (D-1).

Example 4-3

Preparation of Element 16

An element 16 was prepared in the same manner as in Example 2-11 except for using the end product 57 in place of the carbazole derivative (E-1) as a major component (host material) of the light-emitting layer 5 and using the end product 38 in place of the end product 2 (HB-1) in the hole blocking layer.

Light-emitting characteristics of the element 6 are shown in Table 4. The emission maxima of the element 16 was 513 nm, which was identified to be from the organic iridium complex (D-1). Chromaticity was CIE(x, y)=(0.31, 0.61).

TABLE 4

|  | Turn on Voltage [V] @1 cd/m² | Maximum Luminance [cd/m²] @0.25 A/cm² | Luminous efficiency [lm/W] @100 cd/m² | Current Efficiency [cd/A] @100 cd/m² | Voltage [V] @100 cd/m² |
| --- | --- | --- | --- | --- | --- |
| Element 9 | 3.7 | 32,300 | 20.6 | 34.0 | 5.2 |
| Element 10 | 4.0 | 29,800 | 16.7 | 30.4 | 5.8 |
| Element 16 | 4.1 | 35,530 | 16.0 | 27.8 | 5.5 |

Example 4-4

Luminance Lifetime Test of Element 9

The element 9 and the element 1 prepared in Example 2-1 were subjected to luminance lifetime test under the following conditions.

Temperature: room temperature
Initial luminance: 1,000 cd/m²
Driving method: direct current driving (DC driving)

Each element was allowed to continuously emit light by supplying a constant current, and a time required for luminance to decrease by 20% (L/L0=0.8) was determined to compare. Relative time of the element 9 was 1.82 taking the time for the element 1 as 1.00. It is seen that the element 9 wherein the end product 2 (HB-1) in both the organic light-emitting layer and the hole blocking layer had a longer lifetime than the element 1 using the end product 2 (HB-1) only in the hole blocking layer.

Example 5

Preparation of an Element Using the Charge Transporting Material of the Invention in the Light-Emitting Layer (not Having the Hole Blocking Layer)

Example 5-1

Preparation of Element 17

An element 17 was prepared in the same manner as in Example 2-11 except for using the end product 57 synthe sized in Synthesis Example 23 and shown below in place of the carbazole derivative (E-1) as a major component (host material) of the light-emitting layer 5 and directly laminating the electron transport layer on the light-emitting layer without laminating the hole blocking layer.

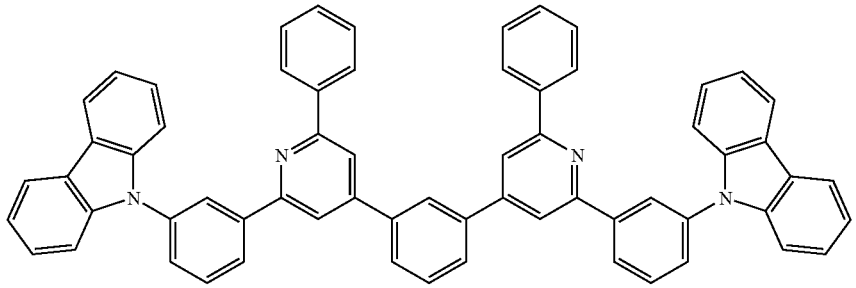

Light-emitting characteristics of the element 17 are shown in Table 5.

In Table 5, the maximum light emission luminance is a value at a current density of 0.25 A/cm², and luminous efficiency, luminance/current, and voltage are values at a luminance of 100 cd/m².

The emission maxima of the element 17 was 513 nm, and was identified to be from the organic iridium complex (D-1). Chromaticity was CIE(x, y)=(0.30, 0.59).

Comparative Example 5-1

Preparation of Comparative Element 4

A comparative element 4 was prepared in the same manner as in (Example 5-1) except for using the carbazole derivative (E-1) in place of the end product 57 in the light-emitting layer.

The light-emitting characteristics of the comparative element 4 are shown in Table 5. The emission maxima of the element was 513 nm, and chromaticity was CIE(x, y)=(0.30, 0.60), which was identified to be from the organic iridium complex (D-1). The initial light-emitting characteristics of the element 17 were more effective than that of the comparative element 4.

TABLE 5

|  | Turn on Voltage [V] @1 cd/m$^2$ | Maximum Luminance [cd/m$^2$] @0.25 A/cm$^2$ | Luminous efficiency [lm/W] @100 cd/m$^2$ | Current Efficiency [cd/A] @100 cd/m$^2$ | Voltage [V] @100 cd/m$^2$ |
|---|---|---|---|---|---|
| Element 17 | 5.0 | 27,950 | 12.8 | 25.2 | 6.2 |
| Comparative element 4 | 3.9 | 30,860 | 4.4 | 7.9 | 5.5 |

Example 6

Evaluation of Elements

Example 6-1

Luminance Lifetime Test

The element 17 was subjected to luminance lifetime test under the following conditions.
Temperature: room temperature
Initial luminance: 1,000 cd/m$^2$
Driving method: direct current driving (DC driving)

Driving characteristics of the element 17 are shown in Table 6. L/L0 is a ratio of luminance after 150 hours/initial luminance.

It is seen that the element 17 had a longer lifetime than the comparative element 4.

TABLE 6

|  | Initial Luminance [cd/m$^2$] | Driving Current Density [mA/cm$^2$] | L/L0 @150 h |
|---|---|---|---|
| Element 17 | 1,000 | 5.9 | 0.91 |
| Comparative element 4 | 1,000 | 7.4 | 0.84 |

Although the invention has been described in detail and by reference to specific embodiments, it is apparent to those skilled in the art that various alterations and modifications may be made without departing from the spirit and scope of the invention.

Additionally, the present application is based on the Japanese Patent Application filed on Jul. 31, 2003 (Japanese Patent Application No. 2003-204947), the Japanese Patent Application filed on Nov. 4, 2003 (Japanese Patent Application No. 2003-374430) and the Japanese Patent Application filed on Feb. 20, 2004 (Japanese Patent Application No. 2004-45219), and the whole contents thereof are included herein by reference.

INDUSTRIAL APPLICABILITY

The organic electroluminescent element using the charge transporting material of the invention can emit light with high luminance and high efficiency, and has an improved stability.

Also, the charge transporting material of the invention has such an excellent heat resistance, filming properties, charge transporting ability and light-emitting properties that it can be applicable as a light-emitting material, a host material, an electron injecting material, an electron transporting material and a hole blocking material depending upon the layer structure of an element.

Therefore, the organic electroluminescent element of the invention is considered to be applied to flat panel display (e.g., for OA computers or as a wall-hanging TV), an onboard display element, display for a cellular phone, a light source utilizing the characteristics as a flat light-emitting body (e.g., a light source for a copying machine or a backlight source for a liquid crystal display or a meter), an indication panel or a beacon light, thus technical values of the element being large.

Since the compound of the invention has a substantially excellent oxidation-reduction stability, it is useful to utilize the compound in an electrophotographic photoreceptor as well as in the organic electroluminescent element.

Further, the compound of the invention has an excellent amorphousness, solubility, heat resistance and durability in addition to the high performance that the charge transporting material of the invention has. Therefore, it is useful for a light-emitting material, a material for solar cell, a material for a battery (e.g., an electrolytic solution, an electrode, at separation membrane or a stabilizer), a material for medical use, a material for paint, a material for coating, a material for organic semi-conductor, a material for toiletries, a material for antistatic material and a material for thermoelectric element as well as for a charge transporting material.

The invention claimed is:

1. A charge transporting material comprising a compound having within the molecule two or more pyridine rings each substituted at least at 2-, 4- and 6-positions thereof by an aromatic ring group having a molecular weight of 400 or less, wherein the pyridine rings are connected to a connector having a molecular weight of 400 or less at the 4-position, and do not conjugate each other through the connector, and wherein the connector is a non-heterocyclic aromatic moiety.

2. The charge transporting material according to claim 1, wherein the compound has within the molecule 2 to 8 pyridyl rings, and the substituents on each ring may be the same or different.

3. The charge transporting material according to claim 1, wherein the molecular weight of the compound is from 200 to 4,000.

4. The charge transporting material according to claim 1, wherein the compound does not have a diarylamine structure within the molecule.

5. The charge transporting material according to claim 1, wherein the compound has at least one carbazole ring within the molecule.

6. The charge transporting material according to claim 1, which is an electron transporting material.

7. An organic electroluminescent element comprising a substrate having provided on a substrate an anode, a cathode and an organic light-emitting layer between these electrodes and comprising the charge transporting material described in claim 1.

8. The organic electroluminescent element according to claim 7, wherein a layer comprising said charge transporting material is the organic light-emitting layer.

9. The organic electroluminescent element according to claim 8, wherein the organic light-emitting layer comprises said charge transporting material as a host material, with the host material being doped with an organometallic complex.

10. The organic electroluminescent element according to claim 7, wherein the organic light-emitting layer comprises an organometallic complex as a light-emitting dye, and a layer comprising said charge transporting material is a hole blocking layer provided in contact with the interface of the organic light-emitting layer on the cathode side.

11. The organic electroluminescent element according to claim 9, wherein the organometallic complex has a 2-arylpyridine-based ligand.

12. The organic electroluminescent element according to claim 7, wherein said charge transporting material is contained in both the organic light-emitting layer and the layer in contact with the interface of the organic light-emitting layer on the cathode side.

13. A compound represented by the following formula (III):

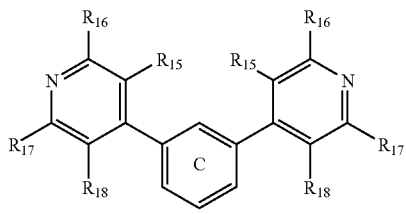

(III)

wherein ring C may have a substituent, the ring and optional substituent having a molecular weight of 400 or less, $R_{15}$ to $R_{18}$ each independently represents an aromatic ring group having a molecular weight of 400 or less, and two $R_{15}$s to $R_{18}$s in the formula (III) may be the same or different from each other.

14. A compound represented by the following formula (IV):

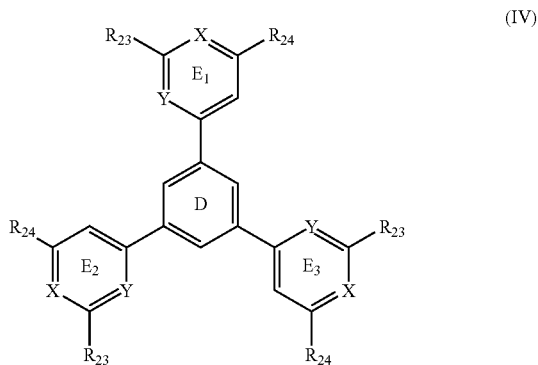

(IV)

wherein X each represents —N=, and Y each represents —CH=, $R_{23}$ and $R_{24}$ each independently represents an arbitrary group, rings $E_1$ to $E_3$ may have a substituent in addition to $R_{23}$ and $R_{24}$, plural $R_{23}$s and $R_{29}$s in the formula (IV) may be the same or different from each other, and ring D may have a substituent.

* * * * *